US011702660B2

(12) United States Patent
Vorechovsky et al.

(10) Patent No.: US 11,702,660 B2
(45) Date of Patent: Jul. 18, 2023

(54) MODULATION OF GENE EXPRESSION AND SCREENING FOR DEREGULATED PROTEIN EXPRESSION

(71) Applicant: University of Southampton, Hampshire (GB)

(72) Inventors: Igor Vorechovsky, Hampshire (GB); Jana Kralovicova, Hampshire (GB)

(73) Assignee: University of Southampton, Hampshire (GB)

( * ) Notice: Subject to any disclaimer, the term of this patent is extended or adjusted under 35 U.S.C. 154(b) by 97 days.

(21) Appl. No.: 17/159,881

(22) Filed: Jan. 27, 2021

(65) Prior Publication Data
US 2021/0155936 A1 May 27, 2021

Related U.S. Application Data

(60) Division of application No. 16/213,535, filed on Dec. 7, 2018, now Pat. No. 10,941,405, which is a continuation of application No. 15/288,415, filed on Oct. 7, 2016, now Pat. No. 10,196,639.

(51) Int. Cl.
*C12N 15/113* (2010.01)
*C12Q 1/6883* (2018.01)
*C12Q 1/6886* (2018.01)

(52) U.S. Cl.
CPC ........ *C12N 15/1137* (2013.01); *C12N 15/113* (2013.01); *C12Q 1/6883* (2013.01); *C12Q 1/6886* (2013.01); C12N 2310/11 (2013.01); C12N 2310/14 (2013.01); C12N 2310/315 (2013.01); C12N 2310/321 (2013.01); C12N 2310/3519 (2013.01); C12N 2320/33 (2013.01); C12N 2320/34 (2013.01); C12Q 2600/106 (2013.01); C12Q 2600/136 (2013.01); C12Q 2600/156 (2013.01); C12Q 2600/158 (2013.01)

(58) Field of Classification Search
None
See application file for complete search history.

(56) References Cited

U.S. PATENT DOCUMENTS

| 4,866,042 | A  | 9/1989  | Neuwelt         |
|-----------|----|---------|-----------------|
| 5,151,510 | A  | 9/1992  | Stec et al.     |
| 5,656,612 | A  | 8/1997  | Monia           |
| 5,665,593 | A  | 9/1997  | Kole et al.     |
| 5,914,396 | A  | 6/1999  | Cook et al.     |
| 5,916,808 | A  | 6/1999  | Kole et al.     |
| 5,976,879 | A  | 11/1999 | Kole et al.     |
| 6,083,482 | A  | 7/2000  | Wang            |
| 6,166,197 | A  | 12/2000 | Cook et al.     |
| 6,210,892 | B1 | 4/2001  | Bennett et al.  |
| 6,294,520 | B1 | 9/2001  | Naito           |
| 6,383,752 | B1 | 5/2002  | Agrawal et al.  |
| 6,436,657 | B1 | 8/2002  | Famodu et al.   |
| 6,451,991 | B1 | 9/2002  | Martin et al.   |
| 6,485,960 | B1 | 11/2002 | Harris et al.   |
| 6,531,591 | B1 | 3/2003  | Fensholdt       |
| 6,573,073 | B2 | 6/2003  | Harris          |
| 6,605,611 | B2 | 8/2003  | Simmonds et al. |
| 6,632,427 | B1 | 10/2003 | Finiels et al.  |
| 6,639,059 | B1 | 10/2003 | Kochkine et al. |
| 6,670,461 | B1 | 12/2003 | Wengel et al.   |
| 6,677,445 | B1 | 1/2004  | Innis et al.    |
| 6,734,291 | B2 | 5/2004  | Kochkine et al. |
| 6,756,523 | B1 | 6/2004  | Kahn et al.     |
| 6,770,748 | B2 | 8/2004  | Imanishi et al. |
| 6,794,499 | B2 | 9/2004  | Wengel et al.   |
| 6,846,921 | B2 | 1/2005  | Innis et al.    |
| 6,936,589 | B2 | 8/2005  | Naito           |
| 6,963,589 | B1 | 11/2005 | Sugata et al.   |
| 6,998,484 | B2 | 2/2006  | Koch et al.     |
| 7,015,315 | B1 | 3/2006  | Cook et al.     |
| 7,034,133 | B2 | 4/2006  | Wengel et al.   |
| 7,053,199 | B2 | 5/2006  | Imanishi et al. |
| 7,053,207 | B2 | 5/2006  | Wengel          |
| 7,060,809 | B2 | 6/2006  | Wengel et al.   |
| 7,071,324 | B2 | 7/2006  | Preparata et al.|
| 7,084,125 | B2 | 8/2006  | Wengel          |
| 7,101,993 | B1 | 9/2006  | Cook et al.     |
| 7,169,594 | B2 | 1/2007  | Guan            |
| 7,214,783 | B2 | 5/2007  | Jeon et al.     |
| 7,217,805 | B2 | 5/2007  | Imanishi et al. |
| 7,314,923 | B2 | 1/2008  | Kaneko et al.   |
| 7,335,765 | B2 | 2/2008  | Kaneko et al.   |
| 7,368,549 | B2 | 5/2008  | Dempcy et al.   |

(Continued)

FOREIGN PATENT DOCUMENTS

CN 103667438 A 3/2014
EP 0549615 A1 7/1993

(Continued)

OTHER PUBLICATIONS

Smith, et al., "Nonsense-mediated RNA decay-a switch and dial for regulating gene expression" Bioessays (2015); 37(6): 612-623.

(Continued)

*Primary Examiner* — Sean McGarry

(74) *Attorney, Agent, or Firm* — Wilson Sonsini Goodrich & Rosati

(57) ABSTRACT

Disclosed herein include compositions and methods of modulating protein expression that utilizes an activator or a repressor of a non-sense mediated RNA decay switch exon (NSE). In some embodiments, also included herein are compositions and methods of modulating protein expression that uses an agent that targets a transposed element.

47 Claims, 31 Drawing Sheets

Specification includes a Sequence Listing.

(56) References Cited

U.S. PATENT DOCUMENTS

| | | |
|---|---|---|
| 7,399,845 B2 | 7/2008 | Seth et al. |
| 7,432,249 B2 | 10/2008 | Crooke |
| 7,432,250 B2 | 10/2008 | Crooke |
| 7,547,684 B2 | 6/2009 | Seth et al. |
| 7,553,644 B2 | 6/2009 | Germino et al. |
| 7,569,575 B2 | 8/2009 | Soerensen et al. |
| 7,569,686 B1 | 8/2009 | Bhat et al. |
| 7,572,582 B2 | 8/2009 | Wengel et al. |
| 7,595,304 B2 | 9/2009 | Zhao et al. |
| 7,615,619 B2 | 11/2009 | Imanishi et al. |
| 7,662,946 B2 | 2/2010 | Ginsburg et al. |
| 7,662,948 B2 | 2/2010 | Kurreck et al. |
| 7,666,854 B2 | 2/2010 | Seth et al. |
| 7,687,617 B2 | 3/2010 | Thrue et al. |
| 7,696,345 B2 | 4/2010 | Allerson et al. |
| 7,741,457 B2 | 6/2010 | Seth et al. |
| 7,750,131 B2 | 7/2010 | Seth et al. |
| 7,816,333 B2 | 10/2010 | Kaneko et al. |
| 7,846,686 B2 | 12/2010 | Kramer |
| 7,951,934 B2 | 5/2011 | Freier |
| 7,994,145 B2 | 8/2011 | Imanishi et al. |
| 8,022,193 B2 | 9/2011 | Seth et al. |
| 8,030,467 B2 | 10/2011 | Seth et al. |
| 8,048,998 B2 | 11/2011 | Rasmussen et al. |
| 8,067,569 B2 | 11/2011 | Iversen et al. |
| 8,084,458 B2 | 12/2011 | Soerensen et al. |
| 8,088,746 B2 | 1/2012 | Seth et al. |
| 8,110,674 B2 | 2/2012 | Manoharan et al. |
| 8,124,745 B2 | 2/2012 | Allerson et al. |
| 8,129,515 B2 | 3/2012 | Esau et al. |
| 8,168,605 B2 | 5/2012 | Zhao et al. |
| 8,258,109 B2 | 9/2012 | Bennett et al. |
| 8,268,980 B2 | 9/2012 | Seth et al. |
| 8,278,036 B2 | 10/2012 | Kariko et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,293,684 B2 | 10/2012 | Mouritzen et al. |
| 8,361,979 B2 | 1/2013 | Aartsma-Rus et al. |
| 8,383,792 B2 | 2/2013 | Okamoto et al. |
| 8,394,947 B2 | 3/2013 | Bhat et al. |
| 8,415,465 B2 | 4/2013 | Freier |
| 8,436,163 B2 | 5/2013 | Iversen et al. |
| 8,450,467 B2 | 5/2013 | Manoharan et al. |
| 8,461,124 B2 | 6/2013 | Chattopadhyaya |
| 8,492,390 B2 | 7/2013 | Detlef et al. |
| 8,501,703 B2 | 8/2013 | Bennett et al. |
| 8,501,805 B2 | 8/2013 | Seth et al. |
| 8,518,908 B2 | 8/2013 | Hrdlicka et al. |
| 8,530,640 B2 | 9/2013 | Seth et al. |
| 8,541,562 B2 | 9/2013 | Obika et al. |
| 8,546,556 B2 | 10/2013 | Seth et al. |
| 8,592,156 B2 | 11/2013 | Liu et al. |
| 8,637,478 B2 | 1/2014 | Bennett |
| RE44,779 E | 2/2014 | Imanishi et al. |
| 8,653,252 B2 | 2/2014 | Elmen et al. |
| 8,673,560 B2 | 3/2014 | Leamon et al. |
| 8,680,254 B2 | 3/2014 | Lutz et al. |
| 8,691,783 B2 | 4/2014 | Thum et al. |
| 8,703,728 B2 | 4/2014 | Swayze et al. |
| 8,710,021 B2 | 4/2014 | Anro et al. |
| 8,735,366 B2 | 5/2014 | Bauer et al. |
| 8,748,089 B2 | 6/2014 | Kariko et al. |
| 8,779,118 B2 | 7/2014 | Allerson et al. |
| 8,796,437 B2 | 8/2014 | Swayze et al. |
| 8,809,516 B2 | 8/2014 | Manoharan et al. |
| 8,846,386 B2 | 9/2014 | Ambati et al. |
| 8,846,637 B2 | 9/2014 | Seth et al. |
| 8,846,639 B2 | 9/2014 | Swayze et al. |
| 8,846,885 B2 | 9/2014 | Hirai et al. |
| 8,895,722 B2 | 11/2014 | Iversen et al. |
| 8,957,040 B2 | 2/2015 | Bennett et al. |
| 8,957,200 B2 | 2/2015 | Seth et al. |
| 8,957,201 B2 | 2/2015 | Kaneko et al. |
| 9,005,906 B2 | 4/2015 | Swayze et al. |
| 9,006,194 B2 | 4/2015 | Katsikis et al. |
| 9,006,415 B2 | 4/2015 | Ren et al. |
| 9,012,139 B2 | 4/2015 | Collard et al. |
| 9,029,335 B2 | 5/2015 | Prakash et al. |
| 9,045,518 B2 | 6/2015 | Christensen et al. |
| 9,045,754 B2 | 6/2015 | Bhanot et al. |
| 9,057,066 B2 | 6/2015 | Hung et al. |
| 9,109,001 B2 | 8/2015 | Parsy et al. |
| 9,127,272 B2 | 9/2015 | Esau et al. |
| 9,127,276 B2 | 9/2015 | Prakash et al. |
| 9,156,873 B2 | 10/2015 | Prakash et al. |
| 9,157,081 B2 | 10/2015 | Bennett et al. |
| 9,181,549 B2 | 11/2015 | Prakash et al. |
| 9,187,515 B2 | 11/2015 | Mayes et al. |
| 9,192,621 B2 | 11/2015 | Mayes et al. |
| 9,193,752 B2 | 11/2015 | Migawa et al. |
| 9,193,969 B2 | 11/2015 | Montefeltro et al. |
| 9,211,300 B2 | 12/2015 | Mayes et al. |
| 9,217,147 B2 | 12/2015 | Singh et al. |
| 9,221,864 B2 | 12/2015 | Seth et al. |
| 9,243,245 B2 | 1/2016 | De Kimpe et al. |
| 9,290,534 B2 | 3/2016 | Seth et al. |
| 9,296,778 B2 | 3/2016 | Parsy et al. |
| 9,309,275 B2 | 4/2016 | Stewart et al. |
| 9,315,535 B2 | 4/2016 | Mitsuoka et al. |
| 9,334,495 B2 | 5/2016 | Khvorova et al. |
| 9,339,541 B2 | 5/2016 | Dousson et al. |
| 9,347,068 B2 | 5/2016 | Dhugga et al. |
| 9,359,445 B2 | 6/2016 | Finkbeiner et al. |
| 9,359,603 B2 | 6/2016 | Lutz et al. |
| 9,359,609 B2 | 6/2016 | Duffield et al. |
| 9,410,155 B2 | 8/2016 | Collard et al. |
| 9,428,534 B2 | 8/2016 | Christensen et al. |
| 9,447,166 B2 | 9/2016 | Ambati et al. |
| 9,453,261 B2 | 9/2016 | Lee et al. |
| 9,464,292 B2 | 10/2016 | Okumura et al. |
| 9,499,818 B2 | 11/2016 | Van |
| 9,518,259 B2 | 12/2016 | Rigo et al. |
| 9,534,222 B2 | 1/2017 | Ambati et al. |
| 9,550,988 B2 | 1/2017 | Swayze |
| 9,714,422 B2 | 7/2017 | Vorechovsky et al. |
| 9,745,577 B2 | 8/2017 | Vorechovsky et al. |
| 9,771,579 B2 | 9/2017 | Collard et al. |
| 9,976,143 B2 | 5/2018 | Krainer et al. |
| 10,119,168 B2 | 11/2018 | Vaidya et al. |
| 10,196,639 B2 | 2/2019 | Vorechovsky et al. |
| 10,517,853 B2 | 12/2019 | Welch et al. |
| 10,583,128 B2 | 3/2020 | Collard et al. |
| 2003/0148974 A1 | 8/2003 | Monia et al. |
| 2004/0063129 A1 | 4/2004 | Gaarde et al. |
| 2004/0219515 A1 | 11/2004 | Bentwich |
| 2005/0221354 A1 | 10/2005 | Mounts |
| 2005/0233327 A1 | 10/2005 | Welch et al. |
| 2006/0062790 A1 | 3/2006 | Reinhard et al. |
| 2006/0134670 A1 | 6/2006 | Piu |
| 2007/0009899 A1 | 1/2007 | Mounts |
| 2007/0087376 A1 | 4/2007 | Potashkin |
| 2007/0249538 A1 | 10/2007 | Sazani et al. |
| 2008/0269123 A1 | 10/2008 | Li et al. |
| 2009/0186846 A1 | 7/2009 | Chabot et al. |
| 2009/0186946 A1 | 7/2009 | Taketomi et al. |
| 2009/0264353 A1 | 10/2009 | Orum et al. |
| 2009/0270332 A1 | 10/2009 | Bare et al. |
| 2010/0150839 A1 | 6/2010 | Kelleher |
| 2010/0166784 A1 | 7/2010 | Murphy et al. |
| 2011/0124591 A1 | 5/2011 | Bennett |
| 2011/0229891 A1 | 9/2011 | Michaud et al. |
| 2012/0190728 A1 | 7/2012 | Bennett et al. |
| 2012/0252877 A1 | 10/2012 | Lo |
| 2013/0072671 A1 | 3/2013 | Van Deutekom |
| 2013/0096183 A1 | 4/2013 | Collard et al. |
| 2013/0109850 A1 | 5/2013 | Prakash et al. |
| 2013/0136732 A1 | 5/2013 | Wagner et al. |
| 2013/0184223 A1 | 7/2013 | Land et al. |
| 2013/0253036 A1 | 9/2013 | Collard et al. |
| 2013/0266560 A1 | 10/2013 | Demopulos et al. |
| 2013/0289092 A1 | 10/2013 | Rigo et al. |
| 2014/0011761 A1 | 1/2014 | Hotamisligil et al. |
| 2014/0128449 A1 | 5/2014 | Liu et al. |

(56) References Cited

U.S. PATENT DOCUMENTS

| | | |
|---|---|---|
| 2014/0186839 A1 | 7/2014 | Margulies et al. |
| 2014/0194610 A1 | 7/2014 | Verdine et al. |
| 2014/0235605 A1 | 8/2014 | Shiffman et al. |
| 2014/0309181 A1 | 10/2014 | Collard et al. |
| 2014/0336238 A1 | 11/2014 | Collin et al. |
| 2014/0343127 A1 | 11/2014 | Kammler |
| 2014/0349290 A1 | 11/2014 | Watnick et al. |
| 2014/0378526 A1 | 12/2014 | Rossi et al. |
| 2014/0378527 A1 | 12/2014 | Van |
| 2014/0378533 A1 | 12/2014 | Freier |
| 2015/0004217 A1 | 1/2015 | Guild et al. |
| 2015/0018540 A1 | 1/2015 | Prakash et al. |
| 2015/0184153 A1 | 7/2015 | Freier et al. |
| 2015/0211006 A1 | 7/2015 | Butler et al. |
| 2015/0211010 A1 | 7/2015 | Kerem et al. |
| 2015/0232845 A1 | 8/2015 | Ozsolak |
| 2015/0232858 A1 | 8/2015 | Ozsolak |
| 2015/0238516 A1 | 8/2015 | Dowdy et al. |
| 2015/0267192 A1 | 9/2015 | Heartlein et al. |
| 2015/0291957 A1 | 10/2015 | Smith |
| 2015/0329918 A1 | 11/2015 | Kang et al. |
| 2015/0337310 A1 | 11/2015 | Walker et al. |
| 2015/0361497 A1 | 12/2015 | Rose |
| 2016/0017322 A1 | 1/2016 | Vorechovsky et al. |
| 2016/0024500 A1 | 1/2016 | Popplewell et al. |
| 2016/0046935 A1 | 2/2016 | Bentwich et al. |
| 2016/0122767 A1 | 5/2016 | Gouya et al. |
| 2016/0201063 A1 | 7/2016 | Ozsolak |
| 2016/0201064 A1 | 7/2016 | Ozsolak |
| 2016/0208264 A1 | 7/2016 | Wilton et al. |
| 2016/0215291 A1 | 7/2016 | Garcia et al. |
| 2016/0244762 A1 | 8/2016 | Vorechovsky et al. |
| 2016/0244767 A1 | 8/2016 | Hastings |
| 2016/0298121 A1 | 10/2016 | Krainer et al. |
| 2017/0159049 A9 | 6/2017 | Krainer et al. |
| 2017/0240904 A1 | 8/2017 | Tallent et al. |
| 2018/0002694 A1 | 1/2018 | Vorechovsky et al. |
| 2018/0296501 A1 | 10/2018 | During |
| 2018/0362987 A1 | 12/2018 | Krainer et al. |
| 2018/0369275 A1 | 12/2018 | Arnarez et al. |
| 2019/0024118 A1 | 1/2019 | Tagliatela et al. |
| 2019/0024119 A1 | 1/2019 | Tagliatela et al. |
| 2019/0024120 A1 | 1/2019 | Tagliatela et al. |
| 2019/0024121 A1 | 1/2019 | Tagliatela et al. |
| 2019/0070213 A1 | 3/2019 | Aznarez et al. |
| 2019/0192691 A1 | 6/2019 | Barrett et al. |
| 2019/0218255 A1 | 7/2019 | Chung et al. |
| 2019/0225939 A1 | 7/2019 | Chambers et al. |
| 2019/0264211 A1 | 8/2019 | Vorechovsky et al. |
| 2020/0085838 A1 | 3/2020 | Martinez Botella et al. |
| 2020/0101174 A1 | 4/2020 | Coller et al. |

FOREIGN PATENT DOCUMENTS

| | | |
|---|---|---|
| EP | 1201678 B1 | 9/2004 |
| EP | 1409497 B1 | 1/2005 |
| EP | 1007714 B1 | 12/2005 |
| EP | 1334109 B1 | 5/2006 |
| EP | 1178999 B1 | 3/2007 |
| EP | 1203827 B1 | 5/2007 |
| EP | 1501848 B1 | 8/2007 |
| EP | 1569661 B1 | 9/2009 |
| EP | 1161439 B1 | 4/2010 |
| EP | 1984381 B1 | 9/2010 |
| EP | 1013661 B1 | 1/2012 |
| EP | 2092065 B1 | 1/2012 |
| EP | 2099461 B1 | 3/2012 |
| EP | 2170917 B1 | 6/2012 |
| EP | 2066684 B1 | 7/2012 |
| EP | 2284269 A3 | 8/2012 |
| EP | 2356129 B1 | 4/2013 |
| EP | 2376516 B1 | 4/2013 |
| EP | 2114981 B1 | 5/2013 |
| EP | 2149605 B1 | 7/2013 |
| EP | 2285819 B1 | 10/2013 |
| EP | 2161038 B1 | 12/2013 |
| EP | 1562971 B1 | 2/2014 |
| EP | 2295441 B1 | 5/2014 |
| EP | 2314594 B1 | 7/2014 |
| EP | 2410053 B1 | 10/2014 |
| EP | 2176280 B2 | 6/2015 |
| EP | 2361921 B1 | 6/2015 |
| EP | 2462153 B1 | 7/2015 |
| EP | 1015469 B2 | 11/2015 |
| EP | 2173760 B2 | 11/2015 |
| EP | 1937312 B1 | 6/2016 |
| EP | 2141233 B1 | 10/2016 |
| EP | 2410054 B1 | 1/2017 |
| EP | 3329909 A1 | 6/2018 |
| EP | 2753317 B1 | 2/2020 |
| GB | 2546719 A | 8/2017 |
| WO | WO-9402501 A1 | 2/1994 |
| WO | WO-9426887 A1 | 11/1994 |
| WO | WO-2005049651 A2 | 6/2005 |
| WO | WO-2006107846 A2 | 10/2006 |
| WO | WO-2007002390 A2 | 1/2007 |
| WO | WO-2007048628 A2 | 5/2007 |
| WO | WO-2007048629 A2 | 5/2007 |
| WO | WO-2007002390 A3 | 11/2007 |
| WO | WO-2009084472 A1 | 7/2009 |
| WO | WO-2010148249 A1 | 12/2010 |
| WO | WO-2011057350 A1 | 5/2011 |
| WO | WO-2012168435 A1 | 12/2012 |
| WO | WO-2012178146 A1 | 12/2012 |
| WO | WO-2013036105 A1 | 3/2013 |
| WO | WO-2013081755 A1 | 6/2013 |
| WO | WO-2013106770 A1 | 7/2013 |
| WO | WO-2013119916 A2 | 8/2013 |
| WO | WO-2014012081 A2 | 1/2014 |
| WO | WO-201428459 A1 | 2/2014 |
| WO | WO-2014028459 A1 | 2/2014 |
| WO | WO-2014031575 A1 | 2/2014 |
| WO | WO-2014049536 A2 | 4/2014 |
| WO | WO-2014121287 A2 | 8/2014 |
| WO | WO-2014172698 A1 | 10/2014 |
| WO | WO-2014201413 A1 | 12/2014 |
| WO | WO-2014209841 A2 | 12/2014 |
| WO | WO-2015035091 A1 | 3/2015 |
| WO | WO-2015024876 A3 | 7/2015 |
| WO | WO-2015190922 A1 | 12/2015 |
| WO | WO-2015193651 A1 | 12/2015 |
| WO | WO-2015198054 A1 | 12/2015 |
| WO | WO-2016027168 A2 | 2/2016 |
| WO | WO-2016054615 A2 | 4/2016 |
| WO | WO-2016061509 A1 | 4/2016 |
| WO | WO-2016077837 A1 | 5/2016 |
| WO | WO-2016087842 A1 | 6/2016 |
| WO | WO-2016118697 A1 | 7/2016 |
| WO | WO-2016128343 A1 | 8/2016 |
| WO | WO-2016138534 A2 | 9/2016 |
| WO | WO-2016161429 A1 | 10/2016 |
| WO | WO-2016196386 A1 | 12/2016 |
| WO | WO-2017053982 A1 | 3/2017 |
| WO | WO-2017060731 A1 | 4/2017 |
| WO | WO-2017106210 A1 | 6/2017 |
| WO | WO-2017106211 A1 | 6/2017 |
| WO | WO-2017106283 A1 | 6/2017 |
| WO | WO-2017106292 A1 | 6/2017 |
| WO | WO-2017106364 A2 | 6/2017 |
| WO | WO-2017106370 A1 | 6/2017 |
| WO | WO-2017106375 A1 | 6/2017 |
| WO | WO-2017106377 A1 | 6/2017 |
| WO | WO-2017106382 A1 | 6/2017 |
| WO | WO-2017106364 A3 | 7/2017 |
| WO | WO-2018187363 A1 | 10/2018 |
| WO | WO-2018191482 A2 | 10/2018 |
| WO | WO-2018206924 A1 | 11/2018 |
| WO | WO-2019040923 A1 | 2/2019 |
| WO | WO-2019084050 A1 | 5/2019 |
| WO | WO-2019109051 A1 | 6/2019 |
| WO | WO-2019191341 A1 | 10/2019 |
| WO | WO-2019199867 A1 | 10/2019 |
| WO | WO-2019227096 A1 | 11/2019 |

(56) References Cited

FOREIGN PATENT DOCUMENTS

| | | |
|---|---|---|
| WO | WO-2019236750 A2 | 12/2019 |
| WO | WO-2019243430 A1 | 12/2019 |
| WO | WO-2020041348 A1 | 2/2020 |

OTHER PUBLICATIONS

Aartsma-Rus, et al. Antisense-mediated exon skipping: a versatile tool with therapeutic and research applications.RNA. Oct. 2007;13(10):1609-24. Epub Aug. 7, 2007.
Aceti, et al. "Syngap1 haploinsufficiency damages a postnatal critical period of pyramidal cell structural maturation linked to cortical circuit assembly", (2015) Biol Psychiatry, 77(9): 805-815.
Aizer AA, et al. Lack of reduction in racial disparities in cancer-specific mortality over a 20-year period. Cancer. 2014;120:1532-9.
Altschul SF et al.Basic local alignment search tool. J. Mol. Biol., vol. 215, No. 3, pp. 403-410, (Oct. 5, 1990).
Aly, et al. Extreme genetic risk for type 1A diabetes. Proc Natl Acad Sci U S A. Sep. 19, 2006;103(38):14074-9. Epub Sep. 11, 2006.
Amarnath, S. et al. The PDL1-PD1 Axis Converts Human TH1 Cells into Regulatory T Cells. Science Translational Medicine, vol. 3, No. 111, pp. 1-13. (Nov. 30, 2011).
Anders S. et al. Detecting differential usage of exons from RNA-seq data. Genome Res. 2012;22(10):2008-17. Epub Jun. 23, 2012.doi: gr.133744.111 [pii] 10.1101/gr.133744.111. PubMed PMID: 22722343.
Au, K.S. et al. Molecular Genetic Basis of Tuberous Sclerosis Complex: From Bench to Bedside.Journal of Child Neurology. vol. 19, No. 9 (Sep. 2004).
Audentes Therapeutics Announces Expansion of AAV Technology Platform and Pipeline with New Development Programs for Duchenne Muscular Dystrophy and Myotonic Dystrophy. PRNewswire Apr. 8, 2019 (7 pgs).
Aznarez, et al. TANGO-Targeted augmentation of nuclear gene output—for the treatment of genetic diseases [abstract]. In: 2018 Annual Meeting Abstract of the American Society of Gene and Cell Therapy; May 16-19, 2018; Chicago, IL; 2018. Abstract No. 304.
Bakkenist CJ, Kastan MB. DNA damage activates ATM through intermolecular autophosphorylation and dimer dissociation. Nature. 2003;421(6922):499-506. doi: 10.1038/nature01368. PubMed PMID: 12556884.
Balagurumoorthy, et al. Hairpin and parallel quartet structures for telomeric sequences. Nucleic Acids Res. Aug. 11, 1992;20(15):4061-7.
Balkwill, et al. Repression of translation of human estrogen receptor alpha by G-quadruplex formation. Biochemistry. Dec. 8, 2009;48(48):11487-95. doi: 10.1021/bi901420k.
Barratt, et al. Remapping the insulin gene/IDDM2 locus in type 1 diabetes. Diabetes. Jul. 2004;53(7):1884-9.
Bassi et al. A novel mutation in the ATP1A2 gene causes alternating hemiplegia of childhood. J. Med. Genet. 41:621-628 (2004).
Battistini et al. A new CACNA1A gene mutation in acetazolamide-responsive familial hemiplegic migraine and ataxia.Neurology, vol. 53, No. 1, pp. 38-43 (Jul. 13, 1999).
Baughan, et al. Delivery of bifunctional RNAs that target an intronic repressor and increase SMN levels in an animal model of spinal muscular atrophy. Hum Mol Genet. May 1, 2009;18(9):1600-11. doi: 10.1093/hmg/ddp076. Epub Feb. 19, 2009.
Bauman et al. Therapeutic potential of splice-switching oligonucleotides. Oligonucleotides 19.1 (2009): 1-13.
Beaudoin, et al. 5'-UTR G-quadruplex structures acting as translational repressors. Nucleic Acids Res. Nov. 2010;38(20):7022-36. doi: 10.1093/nar/gkq557. Epub Jun. 22, 2010.
Beli P, et al., Proteomic investigations reveal a role for RNA processing factor THRAP3 in the DNA damage response. Mol Cell. 2012;46(2):212-25. doi: 10.1016/j.molcel.2012.01.026. PubMed PMID: 22424773; PubMed Central PMCID: PMC3565437.
Berge, SM et al. Pharmaceutical Salts Journal of Pharmaceutical Sciences, vol. 66, No. 1, pp. 1-19 (1977).

Berger, W. et al. The molecular basis of human retinal and vitreoretinal diseases. Progress in Retinal and Eye Research . vol. 29, pp. 335-375 (2010).
Bethke L, et al. Comprehensive analysis of the role of DNA repair gene polymorphisms on risk of glioma. Hum Mol Genet. 2008;17(6):800-5. Epub 2007/12/01.doi: ddm351 [pii] 10.1093/hmg/ddm351. PubMed PMID: 18048407.
Bicknell, et al. Introns in UTRs: why we should stop ignoring them. Bioessays. Dec. 2012;34(12):1025-34. doi: 10.1002/bies.201200073. Epub Oct. 26, 2012.
Blencowe, Benjamin. Reflections for the 20th anniversary issue of RNA journal.RNA Journal, vol. 21, No. 4, pp. 573-575 (2015).
Blencowe BJ. Splicing regulation: the cell cycle connection. Curr Biol. 2003;13(4):R149-51. PubMed PMID: 12593819.
Bonnen, P.E., et al. Haplotypes at ATM identify coding-sequence variation and indicate a region of extensive linkage disequilibrium. Am J Hum Genet. 2000;67(6):1437-51. Epub 2000/11/15.doi: S0002-9297(07)63213-3 [pii] 10.1086/316908. PubMed PMID: 11078475.
Boothby, T. et al. Removal of Retained Introns Regulates Translation in the Rapidly Developing Gametophyte of Marsilea vestita. Developmental Cell vol. 24, pp. 517-529, (Mar. 11, 2013).
Booy, et al. The RNA helicase RHAU (DHX36) unwinds a G4-quadruplex in human telomerase RNA and promotes the formation of the P1 helix template boundary. Nucleic Acids Res. May 2012;40(9):4110-24. doi: 10.1093/nar/gkr1306. Epub Jan. 11, 2012.
Boutz, et al. Detained introns are a novel, widespread class of post-transcriptionally spliced introns. Genes Dev. Jan. 1, 2015;29(1):63-80. doi: 10.1101/gad.247361.114.
Braunschweig, et al. Widespread intron retention in mammals functionally tunes transcriptomes. Widespread intron retention in mammals functionally tunes transcriptomes. Genome Res. Nov. 2014;24(11):1774-86. doi: 10.1101/gr.177790.114. Epub Sep. 25, 2014.
Bravo-Gil, et al., Improving the management of Inherited Retinal Dystrophies by targeted sequencing of a population-specific gene panel, Scientific Reports, 6:23910, 10 pages, 2016.
Brooks, A.N., et al. A pan-cancer analysis of transcriptome changes associated with somatic mutations in U2AF1 reveals commonly altered splicing events. PLoS One. 2014; 9(1):e87361. Epub Feb. 6, 2014.doi: 10.1371/journal.pone.0087361 PONE-D-13-26905 [pii], PubMed PMID: 24498085.
Buchman, et al. Comparison of intron-dependent and intron-independent gene expression. Mol Cell Biol. Oct. 1988;8(10):4395-405.
Buckley, P.T. et al. Cytoplasmic intron retention, function, splicing, and the sentinel RNA hypothesis.WIREs RNA, vol. 5, pp. 223-2330 (Mar./Apr. 2014).
Bugaut, et al. 5'-UTR RNA G-quadruplexes: translation regulation and targeting. Nucleic Acids Res. Jun. 2012;40(11):4727-41. doi: 10.1093/nar/gks068. Epub Feb. 20, 2012.
Bugaut, et al. An RNA hairpin to G-quadruplex conformational transition. J Am Chem Soc. Dec. 12, 2012;134(49):19953-6. doi: 10.1021/ja308665g. Epub Nov. 29, 2012.
Buratti, et al. DBASS3 and DBASS5: databases of aberrant 3'- and 5'-splice sites. Nucleic Acids Res. Jan. 2011;39(Database issue):D86-91. doi: 10.1093/nar/gkq887. Epub Oct. 6, 2010.
Buratti, et al. RNA folding affects the recruitment of SR proteins by mouse and human polypurinic enhancer elements in the fibronectin EDA exon. Mol Cell Biol. Feb. 2004;24(3):1387-400.
Burnette et al. Subdivision of large introns in *Drosophila* by recursive splicing at non-exonic elements. Genetics (2005).
Burns, CG, et al. Connections between pre-mRNA processing and regulation of the eukaryotic cell cycle. Front Horm Res. 1999; 25:59-82.
Buschmann et al. Chitosans for delivery of nucleic acids. Advanced drug delivery reviews 65.9 (2013): 1234-1270.
Busslinger, et al. β+ Thalassemia: Aberrant splicing results from a single point mutation in an intron. Cell 27.2 (1981): 289-298.
Callis, et al. Introns increase gene expression in cultured maize cells. Genes Dev. Dec. 1987;1(10):1183-200.
Catterall, et al. Nav1.1 channels and epilepsy. J Physiol. Jun. 1, 2010;588(Pt 11):1849-59.

(56) References Cited

OTHER PUBLICATIONS

Cavaloc, et al. The splicing factors 9G8 and SRp20 transactivate splicing through different and specific enhancers. RNA. Mar. 1999;5(3):468-83.

Cazzola, et al. Translational pathophysiology: a novel molecular mechanism of human disease. Blood. Jun. 1, 2000;95(11):3280-8.

Chambers, A.L., et al. The INO80 chromatin remodeling complex prevents polyploidy and maintains normal chromatin structure at centromeres. Genes Dev. 2012; 26(23):2590-603. Epub Dec. 5, 2012.doi: 26/23/2590 [pii] 10.1101/gad.199976.112. PubMed PMID: 23207916.

Chen, M.S., et al. Chk1 kinase negatively regulates mitotic function of Cdc25A phosphatase through 14-3-3 binding. Mol Cell Biol. 2003; 23(21):7488-97. PubMed PMID: 14559997; PubMed Central PMCID: PMC207598.

Chen, T., et al. A functional single nucleotide polymorphism in promoter of ATM is associated with longevity. Meeh Ageing Dev. 2010; 131:636-40.

Choi, HH, et al. CHK2 kinase promotes pre-mRNA splicing via phosphorylating CDK11p110. Oncogene. 2014; 33:108-15.

Colla, S., et al. Telomere dysfunction drives aberrant hematopoietic differentiation and myelodysplastic syndrome. Cancer Cell. 2015; 27(5):644-57. doi: 10.1016/j.ccell.2015.04.007. PubMed PMID: 25965571.

Collie, et al. The application of DNA and RNA G-quadruplexes to therapeutic medicines. Chem Soc Rev. Dec. 2011;40(12):5867-92. doi: 10.1039/c1cs15067g. Epub Jul. 25, 2011.

Collin, et al., "Antisense Oligonucleotide (AON)-based Therapy for Leber Congenital Amaurosis caused by a Frequent Mutation in CEP290", (2012) Molecular Therapy-Nucleic Acids, pp. 1-7.

Consortium. TGP. An integrated map of genetic variation from 1,092 human genomes. Nature (London). 2012; 491:56-65.

Corallini et al. Transcriptional and Posttranscriptional Regulation of the CTNS Gene. Pediatric Research 70(2):130-135 (Aug. 2011).

Corey, S.J., et al. A non-classical translocation involving 17q12 (retinoic acid receptor alpha) in acute promyelocytic leukemia (APML) with atypical features. Leukemia. 1994; 8(8):1350-3. PubMed PMID: 8057672.

Corvelo, A., et al. Genome-wide association between branch point properties and alternative splicing. PLoS Comput Biol. 2010; 6(11):e1001016. Epub Dec. 3, 2010.doi: 10.1371/journal.pcbi.1001016. PubMed PMID: 21124863.

Coulombe-Huntington J., et al. Fine-Scale Variation and Genetic Determinants of Alternative Splicing across Individuals. PLoS Genet. 2009; 5(12):e1000766. Epub Dec. 17, 2009.doi: 10.1371/journal.pgen.1000766. PubMed PMID: 20011102.

Coutinho, G., et al. Functional significance of a deep intronic mutation in the ATM gene and evidence for an alternative exon 28a. Hum Mutat. 2005; 25(2):118-24. Epub Jan. 12, 2005.doi: 10.1002/humu.20170. PubMed PMID: 15643608.

Creacy, et al. G4 resolvase 1 binds both DNA and RNA tetramolecular quadruplex with high affinity and is the major source of tetramolecular quadruplex G4-DNA and G4-RNA resolving activity in HeLa cell lysates. J Biol Chem. Dec. 12, 2008;283(50):34626-34. doi: 10.1074/jbc.M806277200. Epub Oct. 7, 2008.

Creson, et al. "Re-expression of SynGAP Protein in Adulthood Improves Translatable Measures of Brain Function and Behavior in a Model of Neurodevelopmental Disorders" (2018) Departments of Neuroscience and Molecular medicine, The Scripps Research Institute.

Culler, et al. Functional selection and systematic analysis of intronic splicing elements identify active sequence motifs and associated splicing factors. Nucleic Acids Res. Aug. 2010;38(15):5152-65. doi: 10.1093/nar/gkq248. Epub Apr. 12, 2010.

DATABASE Geneseq [Online], Nov. 13, 2008 (Nov. 13, 2008), Dual label detection probe, QF probe 1, 5. 3.11, XP055572852, retrieved from EBI Accession No. GSN:ARK21623.

Davies, et al. A genome-wide search for human type 1 diabetes susceptibility genes. Nature. Sep. 8, 1994;371(6493):130-6.

Decorsiere, et al. Essential role for the interaction between hnRNP H/F and a G quadruplex in maintaining p53 pre-mRNA 3'-end processing and function during DNA damage. Genes Dev. Feb. 1, 2011;25(3):220-5. doi: 10.1101/gad.607011.

Dedic, T. et al. Alagille Syndrome Mimicking Biliary Atresia in Early Infancy, PLOS OONE, 10(11):e0143939: pp. 1-7 (Nov. 20, 2015).

Deere, J. et al. Antisense Phosphorodiamidate Morpholino OligomerLengthand TargetpositionEffects on Gene-SpecificInhibitionin *Escherichia coli.* Antimicrobial Agents Andchemotherapy, vol. 49, No. 1, p. 249-255(Jan. 2005).

Derecka, et al. Occurrence of a quadruplex motif in a unique insert within exon C of the bovine estrogen receptor alpha gene (ESR1). Biochemistry. Sep. 7, 2010;49(35):7625-33. doi: 10.1021/bi100804f.

Dias, N. et al. Antisense oligonucleotides: basic concepts and mechanisms Mol. Cancer Ther. vol. 1, pp. 347-355, (Mar. 2002).

Didiot, et al. The G-quartet containing FMRP binding site in FMR1 mRNA is a potent exonic splicing enhancer. Nucleic Acids Res. Sep. 2008;36(15):4902-12. doi: 10.1093/nar/gkn472. Epub Jul. 24, 2008.

Ding, H. et al. DeliveringPD-1 inhibitory signal concomitant with blocking ICOS co-stimulation suppresses lupus-like syndrome in autoimmune BXSB mice.Clinical Immunology, vol. 118, pp. 258-267, (2006).

Divina, P. et al. Ab initio prediction of cryptic splice-site activation and exon skipping. Eur J Hum Genet. 2009; 17:759-65.

Dominski, et al. Restoration of correct splicing in thalassemic pre-mRNA by antisense oligonucleotides. Proc Natl Acad Sci U S A. Sep. 15, 1993;90(18):8673-7.

Dredge, et al. NeuN/Rbfox3 Nuclear and Cytoplasmic Isoforms Differentially Regulate Alternative Splicing and Nonsense-Mediated Decay of Rbfox2. PLoS One. 2011; 6(6): e21585.

Du, et al. Correction of prototypic ATM splicing mutations and aberrant ATM function with antisense morpholino oligonucleotides. Proc Natl Acad Sci U S A. Apr. 3, 2007;104(14):6007-12. Epub Mar. 26, 2007.

Du, et al. "Correction of prototypic ATM splicing utations and aberrant ATM function with antisense morpholino oligonucleotides" (2007) PNAS, vol. 104, No. 14, pp. 6007-6012.

Ducros et al.Recurrence of the T666M calcium channel CACNA1A gene mutation in familial hemiplegic migraine with progressive cerebellar ataxia.Am J Hum Genet. vol. 64, No. 1, pp. 89-98 (Jan. 1999).

Duikers, et al. "Antisense Oligonucleotide-Based Splicing Correction in Individuals with Leber Congenital Amaurosis due to Compound Heterozygosity for the C.2991+1655AG Mutation in CEP290" (2018) International Journal of Molecular Sciences, 19, 753, pp. 1-12.

Dulla, et al., "Splice-Modulating Oligonucleotide QR-110 Restores CEP200 mRNA and Function in Human C.2991+1655AG LCA10 Models" (2018) Molecular Therapy: Nucleic Acids, vol. pp. 730-740.

Duryagina R, et al. Overexpression of Jagged-1 and its intracellular domain in human mesenchymal stromal cells differentially affect the interaction with hematopoietic stem and progenitor cells.Stem Cells Dev. vol. 22, No. 20, pp. 2736-2750 (2013).

Dutertre, M., et al. et al. DNA damage: RNA-binding proteins protect from near and far. Trends Biochem Sci. 2014; 39(3):141-9. Epub Feb. 19, 2014.doi: S0968-0004(14)00015-2 [pii] 10.1016/j.tibs.2014.01.003. PubMed PMID: 24534650.

Eddy, et al. G4 motifs correlate with promoter-proximal transcriptional pausing in human genes. Nucleic Acids Res. Jul. 2011;39(12):4975-83. doi: 10.1093/nar/gkr079. Epub Mar. 3, 2011.

El Bougrini, J., et al. PML positively regulates interferon gamma signaling. Biochimie. 2011; 93(3):389-98. doi: 10.1016/j.biochi.2010.11.005. PubMed PMID: 21115099.

Emerick, et al. Multivariate analysis and visualization of splicing correlations in single-gene transcriptomes. BMC Bioinformatics. Jan. 18, 2007;8:16.

EP 15846242.4 Partial Supplementary Search Report and Search Opinion dated May 2, 2018.

EP 16876621.0 Extended European Search Report and Search Opinion dated Mar. 7, 2019.

(56) References Cited

OTHER PUBLICATIONS

EP15729929.8 Office Action dated Dec. 22, 2017.
EP15729929.8 Office Action dated Oct. 30, 2018.
EP15846242.4 Extended European Search Report dated Aug. 21, 2018.
EP16781187.6 Office Action dated May 20, 2019.
EP16876499.1 Extended Search Report dated Jun. 14, 2019.
EP168766061.1 Extended Search Report dated May 24, 2019.
Fairbrother, W.G., et al. Predictive identification of exonic splicing enhancers in human genes. Science. 2002; 297(5583):1007-13. PubMed PMID: 12114529.
Fededa, et al. A polar mechanism coordinates different regions of alternative splicing within a single gene. Mol Cell. Aug. 5, 2005;19(3):393-404.
Ferreira, P.G., et al. Transcriptome characterization by RNA sequencing identifies a major molecular and clinical subdivision in chronic lymphocytic leukemia. Genome Res. 2014; 24:212-26.
Fletcher, Sue et al. Antisense suppression of donor splice site mutations in the dystrophin gene transcript.Molecular Genetics & Genomic Medicine, vol. 1, No. 3, pp. 162-173, Jun. 13, 2013.
Fred, et al. The human insulin mRNA is partly translated via a cap- and eIF4A-independent mechanism. Biochem Biophys Res Commun. Sep. 9, 2011;412(4):693-8. doi: 10.1016/j.bbrc.2011.08.030. Epub Aug. 16, 2011.
Friedman, et al., "Correction of Aberrant Splicing of the Cystic Fibrosis Transmembrane conductance Regulator (CFTR) Gene by Antisense Oligonucleotides" (1999) The Journal of Biological Chemistry, vol. 274, No. 51, pp. 36193-36199.
Friedman, KJ et al. Correction of aberrant splicing of the cystic fibrosis transmembrane conductance regulator (CFTR) gene by antisense oligonucleotides. J Biol Chem. Dec. 17, 1999;274(51):36193-36199.
Friend, KL et al. Detection of a novel missense mutation and second recurrent mutation in the CACNA1A gene in individuals with EA-2 and FHM. Hum Genet. vol. 105(3):261-5 (Sep. 1999).
Furukawa & Kish 2008, GeneReviews Pagon Ra et al. eds. Univ. of WA Seattle, NCBI Bookshelf ID NBK1437.
Galante, et al. Detection and evaluation of intron retention events in the human transcriptome. RNA. May 2004;10(5):757-65.
Garanto, et al., "In vitro and in vivo rescue of aberrant splicing in CEP290-associted LCA by antisense oligonucleotide delivery" (2016) Human Molecular Genetics, vol. 25, No. 12, pp. 2552-2563.
Garner, et al. Selectivity of small molecule ligands for parallel and anti-parallel DNA G-quadruplex structures. Org Biomol Chem. Oct. 21, 2009;7(20):4194-200. doi: 10.1039/b910505k. Epub Aug. 14, 2009.
Geary et al. Absolute Bioavailability of 29-O-(2-Methoxyethyl)-Modified Antisense Oligonucleotides following Intraduodenal Instillation in Rats. J Pharmacal Exp Ther. vol. 296, No. 3, pp. 898-904 (Mar. 2001).
Geary, et al., "Pharmacokinetics, biodistribution and cell uptake of antisense oligonucleotides", (2015) Advance Drug Delivery Reviews.
Geary, RS, et al., Pharmacokinetic properties of 2'-O-(2-methoxyethyl)-modified oligonucleotide analogs in ratsJ Pharmacal Exp Ther. vol. 296, No. 3, pp. 890-897 (Mar. 2001).
Gerard, et al., "AON-mediated Exon Skipping Restores ciliation in Fibroblasts Harboring the Common Leber Congenital Amaurosis CEP290 Mutation" (2012) Molecular Therapy—Nucleic Acids, pp. 1-9.
Gianchecchi et al. Recent insights into the role of the PD-1/PD-L1 pathway in immunological tolerance and autoimmunity. Autoimmunity Reviews 12:1091-1100 (2013).
Gibson, G. Hints of hidden heritability in GWAS. Nat Genet. 2010; 42(7):558-60. Epub Jun. 29, 2010.doi: ng0710-558 [pii] 10.1038/ng0710-558. PubMed PMID: 20581876.
Gohring, J. et al. Imaging of Endogenous MessengerRNA Splice Variants in Living Cells Reveals Nuclear Retention of Transcripts Inaccessible to Nonsense-Mediated Decay in *Arabidopsis*.The Plant Cell.vol. 26, pp. 754-764.(Feb. 2014).
Gomes et al. Translating chitosan to clinical delivery of nucleic acid-based drugs. MRS bulletin 39.1 (2014): 60-70.
Gomez, et al. Telomerase downregulation induced by the G-quadruplex ligand 12459 in A549 cells is mediated by hTERT RNA alternative splicing. Nucleic Acids Res. Jan. 16, 2004;32(1):371-9. Print 2004.
Goncharova et al. Tuberin regulates p70 S6 kinase activation and ribosomal protein S6 phosphorylation. A role for the TSC2 tumor suppressor gene in pulmonary lymphangioleiomyomatosis (LAM). J. Biol. Chem. (Aug. 23, 2002) 277(34);30958-67. EPub Jun. 3, 2002.
Gonzalez-Santos, et al., Mutation in the splicing factor Hprp3p linked to retinitis pigmentosa impairs interactions within the U4/U6 snRNP pigmentosa impairs interactions within the U4/U6 snRNP complex, PubMed Central Canada , Author Manuscript, 29 pages, 2008.
Goto, et al., "Targeted skipping of a Single Exon Harboring a Premature termination Codon Mutation: Implications and Potential for Gene Correction Therapy for Selective Dystrophic Epiderolysis Bullosa Patients" (2006) Journal of Investigative Dermatology, vol. 126, pp. 2614-262.
Goyenvalie, et al. Therapeutic approaches to muscular dystrophy. Hum Mol Genet. Apr. 15, 2011;20(R1):R69-78. doi: 10.1093/hmg/ddr105. Epub Mar. 24, 2011.
Gozani, O., et al. A potential role for U2AF-SAP 155 interactions in recruiting U2 snRNP to the branch site. Mol Cell Biol. 1998; 18(8):4752-60. PubMed PMID: 9671485.
Graveley, B.R. The haplo-spliceo-transcriptome: common variations in alternative splicing in the human population. Trends Genet. 2008; 24(1):5-7. Epub Dec. 7, 2007.doi: S0168-9525(07)00349-6 [pii] 10.1016/j.tig.2007.10.004. PubMed PMID: 18054116.
Gutell, R.R., et al. A story: unpaired adenosine bases in ribosomal RNAs. J Mol Biol. 2000; 304(3):335-54. Epub Nov. 25, 2000.doi: 10.1006/jmbi.2000.4172 S0022-2836(00)94172-X [pii], PubMed PMID: 11090278.
Guth, S., et al. Dual function for U2AF(35) in AG-dependent pre-mRNA splicing. Mol Cell Biol. 2001;21(22):7673-81. PubMed PMID: 11604503.
Guy et al. A mouse Mecp2-null mutation causes neurological symptoms that mimic Rett syndrome. Nat Genet 27:322-326 (2001).
Hai, et al. A G-tract element in apoptotic agents-induced alternative splicing. Nucleic Acids Res. Jun. 2008;36(10):3320-31. doi: 10.1093/nar/gkn207. Epub Apr. 24, 2008.
Hamdan, F. et al. Mutations in SYNGAP1 in Autosomal Nonsyndromic Mental Retardation.The New England Journal of Medicine.N.Engl. Med. vol. 360, No. 6, pp. 599, (Feb. 5, 2009).
Hamdan, F. F. et al. De Novo SYNGAP1 Mutations in Nonsyndromic Intellectual Disability and Autism, Biol. Psychiatry, 69:898-901 (2011).
Hammond, et al."Genetic therapies for RNA mis-splicing diseases" (2011) Cell Press 10 pages.
Han, et al., "Antisense oligonucleotides increase Scn1a expression and reduce seizures and SUDEP incidence in a mouse model of Dravet syndrome" (2020) Science Translational Medicine, 12, pp. 1-14.
Han, et al. TANGO-Targeted augmentation of nuclear gene output for the treatment of genetic diseases. Poster session presented at the American Society of Gene and Cell Therapy, Chicago, IL. (May 2018).
Hargous, et al. Molecular basis of RNA recognition and TAP binding by the SR proteins SRp20 and 9G8. EMBO J. Nov. 1, 2006;25(21):5126-37. Epub Oct. 12, 2006.
Harkin, et al. The spectrum of SCN1A-related infantile epileptic encephalopathies. Brain. Mar. 2007;130(Pt 3):843-52.
Hastings, M.L., et al. Control of pre-mRNA splicing by the general splicing factors PUF60 and U2AF. PLoS ONE. 2007;2:e538. PubMed PMID: 17579712.
Havens, et al., "Targeting RNA Splicing fo rDisease Therapy" (2013) Wiley Interdiscip Rev RNA , 4(3): 247-266.
He, Y.H., et al. Association of the insulin-like growth factor binding protein 3 (IGFBP-3) polymorphism with longevity in Chinese nonagenarians and centenarians. Aging (Milano). 2014;6:944-56.

(56) References Cited

OTHER PUBLICATIONS

Hegele, et al. Dynamic protein-protein interaction wiring of the human spliceosome. Mol Cell. Feb. 24, 2012;45(4):567-80. doi: 10.1016/j.molcel.2011.12.034.

Hernan, I. et al. Cellular Expression and siRNA-Mediated Interference of Rhodopsin cis-Acting Splicing Mutants Associated with Autosomal Dominant Retinitis Pigmentosa, Invest Ophthalmol. Vis. Sci. (2011) 52:3723-3729.

Heyn, P. et al. Introns and gene expression: Cellular constraints, transcriptional regulation, and evolutionary consequences. Bioessays vol. 37, pp. 148-154 (2014).

Hiller et al. Pre-mRNA secondary structures influence exon recognition. PLoS genetics 3.11 (2007): e204.

Hirata et al.Prevention of Experimental Autoimmune Encephalomyelitis by Transfer of Embryonic Stem Cell-Derived Dendritic Cells Expressing Myelin Oligodendrocyte Glycoprotein Peptide along with TRAIL or Programmed Death-1 Ligand.J. Immunology vol. 174 pp. 1888-1897 (2005).

Hishida, A. et al. Polymorphisms in PPAR Genes (PPARD, PPARG, and PPARGC1A) and the Risk of Chronic Kidney Disease in Japanese: Cross-Sectional Data from the J-MICC Study. PPAR 2013; 980471 pp. 1-8.

*Homo sapiens* pre-mRNA processing factors (PRPF3), mRNA, NCBI Reference Sequence: NM_004698.2 Accessed Apr. 6, 2017.

Hua et al. Antisense masking of an hnRNP A1/A2 intronic splicing silencer corrects SMN2 splicing in transgenic mice. Am. J. Hum. Genet. 82:834-848 (Mar. 27, 2008).

Hua, et al. Antisense correction of SMN2 splicing in the CNS rescues necrosis in a type III SMA mouse model. Genes Dev. Aug. 1, 2010;24(15):1634-44. doi: 10.1101/gad.1941310. Epub Jul. 12, 2010.

Hua, Y., et al. Enhancement of SMN2 exon 7 inclusion by antisense oligonucleotides targeting the exon. PLoS Biol. 2007;5(4):e73. Epub Mar. 16, 2007.doi: 06-PLBI-RA-1492R3 [pii] 10.1371/journal. pbio.0050073. PubMed PMID: 17355180.

Hunt, et al. Negligible impact of rare autoimmune-locus coding-region variants on missing heritability. Nature. Jun. 13, 2013;498(7453):232-5. doi: 10.1038/nature12170. Epub May 22, 2013.

Huynh, K.D., et al. BCoR, a novel corepressor involved in BCL-6 repression. Genes Dev. 2000;14(14):1810-23. PubMed PMID: 10898795; PubMed Central PMCID: PMC316791.

International Application No. PCT/GB2015/051756 International Preliminary Report on Patentability, dated Dec. 26, 2016.

International Application No. PCT/GB2015/051756 International Search Report and Written Opinion dated Nov. 30, 2015.

International Application No. PCT/GB2016/053136 International Search Report and Written Opinion dated Mar. 6, 2017.

International Application No. PCT/GB2016/053136 Partial International Search Report dated Jan. 19, 2017.

International Application No. PCT/US16/66576 International Search Report and Written Opinion dated May 4, 2017.

International Application No. PCT/US16/66691 International Search Report and Written Opinion dated May 10, 2017.

International Application No. PCT/US16/66708 International Search Report and Written Opinion dated May 8, 2017.

International Application No. PCT/US16/66721 International Search Report and Written Opinion dated May 1, 2017.

International Application No. PCT/US2015/053896 International Preliminary Report on Patentability dated Apr. 4, 2017.

International Application No. PCT/US2015/53896 International Search Report and Written Opinion dated Mar. 3, 2016.

International Application No. PCT/US2016/066414 International Search Report and Written Opinion dated Apr. 19, 2017.

International Application No. PCT/US2016/066417 International Search Report and Written Opinion dated Apr. 19, 2017.

International Application No. PCT/US2016/066564 International Search Report and Written Opinion dated May 4, 2017.

International Application No. PCT/US2016/066705 International Search Report and Written Opinion dated Apr. 24, 2017.

International Application No. PCT/US2018/048031 International Search Report and Written Opinion dated Jan. 22, 2019.

International search report and written opinion dated Jun. 5, 2017 for PCT Application No. PCT/US2016/066684.

International Search Report and Written Opinion dated Mar. 28, 2019 for PCT/US2018/057165.

Itoh et al. Methyl CpG-binding Protein Isoform MeCP2_e2 Is Dispensable for Rett Syndrome Phenotypes but Essential for Embryo Viability and Placenta Development. J Biol Chem 287:13859-13867 (2012).

Iwamoto, et al. Transcription-dependent nucleolar cap localization and possible nuclear function of DExH RNA helicase RHAU. Exp Cell Res. Apr. 1, 2008;314(6):1378-91. doi: 10.1016/j.yexcr.2008. 01.006. Epub Jan. 16, 2008.

Jacob et al. Intron retention as a component of regulated gene expression programs. Hum Genet 136:1043-1057 (2017).

Jarver, P. et al., A Chemical View of Oligonucleotides for Exon Skipping and Related Drug Applications, Nucleic Acid Therapeutics vol. 24, No. 1, pp. 37-47, (2014).

Jearawiriyapaisarn et al. Sustained Dystrophin Expression Induced by Peptide-conjugated Morpholino Oligomers in the Muscles of mdx Mice. Mol Ther. 16(9): 1624-1629 (2008).

Jurka et al. Identification of new medium reiteration frequency repeats in the genomes of Primates, Rodentia and Lagomorpha. Genetica98.3 (1996): 235-247.

Jurkiewicz, D. et al. Spectrum of JAG1 gene mutations in Polish patients with Alagille syndrome J. Appl. Genetics vol. 55, pp. 329-336, (2014).

Kach et al. A novel antisense oligonucleotide approach to treat eye diseases by increasing target gene expression. No. 3423-A0194 ARVO Poster Apr. 19, 2019 (1 pg.).

Kaminker, P.G., et al. A novel form of the telomere-associated protein TIN2 localizes to the nuclear matrix. Cell Cycle. 2009;8(6):931-9. PubMed PMID: 19229133; PubMed Central PMCID: PMC2751576.

Kang et al. Up-regulation of luciferase gene expression with antisense oligonucleotides: implications and applications in functional assay development. Biochemistry 37.18 (1998): 6235-6239.

Kaplan et al. Medium reiteration frequency repetitive sequences in the human genome. Nucleic acids research 19.17 (1991): 4731-4738.

Katsani, K.R. et al. Functional Genomics Evidence Unearths New Moonlighting Roles of Outer Ring Coat Nucleoporins Scientific Reports vol. 4, No. 4655 (Apr. 11, 2014).

Kawamata, N., et al. Genetic differences between Asian and Caucasian chronic lymphocytic leukemia. Int J Oncol. 2013;43(2):561-5. doi: 10.3892/ijo.2013.1966. PubMed PMID: 23708256; PubMed Central PMCID: PMC3775563.

Ke, et al. Quantitative evaluation of all hexamers as exonic splicing elements. Genome Res. Aug. 2011;21(8):1360-74. doi: 10.1101/gr. 119628.110. Epub Jun 9, 2011.

Keir, M.E. et al. PD-1 and Its Ligands in Tolerance and Immunity. Annu. Rev. Immunol. vol. 26, pp. 677-704 (2008).

Kervestin et al. NMD: a multifaceted response to premature translational termination. Nature reviews Molecular cell biology13.11 (2012): 700.

Kikin, et al. QGRS Mapper: a web-based server for predicting G-quadruplexes in nucleotide sequences. Nucleic Acids Res. Jul. 1, 2006;34(Web Server issue):W676-82.

Kim, E., et al. SRSF2 Mutations Contribute to Myelodysplasia by Mutant-Specific Effects on Exon Recognition. Cancer Cell. 2015;27(5):617-30. doi: 10.1016/j.ccell.2015.04.006. PubMed PMID: 25965569; PubMed Central PMCID: PMC4429920.

Kim et al. The role of synaptic GTPase-activating protein in neuronal development and synaptic plasticity. J. Neurosci. 23(4):1119-1124 (Feb. 15, 2003).

Kim, J. et al. The splicing factor U2AF65 stabilizes TRF1 protein by inhibiting its ubiquitin-dependent proteolysis. Biochem Biophys Res Commun. 2014;443(3):1124-30. doi: 10.1016/j.bbrc.2013.12. 118. PubMed PMID: 24389012.

Kim P., et al. ChimerDB 2.0—a knowledgebase for fusion genes updated. Nucleic Acids Res. 2009;38(Database issue):D81-5. Epub Nov. 13, 2009.doi: gkp982 [pii] 10.1093/nar/gkp982. PubMed PMID: 19906715.

(56) References Cited

OTHER PUBLICATIONS

Knudsen et al. Increased skewing of X chromosome inactivation in Rett syndrome patients and their mothers. Eur J Hum Genet 14:1189-1194(2006).
Kole, et al. RNA therapeutics: beyond RNA interference and antisense oligonucleotides. Nat Rev Drug Discov. Jan. 20, 2012;11(2):125-40. doi: 10.1038/nrd3625.
Kralovicova, et al. Allele-specific recognition of the 3' splice site of INS intron 1. Hum Genet. Oct. 2010;128(4):383-400. doi: 10.1007/s00439-010-0860-1. Epub Jul. 14, 2010.
Kralovicova, et al. Compensatory signals associated with the activation of human GC 5' splice sites. Nucleic Acids Res. Sep. 1, 2011;39(16):7077-91. doi: 10.1093/nar/gkr306. Epub May 23, 2011.
Kralovicova et al. Exon-centric regulation of ATM expression is population-dependent and amenable to antisense modification by pseudoexon targeting, Scientific Reports, 6:18741, doi:10.1038/srep18741, Jan. 6, 2016, 13 pages.
Kralovicova, et al. Global control of aberrant splice-site activation by auxiliary splicing sequences: evidence fora gradient in exon and intron definition. Nucleic Acids Res. Oct. 2007; 35(19): 6399-6413.
Kralovicova, et al. Identification of U2AF(35)-dependent exons by RNA-Seq reveals a link between 3' splice-site organization and activity of U2AF-related proteins. Nucleic Acids Res. Apr. 20, 2015;43(7):3747-63. doi: 10.1093/nar/gkv194. Epub Mar. 16, 2015.
Kralovicova, et al. Optimal antisense target reducing INS intron 1 retention is adjacent to a parallel G quadruplex. Nucleic Acids Res. Jul. 2014;42(12):8161-73. doi: 10.1093/nar/gku507. Epub Jun. 17, 2014.
Kralovicova, et al. Phenotypic consequences of branch point substitutions. Hum Mutat. Aug. 2006;27(8):803-13.
Kralovicova, et al. Position-dependent repression and promotion of DQB1 intron 3 splicing by GGGG motifs. J Immunol. Feb. 15, 2006;176(4):2381-8.
Kralovicova, et al. Variants in the human insulin gene that affect pre-mRNA splicing: is—23Hphl a functional single nucleotide polymorphism at IDDM2? Diabetes. Jan. 2006;55(1):260-4.
Kralovicova, et al. Antisense Oligonucleotides Modulating Activation of a Nonsense-Mediated RNA Decay Switch Exon in the ATM Gene.Nucleic Acid Ther. Dec. 1, 2016; 26(6): 392-400.
Kralovicova, J. et al. Branch sites haplotypes that control alternative splicing. Hum Mol Genet. 2004;13:3189-202.
Kralovicova, J. et al. The role of short RNA loops in recognition of a single-hairpin exon derived from a mammalian-wide interspersed repeat. RNA Biol. 2015;12(1):54-69. doi: 10.1080/15476286.2015.1017207. PubMed PMID: 25826413.
Kriaucionis et al. The major form of MeCP2 has a novel N-terminus generated by alternative splicing. Nucleic Acids Res 32:1818-1823 (2004).
Krishnaraj et al. RettBASE: Rett syndrome database update. Hum Mutat 38:922-931 (2017).
Laceerra, et al., "Restoration of hemoglobin A synthesis in erythroid cells from peripheral blood of thalassemic patients" (2000) PNAS, vol. 97, No. 17, pp. 9591-9596.
Lander, et al. Initial sequencing and analysis of the human genome. Nature, 409 (Feb. 15, 2001): 860-921.
Laplanche et al. Phosphorothioate-modified oligodeoxyribonucleotides. III. NMR and UV spectroscoptc studies of thRp-Rp,Sp-Sp, anRp-Sduplexes, [d(GGsAATTCC)]2, derived from diastereomeriO-ethyl phosphorothioates Nucleic Acids Res. Vol. 14, No. 22, pp. 9081-9093 (Nov. 25, 1986).
Le Hir, et al. How introns influence and enhance eukaryotic gene expression. Trends Biochem Sci. Apr. 2003;28(4):215-20.
Lee, E.S. et al. The Consensus 5' Splice Site Motif Inhibits mRNA Nuclear Export.PLoS One vol. 10, No. 3, p. e0122743 (Mar. 31, 2015).
Lee, J., et al. Metastasis of neuroendocrine tumors are characterized by increased cell proliferation and reduced expression of the ATM gene. PLoS ONE. 2012;7:e34456.

LeFave,et al., "Splicing factor hnRNPH drives an oncogenic splicing switch in gliomas",(2011) The EMBO Journal, vol. 30, No. 19, pp. 4084-4097.
Lehir, H. et al. 5'-End RET Splicing: Absence of Variants in Normal Tissues and Intron Retention in Pheochromocytomas, Oncology 63:84-91 (2002).
Lei et al. Exonization of Alu Ya5 in the human ACE gene requires mutations in both 3' and 5' splice sites and is facilitated by a conserved splicing enhancer. Nucleic acids research 33.12 (2005): 3897-3906.
Lei, et al. Identification of splicing silencers and enhancers in sense Alus: a role for pseudoacceptors in splice site repression. Mol Cell Biol. Aug. 2005;25(16):6912-20.
Lemaire, M. et al. CDC25B phosphorylation by p38 and MK-2. Cell Cycle. 2006;5(15):1649-53. PubMed PMID: 16861915.
Levin, et al., "Treating Disease at the RNA Level with Oligonucleotides" (2019) The New England Journal of Medicine 380:57-70.
Lev-Maor et al. Intronic Alus influence alternative splicing. PLoS genetics 4.9 (2008): e1000204.
Lev-Maor et al. The birth of an alternatively spliced exon: 3'splice-site selection in Alu exons. Science 300.5623 (2003): 1288-1291.
Levy et al.TranspoGene and microTranspoGene: transposed elements influence on the transcriptome of seven vertebrates and invertebrates. Nucleic acids research 36.suppl_1 (2007): D47-D52.
Li et al. JAG1 Mutation Spectrum and Origin in Chinese Children with Clinical Features of Alagille Syndrome. PLoS One 10(6):e0130355 (2015).
Li et al. PD-L1-Driven Tolerance Protects Neurogenin3-Induced Islet Neogenesis to Reverse Established Type 1 Diabetes in NOD Mice.Diabetes vol. 64, pp. 529-540 (Feb. 2015; epub Oct. 20, 2014).
Liang et al. Short intronic repeat sequences facilitate circular RNA production. Genes & development (2014): gad-251926.
Liang, Xue-Hai et al., T ranslation efficiency of mRNAs is increased by antisense oligonucleotides targeting upstream open reading frames,Nature Biotechnology, 34(8):875-882 (Aug. 2016).
Lianoglou, S., et al. Ubiquitously transcribed genes use alternative polyadenylation to achieve tissue-specific expression. Genes Dev. 2013;27(21):2380-96. Epub Oct. 23, 2013.doi: gad.229328.113 [pii] 10.1101/gad.229328.113. PubMed PMID: 24145798.
Lim et al. A computational analysis of sequence features involved in recognition of short introns. Proceedings of the National Academy of Sciences98.20 (2001): 11193-11198.
Lim, et al., "Antisense oligonucleotide modulation of nonproductive alternative splicing upregulates gene expression" (2020) Nature Communication.
Litchfield, D.W., et al. Pin1: Intimate involvement with the regulatory protein kinase networks in the global phosphorylation landscape. Biochem Biophys Acta. 2015. doi: 10.1016/j.bbagen.2015.02.018. PubMed PMID: 25766872.
Liu et al. Alternative splicing and retinal degeneration. Clinical Genetics 84(2):142-149 (2013).
Llorian et al. Position-dependent alternative splicing activity revealed by global profiling of alternative splicing events regulated by PTB. Nature structural & molecular biology 17.9 (2010): 1114.
Lo, YL et al. ATM Polymorphisms and risk of lung cancer among never smokers, Lung Cancer 69(2):148-154 (2010).
Long et al. Correction of diverse muscular dystrophy mutations in human engineered heart muscle by single-site genome editing. Sci Adv 4:eaap9004 (2018).
Lorenz, et al. 2D meets 4G: G-Quadruplexes in RNA Secondary Structure Prediction. IEEE/ACM Trans Comput Biol Bioinform. Jul.-Aug. 2013;10(4):832-44. doi: 10.1109/TCBB.2013.7.
Lu, F. Conditional JAG1 MutationShows the Developing Heart Is More Sensitive Than Developing Liver to JAG1 Dosage.Am. J. Hum. Genet. vol. 72, pp. 1065-1070 (2003).
Ludecke et al.Recessively inherited L-DOPA-responsive parkinsonism in infancy caused by a point mutation (L205P) in the tyrosine hydroxylase gene Hum. Mol. Genet. vol 5, pp. 1023-1028, (1996).
Luo et al. Palmitic Acid Suppresses Apolipoprotein M Gene Expression via the Pathway of PPARb/d in HepG2 Cells. Biochemical and Biophysical Research Communications, 445(1):203-207 (Feb. 2014).

(56) References Cited

OTHER PUBLICATIONS

Magi-Galuzzi, C. et al. TMPRSS2-ERG gene fusion prevalence and class are significantly difference in prostate cancer of Caucasian, African-American and Japanese patients. The Prostate. 2011;71:489-97.
Makishima, et al. Mutations in the spliceosome machinery, a novel and ubiquitous pathway in leukemogenesis. Blood. Apr. 5, 2012;119(14):3203-10. doi: 10.1182/blood-2011-12-399774. Epub Feb. 9, 2012.
Maniatis et al. An extensive network of coupling among gene expression machines. Nature 416.6880 (2002): 499.
Mansouri, S. et al. Epstein-Barr Virus EBNA1 Protein Regulates Viral Latency through Effects on let-7 MicroRNA and Dicer.Journal of Virology, vol. 88, No. 19, pp. 11166-11177, (Oct. 2014).
Marcel, et al. G-quadruplex structures in TP53 intron 3: role in alternative splicing and in production of p53 mRNA isoforms. Carcinogenesis. Mar. 2011;32(3):271-8. doi: 10.1093/carcin/bgq253. Epub Nov. 26, 2010.
Marquez, Y. et al. Unmasking alternative splicing inside protein-coding exons defines exitrons and their role inproteome plasticity. Genome vol. 25, pp. 995-1007 (2015).
Matsuoka, S., et al. Ataxia telangiectasia-mutated phosphorylates Chk2 in vivo and in vitro. Proc Natl Acad Sci USA. 2000;97:10389-94.
Matsuoka, S., et al. ATM and ATR substrate analysis reveals extensive protein networks responsive to DNA damage. Science. 2007;316(5828):1160-6. Epub May 26, 2007.doi: 316/5828/1160 [pii] 10.1126/science. 1140321. PubMed PMID: 17525332.
Mayeda, et al. Surveying cis-acting sequences of pre-mRNA by adding antisense 2'-O-methyl oligoribonucleotides to a splicing reaction. J Biochem. Sep. 1990;108(3):399-405.
McKie et al. Mutations in the pre-mRNA splicing factor gene PRPC8 in autosomal dominant retinitis pigmentosa (RP13). Human Molecular Genetics 10(15):1555-1562 (2001).
Melhuish, et al. The Tgif2 gene contains a retained intron within the coding sequence, BMC Molecular Biology 7(2);1-10 (2006).
Melko, et al. Functional characterization of the AFF (AF4/FMR2) family of RNA-binding proteins: insights into the molecular pathology of FRAXE intellectual disability. Hum Mol Genet. May 15, 2011;20(10):1873-85. doi: 10.1093/hmg/ddr069. Epub Feb. 17, 2011.
Mendell, J.T., ap Rhys CM, Dietz HC. Separable roles for rent1/hUpf1 in altered splicing and decay of nonsense transcripts. Science. 2002;298(5592):419-22. Epub Sep. 14, 2002.doi: 10.1126/science. 1074428 1074428 [pii], PubMed PMID: 12228722.
Merendino, L., et al. Inhibition of msl-2 splicing by Sex-lethal reveals interaction between U2AF35 and the 3' splice site AG. Nature. 1999;402(6763):838-41. PubMed PMID: 10617208.
Michael, et al. Mfold web server for nucleic acid folding and hybridization prediction. Nucleic Acids Research. 31 (2003): 3406-3415.
Miller at al. 1993-2015 GeneReviews Eds. Pagon RA et al. Seattle (WA); University of WA, Seattle Bookshelf ID NBK1318.
Millevoi, et al. G-quadruplexes in RNA biology. Wiley Interdiscip Rev RNA. Jul.-Aug. 2012;3(4):495-507. doi: 10.1002/wrna.1113. Epub Apr. 4, 2012.
Min et al. Optimization of a novel series of ataxia-telangiectasia mutated kinase inhibitors as potential radiosensitizing agents. Journal of medicinal chemistry 59.2 (2016): 559-577.
Mirey, G., et al. CDC25B phosphorylated by pEg3 localizes to the centrosome and the spindle poles at mitosis. Cell Cycle. 2005;4(6):806-11. PubMed PMID: 15908796.
Mitelman, F., et al. The impact of translocations and gene fusions on cancer causation. Nat Rev Cancer. 2007;7(4):233-45. Epub Mar. 16, 2007.
Mnatzakanian et al. A previously unidentified MECP2 open reading frame defines a new protein isoform relevant to Rett syndrome. Nat Genet 36:339-341 (2004).

Mochizuki, T. et al. PKD2, a gene for polycystic kidney disease that encodes an integral membrane protein.Science vol. 272, pp. 1339-1342 (1996).
Montecucco, A., et al. Pre-mRNA processing factors meet the DNA damage response. Front Genet. 2013;4:102. doi: 10.3389/fgene. 2013.00102. PubMed PMID: 23761808; PubMed Central PMCID: PMC3674313.
Moreno et al. Delivery of splice switching oligonucleotides by amphiphilic chitosan-based nanoparticles. Molecular pharmaceutics13.2 (2016): 344-356.
Morris, et al. An RNA G-quadruplex is essential for cap-independent translation initiation in human VEGF IRES. J Am Chem Soc. Dec. 22, 2010;132(50):17831-9. doi: 10.1021/ja106287x. Epub Nov. 24, 2010.
Morrison, A.J., et al. Mec1/Tel1 phosphorylation of the INO80 chromatin remodeling complex influences DNA damage checkpoint responses. Cell. 2007;130(3):499-511. doi: 10.1016/j.cell.2007.06.010. PubMed PMID: 17693258.
Moskowitz, et al., Mutation in Scheie syndrome (MPS IS): a G→A transition creates new splice site in intron 5 of one IDUA allele, Hum. Mutat. 2(2):141-144 (1993).
Mulley et al. A new molecular mechanism for severe myoclonic epilepsy of infancy: Exonic deletions in SCN1A.Neurol. vol. 67, pp. 1094-1095 (2006).
Mulley et al. SCN1A mutations and epilepsy.Hum. Muta. vol. 25, pp. 535-542 (2005).
Murray, S.F. et al. Allele-Specific Inhibition of Rhodopsin with an Antisense Oligonucleotide Slows Photoreceptor Cell Degeneration, Invest Ophthalmol. Vis. Sci. 56:6362-6375 (Oct. 2015).
Neidle, S. and Balasubramanian, S. (2006) Quadruplex Nucleic Acids. RSC Biomolecular Sciences, Cambridge, UK.
Nemeroff et al. Identification of cis-acting intron and exon regions in influenza virus NS1 mRNA that inhibit splicing and cause the formation of aberrantly sedimenting presplicing complexes. Molecular and cellular biology 12.3 (1992): 962-970.
Nguyen, L.A., et al. Physical and functional link of the leukemia-associated factors AML1 and PML. Blood. 2005;105(1):292-300. doi: 10.1182/blood-2004-03-1185. PubMed PMID: 15331439.
Nishi, M. et al. Insulin gene mutations and diabetes. Journal of Diabetes Investigation vol. 2 Issue 2 (Apr. 2011).
Nishida, A. et al. Tissue- and Case-specific retention of intron 40 in mature dystrophin mRNA, Journal of Human Genetic 60;327-333 (2015).
Nisole, S., et al. Differential Roles of PML Isoforms. Front Oncol. 2013;3:125. doi: 10.3389/fonc.2013.00125. PubMed PMID: 23734343; PubMed Central PMCID: PMC3660695.
Nomakuchi et al. Antisense-oligonucleotide-directed inhibition of nonsense-mediated mRNA decay. Nat. Biotechnol. 34(2):164-166 (Feb. 2016).
Nozu et al. Alport syndrome caused by a COL4A5 deletion and exonization of an adjacent AluY. Molecular genetics & genomic medicine 2.5 (2014): 451-453.
Nussinov. Conserved quartets near 5' intron junctions in primate nuclear pre-mRNA. J Theor Biol. Jul. 8, 1988;133(1):73-84.
Oda, T. et al. Identification and cloning of the human homolog (JAG) of the rat Jagged1 gene from the Alagille syndrome critical region at 20p12.Genomics vol. 43, No. 3, pp. 376-379 (1997).
Okazaki, T. et al. PD-1 and PD-1 ligands: from discovery to clinical application. International Immunology(The Japanese Society for Immunology), vol. 19, No. 7, pp. 813-824, (2007).
Oustric, V. et al. Antisense oligonucleotide-based therapy in human erythropoietic protoporphyria. Am J Hum Genet. 2014;94(4):611-7. doi: 10.1016/j.ajhg.2014.02.010. PubMed PMID: 24680888; PubMed Central PMCID: PMC3980518.
Pacheco, et al. Diversity of vertebrate splicing factor U2AF35: identification of alternatively spliced U2AF1 mRNAS. J Biol Chem. Jun. 25, 2004;279(26):27039-49. Epub Apr. 19, 2004.
Pacheco, et al. RNA interference knockdown of hU2AF35 impairs cell cycle progression and modulates alternative splicing of Cdc25 transcripts. Mol Biol Cell. Oct. 2006;17(10):4187-99. Epub Jul. 19, 2006.
Page-McCaw, P.S., et al. PUF60: a novel U2AF65-related splicing activity. RNA. 1999;5(12):1548-60. PubMed PMID: 10606266.

(56) References Cited

OTHER PUBLICATIONS

Palazzo et al. Non-coding RNA: what is functional and what is junk?. Frontiers in genetics 6 (2015): 2.
Pandit et al. Genome-wide analysis reveals SR protein cooperation and competition in regulated splicing. Molecular cell 50.2 (2013): 223-235.
Papaemmanuil, et al. Clinical and biological implications of driver mutations in myelodysplastic syndromes. Blood. Nov. 21, 2013;122(22):3616-27; quiz 3699. doi: 10.1182/blood-2013-08-518886. Epub Sep. 12, 2013.
Passamonti, C. et al. A novel inherited SCN1A mutation associated with different neuropsychological phenotypes: Is there a common core deficit? Epilepsy & Behavior 43:89-92 (2015).
Pastor, et al. Interaction of hnRNPA1/A2 and DAZAP1 with an Alu-derived intronic splicing enhancer regulates ATM aberrant splicing. PLoS One. 2011;6(8):e23349. doi: 10.1371/journal.pone. 0023349. Epub Aug. 8, 2011.
Pastor, F., et al. Induction of tumour immunity by targeted inhibition of nonsense-mediated mRNA decay. Nature. 2010;465(7295):227-30. doi: 10.1038/nature08999. PubMed PMID: 20463739; PubMed Central PMCID: PMC3107067.
Paz, A., et al. SPIKE: a database of highly curated human signaling pathways. Nucleic Acids Res. 2011;39(Database issue):D793-9. doi: 10.1093/nar/gkq1167. PubMed PMID: 21097778; PubMed Central PMCID: PMC3014840.
Pear, Warren S. New roles for Notch in tuberous sclerosis, Journal of Clinical Investigation, 120(1):84-87 (Jan. 4, 2010).
Pecarelli et al. Regulation of natural mRNAs by the nonsense-mediated mRNA decay pathway. Eukaryotic cell(2014): EC-00090.
Pellagatti, A., et al. Deregulated gene expression pathways in myelodysplastic syndrome hematopoietic stem cells. Leukemia. 2010;24(4):756-64. doi: 10.1038/leu.2010.31. PubMed PMID: 20220779.
Peng, et al. Functional importance of different patterns of correlation between adjacent cassette exons in human and mouse. BMC Genomics. Apr. 26, 2008;9:191. doi: 10.1186/1471-2164-9-191.
Penton, A.L.Notch signaling in humandevelopment and disease. Seminars in Cell & Developmental Biology. vol. 23, pp. 450-457 (2012).
Perdiguero, E., et al. Regulation of Cdc25C activity during the meiotic G2/M transition. Cell Cycle. 2004;3(6):733-7. PubMed PMID: 15136768.
Piaceri, I., et al. Ataxia-telangiectasia mutated (ATM) genetic variant in Italian centenarians. Neurophysiology. 2013;34:573-5.
Pilia et al. Jagged-1 mutation analysis in Italian Alagille syndrome patients. Hum Mut 14(5):394-400 (1999).
Pomentel et al. A dynamic intron retention program enriched in RNA processing genes regulates gene expression during terminal erythropoiesis. Nucleic acids research 44.2 (2015): 838-851.
Precursor mRNA-Processing Factor 3, S. Cerevisiae, Homolog OF; PRPF3m, 3 pages.
Przychodzen, B., et al. Patterns of missplicing due to somatic U2AF1 mutations in myeloid neoplasms. Blood. 2013;122:999-1006. Epub Jun. 19, 2013.doi: blood-2013-01-480970 [pii] 10.1182/blood-2013-01-480970. PubMed PMID: 23775717.
Pugliese, et al. The insulin gene is transcribed in the human thymus and transcription levels correlated with allelic variation at the INS VNTR-IDDM2 susceptibility locus for type 1 diabetes. Nat Genet. Mar. 1997;15(3):293-7.
Rainey et al. Transient inhibition of ATM kinase is sufficient to enhance cellular sensitivity to ionizing radiation. Cancer research68. 18 (2008): 7466-7474.
Ramocki et al. The MECP2 duplication syndrome. Am J Med Genet A 152A:1079-1088 (2010).
Rangasamy et al. Reduced neuronal size and mTOR pathway activity in the Mecp2 A140V Rett syndrome mouse model. F1000research 5:2269 (2016).
Ray, D. et al. A compendium of RNA-binding motifs for decoding gene regulation. Nature. vol. 499, No. 7457, pp. 172-177 (Jul. 11, 2013).

Reineke, E.L., et al. Degradation of the tumor suppressor PML by Pin1 contributes to the cancer phenotype of breast cancer MDA-MB-231 cells. Mol Cell Biol. 2008;28(3):997-1006. doi: 10.1128/MCB.01848-07. PubMed PMID: 18039859; PubMed Central PMCID: PMC2223389.
Rendu, J. et al. Hum Gene Ther. Exon skipping as a therapeutic strategy applied to an RYR1 mutation with pseudo-exon inclusion causing a severe core myopathy. Jul. 2013;24(7):702-13. doi: 10.1089/hum.2013.052.
Reynolds, DM et al.Aberrant Splicing in the PKD2 Gene as a Cause of Polycystic Kidney Disease.Am. Soc. Nephrol. vol. 10, pp. 2342-2351 (1999).
Ritprajak et al. Keratinocyte-Associated B7-H1 Directly Regulates Cutaneous Effector CD8+ T Cell Responses.J Immunology vol. 184, pp. 4918-4925 (2010).
RNA 2-14 The Nineteenth Annual Meeting of the RNA Society. Quebec City, Canada. (Jun. 3-8, 2014).
Roberts, Jennifer et al. Efficient and Persistent Splice Switching by Systemically Delivered LNA Oligonucleotides in Mice. Molecular Therapy, Nature Publishing, vol. 14, No. 4, pp. 471-475, Oct. 1, 2006.
Romero, P.R., et al. Alternative splicing in concert with protein intrinsic disorder enables increased functional diversity in multicellular organisms. Proc Natl Acad Sci USA. 2006;103(22):8390-5. Epub May 24, 2006.doi: 0507916103 [pii] 10.1073/pnas.0507916103. PubMed PMID: 16717195.
Rosenbloom et al. The UCSC Genome Browser database: 2015 Update. Nucleic Acids Research 43, Database Issue doi:101093/nar/gku1177.
Ruchlemer, R., et al. Geography, ethnicity and "roots" in chronic lymphocytic leukemia. Leuk Lymphoma. 2013;54(6):1142-50. doi: 10.3109/10428194.2012.740670. PubMed PMID: 23121522.
Rudd, M.F., et al. Variants in the ATM-BRCA2-CHEK2 axis predispose to chronic lymphocytic leukemia. Blood. 2006;108(2):638-44. Epub Apr. 1, 2006.doi: 2005-12-5022 [pii] 10.1182/blood-2005-12-5022. PubMed PMID: 16574953.
Ruskin, et al. A factor, U2AF, is required for U2 snRNP binding and splicing complex assembly. Cell. Jan. 29, 1988;52(2):207-19.
Sadleir, et al. Not all SCN1A epileptic encephalopathies are Dravet syndrome. Neurology. Sep. 5, 2017; 89(10): 1-8.
Sahashi et al. Pathological impact of SMN2 mis-splicing in adult SMA mice. EMBO Mol. Med. 5(10):1586-601 (Oct. 2013).
Sahashi et al. TSUNAMI: an antisense method to phenocopy splicing-associated diseases in animals. Genes Dev. 26(16):1874-1884 (Aug. 15, 2012).
Sakabe, et al. Sequence features responsible for intron retention in human. BMC Genomics. Feb. 26, 2007;8:59.
Samatanga, et al. The high kinetic stability of a G-quadruplex limits hnRNP F qRRM3 binding to G-tract RNA. Nucleic Acids Res. Feb. 1, 2013;41(4):2505-16. doi: 10.1093/nar/gks1289. Epub Dec. 28, 2012.
Sazani, et al., "Therapeutic potential of antisense oligonucleotides as modulators of alternative splicing" (2003) The Journal of clinical Investigation, 112(4):481-486.
Schanen et al. A Severely Affected Male Born into a Rett Syndrome Kindred Supports X-Linked Inheritance and Allows Extension of the Exclusion Map. Am J Hum Genetics 63:267-269 (1998).
Schwarze, et al. Redefinition of exon 7 in the COL1A1 gene of type I collagen by an intron 8 splice-donor-site mutation in a form of osteogenesis imperfecta: influence of intron splice order on outcome of splice-site mutation. Am J Hum Genet. Aug. 1999;65(2):336-44.
Scott, S.P., et al. Missense mutations but not allelic variants alter the function of ATM by dominant interference in patients with breast cancer. Proc Natl Acad Sci USA. 2002;99:925-30.
SG 11201702682P Search Report and Written Opinion dated Apr. 9, 2018.
Shao, C., et al. Mechanisms for U2AF to define 3' splice sites and regulate alternative splicing in the human genome. Nat Struct Mol Biol. 2014;doi: 10.1038/nsmb.2906.
Shcherbakova, I., et al. Alternative spliceosome assembly pathways revealed by single-molecule fluorescence microscopy. Cell Rep. 2013;5(1):151-65. Epub Oct. 1, 2013.doi: S2211-1247(13)00467-1 [pii] 10.1016/j.celrep.2013.08.026. PubMed PMID: 24075986.

(56) References Cited

OTHER PUBLICATIONS

Shen, M., et al. Characterization and cell cycle regulation of the related human telomeric proteins Pin2 and TRF1 suggest a role in mitosis. Proc Natl Acad Sci USA. 1997;94(25):13618-23. PubMed PMID: 9391075; PubMed Central PMCID: PMC28355.

Shiloh, Y., et al. The ATM protein kinase: regulating the cellular response to genotoxic stress, and more. Nat Rev Mol Cell Biol. 2013;14(4):197-210. doi: 10.1038/nrm3546. PubMed PMID: 23486281.

Shiria, C.L. et al. Mutant U2AF1 Expression Alters Hematopoiesis and Pre-mRNA Splicing In Vivo. Cancer Cell. 2015;27(5):631-43. doi: 10.1016/j.ccell.2015.04.008. PubMed PMID: 25965570; PubMed Central PMCID: PMC4430854.

Shirley, M.H., et al Incidence of haematological malignancies by ethnic group in England, Jul. 2001. Br J Haematol. 2013;163(4):465-77. doi: 10.1111/bjh.12562. PubMed PMID: 24033296.

Sierakowska, H et al. Repair of thalassemic human beta-globin mRNA in mammalian cells by antisense oligonucleotides. Proc Natl Acad Sci U S A. Nov. 12, 1996;93(23):12840-4.

Singh, et al. An antisense microwalk reveals critical role of an intronic position linked to a unique long-distance interaction in pre-mRNA splicing. RNA. Jun. 2010;16(6):1167-81. doi: 10.1261/rna.2154310. Epub Apr. 22, 2010.

Sirand-Pugnet, et al. An intronic (A/U)GGG repeat enhances the splicing of an alternative intron of the chicken beta-tropomyosin pre-mRNA. Nucleic Acids Res. Sep. 11, 1995;23(17):3501-7.

Skjevik et al. The N-Terminal Sequence of Tyrosine Hydroxylase Is a Conformationally Versatile Motif That Binds 14-3-3 Proteins and Membranes.J. Mol. Bio. vol. 426, pp. 150-168 (2014).

Smith, C.W., et al. Scanning and competition between AGs are involved in 3' splice site selection in mammalian introns. Mol Cell Biol. 1993;13(8):4939-52. PubMed PMID: 8336728.

Smith, et al. Alternative pre-mRNA splicing: the logic of combinatorial control. Trends Biochem Sci. Aug. 2000;25(8):381-8.

Smith, P.J., et al. An increased specificity score matrix for the prediction of SF2/ASF-specific exonic splicing enhancers. Hum Mol Genet. 2006;15(16):2490-508. PubMed PMID: 16825284.

Soo, R.A., et al. Ethnic differences in survival outcome in patients with advanced stage non-small cell lung cancer. J Thorac Oncol. 2011;6:1030-8.

Sorek et al. Minimal conditions for exonization of intronic sequences: 5' splice site formation in alu exons. Molecular cell 14.2 (2004): 221-231.

Soutar et al. Mechanisms of disease: genetic causes of familial hpercholesterolemia. Nat. Clin. Pract. Cardiovasc. Med. 4:214-255 (Apr. 1, 2007).

Spellman et al. Regulation of alternative splicing by PTB and associated factors. (2005): 457-460.

Spinner et al. Jagged1 mutations in alagille syndrome. Hum Mutat 17(1):18-33 (2001).

Stamm, S. Regulation of alternative splicing by reversible protein phosphorylation. J Biol Chem. 2008;283(3):1223-7. PubMed PMID: 18024427.

Stankovic, T., et al. Inactivation of ataxia telangiectasia mutated gene in B-cell chronic lymphocytic leukaemia. Lancet. 1999;353(9146):26-9. doi: 10.1016/S0140-6736(98)10117-4. PubMed PMID: 10023947.

Staropoli et al. Rescue of gene-expression changes in an induced mouse model of spinal muscular atrophy by an antisense oligonucleotide that promotes inclusion of SMN2 exon 7. Genomics 105:220-228 (2015).

Stead, et al. Global haplotype diversity in the human insulin gene region. Genome Res. Sep. 2003;13(9):2101-11.

Stec et al. Automated solid-phase synthesis, separation, and stereochemistry of phosphorothioate analogs of oligodeoxyribonucleotides J. Am. Chem. Soc., 1984, 106 (20), pp. 6077-6079 (1984).

Stein et al. FDA-Approved Oligonucleotide Therapies in 2017. Mol Ther 25:1069-1075 (2017).

Stein et al. Physicochemical properties of phosphorothioate oligodeoxynucleotides. Nucleic Acids Res. Apr. 25, 1988;16(8):3209-21.

Story, M.D. et al. ATM has a major role in the double-stand break repair pathway dysregulation in sporadic breast carcinomas and is an independent prognostic marker at both mRNA and protein levels, Breast Diseases: A Yearbook Quarterly, 26(4);297-299 (Mar. 17, 2015).

Strausfeld, U., et al. Activation of p34cdc2 protein kinase by microinjection of human cdc25C into mammalian cells. Requirement for prior phosphorylation of cdc25C by p34cdc2 on sites phosphorylated at mitosis. J Biol Chem. 1994;269(8):5989-6000. PubMed PMID: 8119945.

Suarez, F. et al. Incidence, presentation, and prognosis of malignancies in ataxia-telangiectasia: a report from the French national registry of primary immune deficiencies. J Clin Oncol. 2015;33(2):202-8. doi: 10.1200/JCO.2014.56.5101. PubMed PMID: 25488969.

Summerton, James. Morpholino Antisense Oligos: Applications in Biopharmaceutical ResearchMorpholinos constitute a radical redesign of DNA, providing decisive advantages over the moreconventional oligo types used for modulating gene expression. Innovations in Pharmaceutical Technology Issue No. 17 (2005).

Sun, H., et al. Multiple splicing defects in an intronic false exon. Mol Cell Biol. 2000;20(17):6414-25. PubMed PMID: 10938119.

Supplementary European Search Report dated Apr. 18, 2019 for EP16876615.2.

Svasti, et al. RNA repair restores hemoglobin expression in IVS2-654 thalassemic mice. Proc Natl Acad Sci U S A. Jan. 27, 2009; 106(4): 1205-1210.

Swaans, RJM et al.Four novel mutations in the Tyrosine Hydroxylase gene in patients with infantile parkinsonism Annals of Human Genetic, vol. 64, No. 1, pp. 25-31, (Jan. 2000).

Tabrez, S. et al. A Synopsis of the Role of Tyrosine Hydroxylase in Parkinson's Disease.CNS & Neurological Disorders—Drug Targets vol. 11, No. 4 (2012).

Takahashi et al. Skewed X chromosome inactivation failed to explain the normal phenotype of a carrier female with MECP2 mutation resulting in Rett syndrome. Clin Genet 73:257-261 (2008).

Tavanez, J.P., et al. hnRNP A1 proofreads 3' splice site recognition by U2AF. Mol Cell. 2012;45(3):314-29. Epub Feb. 14, 2012. doi: S1097-2765(12)00032-9 [pii] 10.1016/j.molcel.2011.11.033. PubMed PMID: 22325350.

Taylor, A.M., et al. Ataxia telangiectasia: more variation at clinical and cellular levels. Clin Genet. 2015;87(3):199-208. doi: 10.1111/cge.12453. PubMed PMID: 25040471.

Taylor, A.M., et al. Leukemia and lymphoma in ataxia telangiectasia. Blood. 1996;87(2):423-38. PubMed PMID: 8555463.

Thisted, et al. Optimized RNA targets of two closely related triple KH domain proteins, heterogeneous nuclear ribonucleoprotein K and alphaCP-2KL, suggest Distinct modes of RNA recognition. J Biol Chem. May 18, 2001;276(20):17484-96. Epub Feb. 2, 2001.

Tilgner et al. Deep Sequencing of subcellular RNA factions shows splicing to be predominantly co-transcriptional in the human genome but inefficient for lncRNAs.Genome Research vol. 22, No. 9, pp. 1616-1625 (2012).

Tillotson et al. Radically truncated MeCP2 rescues Rett syndrome-like neurological defects. Nature 550:398 (2017).

Torres, V.E. et al. Autosomal dominant polycystic kidney disease: the last 3 years.Kidney International vol. 76, pp. 149-168 (May 20, 2009).

Trabattoni, M. et al.Costimulatory Pathways in Multiple Disease Sclerosis: Distinctive Expression of PD-1 and PD-L1 in Patients with Different Patterns of Disease.J. Immunol. vol. 183, pp. 4984-4993 (2009).

Trapnell, C. et al. Differential gene and transcript expression analysis of RNA-seq experiments with Top Hat and Cufflinks. Nat Protoc. 2012;7(3):562-78. Epub Mar. 3, 2012.doi: nprot.2012.016 [pii] 10.1038/nprot.2012.016. PubMed PMID: 22383036.

Turnpenny, P.D. et al. Alagille syndrome: pathogenesis, diagnosis and management.European Journal of Human Genetics vol. 20, pp. 251-257 (2012.

(56) References Cited

OTHER PUBLICATIONS

Uhlmann, E. et al. Antisense oligonucleotides: a new therapeutic principle. Chemical Reviews vol. 90, No. 4, pp. 543-584 (Jun. 1990).
U.S. Appl. No. 14/741,071 Non-Final Office Action dated Dec. 1, 2016.
U.S. Appl. No. 14/874,420 Non-Final Office Action dated Mar. 21, 2017.
U.S. Appl. No. 14/874,420 Office Action dated Oct. 24, 2017.
U.S. Appl. No. 15/619,984 Office Action dated Dec. 17, 2018.
U.S. Appl. No. 15/949,902 Office Action dated Mar. 1, 2019.
U.S. Appl. No. 15/288,415 Office Action dated Jun. 26, 2018.
Vafiadis, et al. Insulin expression in human thymus is modulated by INS VNTR alleles at the IDDM2 locus. Nat Genet. Mar. 1997;15(3):289-92.
Van Nostrand et al. Robust transcriptome-wide discovery of RNA-binding protein binding sites with enhanced CLIP (eCLIP). Nature methods 13.6 (2016): 508.
Verhaart, I.E.C. AON-Mediated Exon Skipping for Duchenne Muscular Dystrophy. Chapter 3. pp. 1-26 (Aug. 1, 2012).
Verret et al., Inhibitory Interneuron Deficit Links Altered Network Activity and Cognitive Dysfunction in Alzheimer Model, Cell, 149(3): 708-721 (2012).
Vieira, N. et al. Jagged 1 Rescues the Duchenne Muscular Dystrophy Phenotype. Cell vol. 163, pp. 1204-1213 (Nov. 19, 2015).
Voelker, et al. A comprehensive computational characterization of conserved mammalian intronic sequences reveals conserved motifs associated with constitutive and alternative splicing. Genome Res. Jul. 2007;17(7):1023-33. Epub May 24, 2007.
Vorechovsky Correspondence Pediatric Research 2010.
Vorechovsky, I. Letter to the Editor: MER91B-assisted cryptic exon activation in Gitelman syndrome. Pediatric research 67.4 (2010): 444-445.
Vorechovsky Transposable elements in disease-associated cryptic exons. Human genetics 127.2 (2010): 135-154.
Wahl, et al. The spliceosome: design principles of a dynamic RNP machine. Cell. Feb. 20, 2009;136(4):701-18. doi: 10.1016/j.cell.2009.02.009.
Wan et al.Synthesis, biophysical properties and biological activity of second generation antisense oligonucleotides containing chiral phosphorothioate linkages.Nucleic Acids Research, vol. 42, No. 22, pp. 13456-13468 (2014).
Wang, et al. A complex network of factors with overlapping affinities represses splicing through intronic elements. Nat Struct Mol Biol. Jan. 2013;20(1):36-45. doi: 10.1038/nsmb.2459. Epub Dec. 16, 2012.
Wang et al. Alternative isoform regulation in human tissue transcriptomes. Nature. 2008;456(November):470-476.
Wang et al. Human Adenovirus Type 36 Enhances Glucose Uptake in Diabetic and Nondiabetic Human Skeletal Muscle Cells Independent of Insulin Signaling.Diabetes vol. 57, pp. 1861-1869 (2008).
Wang, et al. Intronic splicing enhancers, cognate splicing factors and context-dependent regulation rules. Nat Struct Mol Biol. Oct. 2012;19(10):1044-52. doi: 10.1038/nsmb.2377. Epub Sep. 16, 2012.
Wang, et al. Regulation of insulin preRNA splicing by glucose. Proc Natl Acad Sci U S A. Apr. 29, 1997;94(9):4360-5.
Wang, Z. et al. Systematic identification and analysis of exonic splicing silencers. Cell. 2004;119(6):831-45. PubMed PMID: 15607979.
Warf, M.B., et al. Role of RNA structure in regulating pre-mRNA splicing. Trends Biochem Sci. 2010;35(3):169-78. Epub Dec. 5, 2009.doi: S0968-0004(09)00196-0 [pii].
Wieland, et al. RNA quadruplex-based modulation of gene expression. Chem Biol. Jul. 2007;14(7):757-63.
Wilton, et al. Splice modification to restore functional dystrophin synthesis in Duchenne muscular dystrophy. Current pharmaceutical design 16.8 (2010): 988-1001.
Wong et al. Orchestrated intron retention regulates normal granulocyte differentiation. Cell 154.3 (2013): 583-595.
Wu et al. AT-AC Pre-mRNA Splicing Mechanisms and Conservation of Minor Introns in Voltage-Gated Ion Channel Genes. Molecular and Cellular Biology 19(5): 3225-3236 (May 1999).
Wu, J.Y., et al. Specific interactions between proteins implicated in splice site selection and regulated alternative splicing. Cell. 1993;75(6):1061-70. Epub Dec. 17, 1993.doi: 0092-8674(93)90316-I [pii]. PubMed PMID: 8261509.
Wu, S. et al. Functional recognition of the 3' splice site AG by the splicing factor U2AF35.Nature. 1999;402(6763):832-5. PubMed PMID: 10617206.
Wu, Y. et al. MRE11-RAD50-NBS1 and ATM function as co-mediators of TRF1 in telomere length control. Nat Struct Mol Biol. 2007;14(9):832-40. doi: 10.1038/nsmb1286. PubMed PMID: 17694070.
Xia, Y. et al. Frequencies of SF3B1, NOTCH1, MYD88, BIRC3 and IGHV mutations and TP53 disruptions in Chinese with chronic lymphocytic leukemia: disparities with Europeans. Oncotarget. 2015;6(7):5426-34. PubMed PMID: 25605254.
Xing, et al. The multiassembly problem: reconstructing multiple transcript isoforms from EST fragment mixtures. Genome Res. Mar. 2004;14(3):426-41. Epub Feb. 12, 2004.
Yamamoto et al. Mib-Jag1-Notch signalling regulates patterning and structural roles of the notochord by controlling cell-fate decisions. Development 137(15):2527-2537 (2010).
Yamamoto, Y., et al. BCOR as a novel fusion partner of retinoic acid receptor alpha in a t(X;17)(p11;q12) variant of acute promyelocytic leukemia. Blood. 2010;116(20):4274-83. doi: 10.1182/blood-2010-01-264432. PubMed PMID: 20807888.
Yan, et al. Systematic discovery of regulated and conserved alternative exons in the mammalian brain reveals NMD modulating chromatin regulators. Proc Natl Acad Sci U S A. Mar. 17, 2015; 112(11): 3445-3450.
Yang et al. Biophysical analysis and small-angle X-ray scattering-derived structures of MeCP2-nucleosome complexes. Nucleic Acids Res 39:4122-4135 (2011).
Yang, S. et al. PML-dependent apoptosis after DNA damage is regulated by the checkpoint kinase hCds1/Chk2. Nat Cell Biol. 2002;4(11):865-70. doi: 10.1038/ncb869. PubMed PMID: 12402044.
Yang, S., et al. Promyelocytic leukemia activates Chk2 by mediating Chk2 autophosphorylation. J Biol Chem. 2006;281(36):26645-54. doi: 10.1074/jbc.M604391200. PubMed PMID: 16835227.
Yang, Y. et al.Oligomerization of the polycystin-2 C-terminal tail and effects on its Ca2+binding properties.J. Bio. Chem. vol. 290, No. 16, pp. 10544-10554 (2015).
Yeo, et al. Discovery and analysis of evolutionarily conserved intronic splicing regulatory elements. PLoS Genet. May 25, 2007;3(5):e85. Epub Apr. 13, 2007.
Yoshida, et al. Frequent pathway mutations of splicing machinery in myelodysplasia. Nature. Sep. 11, 2011;478(7367):64-9. doi: 10.1038/nature10496.
Yoshida, K., et al. Splicing factor mutations and cancer. Wiley Interdiscip Rev RNA. 2014;5(4):445-59. doi: 10.1002/wrna.1222. PubMed PMID: 24523246.
Young et al. 915—a GABA-Selective AAV Vector-Based Approach to Up-Regulate Endogenous Senia Expression reverses key Phenotypes in a Mouse Model of Dravet Syndrome. 22nd Annual Meeting American Society of Gene & Cell Therapy. Washington, D.C. Apr. 29-May 2, 2019 (Abstract).
Yu, E.Y., et al. Regulation of telomere structure and functions by subunits of the INO80 chromatin remodeling complex. Mol Cell Biol. 2007;27(16):5639-49. doi: 10.1128/MCB.00418-07. PubMed PMID: 17562861; PubMed Central PMCID: PMC1952117.
Yuan et al. Brain localization and neurotoxicity evaluation of polysorbate 80-modified chitosan nanoparticles in rats. PloS one 10.8 (2015): e0134722.
Yuan X., et al. Nuclear protein profiling of Jurkat cells during heat stress-induced apoptosis by 2-DE and MS/MS. Electrophoresis. 2007;28(12):2018-26. doi: 10.1002/elps.200600821. PubMed PMID: 17523140.
Zammarchi, et al. "Antitumorigenic potential of STAT3 alternative splicing modulation", (2011) PNAS, vol. 108, No. 43, pp. 17779-17784.

(56) References Cited

OTHER PUBLICATIONS

Zamore, P.D., et al. Identification, purification, and biochemical characterization of U2 small nuclear ribonucleoprotein auxiliary factor. Proc Natl Acad Sci USA. 1989;86(23):9243-7. PubMed PMID: 2531895.

Zarnack K., et al. Direct competition between hnRNP C and U2AF65 protects the transcriptome from the exonization of Alu elements. Cell. 2013;152(3):453-66. Epub Feb. 5, 2013.doi: S0092-8674(12)01545-0 [pii] 10.1016/j.cell.2012.12.023. PubMed PMID: 23374342.

Zhang C., et al. RNA landscape of evolution for optimal exon and intron discrimination. Proc Natl Acad Sci USA. 2008;105(15):5797-802. Epub Apr. 9, 2008.doi: 0801692105 [pii] 10.1073/pnas.0801692105. PubMed PMID: 18391195.

Zhang, et al. Insulin as an autoantigen in NOD/human diabetes. Curr Opin Immunol. Feb. 2008;20(1):111-8. doi: 10.1016/j.coi.2007.11.005.

Zhang, et al. The kinetics and folding pathways of intramolecular G-quadruplex nucleic acids. J Am Chem Soc. Nov. 21, 2012;134(46):19297-308. doi: 10.1021/ja309851t. Epub Nov. 12, 2012.

Zhang, J. et al. PowerBLAST: A New Network BLAST Application for Interactive or Automated Sequence Analysis and Annotation Genome Res., vol. 7, pp. 649-656, (1997).

Zhang, X.H., et al. Computational definition of sequence motifs governing constitutive exon splicing. Genes Dev. 2004;18:1241-50. PubMed PMID: 15145827.

Zimrin et al. An Antisense Oligonucleotide to the Notch Ligand Jagged Enhances Firbroblast Growth Factor-induced Angiogenesis in Vitro. J. Biol. Chem. 271(51):32499-502 (Dec. 20, 1996).

Zon et al. Phosphorothioate oligonucleotides: chemistry, purification, analysis, scale-up and future directions. Anti Cancer Drug Design vol. 6, No. 6, pp. 539-568 (1991).

Zon G. and Stec.W.J. (1991) In Eckstein,F. (ed.), Oligonucleotides and Analogues: A Practical Approach. Oxford University Press, Oxford, UK, pp. 87-108.

Zorio, D.A., et al. Both subunits of U2AF recognize the 3' splice site in Caenorhabditis elegans. Nature. 1999;402(6763):835-8. PubMed PMID: 10617207.

Zuker, M. Mfold web server for nucleic acid folding and hybridization prediction. Nucleic Acids Res. 31, 3406-3415 (2003).

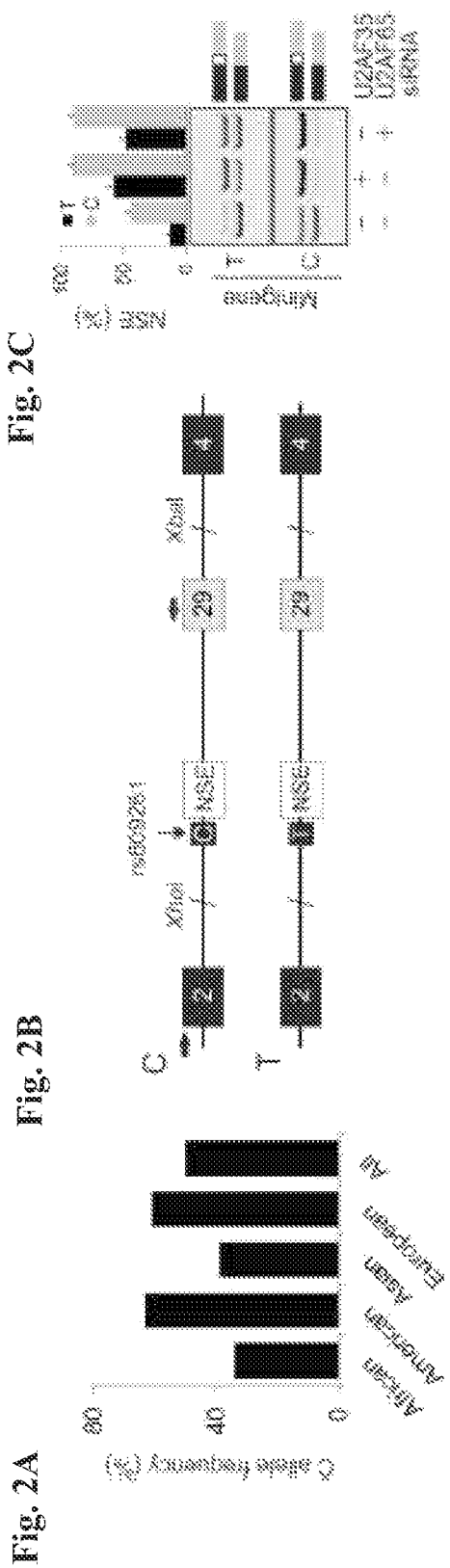

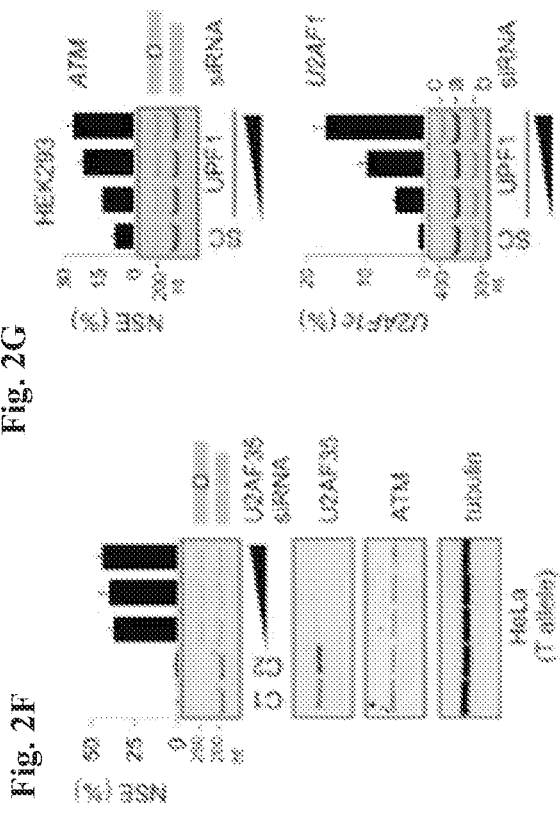
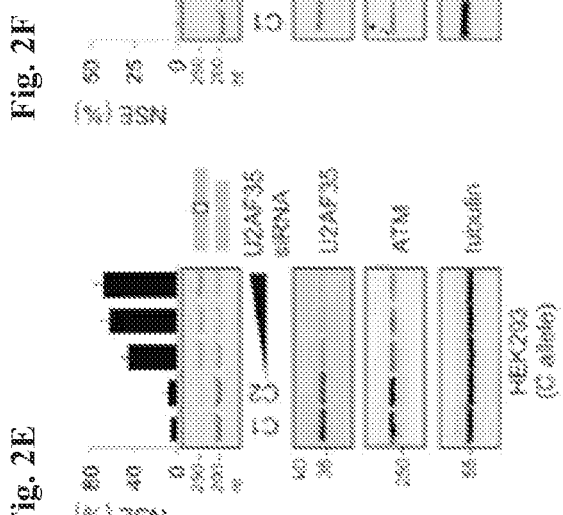
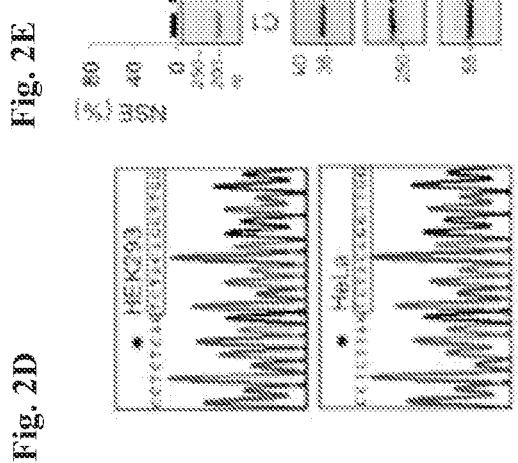
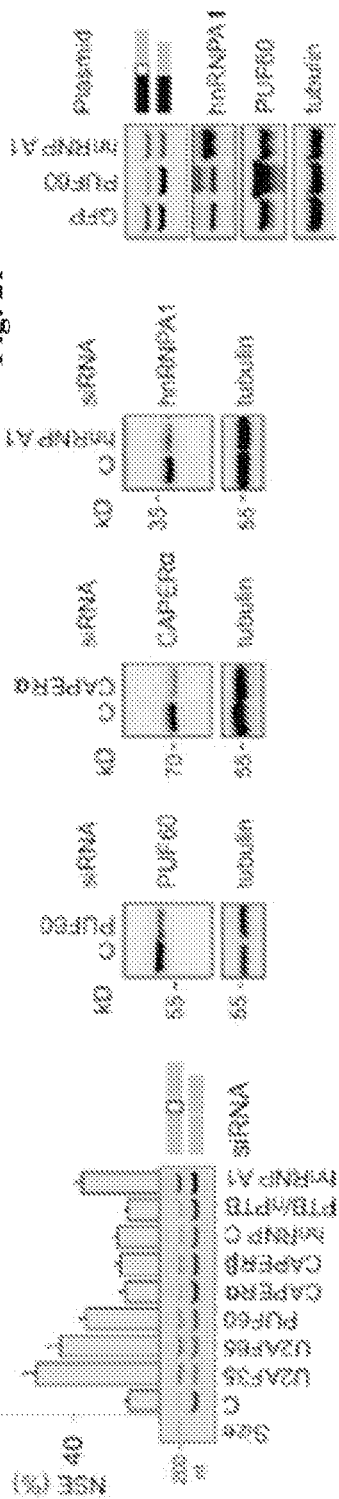

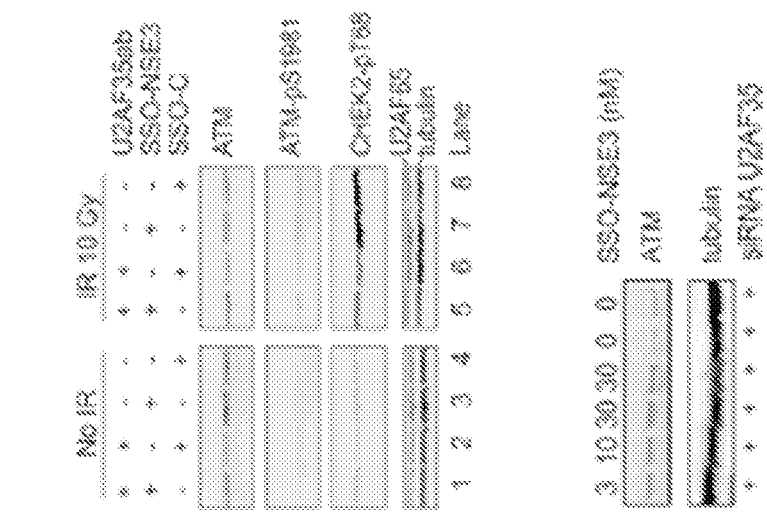
Fig. 3C
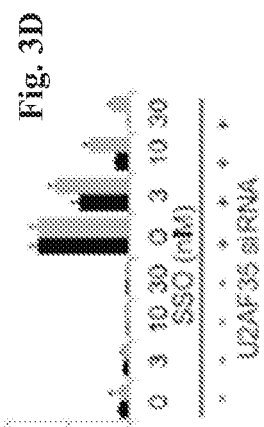
Fig. 3D
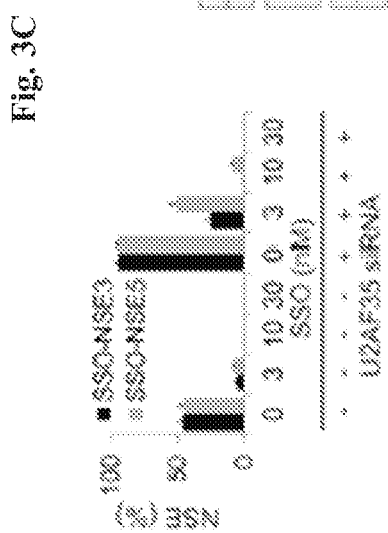
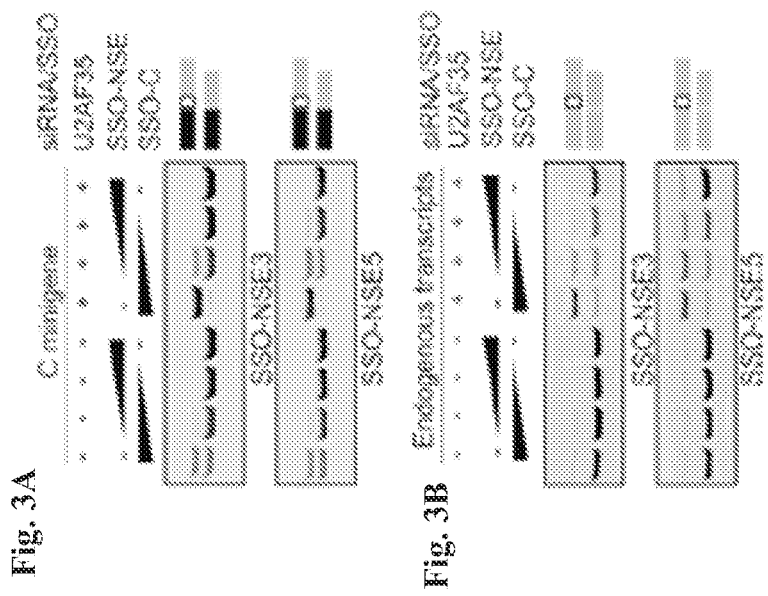
Fig. 3A
Fig. 3B

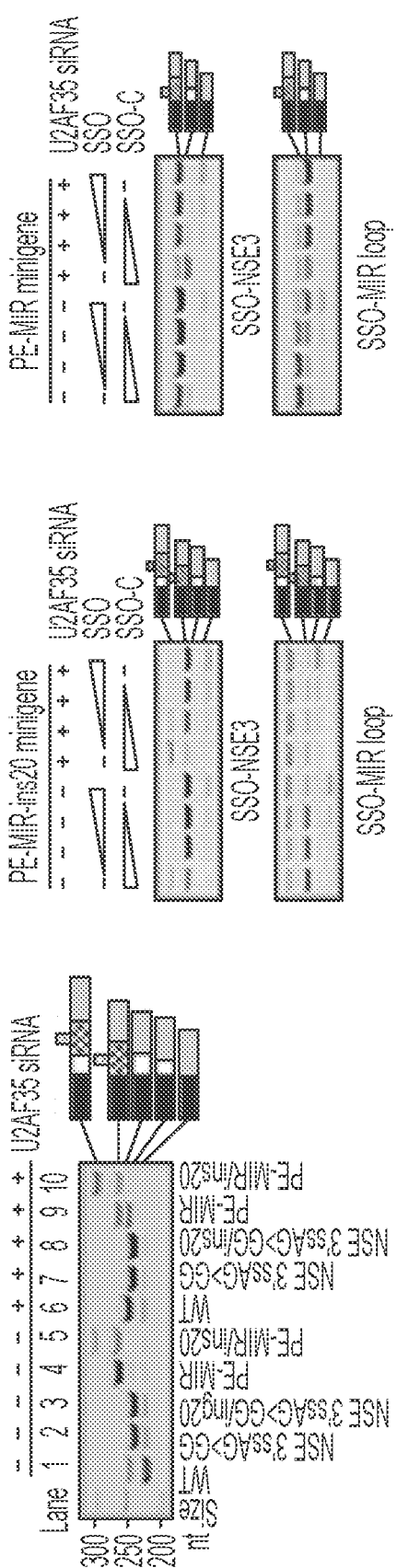
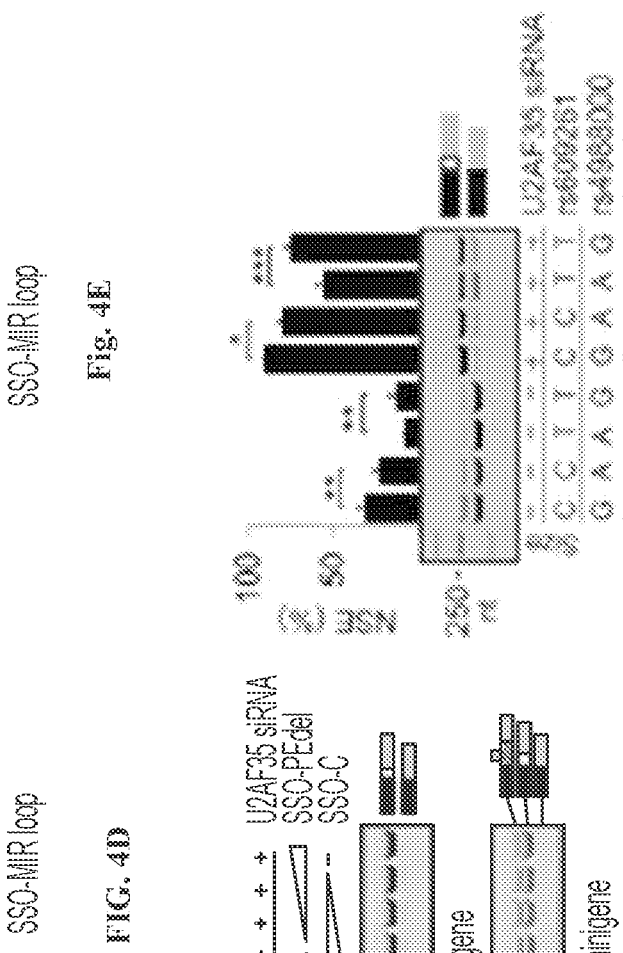
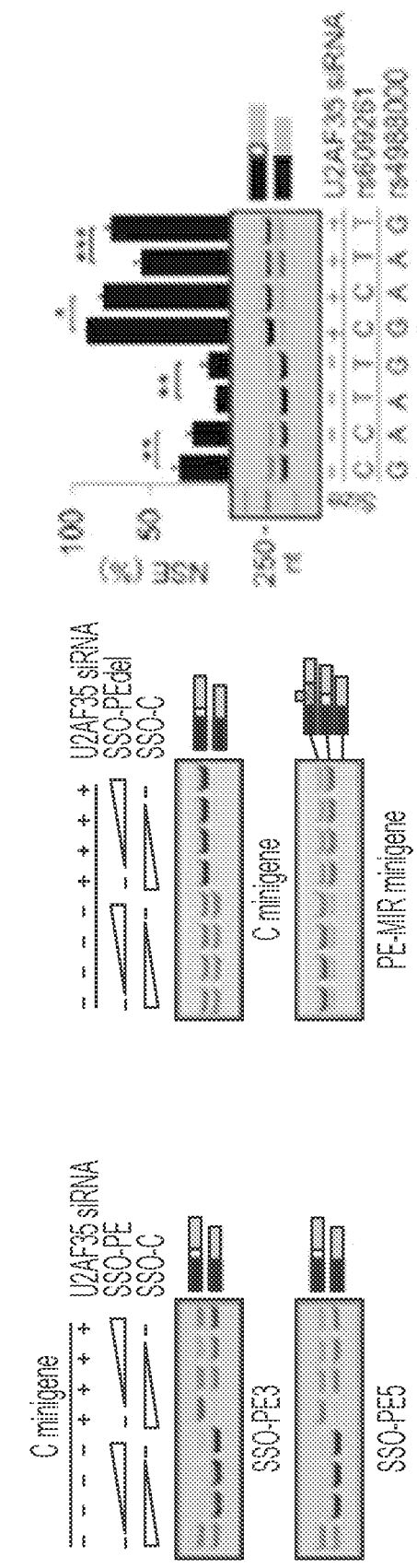
FIG. 4C
FIG. 4D
FIG. 4E
FIG. 4F
FIG. 4G
FIG. 4H

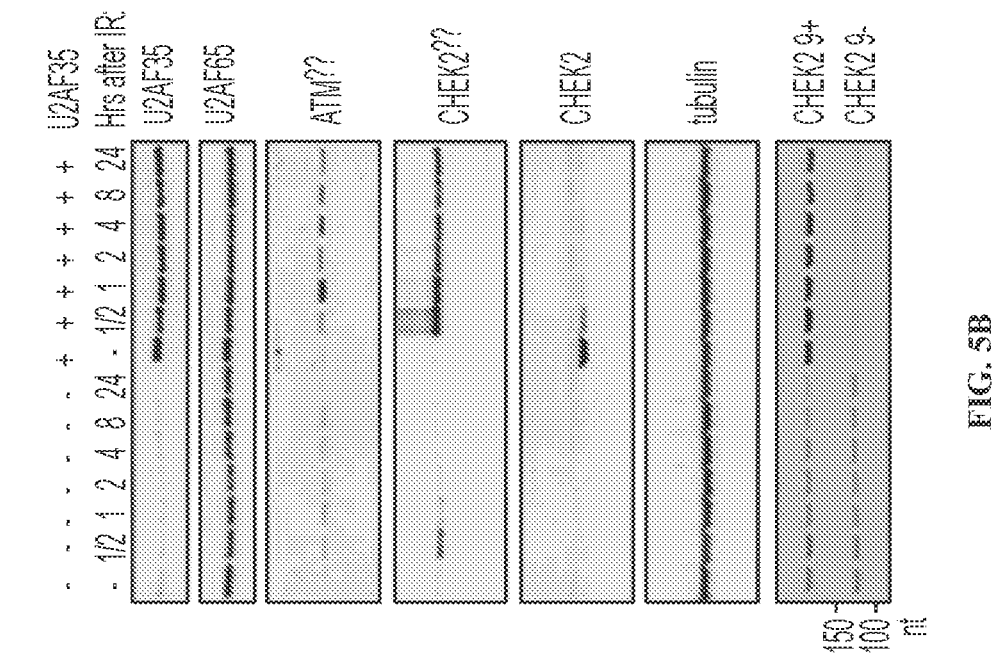
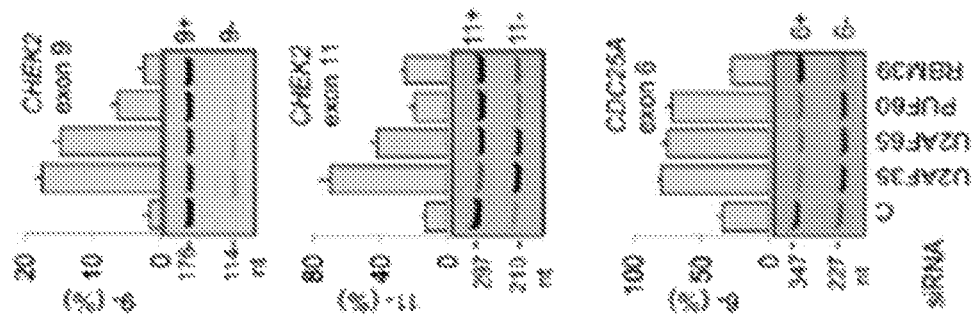
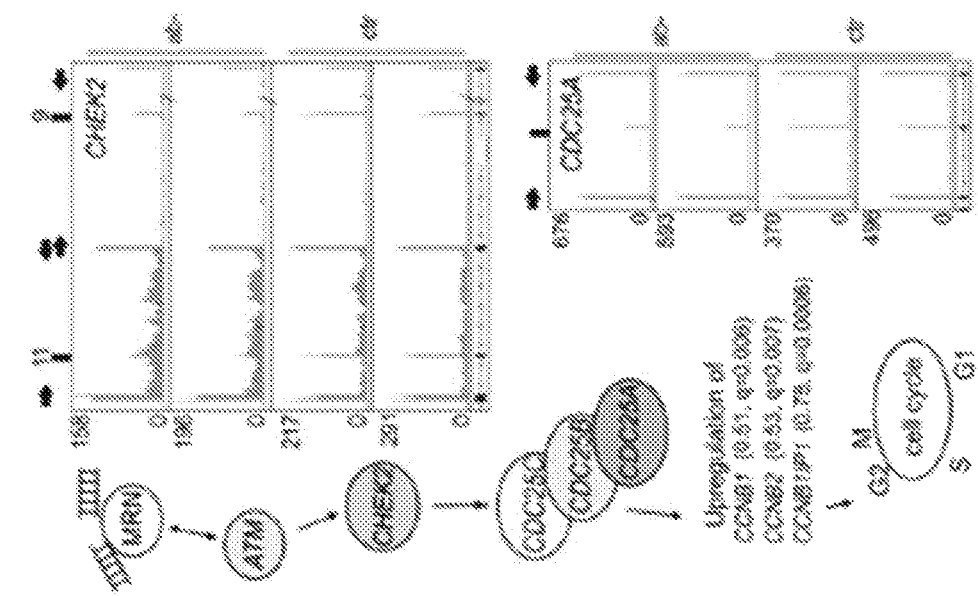
FIG. 5A
FIG. 5B

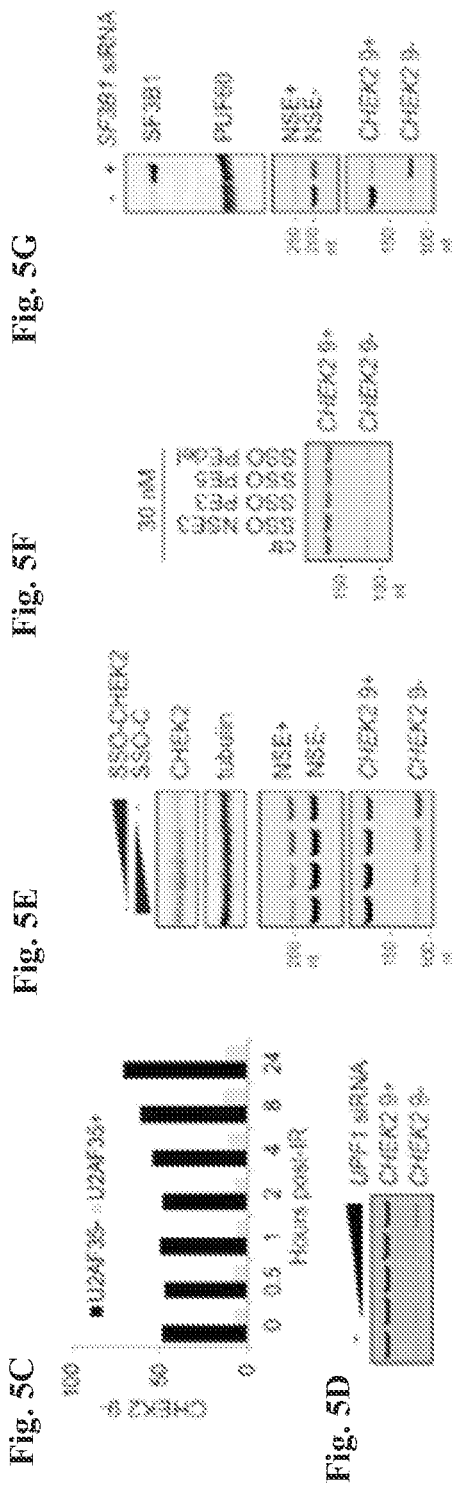

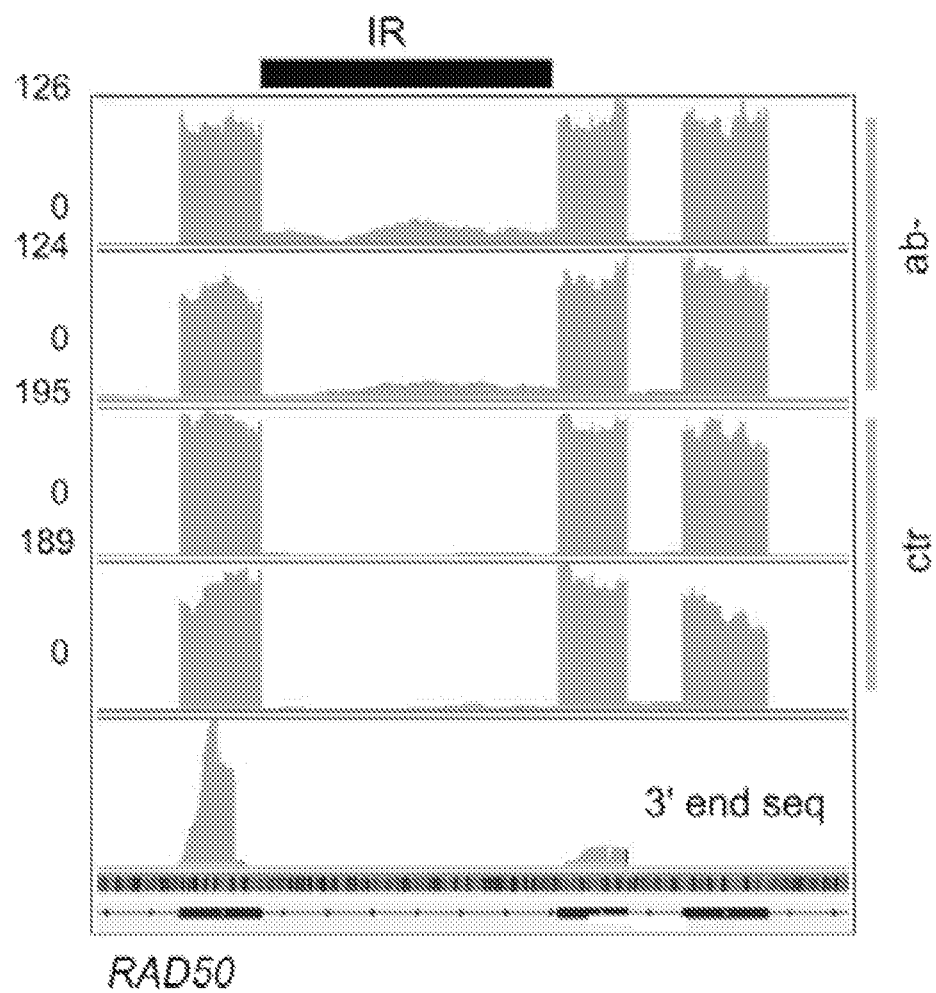

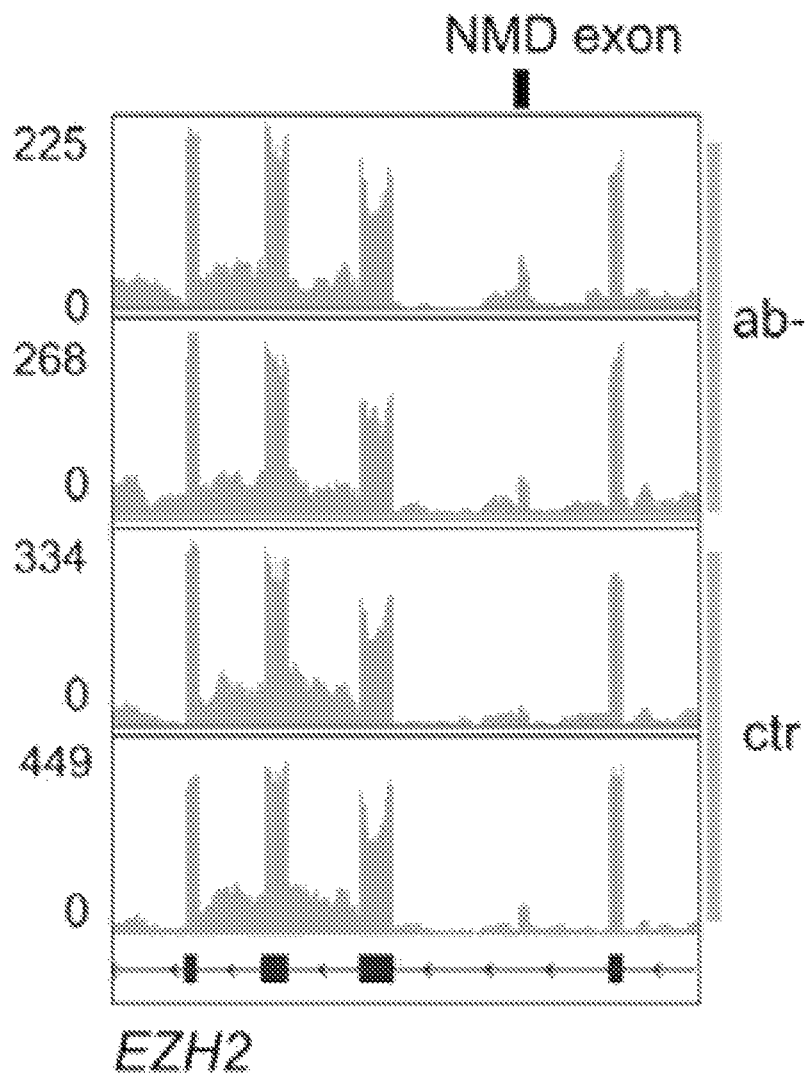

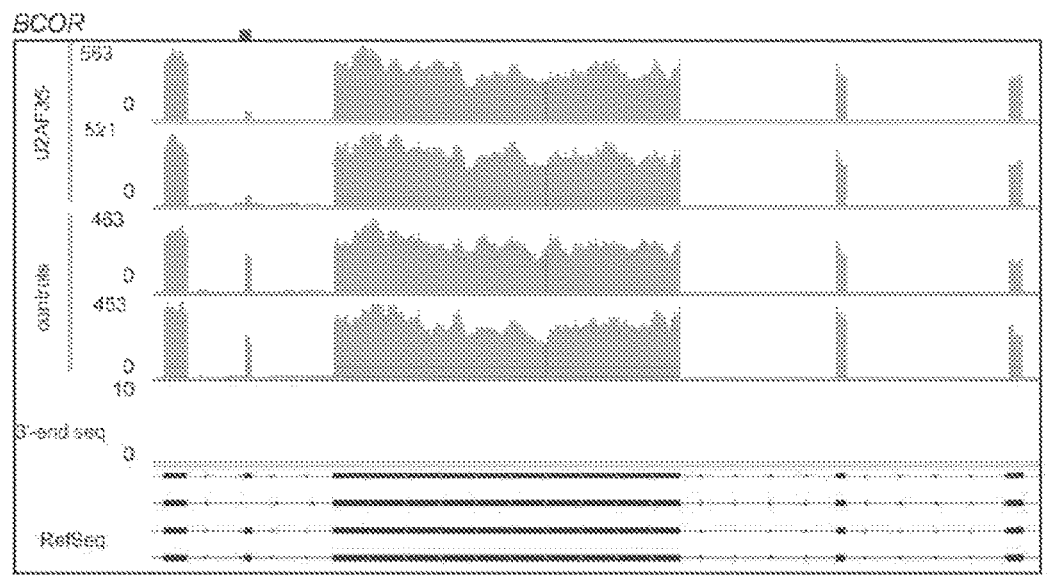
Fig. 14C BCOR
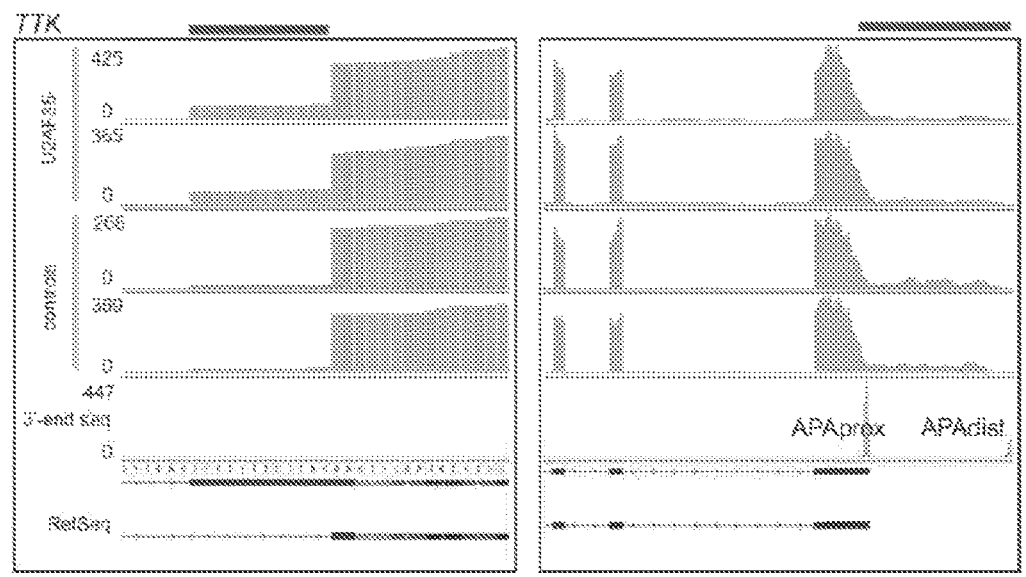
Fig. 14D TTK

ACCESSION NUMBER

Accession number for RNA-Seq data is E-MTAB-2682 (ArrayExpress).

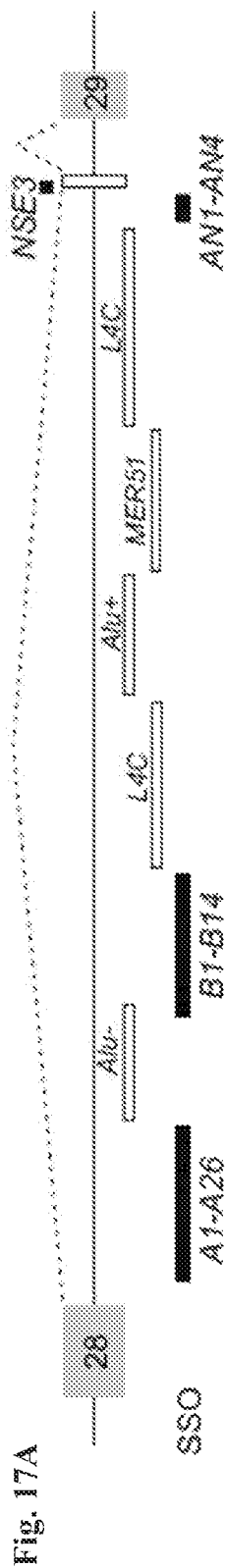
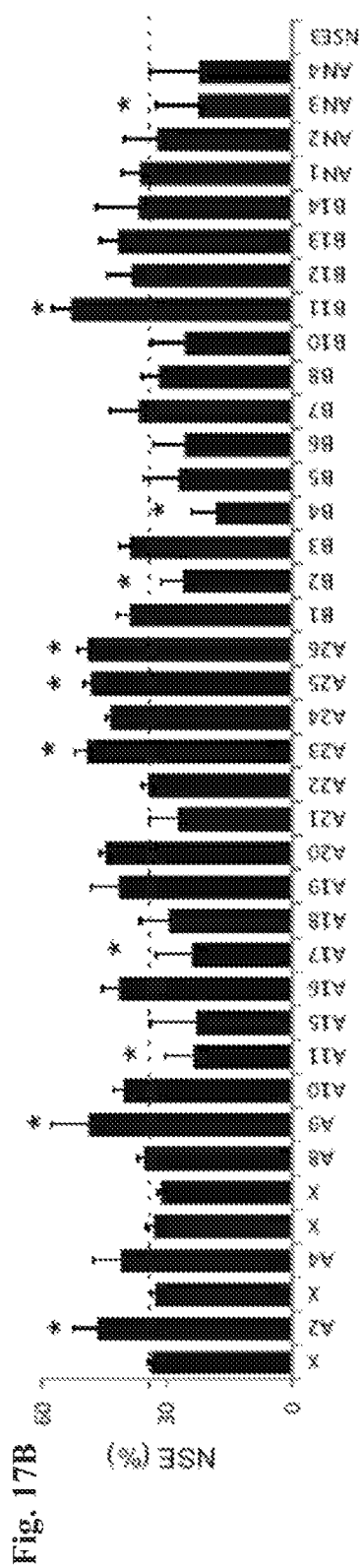
Fig. 17A
Fig. 17B

Fig. 19

```
ATM intron 28      UUGUAUAAAACACACAAACAAAGCAAGGAAAGAAUGAAGCAACAAAGCCA
                        v  i      i                            iv
MER51A#LTR/ER      UUGGACAAAACGCACAAACAAAGCAAGGAAAGAAUGAAGCAACAAAAGCA ATM intron 28      GAGAUUACUGAAAUGAAAUUAUACUCCACAGAGUUGGAGUC░░░░░░░░
                        i     i v i      i      i
MER51A#LTR/ER      GAGAUUAUUGAAAACGAAAGUACACUCCACAGGGUGGGAGCGGGCCC-G ATM intron 28      ░░AGUC░░░░░░░░░░░░░░░░░░░░AUUUCUGGGGUUAAAUACC
                        i                     i
MER51A#LTR/ER      AGCAAGCGGCUCAAGGGCCCGGUUACAGAAUUUCUGGGGUUAAAUACC ATM intron 28      CUUCAGAGGUUUUCCAUUGGUUACUGGUAUACACCCUAUGUAAAUGAAG
                         ii    i               i
MER51A#LTR/ER      CUCUAGAGGUUUCCCAUUGGUUACUGGUGUACACCCUAUUUAAAUGAAG ATM intron 28      UAGUGG░░░░░░░░░░░░░░░░░░░░AUACUA░GG░░░░░░░░░░░░
                        iii                     iii ii v
MER51A#LTR/ER      UAGUGGCCCGCAAUCAGUCUGAUUGGUUGCGGAAAGCGACCAAUCAGAGG ATM intron 28      UACAC-CCUAUGUAAAUGAAGUAGUGGUCUGUAAUCAGUCUGAUGGUUA
                        -   i       vv    i iii                i
MER51A#LTR/ER      UACACUCCUAUGCAAAUGAAGACUGGCCCCGCGACCAGUCUGAUGGUUG ATM intron 28      UUCAAUUUCUUAUCUGCCA---CAGUAAAAGCG░░░░░░░░AAACGGA░
                        ii         --- -      vi
MER51A#LTR/ER      UUCAAUUCCCAUCUGCCACGCAG-AAAAGGCUGGGGUUGCAAAGGGAG ATM intron 28      ░░░░░░░░░░GUCCUUUUGUUACUUGCAGCAUGGAAAGUUGGGGUUUCCUU
                        v                   i  i
MER51A#LTR/ER      UAGCCUCUGGUCCUUUUGUUACUGGGCGUGGAAAGUGGGGUUUCCUU ATM intron 28      UUGAUUUCGUUCUAGGAGGUCAGCAUGGAUUGACCUUAGGUUCCCUGCCU
                        i        i      i i    ii        i
MER51A#LTR/ER      UCGAUUUAGUUCUAGGAAGUCAGCGUGAAUCGCCUUAGGUUCCCUGCCU ATM intron 28      CCAGACCUAUUGCCCUGCCUCA
                        i    vi
MER51A#LTR/ER      CCAGACCUAUUCUCCUGCCUCA
```

Fig. 20

| RT-PCR primers | Sequence (5'-3') | Reference |
|---|---|---|
| ATM-F | GAGGGTACCAGAGACAGTGGGATGGC | This study |
| ATM-R | GGCTCATGTAACGTCATCAAT | This study |
| PL3 | GGGAGACCCAAGCTGGCTA | [1] |
| CHEK2-E9-F | AGACCCAGCTCTCAATGTTG | This study |
| CHEK2-E9-R | TAGCTTCTTTCAGGCGTTTA | This study |
| CHEK2-E11F1 | AGTGGTGGGGAATAAACG | This study |
| CHEK2-E11R | CAGCAGTCCACAGCACGGT | This study |
| CDC25B-F | CTCAGTCCAGCAGGCGTGTG | This study |
| CDC25B-R | GGTCTCTGGGCAAAGGCTTC | This study |
| CDC25A-F | CAGAAGCTGTTGGGATGTAG | This study |
| CDC25A-R | TCTCCATCGAGAAGGTCCAC | This study |
| CDC25C-F | TGGCTCAGGACCCAGTTTTA | [2] |
| CDC25C-R | TCTTCTGCCTGGTCTTCTCC | [2] |
| TIN2-F1 | CCTGGCTTGGTTCGCTACC | This study |
| TIN2-R3 | TGCTTCACCTGCTGGTAAAA | This study |
| TIN2-F6 | GAAGAACATGCGATATACACA | This study |
| TIN2-R8 | GTCTAAAACCAAGTCCCCTAT | This study |
| PIN1-F | GAGGGAAGATGGCGGACGAG | This study |
| PIN1-R | TCCTCCTTGGTCCGGGTGAT | This study |
| TERF1-F | GCAGCGGCAAAAGTAGTAGA | This study |
| TERF1-R | GTCTTGTTGCTGGGTTCCA | This study |
| RAD50-cr5-F | AAAATCATCAAAACAGCGAG | This study |
| RAD50-cr5-R | TGGAGCAAGTCGCAGTTTAG | This study |
| RAD50-E-F | GGCGACAGAAAGGTTATGAA | This study |
| RAD50-E-R | CGCCACAGGTCACGTATAAT | This study |
| Cloning primers | | |
| ATM-XhoI | ATAGAATTCTCGAGGGGAGGGTTTTATTCTACTA | This study |
| ATM-XbaI | ATAGGGCCCTCTAGACTGTGGGGAGACTATGGTAA | This study |
| CHEK2-EcoRI | ATTAGAATTCTCTCGGGAGTCGGATGTTG | This study |
| CHEK2-NotI | ATTAGCGGCCGCGGTACATTTCTTTCGTGTTCA | This study |
| Modified antisense oligonucleotides | | |
| SSO-NSE3 | CUUCUAUGCAGCCAACCUGUAGACU | This study |
| SSO-NSE5 | ACCUUUUUCUUCUAUGCAGCCAAC | This study |
| SSO-PE3 | AUUCCAAAAGUAUUCGAUGACUG | This study |
| SSO-PE5 | UAUAUUACCUUAUUUCCAAAAGUA | This study |
| SSO-PE8P | CUGUAAAAGAAAAUAGAUGACUCAA | This study |
| SSO-PEdel | CUGUAAAGAAAAUAGA | This study |
| SSO-CHEK2-ex3 | ACUUACAAUUCCAAAACAAUAUAAU | This study |
| SSO-C | AGGUGCUCGCGGUGG | [3] |
| SSO-MIR loop | AGUUGCUUCAUCU | [4] |
| siRNA | | |
| U2AF35ab | GGCUGUGAUUGACUUGAAU | [5] |
| U2AF65 | GCAAGUACGGGCUUGUCAA | [6] |
| RBM39 | GGAUCUACUGUCAUUUGUA | [7] |
| PUF60 | GCAGAUGAACUCGGUGAUG | [6] |
| UPF1 | AAGAUGCAGUUCCGCUCCAUU | [8] |

| Pseudoexon | Allele | FAS-ESS[1] | PES G[1] | PES E[1] | RESCUE-ESE[1] | SE 1/A/SF ESE[1] | ESE density[1] |
|---|---|---|---|---|---|---|---|
| NSE | C | 3.45 | 3.45 | 5 | 6 | 9.3 | 975.4 |
| NSE | T | 3.45 | 3.45 | 5 | 6 | 9.3 | 975.4 |
| PE | G | 4.17 | 0 | 0 | 3 | 0 | 403.8 |
| PE | A | 4.17 | 0 | 0 | 5 | 0 | 334.2 |
| Reference | | [10] | [11] | [11] | [12] | [13] | [14] |

Legend: [1]Densities of the indicated enhancers and silencers predicted in NSE and PE were computed as described [15]. Support vector machine scores for the best predicted BPS of NSE and PE [16] were 1.3 and 0.5.

Fig. 23

| Transcript | Levels in depleted cells |
|---|---|
| UPF3A | Down (q=0.002) |
| UPF3B[1] | Down (q=0.0006), skipping of a 39-nt exon |
| SMG7 | Up (q=0.002) |
| SMG8 | Up (q=0.01) |
| DHX34 | Up (q=0.02) |
| CASC3 | Up (q=0.04) |
| RNPS1 | Up (q=0.03) through putative intronic alternative polyadenylation site |
| RBFOX2 | Up (q=0.007) |

[1] UPF3B was implicated as exhibiting a distinct level of exon inclusion in patients with myeloid neoplasms [17].

SEQUENCE LISTING

```
<160> NUMBER OF SEQ ID NOS: 127

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ataaagcttc ttgttataag gttttgattc c                                  31

<210> SEQ ID NO 2
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
atatctagat gtacataccc tgaaaagtca c                                  31

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
agtcgaggct gatcagcgg                                                19

<210> SEQ ID NO 4
<211> LENGTH: 26
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gagggtacca gagacagtgg gatggc                                          26

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggctcatgta acgtcatcaa t                                               21

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
atacaattta ccataattta cttttgaatt atgtt                                35

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aagtaaatta tggtaaattg tatcatacat tag                                  33

<210> SEQ ID NO 8
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ccttgccaga ccagtttcct agttatctat attgaac                              37

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
taactaggaa actggtctgg caaggtggct ta                                   32

<210> SEQ ID NO 10
<211> LENGTH: 31
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 10
cttcaaggga ccttggccgg gtgcggtggc t                              31

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcacccggcc aaggtccctt gaagtttatc taa                            33

<210> SEQ ID NO 12
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
acacaaacaa agcttaggtt tctttcttgt caccttcta                      39

<210> SEQ ID NO 13
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
agaaagaaac ctaagctttg tttgtgtgtt ttatacaa                       38

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tgcctcattt acgtcataca acttaatgat agacct                         36

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ttaagttgta tgacgtaaat gaggcagggc aa                             32

<210> SEQ ID NO 16
<211> LENGTH: 37
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 16
tgatacaatt tacctcatac aacttaatga tagacct                            37

<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
attaagttgt atgaggtaaa ttgtatcata cattag                             36

<210> SEQ ID NO 18
<211> LENGTH: 19
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 18
aacuuaaagg uuauaucuc                                                19

<210> SEQ ID NO 19
<211> LENGTH: 20
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 19
uauaaauacg aauaaaucga                                               20

<210> SEQ ID NO 20
<211> LENGTH: 19
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 20
cauggguugg cuaugcuag                                                19

<210> SEQ ID NO 21
<211> LENGTH: 18
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 21
caacacgaca uaaccaaa                                                 18

<210> SEQ ID NO 22
<211> LENGTH: 20
<212> TYPE: RNA
<213> ORGANISM: Artificial Sequence
<220> FEATURE:
```

```
<223> OTHER INFORMATION: Description of Artificial Sequence: Synthetic
      primer

<400> SEQUENCE: 22
aagccaauca gagggagaca                                              20

<210> SEQ ID NO 23
<211> LENGTH: 23
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 23
aacauuucua uuuaguuaaa agc                                          23

<210> SEQ ID NO 24
<211> LENGTH: 20
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 24
ucguguauua caacaguuaa                                              20

<210> SEQ ID NO 25
<211> LENGTH: 18
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 25
caaccaguuu gcauucgu                                                18

<210> SEQ ID NO 26
<211> LENGTH: 19
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 26
uuaguauucc uugacuuua                                               19

<210> SEQ ID NO 27
<211> LENGTH: 23
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 27
uucuguacac uguuuaguau ucc                                          23

<210> SEQ ID NO 28
<211> LENGTH: 18
<212> TYPE: RNA
<213> ORGANISM: Artificial Sequence
<220> FEATURE:
<223> OTHER INFORMATION: Description of Artificial Sequence: Synthetic
```

```
                                          primer

<400> SEQUENCE: 28
gaagagggag ugaagguu                                                      18

<210> SEQ ID NO 29
<211> LENGTH: 18
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 29
aaagcuuggu gagauuga                                                      18

<210> SEQ ID NO 30
<211> LENGTH: 23
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 30
uuucuugaaa aguggaaagc uug                                                23

<210> SEQ ID NO 31
<211> LENGTH: 24
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 31
uggaaugagg gacgguuguu uuuc                                               24

<210> SEQ ID NO 32
<211> LENGTH: 18
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 32
gguaugagaa cuauagga                                                      18

<210> SEQ ID NO 33
<211> LENGTH: 18
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 33
aaacaaacag caggguau                                                      18

<210> SEQ ID NO 34
<211> LENGTH: 18
<212> TYPE: RNA
<213> ORGANISM: Artificial Sequence
<220> FEATURE:
<223> OTHER INFORMATION: Description of Artificial Sequence: Synthetic
      primer
```

```
<400> SEQUENCE: 34
gguaauaagu gucacaaa                                               18

<210> SEQ ID NO 35
<211> LENGTH: 18
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 35
guaucauaca uuagaagg                                               18

<210> SEQ ID NO 36
<211> LENGTH: 20
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 36
ucaaaaguaa auuauggucu                                             20

<210> SEQ ID NO 37
<211> LENGTH: 25
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 37
gacugguaaa uaauaaacau aauuc                                       25

<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 38
aaauguauac uggagaagac u                                           21

<210> SEQ ID NO 39
<211> LENGTH: 22
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 39
auauauuaga gauacaucag cc                                          22

<210> SEQ ID NO 40
<211> LENGTH: 24
<212> TYPE: RNA
<213> ORGANISM: Artificial Sequence
<220> FEATURE:
<223> OTHER INFORMATION: Description of Artificial Sequence: Synthetic
      primer
```

```
<400> SEQUENCE: 40
gacaaacauu uaaugaauac ucaa                                          24

<210> SEQ ID NO 41
<211> LENGTH: 24
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 41
uugacuccuu cuuuugacaa acau                                          24

<210> SEQ ID NO 42
<211> LENGTH: 19
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 42
uuuaaauccu uccuuacuu                                                19

<210> SEQ ID NO 43
<211> LENGTH: 20
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 43
gauuauaaaa caaacgaagc                                               20

<210> SEQ ID NO 44
<211> LENGTH: 23
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 44
uguuuuaaua uaaguugcuu caa                                           23

<210> SEQ ID NO 45
<211> LENGTH: 19
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 45
ugugggguga ccacagcuu                                                19

<210> SEQ ID NO 46
<211> LENGTH: 18
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 46
```

```
ucccuuacuu auauccaa                                              18

<210> SEQ ID NO 47
<211> LENGTH: 19
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 47
ccaaguuugg uuacuuauc                                             19

<210> SEQ ID NO 48
<211> LENGTH: 21
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 48
gaaguuuauc uaauauugac c                                          21

<210> SEQ ID NO 49
<211> LENGTH: 22
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 49
ggucuaucau uaaguuguau ga                                         22

<210> SEQ ID NO 50
<211> LENGTH: 21
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 50
uuaaauaaga cuucaggucu a                                          21

<210> SEQ ID NO 51
<211> LENGTH: 24
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 51
uuagagaauc auuuuaaaua agac                                       24

<210> SEQ ID NO 52
<211> LENGTH: 24
<212> TYPE: RNA
<213> ORGANISM: Artificial Sequence
<220> FEATURE:
<223> OTHER INFORMATION: Description of Artificial Sequence: Synthetic
      primer

<400> SEQUENCE: 52
```

```
cuuaauccaa uucuucaauu uuag                                              24

<210> SEQ ID NO 53
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
cuucuaugca gccaaccugu agacu                                             25

<210> SEQ ID NO 54
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
accuuuuucu ucuaugcagc caac                                              24

<210> SEQ ID NO 55
<211> LENGTH: 33
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
accuuuuucu ucuaugcagc caaccuguag acu                                    33

<210> SEQ ID NO 56
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
cuguaaaaga aaauaga                                                      17

<210> SEQ ID NO 57
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
tctacaggtt ggctgcatag aagaaaaag                                         29

<210> SEQ ID NO 58
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
agtctacagg ttggctgcat agaagaaaaa ggtagag                                37
```

<210> SEQ ID NO 59
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
tcttagtcta caggttggct gcatagaaga aaaaggtaga g                          41

<210> SEQ ID NO 60
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
tctcagtcta caggttggct gcatagaaga aaaaggtaga g                          41

<210> SEQ ID NO 61
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
tcatcgaata cttttggaaa taag                                             24

<210> SEQ ID NO 62
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
tagtctacag gttggctgca tagaagaaaa aggtagag                              38

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
cctctcagtc tacaggttgg                                                  20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
cctcttagtc tacaggttgg                                                  20

<210> SEQ ID NO 65
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gtagagttat ttataatctt gtaaatcttg gactttgagt catctatttt cttttacgg        59

<210> SEQ ID NO 66
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
gtagagttat ttataatctt gtaaatcttg gactttgagt ca                          42

<210> SEQ ID NO 67
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
gtagagttat ttataattct tgacgttcac agatatactt gtaaatcttg gactttgagt        60
catctatttt cttttacag                                                    79

<210> SEQ ID NO 68
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
gttcagtttt tttcttagaa atggaatccg agg                                    33

<210> SEQ ID NO 69
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
cttagtctac aggttggctg catagaagaa aaaggt                                 36

<210> SEQ ID NO 70
<211> LENGTH: 470
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 70
uuguauaaaa cacacaaaca aagcaaggaa agaaugaagc aacaaagcca gagauuuacu        60

```
gaaaaugaaa uuauacucca cagagugggg gugggcccug agcaagugcc ucaagggccu    120
gguuacagaa uuuucugggg uuuaaauacc cuucagaggu uuccauugg uuacuuggua     180 uacacccuau guaaaugaag uaguggucug uaaucagucu gauugguuau aggaggggac    240
caaucagagg uacacccuau guaaaugaag uaguggucug uaaucagucu gauugguuau    300
ucaauuucuu aucugccaca guaaaaggga gggggduugca aagggaguag ccucuugucc   360
uuuuguuacu ugagcaugga aaguggggu uuuccuuuug auuucguucu aggaggucag     420
cauggauuga ccuuagguuc ccugccucca gaccuuauug cccugccuca               470
```

<210> SEQ ID NO 71
<211> LENGTH: 471
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 71

```
uuggacaaaa cgcacaaaca aagcaaggaa agaaugaagc aacaaaagca gagauuuauu     60 gaaacgaaa guacacucca cagggugggga gcgggcccga gcaagcggcu caagggcccg    120
guuacagaau uuucuggggu uuaaauaccc ucuagagguu ucccauuggu acuuggugu     180 acacccuaug uaaaugaagu aguggccgc aaucagucug auugguucg gaaagcgacc      240 aaucagaggu acacuccuau gcaaaugaag acuggcccg cgaccagucu gauugguugu     300
ucaauucccc aucugccacg cagaaaaggu gggggguugc aaagggagua gccucuggc     360 cuuugguac ugggcgugg aaaguggggg uuuccuuuc gauuuaguuc uaggaagca       420 gcgugaaucg gccuuagguu cccgccucc agacccuauu cuccugccuc a              471
```

<210> SEQ ID NO 72
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
gagggtacca gagacagtgg gatggc                                          26

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
ggctcatgta acgtcatcaa t                                               21

<210> SEQ ID NO 74
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74

```
gggagaccca agctggcta                                                    19
```

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75

```
agacccagct ctcaatgttg                                                   20
```

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76

```
tagcttcttt caggcgttta                                                   20
```

<210> SEQ ID NO 77
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77

```
agtggtgggg aataaacg                                                     18
```

<210> SEQ ID NO 78
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78

```
cagcagtcca cagcacggt                                                    19
```

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79

```
ctcagtccag caggcgtgtg                                                   20
```

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80

```
ggtctctggg caaaggcttc                                                   20
```

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
cagaagctgt tgggatgtag                                              20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
tctccatcga gaaggtccac                                              20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
tggctcagga cccagtttta                                              20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
tcttctgcct ggtcttctcc                                              20

<210> SEQ ID NO 85
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
cctggcttgg ttcgctacc                                               19

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
tgcttcacct gctggtaaaa                                              20

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
gaagaacatg cgatatacac a                                              21

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
gtctaaaacc aagtcccta t                                               21

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
gagggaagat ggcggacgag                                                20

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
tcctccttgg tccgggtgat                                                20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
gcagcggcaa aagtagtaga                                                20

<210> SEQ ID NO 92
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
gtcttgttgc tgggttcca                                                 19

```
<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
aaaatcatca aaacagcgag                                                 20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
tggagcaagt cgcagtttag                                                 20

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
ggcgacagaa aggttatgaa                                                 20

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
cgccacaggt cacgtataat                                                 20

<210> SEQ ID NO 97
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
atagaattct cgaggggagg gttttattct acta                                 34

<210> SEQ ID NO 98
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
atagggccct ctagactgtg gggagactat ggtaa                                35

<210> SEQ ID NO 99
```

```
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
attagaattc tctcgggagt cggatgttg                                       29

<210> SEQ ID NO 100
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
attagcggcc gcggtacatt tctttcgtgt tca                                  33

<210> SEQ ID NO 101
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
cuucuaugca gccaaccugu agacu                                           25

<210> SEQ ID NO 102
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
accuuuuucu ucuaugcagc caac                                            24

<210> SEQ ID NO 103
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
auuuccaaaa guauucgaug acug                                            24

<210> SEQ ID NO 104
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
uauauuaccu uauuuccaaa agua                                            24

<210> SEQ ID NO 105
<211> LENGTH: 25
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
cuguaaaaga aaauagauga cucaa                                          25

<210> SEQ ID NO 106
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
cuguaaaaga aaauaga                                                   17

<210> SEQ ID NO 107
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
acuuacaauu ccaaaacaau auaau                                          25

<210> SEQ ID NO 108
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
aggugcucgc gggugg                                                    16

<210> SEQ ID NO 109
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
aguugcuuca ucu                                                       13

<210> SEQ ID NO 110
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
ggcugugauu gacuugaau                                                 19

<210> SEQ ID NO 111
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 111
gcaaguacgg gcuugucaa                                                   19

<210> SEQ ID NO 112
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
ggaucuacug ucauuugua                                                   19

<210> SEQ ID NO 113
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
gcagaugaac ucggugaug                                                   19

<210> SEQ ID NO 114
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
aagaugcagu uccgcuccau u                                                21

<210> SEQ ID NO 115
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 115
cagtctacag gttggctgca tagaagaaaa aggtagagtt atttataatc ttgtaaatct       60
tggactttga gtcatctatt ttctttaca gtcatcgaat acttttggaa ataaggt         117

<210> SEQ ID NO 116
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 116
cggtctacag gttggctgca tagaagaaaa aggtagagtt atttataatc ttgtaaatct       60
tggactttga gtcatctatt ttctttaca gtcatcgaat acttttggaa ataaggt         117
```

```
<210> SEQ ID NO 117
<211> LENGTH: 137
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 117
cggtctacag gttggctgca tagaagaaaa aggtagagtt atttataatt cttgacgttc      60
acagatatac ttgtaaatct tggactttga gtcatctatt ttcttttaca gtcatcgaat     120
acttttggaa ataaggt                                                    137

<210> SEQ ID NO 118
<211> LENGTH: 141
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Description of Combined DNA/RNA Molecule:
      Synthetic polynucleotide

<400> SEQUENCE: 118
cagtctacag gttggctgca tagaagaaaa aggtagagtt atttataatc ttgtaaatct      60
tggactttga gtcatctatt ttcttttaca gtcatcgaat actgggcaca gaugaagcaa     120
cuugcccttt ggaaataagg t                                               141

<210> SEQ ID NO 119
<211> LENGTH: 161
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Description of Combined DNA/RNA Molecule:
      Synthetic polynucleotide

<400> SEQUENCE: 119
cagtctacag gttggctgca tagaagaaaa aggtagagtt atttataatt cttgacgttc      60
acagatatac ttgtaaatct tggactttga gtcatctatt ttcttttaca gtcatcgaat     120
actgggcaca gaugaagcaa cuugcccttt ggaaataagg t                         161

<210> SEQ ID NO 120
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(6)
<223> OTHER INFORMATION: D-Arg or L-Arg

<400> SEQUENCE: 120

Arg Arg Arg Arg Arg Arg
1               5

<210> SEQ ID NO 121
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 121

Pro Lys Lys Lys Arg Lys Val
1               5

<210> SEQ ID NO 122
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ahx
<220> FEATURE:
<221> NAME/KEY: MOD_RES
<222> LOCATION: (5)..(5)
<223> OTHER INFORMATION: Ahx
<220> FEATURE:
<221> NAME/KEY: MOD_RES
<222> LOCATION: (8)..(8)
<223> OTHER INFORMATION: Ahx
<220> FEATURE:
<221> NAME/KEY: MOD_RES
<222> LOCATION: (11)..(11)
<223> OTHER INFORMATION: Ahx

<400> SEQUENCE: 122

Arg Xaa Arg Arg Xaa Arg Arg Xaa Arg Arg Xaa Arg
1               5                   10

<210> SEQ ID NO 123
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Ahx
<220> FEATURE:
<221> NAME/KEY: MOD_RES
<222> LOCATION: (12)..(12)
<223> OTHER INFORMATION: Beta-Ala

<400> SEQUENCE: 123

Arg Phe Phe Arg Phe Phe Arg Phe Phe Arg Xaa Ala
1               5                   10

<210> SEQ ID NO 124
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Lys Phe Phe Lys Phe Phe Lys Phe Phe Lys
1               5                   10

<210> SEQ ID NO 125
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(15)
<223> OTHER INFORMATION: D-Arg or L-Arg

<400> SEQUENCE: 125

Arg Arg Arg Arg Arg Arg Arg Arg Arg Arg Arg Arg Arg Arg Arg
1               5                   10                  15

<210> SEQ ID NO 126
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(9)
<223> OTHER INFORMATION: D-Arg or L-Arg

<400> SEQUENCE: 126

Arg Arg Arg Arg Arg Arg Arg Arg Arg
1               5

<210> SEQ ID NO 127
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
actgttcagt tttttctta gaaatggaat ccgaggat                              38
```

MODULATION OF GENE EXPRESSION AND SCREENING FOR DEREGULATED PROTEIN EXPRESSION

CROSS-REFERENCE

This application is a divisional application of U.S. patent application Ser. No. 16/213,535, filed on Dec. 7, 2018, which is a continuation of U.S. patent application Ser. No. 15/288,415, filed on Oct. 7, 2016, now U.S. Pat. No. 10,196,639, issued on Feb. 5, 2019, which claims the benefit of United Kingdom Patent Application No: 1517937.7, filed on Oct. 9, 2015, and United Kingdom Patent Application No: 1614744.9, filed on Aug. 31, 2016, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Dec. 1, 2016, is named 47991_718_201_SL.txt and is 32,036 bytes in size.

BACKGROUND OF THE INVENTION

The ATM protein belongs to the PI3/PI4-kinase family and is involved in the developments of the nervous system and the immune system. The ATM protein kinase is activated upon DNA damage and subsequently coordinates the DNA repair mechanism.

SUMMARY OF THE INVENTION

In certain embodiments, described herein include methods of screening a subject susceptible to functional-ATM protein deficiency and associated conditions, methods for selecting subjects for treatment, methods for treatment or prevention of conditions associated with functional-ATM protein deficiency, methods of modifying a cells susceptibility to DNA damaging radio- and chemotherapy, methods for treatment of cancer, and associated compositions and kits.

Disclosed herein, in certain embodiments, is a method of screening a subject for susceptibility to functional-ATM protein deficiency, wherein the screening comprises determining the presence of a non-thymine variant residue rs609261 located at position −3 relative to the 3' splice site of NSE (cryptic exon in ATM intron 28) of the human genome, wherein the presence of a non-thymine variant residue rs609261 indicates that the subject has, or is susceptible to, functional-ATM protein deficiency. In some embodiments, the NSE comprises a sequence comprising tctacaggttggctgcatagaagaaaaag. In some embodiments, the NSE repressor agent binds to the NSE within a sequence comprising agTCTACAGGTTGGCTGCATAGAAGAAAAAGgtagag; or tcttagTCTACAGGTTGGCTGCATAGAAGAAAAAGgtagag; or tctcagTCTACAGGTTGGCTGCATAGAAGAAAAAGgtagag. In some embodiments, the NSE repressor agent binds to the NSE or its 5' or 3' splice site in ATM intron 28 of the NSE. In some embodiments, the NSE repressor agent and/or NSE activator agent comprises a polynucleic acid polymer. In some embodiments, the NSE repressor agent and/or NSE activator agent is an SSO (Splice Switching Oligonucleotide). In some embodiments, the NSE repressor agent and/or NSE activator agent is associated with a delivery vehicle suitable for delivering the NSE repressor agent and/or NSE activator agent to cells. In some embodiments, the NSE repressor agent comprises: an SSO of the sequence cuucuaugcagccaaccuguagacu (SSO-NSE3), or a nucleic acid analogue thereof; or an SSO of the sequence accuuuucuucuaugcagccaac (SSO-NSE5), or a nucleic acid analogue thereof; and/or the NSE repressor agent comprises or consists of any one SSO selected from the group comprising: aacauuucuauuuaguuaaaagc (SSO A11); uuaguauuccuugacuuua (SSO A17); gacugguaaauaauaaacauaauuc (SSO B2); auauauuagagauacaucagcc (SSO B4); and uuagagaaucauuuuaaauaagac (SSO AN3), or combinations thereof.

Disclosed herein, in certain embodiments, is a method of selecting a subject for treatment, wherein the subject is susceptible to a functional-ATM protein deficiency, the method comprising determining the presence of a non-thymine variant residue rs609261 located at position −3 relative to the 3' splice site of NSE (cryptic exon in ATM intron 28) of the human genome, wherein the presence of a non-thymine variant residue rs609261 indicates that the subject has, or is susceptible to, a functional-ATM protein deficiency, and selecting such subject for treatment with an agent thereby increasing a functional-ATM levels in the subject. In some embodiments, the method further comprises administering the agent for treatment of the selected subject. In some embodiments, the agent comprises a NSE repressor agent. In some embodiments, the NSE comprises a sequence comprising tctacaggttggctgcatagaagaaaaag. In some embodiments, the NSE repressor agent binds to the NSE within a sequence comprising agTCTACAGGTTGGCTGCATAGAAGAAAAAGgtagag; or tcttagTCTACAGGTTGGCTGCATAGAAGAAAAAGgtagag; or tctcagTCTACAGGTTGGCTGCATAGAAGAAAAAGgtagag. In some embodiments, the NSE repressor agent binds to the NSE or its 5' or 3' splice site in ATM intron 28 of the NSE. In some embodiments, the NSE repressor agent and/or NSE activator agent comprises a polynucleic acid polymer. In some embodiments, the NSE repressor agent and/or NSE activator agent is an SSO (Splice Switching Oligonucleotide). In some embodiments, the NSE repressor agent and/or NSE activator agent is associated with a delivery vehicle suitable for delivering the NSE repressor agent and/or NSE activator agent to cells. In some embodiments, the NSE repressor agent comprises: an SSO of the sequence cuucuaugcagccaaccuguagacu (SSO-NSE3), or a nucleic acid analogue thereof; or an SSO of the sequence accuuuucuucuaugcagccaac (SSO-NSE5), or a nucleic acid analogue thereof; and/or the NSE repressor agent comprises or consists of any one SSO selected from the group comprising: aacauuucuauuuaguuaaaagc (SSO A11); uuaguauuccuugacuuua (SSO A17); gacugguaaauaauaaacauaauuc (SSO B2); auauauuagagauacaucagcc (SSO B4); and uuagagaaucauuuuaaauaagac (SSO AN3), or combinations thereof.

Disclosed herein, in certain embodiments, is a method of treatment or prevention of a functional-ATM protein deficiency in a subject, the method comprising identifying a presence of a non-thymine variant residue rs609261 located at position −3 relative to the 3' splice site of NSE (cryptic exon in ATM intron 28) of the human genome, wherein the presence of a non-thymine variant residue rs609261 indicates that the subject has, or is susceptible to, a functional-ATM protein deficiency, and administration of an agent to the subject, which is arranged to increase functional-ATM levels. In some embodiments, the NSE comprises a sequence comprising tctacaggttggctgcatagaagaaaaag. In some embodiments, the NSE repressor agent binds to the NSE within a sequence comprising agTCTACAGGTTGGCTGCATAGAAGAAAAAGgtagag; or tcttagTCTACAGGTTGGCTGCATAGAAGAAAAG gtagag; or tctc agTCTACAGGTTGGCTGCATAGAAGAAAAAGgtagag. In some embodiments, the NSE repressor agent binds to the NSE or its 5' or 3' splice site in ATM intron 28 of the NSE. In some embodiments, the NSE repressor agent and/or NSE activator agent comprises a polynucleic acid polymer. In some embodiments, the NSE repressor agent and/or NSE activator agent is an SSO (Splice Switching Oligonucleotide). In some embodiments, the NSE repressor agent and/or NSE activator agent is associated with a delivery vehicle suitable for delivering the NSE repressor agent and/or NSE activator agent to cells. In some embodiments, the NSE repressor agent comprises: an SSO of the sequence cuucuaugcagccaaccuguagacu (SSO-NSE3), or a nucleic acid analogue thereof; or an SSO of the sequence accuuuuucuucuaugcagccaac (SSO-NSE5), or a nucleic acid analogue thereof; and/or the NSE repressor agent comprises or consists of any one SSO selected from the group comprising: aacauuucuauuuaguuaaaagc (SSO A11); uuaguauuccuugacuuua (SSO A17); gacugguaaauaauaaacauaauuc (SSO B2); auauauuagagauacaucagcc (SSO B4); and uuagagaaucauuuuaaauaagac (SSO AN3), or combinations thereof.

Disclosed herein, in certain embodiments, is a method of treatment or prevention of a condition associated with a functional-ATM protein deficiency, comprising the administration of a NSE repressor agent thereby increasing a functional ATM protein level, wherein the agent binds to a NSE in ATM intron 28 of a pre-mRNA transcript thereby decreasing inclusion of the NSE in the mature RNA transcript. In some embodiments, the decreasing inclusion of the NSE in the mature RNA transcript provides an increase in functional ATM protein expression. In some embodiments, the method is for treatment or prevention of functional-ATM protein deficiency in a subject or an at-risk population of subjects is for treatment or prevention of a condition or symptoms associated with a functional-ATM protein deficiency. In some embodiments, the condition is ataxia-telangiectasia; cancer; immune deficiency; cellular radiosensitivity; or chromosomal instability. In some embodiments, the NSE comprises a sequence comprising tctacaggttggctgcatagaagaaaaag. In some embodiments, the NSE repressor agent binds to the NSE within a sequence comprising agTCTACAGGTTGGCTGCATAGAAGAAAAGgtagag; or tcttagTCTACAGGTTGGCTGCATAGAAGAAAAG gtagag; or tctc agTCTACAGGTTGGCTGCATAGAAGAAAAAGgtagag. In some embodiments, the NSE repressor agent binds to the NSE or its 5' or 3' splice site in ATM intron 28 of the NSE. In some embodiments, the NSE repressor agent and/or NSE activator agent comprises a polynucleic acid polymer. In some embodiments, the NSE repressor agent and/or NSE activator agent is an SSO (Splice Switching Oligonucleotide). In some embodiments, the NSE repressor agent and/or NSE activator agent is associated with a delivery vehicle suitable for delivering the NSE repressor agent and/or NSE activator agent to cells. In some embodiments, the NSE repressor agent comprises: an SSO of the sequence cuucuaugcagccaaccuguagacu (SSO-NSE3), or a nucleic acid analogue thereof; or an SSO of the sequence accuuuuucuucuaugcagccaac (SSO-NSE5), or a nucleic acid analogue thereof; and/or the NSE repressor agent comprises or consists of any one SSO selected from the group comprising: aacauuucuauuuaguuaaaagc (SSO A11); uuaguauuccuugacuuua (SSO A17); gacugguaaauaauaaacauaauuc (SSO B2); auauauuagagauacaucagcc (SSO B4); and uuagagaaucauuuuaaauaagac (SSO AN3), or combinations thereof.

Disclosed herein, in certain embodiments, is a method of treatment or prevention of a condition associated with deregulation of ATM expression in a subject comprising administering a NSE-activator agent to the subject, wherein the NSE-activator agent increases inclusion of a NSE in an ATM mature RNA transcript by binding to a regulatory motif in ATM intron 28, or by binding to a U2AF65 binding site upstream of a pseudoexon located 3' of a NSE in ATM intron 28 of an ATM pre-mRNA transcript. In some embodiments, disclosed herein is a method of treatment or prevention of a condition associated with deregulation of ATM expression in a subject comprising administering a NSE-activator agent to the subject, wherein the NSE-activator agent increases inclusion of a NSE in an ATM mature RNA transcript by binding to a regulatory motif in ATM intron 28, optionally wherein the regulatory motifs in ATM intron 28 compete with NSE for spliceosomal components, and further optionally wherein such motifs comprise a 24 nucleotide pseudoexon (PE) located 3' of NSE in ATM intron 28 of the pre-mRNA transcript or binding to a U2AF65 binding site upstream of the pseudoexon. In some embodiments, increasing inclusion of the NSE in the mature RNA transcript provides a decrease in functional ATM protein expression. In some embodiments, the pseudoexon comprises the sequence tcatcgaatactttgaaataag. In some embodiments, the regulatory motif in ATM intron 28 competes with the NSE for spliceosomal components. In some embodiments, the regulatory motif in ATM intron 28 comprises a 24 nucleotide pseudoexon (PE) located 3' of the NSE in ATM intron 28 of the pre-mRNA transcript. In some embodiments, the NSE repressor agent and/or NSE activator agent comprises a polynucleic acid polymer. In some embodiments, the NSE repressor agent and/or NSE activator agent is an SSO (Splice Switching Oligonucleotide). In some embodiments, the NSE repressor agent and/or NSE activator agent is associated with a delivery vehicle suitable for delivering the NSE repressor agent and/or NSE activator agent to cells. In some embodiments, the NSE repressor agent comprises: an SSO of the sequence cuucuaugcagccaaccuguagacu (SSO-NSE3), or a nucleic acid analogue thereof; or an SSO of the sequence accuuuuucuucuaugcagccaac (SSO-NSE5), or a nucleic acid analogue thereof and/or the NSE repressor agent comprises or consists of any one SSO selected from the group comprising: aacauuucuauuuaguuaaaagc (SSO A11); uuaguauuccuugacuuua (SSO A17); gacugguaaauaauaaacauaauuc (SSO B2); auauauuagagauacaucagcc (SSO B4); and uuagagaaucauuuuaaauaagac (SSO AN3), or combinations thereof. In some embodiments, the NSE activator agent comprises the SSO PEkr/PEdel; and/or the NSE activator agent comprises or consists of any one SSO selected from the group comprising: aacuuaaagguuauaucuc (SSO A2); uauaaauacgaauaaaucga (SSO A4); caacacgacauaaccaaa (SSO A9); gguaugagaacuauagga (SSO A23); gguaauaagugucacaaa (SSO A25); guaucauacauuagaagg (SSO A26); and ugugggugaccacagcuu (SSO B11), or combinations thereof.

Disclosed herein, in certain embodiments, is a method of treatment or prevention of cancer in a subject comprising administering a NSE-activator agent to the subject, wherein the NSE-activator agent increases a cancer cell's susceptibility to cytotoxic therapy with DNA damaging agents such as radiotherapy, wherein the NSE-activator agent increases inclusion of a NSE in an ATM mature RNA transcript by binding to a regulatory motif in ATM intron 28, or by binding to a U2AF65 binding site upstream of a pseudoexon located 3' of a NSE in ATM intron 28 of an ATM pre-mRNA transcript, and treating the subject with the cytotoxic therapy, such as radiotherapy or chemotherapy. In some embodiments, disclosed herein is a method of treatment or prevention of cancer in a subject comprising the administration of a NSE-activator agent arranged to increase a cancer cell's susceptibility to cytotoxic therapy with DNA damaging agents such as radiotherapy, wherein the NSE-activator agent is arranged to increase NSE inclusion in ATM mature RNA transcript by binding to regulatory motifs in ATM intron 28, optionally wherein the regulatory motifs in ATM intron 28 compete with NSE for spliceosomal components, and further optionally wherein such motifs comprise a 24 nucleotide pseudoexon (PE) located 3' of NSE in ATM intron 28 of the pre-mRNA transcript or binding to a U2AF65 binding site upstream of the pseudoexon; and treating the subject with the cytotoxic therapy, such as radiotherapy or chemotherapy. In some embodiments, increasing inclusion of the NSE in the mature RNA transcript provides a decrease in functional ATM protein expression. In some embodiments, the pseudoexon comprises the sequence tcatcgaatacttttggaaataag. In some embodiments, increasing inclusion of the NSE in the mature RNA transcript provides a decrease in functional ATM protein expression. In some embodiments, the pseudoexon comprises the sequence tcatcgaatacttttggaaataag. In some embodiments, the regulatory motif in ATM intron 28 competes with the NSE for spliceosomal components. In some embodiments, the regulatory motif in ATM intron 28 comprises a 24 nucleotide pseudoexon (PE) located 3' of the NSE in ATM intron 28 of the pre-mRNA transcript. In some embodiments, the NSE repressor agent and/or NSE activator agent comprises a polynucleic acid polymer. In some embodiments, the NSE repressor agent and/or NSE activator agent is an SSO (Splice Switching Oligonucleotide). In some embodiments, the NSE repressor agent and/or NSE activator agent is associated with a delivery vehicle suitable for delivering the NSE repressor agent and/or NSE activator agent to cells. In some embodiments, the NSE repressor agent comprises: an SSO of the sequence cuucuaugcagccaaccuguagacu (SSO-NSE3), or a nucleic acid analogue thereof; or an SSO of the sequence accuuuuucuucuaugcagccaac (SSO-NSE5), or a nucleic acid analogue thereof; and/or the NSE repressor agent comprises or consists of any one SSO selected from the group comprising: aacauuucuauuuaguuaaaagc (SSO A11); uuaguauuccuugacuuua (SSO A17); gacugguaaauaauaaacauaauuc (SSO B2); auauauuagagauacaucagcc (SSO B4); and uuagagaaucauuuuaaauaagac (SSO AN3), or combinations thereof. In some embodiments, the NSE activator agent comprises the SSO PEkr/PEdel; and/or the NSE activator agent comprises or consists of any one SSO selected from the group comprising: aacuuaaagguuauaucuc (SSO A2); uauaaauacgaauaaaucga (SSO A4); caacacgacauaaccaaa (SSO A9); gguaugagaacuauagga (SSO A23); gguaauaagugucacaaa (SSO A25); guaucauacauuagaagg (SSO A26); and uguggggugaccacagcuu (SSO B11), or combinations thereof.

Disclosed herein, in certain embodiments, is a method of increasing a cell's susceptibility to cytotoxic therapy with DNA damaging agents such as radiotherapy or chemotherapy comprising reducing ATM protein expression by administering a NSE-activator agent, wherein the NSE-activator agent increases inclusion of a NSE in an ATM mature RNA transcript by binding to motifs in ATM intron 28, or by binding to a U2AF65 binding site upstream of a pseudoexon located 3' of a NSE in ATM intron 28 of an ATM pre-mRNA transcript. Disclosed herein, in certain embodiments, is a method of increasing a cell's susceptibility to cytotoxic therapy with DNA damaging agents such as radiotherapy or chemotherapy comprising reducing ATM protein expression by administrating a NSE-activator agent arranged to increase NSE inclusion in ATM mature RNA transcript by binding to motifs in ATM intron 28, optionally wherein the regulatory motifs in ATM intron 28 compete with NSE for spliceosomal components, and further optionally wherein such motifs comprise a 24 nucleotide pseudoexon (PE) located 3' of NSE in ATM intron 28 of the pre-mRNA transcript or binding to a U2AF65 binding site upstream of the pseudoexon. In some embodiments, increasing inclusion of the NSE in the mature RNA transcript provides a decrease in functional ATM protein expression. In some embodiments, the pseudoexon comprises the sequence tcatcgaatacttttggaaataag. In some embodiments, the regulatory motif in ATM intron 28 competes with the NSE for spliceosomal components. In some embodiments, the regulatory motif in ATM intron 28 comprises a 24 nucleotide pseudoexon (PE) located 3' of the NSE in ATM intron 28 of the pre-mRNA transcript. In some embodiments, the NSE repressor agent and/or NSE activator agent comprises a polynucleic acid polymer. In some embodiments, the NSE repressor agent and/or NSE activator agent is an SSO (Splice Switching Oligonucleotide). In some embodiments, the NSE repressor agent and/or NSE activator agent is associated with a delivery vehicle suitable for delivering the NSE repressor agent and/or NSE activator agent to cells. In some embodiments, the NSE repressor agent comprises: an SSO of the sequence cuucuaugcagccaaccuguagacu (SSO-NSE3), or a nucleic acid analogue thereof; or an SSO of the sequence accuuuuucuucuaugcagccaac (SSO-NSE5), or a nucleic acid analogue thereof; and/or the NSE repressor agent comprises or consists of any one SSO selected from the group comprising: aacauuucuauuuaguuaaaagc (SSO A11); uuaguauuccuugacuuua (SSO A17); gacugguaaauaauaaacauaauuc (SSO B2); auauauuagagauacaucagcc (SSO B4); and uuagagaaucauuuuaaauaagac (SSO AN3), or combinations thereof. In some embodiments, the NSE activator agent comprises the SSO PEkr/PEdel; and/or the NSE activator agent comprises or consists of any one SSO selected from the group comprising: aacuuaaagguuauaucuc (SSO A2); uauaaauacgaauaaaucga (SSO A4); caacacgacauaaccaaa (SSO A9); gguaugagaacuauagga (SSO A23); gguaauaagugucacaaa (SSO A25); guaucauacauuagaagg (SSO A26); and uguggggugaccacagcuu (SSO B11), or combinations thereof.

Disclosed herein, in certain embodiments, is a method of tailoring functional ATM expression in a subject, cell or tissue, comprising the administration of a NSE-activator agent and/or a NSE-repressor agent described herein. In some embodiments, the NSE repressor agent and/or NSE activator agent comprise a polynucleic acid polymer. In some embodiments, the NSE repressor agent and/or NSE activator agent is an SSO (Splice Switching Oligonucleotide). In some embodiments, the NSE repressor agent and/or NSE activator agent is associated with a delivery vehicle suitable for delivering the NSE repressor agent and/or NSE activator agent to cells. In some embodiments, the NSE repressor agent comprises: an SSO of the sequence cuucuaugcagccaaccuguagacu (SSO-NSE3), or a nucleic acid analogue thereof; or an SSO of the sequence accuuuuucuucuaugcagccaac (SSO-NSE5), or a nucleic acid analogue thereof; and/or the NSE repressor agent comprises or consists of any one SSO selected from the group comprising: aacauuucuauuuaguuaaaagc (SSO A11); uuaguauuccuugacuuua (SSO A17); gacugguaaauaauaaacauaauuc (SSO B2); auauauuagagauacaucagcc (SSO B4); and uuagagaaucauuuaaauaagac (SSO AN3), or combinations thereof; or the method of which the NSE activator agent comprises the SSO PEkr/PEdel; and/or the NSE activator agent comprises or consists of any one SSO selected from the group comprising: aacuuaaagguuauaucuc (SSO A2); uauaaauacgaauaaaucga (SSO A4); caacacgacauaaccaaa (SSO A9); gguaugagaacuauagga (SSO A23); gguaauaagugucacaaa (SSO A25); guaucauacauuagaagg (SSO A26); and uguggggugaccacagcuu (SSO B11), or combinations thereof.

Disclosed herein, in certain embodiments, is use of rs609261 and/or rs4988000 genotyping to predict a subject's response to therapy for conditions associated with ATM deregulation.

Disclosed herein, in certain embodiments, is a composition comprising the NSE repressor agent and/or the NSE activator agent described herein. In some embodiments, the composition is a pharmaceutically acceptable formulation.

Disclosed herein, in certain embodiments, is a method of treatment or prevention of functional-ATM protein deficiency in a subject, the method comprising identifying the presence of a non-thymine variant residue rs609261 located at position −3 relative to the 3' splice site of NSE (cryptic exon in ATM intron 28) of the human genome, wherein the presence of a non-thymine variant residue rs609261 indicates that the subject has, or is susceptible to, functional-ATM protein deficiency, and administration of an agent to the subject, which is arranged to replace the non-thymine variant residue rs609261 with a thymine residue. In some embodiments, replacing the non-thymine variant residue rs609261 comprises administration of an agent to the subject, which is arranged to replace the non-thymine variant residue rs609261 with a thymine residue. In some embodiments, the agent for replacement of the non-thymine residue is a genomic editing molecule. In some embodiments, the agent for replacement of the non-thymine residue is CRISPR-Cas9, or a functional equivalent thereof, together with an appropriate RNA molecule arranged to target rs609261.

Disclosed herein, in certain embodiments, is a method of treatment or prevention of functional-ATM protein deficiency in a subject, the method comprising replacing a non-thymine variant residue rs609261 located at position −3 relative to the 3' splice site of NSE (cryptic exon in ATM intron 28) of the human genome with a thymine residue. In some embodiments, replacing the non-thymine variant residue rs609261 comprises administration of an agent to the subject, which is arranged to replace the non-thymine variant residue rs609261 with a thymine residue. In some embodiments, the agent for replacement of the non-thymine residue is a genomic editing molecule. In some embodiments, the agent for replacement of the non-thymine residue is CRISPR-Cas9, or a functional equivalent thereof, together with an appropriate RNA molecule arranged to target rs609261.

Disclosed herein, in certain embodiments, is a method of treatment or prevention of functional-ATM protein deficiency in a subject, the method comprising identifying the presence of a guanine variant residue at rs4988000 of the human genome, wherein the presence of a guanine variant residue at rs4988000 indicates that the subject has, or is susceptible to, functional-ATM protein deficiency, and administration of an agent to the subject, which is arranged to replace the guanine variant residue at rs4988000 with adenine. In some embodiments, replacing the guanine variant residue at rs4988000 comprises administration of an agent to the subject, which is arranged to replace the guanine variant residue at rs4988000 with an adenine residue. In some embodiments, the agent for replacement of the guanine residue is a genomic editing molecule. In some embodiments, the agent for replacement of the guanine residue is CRISPR-Cas9, or a functional equivalent thereof, together with an appropriate RNA molecule arranged to target rs4988000.

Disclosed herein, in certain embodiments, is a method of treatment or prevention of functional-ATM protein deficiency in a subject, the method comprising replacing a guanine variant residue at rs4988000 of the human genome with an adenine residue; or blocking the guanine residue by the binding of an SSO. In some embodiments, replacing the guanine variant residue at rs4988000 comprises administration of an agent to the subject, which is arranged to replace the guanine variant residue at rs4988000 with an adenine residue. In some embodiments, the agent for replacement of the guanine residue is a genomic editing molecule. In some embodiments, the agent for replacement of the guanine residue is CRISPR-Cas9, or a functional equivalent thereof, together with an appropriate RNA molecule arranged to target rs4988000.

Disclosed herein, in certain embodiments, is a method of screening a subject or a population of subjects for susceptibility to functional-ATM protein deficiency, wherein the screening comprises determining the presence of a guanine variant residue at rs4988000 of the human genome, wherein the presence of a guanine variant residue at rs4988000 indicates that the subject (or group of subjects) has, or is susceptible to, functional-ATM protein deficiency.

Disclosed herein, in certain embodiments, is a method of selecting a subject or a population of subjects for treatment or prophylaxis, wherein the subject is susceptible to functional-ATM protein deficiency, the method comprising determining a presence of a guanine variant residue at rs4988000 of a human subject's genome, wherein the presence of a guanine variant residue at rs4988000 indicates that the subject has, or is susceptible to, the functional-ATM protein deficiency, and selecting the subject for treatment with an agent that increases functional-ATM levels in the subject.

Disclosed herein, in certain embodiments, is a method of treatment or prevention of functional-ATM protein deficiency in a subject, the method comprising identifying a presence of a guanine variant residue at rs4988000 of a human subject's genome, wherein the presence of a guanine variant residue at rs4988000 indicates that the subject has, or is susceptible to, functional-ATM protein deficiency, and administering an agent to the subject, wherein the agent increases functional-ATM levels.

In some embodiments, one or more methods disclosed herein is in combination to modify a CG haplotype to TA.

In some embodiments, one or more methods disclosed herein is in combination to identify a CG haplotype in a subject, and optionally treat or select the patient for treatment.

Disclosed herein, in certain embodiments, is a method of modifying regulation of inclusion of a NSE in a mature RNA transcript, the method comprising inserting or deleting one or more splicing regulatory motifs upstream or downstream of the NSE that compete with the NSE for spliceosomal components, said one or more splicing regulatory motifs comprising a cryptic splice site or a pseudo-exon. In some embodiments, the insertion or the deletion of the one or more splicing regulatory motifs is in genomic DNA of ATM intron 28. In some embodiments, insertion of the one or more splicing regulatory motifs causes a reduction in the inclusion of the NSE in the mature RNA transcript. In some embodiments, the deletion of the one or more splicing regulatory motifs causes an increase in the inclusion of the NSE in the mature RNA transcript. In some embodiments, the insertion or the deletion of the one or more splicing regulatory motifs comprises the use of genome editing technology, such as CRISPR-Cas9.

Disclosed herein, in certain embodiments, is a method of modifying regulation of expression of a functional protein, wherein the expression of a functional protein is regulated by inclusion of a NSE in a mature RNA transcript of a gene encoding the functional protein, the method comprising inserting or deleting one or more splicing regulatory motifs upstream or downstream of the NSE that compete with the NSE for spliceosomal components, said one or more splicing regulatory motifs comprising cryptic splice sites or pseudo-exons. In some embodiments, the insertion or the deletion of the one or more splicing regulatory motifs is in genomic DNA of ATM intron 28. In some embodiments, insertion of the one or more splicing regulatory motifs causes a reduction in the inclusion of the NSE in the mature RNA transcript. In some embodiments, the deletion of the one or more splicing regulatory motifs causes an increase in the inclusion of the NSE in the mature RNA transcript. In some embodiments, the insertion or the deletion of the one or more splicing regulatory motifs comprises the use of genome editing technology, such as CRISPR-Cas9.

Disclosed herein, in certain embodiments, is a kit comprising one or more oligonucleotide probes for identifying rs609261 and/or rs4988000 variants. In some embodiments, the one or more oligonucleotide probes are primers for use in PCR amplifying a region of a nucleic acid comprising the rs609261 and/or the rs4988000 variants.

Disclosed herein, in certain embodiments, is a vector comprising a nucleic acid encoding a NSE activating agent and/or a NSE repressor agent.

Disclosed herein, in certain embodiments, is a method of screening for an agent capable of modifying regulation of a gene's expression comprising: identifying a nonsense-mediated RNA decay switch exon (NSE) that limits functional gene expression; identifying one or more splicing regulatory motifs upstream or downstream of the NSE that compete with the NSE for spliceosomal components, said regulatory motifs comprising cryptic splice sites or pseudoexons; targeting the one or more splicing regulatory motifs with an antisense polynucleic acid comprising a sequence that hybridizes to a splicing regulatory motif of the one or more splicing regulatory motifs through Watson-Crick base pairing; and determining if there is an increased or decreased inclusion of the NSE in a mature RNA transcript of the gene.

Disclosed herein, in certain embodiments, is a method of modulating expression of a gene comprising providing an agent that binds to a splicing regulatory motif, such as a cryptic splice site or a pseudoexon, that competes with a nonsense-mediated RNA decay switch exon (NSE) for spliceosomal components.

Disclosed herein, in certain embodiments, is an agent that binds to a gene splicing regulatory motif, such as a cryptic splice site or a pseudoexon, that competes with a nonsense-mediated RNA decay switch exon (NSE) for spliceosomal components, wherein the gene splicing regulatory motif controls inclusion of the NSE into a mature RNA transcript of the gene.

Disclosed herein, in certain embodiments, is a method of modulating protein expression comprising: (a) contacting an isolated polynucleic acid polymer to a target cell of a subject; (b) hybridizing the contacted polynucleic acid polymer to a target motif on a pre-processed mRNA transcript, wherein a hybridization of the contacted polynucleic acid polymer to the target motif either promotes or represses activation of a non-sense mediated RNA decay switch exon (NSE); (c) processing a mRNA transcript of the pre-processed mRNA transcript, wherein the NSE is either present or absent in the mRNA transcript; and (d) translating the processed mRNA transcript of step c), wherein the presence or absence of the NSE modulates protein expression. In some embodiments, the protein is expressed from the processed mRNA transcript. In some embodiments, the presence of the NSE downregulates protein expression. In some embodiments, the absence of the NSE upregulates protein expression. In some embodiments, the polynucleic acid polymer hybridizes to a motif within ATM intron 28. In some embodiments, the motif is a splicing regulatory motif that competes with the NSE for a spliceosomal component. In some embodiments, the splicing regulatory motif comprises a cryptic splice site or a pseudoexon. In some embodiments, the pseudoexon is a 24 nucleotide pseudoexon located at 3' of a NSE in ATM intron 28 of the pre-mRNA transcript. In some embodiments, the motif is a U2AF65 binding site. In some embodiments, the motif is a motif within a transposed element, upstream of a transposed element, or downstream of a transposed element. In some embodiments, the transposed element is Alu or MER51. In some embodiments, the isolated polynucleic acid polymer hybridizes to a target motif within Alu. In some embodiments, the isolated polynucleic acid polymer hybridizes to a target motif that is either upstream or downstream of Alu. In some embodiments, the isolated polynucleic acid polymer hybridizes to a target motif downstream of MER51. In some embodiments, the polynucleic acid polymer is from about 10 to about 50 nucleotides in length. In some embodiments, the isolated polynucleic acid polymer comprises a sequence with at least 70%, 75%, 80%, 85%, 90%, 95%, or 99% sequence identity to a sequence selected from the group consisting of SEQ ID NOs: 18-52. In some embodiments, the polynucleic acid polymer is modified at a nucleoside moiety, at a phosphate moiety, at a 5' terminus, at a 3' terminus, or a combination thereof. In some embodiments, the polynucleic acid polymer comprises an artificial nucleotide. In some embodiments, the artificial nucleotide is selected from the group consisting of 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), 2'-O—N-methylacetamido (2'-O-NMA), a locked nucleic acid (LNA), an ethylene nucleic acid (ENA), a peptide nucleic acid (PNA), a 1',5'-anhydrohexitol nucleic acid (HNA), a morpholino, a methylphosphonate nucleotide, a thiolphosphonate nucleotide, and a 2'-fluoro N3-P5'-phosphoramidite.

Disclosed herein, in certain embodiments, is a method of modulating protein expression comprising: (a) contacting an isolated polynucleic acid polymer to a target cell of a subject; (b) hybridizing the contacted polynucleic acid polymer to a target motif within a transposed element, wherein a hybridization of the contacted polynucleic acid polymer to the target motif either promotes or represses activation of a non-sense mediated RNA decay switch exon (NSE); (c) processing a mRNA transcript of the pre-processed mRNA transcript, wherein the NSE is either present or absent in the mRNA transcript; and (d) translating the processed mRNA transcript of step c), wherein the presence or absence of the NSE modulates protein expression. In some embodiments, the protein is expressed from the processed mRNA transcript. In some embodiments, the presence of the NSE downregulates protein expression. In some embodiments, the absence of the NSE upregulates protein expression. In some embodiments, the transposed element is Alu or MER51. In some embodiments, the isolated polynucleic acid polymer comprises a sequence with at least 70%, 75%, 80%, 85%, 90%, 95%, or 99% sequence identity to a sequence selected from the group consisting of SEQ ID NOs: 18-52. In some embodiments, the polynucleic acid polymer is from about 10 to about 50 nucleotides in length. In some embodiments, the isolated polynucleic acid polymer hybridizes to a target motif within Alu. In some embodiments, the isolated polynucleic acid polymer hybridizes to a target motif that is either upstream or downstream of Alu. In some embodiments, the isolated polynucleic acid polymer hybridizes to a target motif downstream of MER51. In some embodiments, activation of the NSE further induces exon skipping. In some embodiments, the NSE is located in intron 28. In some embodiments, the NSE modulates ATM protein expression. In some embodiments, the polynucleic acid polymer is modified at a nucleoside moiety, at a phosphate moiety, at a 5' terminus, at a 3' terminus, or a combination thereof. In some embodiments, the polynucleic acid polymer comprises an artificial nucleotide. In some embodiments, the artificial nucleotide is selected from the group consisting of 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), 2'-O—N-methylacetamido (2'-O-NMA), a locked nucleic acid (LNA), an ethylene nucleic acid (ENA), a peptide nucleic acid (PNA), a 1',5'-anhydrohexitol nucleic acid (HNA), a morpholino, a methylphosphonate nucleotide, a thiolphosphonate nucleotide, and a 2'-fluoro N3-P5'-phosphoramidite.

Disclosed herein, in certain embodiments, is a method of modulating protein expression comprising: (a) contacting an isolated polynucleic acid polymer to a target cell of a subject; (b) hybridizing the contacted polynucleic acid polymer to a target motif either upstream or downstream of a transposed element, wherein a hybridization of the contacted polynucleic acid polymer to the target motif promotes or represses activation of a non-sense mediated RNA decay switch exon (NSE); (c) processing a mRNA transcript of the pre-processed mRNA transcript, wherein the NSE is either present or absent in the mRNA transcript; and (d) translating the processed mRNA transcript of step c), wherein the presence or absence of the NSE modulates protein expression. In some embodiments, the protein is expressed from the processed mRNA transcript. In some embodiments, the presence of the NSE downregulates protein expression. In some embodiments, the absence of the NSE upregulates protein expression. In some embodiments, the transposed element is Alu or MER51. In some embodiments, the isolated polynucleic acid polymer comprises a sequence with at least 70%, 75%, 80%, 85%, 90%, 95%, or 99% sequence identity to a sequence selected from the group consisting of SEQ ID NOs: 18-52. In some embodiments, the polynucleic acid polymer is from about 10 to about 50 nucleotides in length. In some embodiments, the isolated polynucleic acid polymer hybridizes to a target motif within Alu. In some embodiments, the isolated polynucleic acid polymer hybridizes to a target motif that is either upstream or downstream of Alu. In some embodiments, the isolated polynucleic acid polymer hybridizes to a target motif downstream of MER51. In some embodiments, activation of the NSE further induces exon skipping. In some embodiments, the NSE is located in intron 28. In some embodiments, the NSE modulates ATM protein expression. In some embodiments, the polynucleic acid polymer is modified at a nucleoside moiety, at a phosphate moiety, at a 5' terminus, at a 3' terminus, or a combination thereof. In some embodiments, the polynucleic acid polymer comprises an artificial nucleotide. In some embodiments, the artificial nucleotide is selected from the group consisting of 2'-O-methyl, 2'-O-methoxyethyl (2'-O-MOE), 2'-O-aminopropyl, 2'-deoxy, T-deoxy-2'-fluoro, 2'-O-aminopropyl (2'-0-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), 2'-O—N-methylacetamido (2'-O-NMA), a locked nucleic acid (LNA), an ethylene nucleic acid (ENA), a peptide nucleic acid (PNA), a 1',5'-anhydrohexitol nucleic acid (HNA), a morpholino, a methylphosphonate nucleotide, a thiolphosphonate nucleotide, and a 2'-fluoro N3-P5'-phosphoramidite.

Disclosed herein, in certain embodiments, is a method of treating or preventing a disease or condition associated with deregulation of ATM expression in a subject in need thereof, the method comprising: administering to the subject a pharmaceutical composition comprising: (i) a non-sense mediated RNA decay switch exon (NSE)-activator agent that interacts with a pre-processed mRNA transcript to promote inclusion of a NSE into a processed mRNA transcript; and (ii) a pharmaceutically acceptable excipient and/or a delivery vehicle; wherein the disease or condition associated with deregulation of ATM expression is treated or prevented in the subject by the administration of the NSE-activator agent. In some embodiments, the NSE-activator agent is an isolated polynucleic acid polymer. In some embodiments, the NSE-repressor agent is an isolated polynucleic acid polymer. In some embodiments, the polynucleic acid polymer hybridizes to a motif within ATM intron 28. In some embodiments, the polynucleic acid polymer hybridizes to a splicing regulatory motif that competes with the NSE for spliceosomal components. In some embodiments, the splicing regulatory motif comprises a cryptic splice site or a pseudoexon. In some embodiments, the pseudoexon is a 24 nucleotide pseudoexon located at 3' of a NSE in ATM intron 28 of the pre-mRNA transcript. In some embodiments, the polynucleic acid polymer hybridizes to a U2AF65 binding site. In some embodiments, the polynucleic acid polymer hybridizes to a motif within a transposed element, upstream of a transposed element, or downstream of a transposed element. In some embodiments, the transposed element is Alu or MER51. In some embodiments, the isolated polynucleic acid polymer hybridizes to a target motif within Alu. In some embodiments, the isolated polynucleic acid polymer hybridizes to a target motif that is either upstream or downstream of Alu. In some embodiments, the isolated polynucleic acid polymer hybridizes to a target motif downstream of MER51. In some embodiments, the polynucleic acid polymer is from about 10 to about 50 nucleotides in length. In some embodiments, the isolated polynucleic acid polymer comprises a sequence with at least 70%, 75%, 80%, 85%, 90%, 95%, or 99% sequence identity to a sequence selected from the group consisting of SEQ ID NOs: 18-52. In some embodiments, the disease or condition is cancer. In some embodiments, the polynucleic acid polymer is modified at a nucleoside moiety, at a phosphate moiety, at a 5' terminus, at a 3' terminus, or a combination thereof. In some embodiments, the polynucleic acid polymer comprises an artificial nucleotide. In some embodiments, the artificial nucleotide is selected from the group consisting of 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), 2'-O—N-methylacetamido (2'-O-NMA), a locked nucleic acid (LNA), an ethylene nucleic acid (ENA), a peptide nucleic acid (PNA), a 1',5'-anhydrohexitol nucleic acid (HNA), a morpholino, a methylphosphonate nucleotide, a thiolphosphonate nucleotide, and a 2'-fluoro N3-P5'-phosphoramidite. In some embodiments, the delivery vehicle comprises a nanoparticle-based delivery vehicle.

Disclosed herein, in certain embodiments, is a method of treating or preventing a disease or condition associated with a functional-ATM protein deficiency in a subject in need thereof, the method comprising: administering to the subject a pharmaceutical composition comprising: (i) a non-sense mediated RNA decay switch exon (NSE)-repressor agent that interacts with a pre-processed mRNA transcript to promote exclusion of a NSE into a processed mRNA transcript; and (ii) a pharmaceutically acceptable excipient and/or a delivery vehicle; wherein the disease or condition associated with a functional-ATM protein deficiency is treated or prevented in the subject by the administration of the NSE-repressor agent. In some embodiments, the NSE-activator agent is an isolated polynucleic acid polymer. In some embodiments, the NSE-repressor agent is an isolated polynucleic acid polymer. In some embodiments, the polynucleic acid polymer hybridizes to a motif within ATM intron 28. In some embodiments, the polynucleic acid polymer hybridizes to a splicing regulatory motif that competes with the NSE for spliceosomal components. In some embodiments, the splicing regulatory motif comprises a cryptic splice site or a pseudoexon. In some embodiments, the pseudoexon is a 24 nucleotide pseudoexon located at 3' of a NSE in ATM intron 28 of the pre-mRNA transcript. In some embodiments, the polynucleic acid polymer hybridizes to a U2AF65 binding site. In some embodiments, the polynucleic acid polymer hybridizes to a motif within a transposed element, upstream of a transposed element, or downstream of a transposed element. In some embodiments, the transposed element is Alu or MER51. In some embodiments, the isolated polynucleic acid polymer hybridizes to a target motif within Alu. In some embodiments, the isolated polynucleic acid polymer hybridizes to a target motif that is either upstream or downstream of Alu. In some embodiments, the isolated polynucleic acid polymer hybridizes to a target motif downstream of MER51. In some embodiments, the polynucleic acid polymer is from about 10 to about 50 nucleotides in length. In some embodiments, the isolated polynucleic acid polymer comprises a sequence with at least 70%, 75%, 80%, 85%, 90%, 95%, or 99% sequence identity to a sequence selected from the group consisting of SEQ ID NOs: 18-52. In some embodiments, the disease or condition is cancer. In some embodiments, the polynucleic acid polymer is modified at a nucleoside moiety, at a phosphate moiety, at a 5' terminus, at a 3' terminus, or a combination thereof. In some embodiments, the polynucleic acid polymer comprises an artificial nucleotide. In some embodiments, the artificial nucleotide is selected from the group consisting of 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), 2'-O—N-methylacetamido (2'-O-NMA), a locked nucleic acid (LNA), an ethylene nucleic acid (ENA), a peptide nucleic acid (PNA), a 1',5'-anhydrohexitol nucleic acid (HNA), a morpholino, a methylphosphonate nucleotide, a thiolphosphonate nucleotide, and a 2'-fluoro N3-P5'-phosphoramidite. In some embodiments, the delivery vehicle comprises a nanoparticle-based delivery vehicle.

Disclosed herein, in certain embodiments, is a method of treating or preventing a disease or condition in a subject in need thereof, the method comprising: administering to the subject a pharmaceutical composition comprising: (i) a non-sense mediated RNA decay switch exon (NSE)-activator agent that interacts with a pre-processed mRNA transcript to promote inclusion of NSE into a processed mRNA transcript; and (ii) a pharmaceutically acceptable excipient and/or a delivery vehicle; wherein the disease or condition is treated or prevented in the subject by the administration of the NSE-activator agent. In some embodiments, the NSE-activator agent is an isolated polynucleic acid polymer. In some embodiments, the NSE-repressor agent is an isolated polynucleic acid polymer. In some embodiments, the polynucleic acid polymer hybridizes to a motif within ATM intron 28. In some embodiments, the polynucleic acid polymer hybridizes to a splicing regulatory motif that competes with the NSE for spliceosomal components. In some embodiments, the splicing regulatory motif comprises a cryptic splice site or a pseudoexon. In some embodiments, the pseudoexon is a 24 nucleotide pseudoexon located at 3' of a NSE in ATM intron 28 of the pre-mRNA transcript. In some embodiments, the polynucleic acid polymer hybridizes to a U2AF65 binding site. In some embodiments, the polynucleic acid polymer hybridizes to a motif within a transposed element, upstream of a transposed element, or downstream of a transposed element. In some embodiments, the transposed element is Alu or MER51. In some embodiments, the isolated polynucleic acid polymer hybridizes to a target motif within Alu. In some embodiments, the isolated polynucleic acid polymer hybridizes to a target motif that is either upstream or downstream of Alu. In some embodiments, the isolated polynucleic acid polymer hybridizes to a target motif downstream of MER51. In some embodiments, the polynucleic acid polymer is from about 10 to about 50 nucleotides in length. In some embodiments, the isolated polynucleic acid polymer comprises a sequence with at least 70%, 75%, 80%, 85%, 90%, 95%, or 99% sequence identity to a sequence selected from the group consisting of SEQ ID NOs: 18-52. In some embodiments, the disease or condition is cancer. In some embodiments, the disease or condition is a disease or condition associated with deregulation of ATM expression. In some embodiments, the disease or condition is a disease or condition associated with a functional-ATM protein deficiency. In some embodiments, the polynucleic acid polymer is modified at a nucleoside moiety, at a phosphate moiety, at a 5' terminus, at a 3' terminus, or a combination thereof. In some embodiments, the polynucleic acid polymer comprises an artificial nucleotide. In some embodiments, the artificial nucleotide is selected from the group consisting of 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), 2'-O—N-methylacetamido (2'-O-NMA), a locked nucleic acid (LNA), an ethylene nucleic acid (ENA), a peptide nucleic acid (PNA), a 1',5'-anhydrohexitol nucleic acid (HNA), a morpholino, a methylphosphonate nucleotide, a thiolphosphonate nucleotide, and a 2'-fluoro N3-P5'-phosphoramidite.

In some embodiments, the delivery vehicle comprises a nanoparticle-based delivery vehicle.

Disclosed herein, in certain embodiments, is a method of treating or preventing a disease or condition in a subject in need thereof, the method comprising: administering to the subject a pharmaceutical composition comprising: (i) a non-sense mediated RNA decay switch exon (NSE)-repressor agent that interacts with a pre-processed mRNA transcript to promote exclusion of an NSE into a processed mRNA transcript; and (ii) a pharmaceutically acceptable excipient and/or a delivery vehicle; wherein the disease or condition is treated or prevented in the subject by the administration of the NSE-repressor agent. In some embodiments, the NSE-activator agent is an isolated polynucleic acid polymer. In some embodiments, the NSE-repressor agent is an isolated polynucleic acid polymer. In some embodiments, the polynucleic acid polymer hybridizes to a motif within ATM intron 28. In some embodiments, the polynucleic acid polymer hybridizes to a splicing regulatory motif that competes with the NSE for spliceosomal components. In some embodiments, the splicing regulatory motif comprises a cryptic splice site or a pseudoexon. In some embodiments, the pseudoexon is a 24 nucleotide pseudoexon located at 3' of a NSE in ATM intron 28 of the pre-mRNA transcript. In some embodiments, the polynucleic acid polymer hybridizes to a U2AF65 binding site. In some embodiments, the polynucleic acid polymer hybridizes to a motif within a transposed element, upstream of a transposed element, or downstream of a transposed element. In some embodiments, the transposed element is Alu or MER51. In some embodiments, the isolated polynucleic acid polymer hybridizes to a target motif within Alu. In some embodiments, the isolated polynucleic acid polymer hybridizes to a target motif that is either upstream or downstream of Alu. In some embodiments, the isolated polynucleic acid polymer hybridizes to a target motif downstream of MER51. In some embodiments, the polynucleic acid polymer is from about 10 to about 50 nucleotides in length. In some embodiments, the isolated polynucleic acid polymer comprises a sequence with at least 70%, 75%, 80%, 85%, 90%, 95%, or 99% sequence identity to a sequence selected from the group consisting of SEQ ID NOs: 18-52. In some embodiments, the disease or condition is cancer. In some embodiments, the disease or condition is a disease or condition associated with deregulation of ATM expression. In some embodiments, the disease or condition is a disease or condition associated with a functional-ATM protein deficiency. In some embodiments, the polynucleic acid polymer is modified at a nucleoside moiety, at a phosphate moiety, at a 5' terminus, at a 3' terminus, or a combination thereof. In some embodiments, the polynucleic acid polymer comprises an artificial nucleotide. In some embodiments, the artificial nucleotide is selected from the group consisting of 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), 2'-O—N-methylacetamido (2'-O-NMA), a locked nucleic acid (LNA), an ethylene nucleic acid (ENA), a peptide nucleic acid (PNA), a 1',5'-anhydrohexitol nucleic acid (HNA), a morpholino, a methylphosphonate nucleotide, a thiolphosphonate nucleotide, and a 2'-fluoro N3-P5'-phosphoramidite. In some embodiments, the delivery vehicle comprises a nanoparticle-based delivery vehicle.

Disclosed herein, in certain embodiments, is a method of modulating protein expression comprising: (a) contacting an isolated polynucleic acid polymer to a target cell of a subject; (b) hybridizing the contacted polynucleic acid polymer to a target motif within a transposed element, wherein a hybridization of the contacted polynucleic acid polymer to the target motif either promotes or represses activation of an alternative splice site; (c) processing a mRNA transcript of the pre-processed mRNA transcript, wherein the alternative splice site is either present or absent in the mRNA transcript; and (d) translating the processed mRNA transcript of step c), wherein the presence or absence of the alternative splice site modulates protein expression. In some embodiments, the transposon element is on the pre-processed mRNA transcript.

Disclosed herein, in certain embodiments, is a method of modulating protein expression comprising: (a) contacting an isolated polynucleic acid polymer to a target cell of a subject; (b) hybridizing the contacted polynucleic acid polymer to a target motif either upstream or downstream of a transposed element, wherein a hybridization of the contacted polynucleic acid polymer to the target motif promotes or represses activation of an alternative splice site; (c) processing a mRNA transcript of the pre-processed mRNA transcript, wherein the alternative splice site is either present or absent in the mRNA transcript; and (d) translating the processed mRNA transcript of step c), wherein the presence or absence of the alternative splice site modulates protein expression. In some embodiments, the transposon element is on the pre-processed mRNA transcript.

Disclosed herein, in certain embodiments, is a method of modulating protein expression comprising: (a) contacting an isolated polynucleic acid polymer to a target cell of a subject; (b) hybridizing the contacted polynucleic acid polymer to a target motif on a pre-processed mRNA transcript, wherein hybridization of the contacted polynucleic acid polymer to the target motif either promotes or represses activation of an alternative splice site; (c) processing a mRNA transcript of the pre-processed mRNA transcript, wherein the alternative splice site is either present or absent in the mRNA transcript; and (d) translating the processed mRNA transcript of step c), wherein the presence or absence of the alternative splice site modulates protein expression. In some embodiments, the protein is expressed from the processed mRNA transcript. In some embodiments, the presence of NSE downregulates protein expression. In some embodiments, the absence of NSE upregulates protein expression. In some embodiments, the polynucleic acid polymer hybridizes to a motif within ATM intron 28. In some embodiments, the motif is a splicing regulatory motif that competes with NSE for a spliceosomal component. In some embodiments, the splicing regulatory motif comprises a cryptic splice site or a pseudoexon. In some embodiments, the pseudoexon is a 24 nucleotide pseudoexon located at 3' of a NSE in ATM intron 28 of the pre-mRNA transcript. In some embodiments, the motif is a U2AF65 binding site. In some embodiments, the motif is a motif within a transposed element, upstream of a transposed element, or downstream of a transposed element. In some embodiments, the transposed element is Alu or MER51. In some embodiments, the isolated polynucleic acid polymer hybridizes to a target motif within Alu. In some embodiments, the isolated polynucleic acid polymer hybridizes to a target motif that is either upstream or downstream of Alu. In some embodiments, the isolated polynucleic acid polymer hybridizes to a target motif downstream of MER51. In some embodiments, the polynucleic acid polymer is from about 10 to about 50 nucleotides in length. In some embodiments, the isolated polynucleic acid polymer comprises a sequence with at least 70%, 75%, 80%, 85%, 90%, 95%, or 99% sequence identity to a sequence selected from the group consisting of SEQ ID NOs: 18-52.

Disclosed herein, in certain embodiments, is a pharmaceutical composition comprising: (a) a non-sense mediated RNA decay switch exon (NSE)-activator agent that interacts with a pre-processed mRNA transcript to promote inclusion of NSE into a processed mRNA transcript, or a non-sense mediated RNA decay switch exon (NSE)-repressor agent that interacts with a pre-processed mRNA transcript to promote exclusion of an NSE into a processed mRNA transcript; and (b) a pharmaceutically acceptable excipient and/or a delivery vehicle. In some embodiments, the NSE-activator agent is an isolated polynucleic acid polymer. In some embodiments, the NSE-repressor agent is an isolated polynucleic acid polymer. In some embodiments, the polynucleic acid polymer hybridizes to a motif within ATM intron 28. In some embodiments, the polynucleic acid polymer hybridizes to a splicing regulatory motif that competes with the NSE for a spliceosomal component. In some embodiments, the splicing regulatory motif comprises a cryptic splice site or a pseudoexon. In some embodiments, the pseudoexon is a 24 nucleotide pseudoexon located at 3' of NSE in ATM intron 28 of the pre-mRNA transcript. In some embodiments, the polynucleic acid polymer hybridizes to a U2AF65 binding site. In some embodiments, the polynucleic acid polymer hybridizes to a motif within a transposed element, upstream of a transposed element, or downstream of a transposed element. In some embodiments, the transposed element is Alu or MER51. In some embodiments, the isolated polynucleic acid polymer hybridizes to a target motif within Alu. In some embodiments, the isolated polynucleic acid polymer hybridizes to a target motif that is either upstream or downstream of Alu. In some embodiments, the isolated polynucleic acid polymer hybridizes to a target motif downstream of MER51. In some embodiments, the polynucleic acid polymer is from about 10 to about 50 nucleotides in length. In some embodiments, the isolated polynucleic acid polymer comprises a sequence with at least 70%, 75%, 80%, 85%, 90%, 95%, or 99% sequence identity to a sequence selected from the group consisting of SEQ ID NOs: 18-52.

Disclosed herein, in certain embodiments, is a cell comprising a pharmaceutical composition comprising: (a) a non-sense mediated RNA decay switch exon (NSE)-activator agent that interacts with a pre-processed mRNA transcript to promote inclusion of NSE into a processed mRNA transcript, or a non-sense mediated RNA decay switch exon (NSE)-repressor agent that interacts with a pre-processed mRNA transcript to promote exclusion of an NSE into a processed mRNA transcript; and (b) a pharmaceutically acceptable excipient and/or a delivery vehicle. In some embodiments, the NSE-activator agent is an isolated polynucleic acid polymer. In some embodiments, the NSE-repressor agent is an isolated polynucleic acid polymer. In some embodiments, the polynucleic acid polymer hybridizes to a motif within ATM intron 28. In some embodiments, the polynucleic acid polymer hybridizes to a splicing regulatory motif that competes with the NSE for a spliceosomal component. In some embodiments, the splicing regulatory motif comprises a cryptic splice site or a pseudoexon. In some embodiments, the pseudoexon is a 24 nucleotide pseudoexon located at 3' of NSE in ATM intron 28 of the pre-mRNA transcript. In some embodiments, the polynucleic acid polymer hybridizes to a U2AF65 binding site. In some embodiments, the polynucleic acid polymer hybridizes to a motif within a transposed element, upstream of a transposed element, or downstream of a transposed element. In some embodiments, the transposed element is Alu or MER51. In some embodiments, the isolated polynucleic acid polymer hybridizes to a target motif within Alu. In some embodiments, the isolated polynucleic acid polymer hybridizes to a target motif that is either upstream or downstream of Alu. In some embodiments, the isolated polynucleic acid polymer hybridizes to a target motif downstream of MER51. In some embodiments, the polynucleic acid polymer is from about 10 to about 50 nucleotides in length. In some embodiments, the isolated polynucleic acid polymer comprises a sequence with at least 70%, 75%, 80%, 85%, 90%, 95%, or 99% sequence identity to a sequence selected from the group consisting of SEQ ID NOs: 18-52.

Disclosed herein, in certain embodiments, is a method, use, composition, vector, or agent substantially described herein, optionally with reference to the accompanying figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIG. 1A shows a schematics of the cryptic exon (termed here NSE for NMD-switch exon) activation. NSE sequence (upper panel) is boxed, asterisk denotes rs609261, and black rectangles show the indicated antisense oligonucleotides. Genome browser views of RNA-Seq data from RNAi- or SSO-mediated depletions of both U2AF35 isoforms (ab−), U2AF35a (a−), U2AF35b (b−) and controls (c) are shown in the lower panel. SSOs targeting 3' ss of U2AF1 exons Ab and 3 and U2AF35 siRNA were as previously described. Y axis, read densities. NSE inclusion/exclusion is schematically shown by dotted lines at the top. ATM exons (gray boxes) are numbered. The 29-nt NS E introduced a stop codon in the ATM mRNA. FIG. 1B shows validation of the NSE activation by RT-PCR (upper panel) in independent depletions (lower panel). RT-PCR primers (ATM-F, ATM-R, FIG. 20) are denoted by arrows in panel A. Spliced products are shown to the right, the percentage of transcripts with NSE is at the top. Error bars denote SDs of two transfections experiments (*, $p<0.0001$, , $p<0.001$). FIG. 1C shows NSE inclusion in mature transcripts inversely correlates with residual U2AF (r=Pearson correlation). Estimates of heterodimer levels were determined.

FIG. 2A-FIG. 2I show NSE activation and ATM expression modified by rs609261. Allelic frequencies at rs609261 are shown in the indicated populations (FIG. 2A). FIG. 2B shows exemplary minigene schematics. An XhoI/XbaI segment of ATM containing NSE and exon 29 was cloned between U2AF1 exons 2 and 4 (black boxes). RT-PCR primers to amplify exogenous transcripts (PL3 and ATM-R, FIG. 20) are denoted by arrows. FIG. 2C shows the rs609261-dependent NSE activation in exogenous pre-mRNAs. HEK293 cells depleted of U2AF35 or U2AF65 were transiently transfected with T (black) and C (grey) minigenes. Final concentration of the U2AF35 and U2AF65 siRNAs was 30 and 60 nM, respectively. FIG. 2D illustrates the identification of cell lines homozygous at rs609261 (asterisk). NSE is boxed. FIG. 2E and FIG. 2F show allele-specific activation of NSE in endogenous transcripts limits ATM expression in a dose-dependent manner. The source of endogenous transcripts is at the bottom, antibodies are to the right Concentration of siRNAs in cultures was 3, 10 and 30 nM. C1, C2, control siRNAs. Transfection efficiency was monitored by a GFP-plasmid and fluorescent microscopy. FIG. 2G shows UPF1 depletion increased NSE activation (upper panel) and upregulated isoform U2AF1c (lower panel). The U2AF1c isoform contains both exons Ab and 3 and is repressed by NMD. Final concentration of the UPF1 siRNA was 7, 20 and 60 nM (SC=a scrambled control). Error bars are SDs of independent transfections. FIG. 2H shows NSE inclusion levels in cells depleted of U2AF-related proteins and a subset of heterogeneous nuclear RNPs. Error bars denote SDs of two transfections. Immunoblots are shown to the right Final concentration of the U2AF35 siRNA was 25 nM; the remaining siRNAs were at 60 nM (C=controls). FIG. 2I shows overexpression of PUF60 induced NSE skipping. Immunoblots are shown below, antibodies to the right.

FIG. 3A-FIG. 3D illustrate rescue of U2AF-repressed ATM expression by SSOs targeting NSE. FIG. 3A and FIG. 3B show efficient SSO-mediated NSE inhibition in exogenous (FIG. 3A) and endogenous (FIG. 3B) ATM transcripts. Mean NSE inclusion levels of two transfection experiments are shown in the right panels. FIG. 3C shows restoration of ATM protein levels by SSOs that blocks access to NSE. Cells lacking U2AF35 and control cells were transfected with the SSO targeting the NSE 3' ss and a control SSOs (FIG. 1A and FIG. 20). After 48 hrs, the cells were exposed to ionizing radiation (IR, 10 Gy) and harvested 1 hr later. Cell lysates were separated using a gradient SDS-PAGE. Western blotting was with antibodies shown to the right FIG. 3D shows dose-dependent reconstitution of ATM expression SSO-NSE3 in depleted cells.

FIG. 4A-FIG. 4H show identification of intronic cis-elements and SSOs that modulate NSE activation. FIG. 4A shows schematics of two pseudoexons in ATM intron 28. Canonical exons (numbered) are shown as grey boxes, NSE as a white box, and PE as a checkered box. Asterisk indicates location of the IVS28-159A>G substitution, causing A-T. In this A-T case, both NSE and PE were included in the ATM mRNA together with the intervening sequence because NSE is separated from PE by less than the minimal size of human intron. Canonical and aberrant transcripts are denoted by dotted lines above and below the pre-mRNA, respectively. Middle panel shows RNA-Seq read densities for NSE in cells depleted of both U2AF35 isoforms (ab−) together with U2AF65 tags/high-confidence binding sites (horizontal lines/rectangles) identified by crosslinking and immunoprecipitation. The 100 basewise vertebrate conservation by Phylop (100 VC) is shown at the bottom. Lower panel shows mutations (in red and underlined) introduced in the C-minigene. FIG. 4B shows splicing pattern of wildtype and mutated C minigenes. Mutations are shown in panel A; RNA products are shown schematically to the right. The largest product produced by clone PE delPPT/AG contains the shortened pseudointron (42 nt). FIG. 4C shows splicing pattern of C minigenes mutated in NSE (lanes 2, 3, 7 and 8) or PE (lanes 4, 5, 9 and 10) in (mock) depleted HEK293 cells. Mutations are at the bottom and minigene sequences in FIG. 21. Spliced products are schematically shown to the right; a hairpin symbol above PE denotes the MIR stem-loop insertion. FIG. 4D and FIG. 4E illustrate SSO-induced pseudoexon switching. Transfected minigenes are shown at the top, spliced products to the right and SSOs at the bottom. SSO sequences are in FIG. 20. Final concentration of SSOs shown in panels D-G was 3, 10 and 30 nM. FIG. 4F shows SSOs targeting PE induced NSE skipping. FIG. 4G shows SSOs targeting a sequence activating NSE upon deletion (PEdelPPT/AG; panel A and B) inhibit PE. FIG. 4H shows NSE activation is haplotype-dependent Minigene haplotypes at the indicated variants are shown at the bottom. Columns represent mean NSE inclusion, error bars are SDs, and asterisks denote statistically significant differences as in FIG. 1B.

FIG. 5A-FIG. 5G show exon-centric regulation of ATM signaling. FIG. 5A shows U2AF-regulated gene- and exon-level expression changes in MRN-ATM-CHEK2-CDC25-cdc2/cyclin B pathway (left panel). Log 2fold- and q-values are shown in parentheses. Exon usage of CHEK2 and CDC25A genes is shown by RNA-Seq browser shots; PCR validation gels are in the right panels. CHEK2 exon 9 is a NMD switch exon; exon 11 encodes a portion of the kinase domain. Full spectrum of U2AF-mediated expression changes in the ATM signaling pathway is shown in FIG. 9; examples of the U2AF-mediated splicing regulation are in Fig. S3-S6. FIG. 5B shows impaired ATM signaling in U2AF35 depleted cells following IR. HEK293 cells were (mock) depleted of U2AF35 and subjected to IR (10 Gy) 48 hrs later. Expression was examined by immunoblotting at the indicated time points. Antibodies are shown to the right CHEK2 exon 9 skipping levels are at the bottom; their measurements in control (U2AF35+) and depleted cells (U2AF35−) are in panel FIG. 5C. FIG. 5D shows CHEK2 exon 9 inclusion in UPF1 depleted cells. Final concentration of the UPF1 siRNA (FIG. 20) was 12.5, 25, 50, and 100 nM. FIG. 5E shows repression of CHEK2 exon 9 by SSO reduced CHEK2 levels and promoted NSE inclusion. Final concentration of SSO targeting CHEK2 exon 9 was 3, 10 and 30 nM. FIG. 5F shows CHEK2 exon 9 inclusion upon transfection of HEK293 cells with the indicated SSOs. FIG. 5G shows a lack of SF3B1 induced CHEK2 exon 9 skipping but did not alter NSE activation. Final concentration of each siRNA targeting SF3B1 was 20 nM.

FIG. 8A shows SSO-NSE3 increased expression of total and activated ATM. HEK293 cells were (mock)-depleted of U2A F35, cotransfected with X press-tagged CHEK2 and SSO NSE3/control (SSO-C), exposed to ionizing radiation (IR) and harvested 30 minutes later. Cell lysates were immunoblotted with the indicated antibodies. Final concentration of siRNA and SSOs was 30 nM. The amount of plasmids expressing CHEK2 was 30, 90 and 270 ng; DNA from the empty vector was added to a final concentration of 270 ng/mL. Ex/enCHEK2, signal from exogenous and endogenous CHEK2, as detected by the D9C6 antibody. FIG. 8B and FIG. 8C show increased expression of exogenous CHEK2 by an SSO targeting NMD switch exon 9 (SSO CHEK2). Constant amounts of SSO CHEK2 were cotransfected with increasing amounts of Xpress-CHEK2 and constant amounts of GFP plasmids as transfection and loading control (B) and vice versa (C). Antibodies are to the right.

FIG. 12A-FIG. 12D show RNA processing of RAD50 and EZH2 in depleted cells. Genomic browser views of RNA-Seq data in control (ctr) and depleted (ab−) cells (left panels in FIG. 12A and FIG. 12B and in FIG. 12C and FIG. 12D). PCR primers are shown by arrows, differentially used exons are denoted by black rectangles. RefSeq exon annotation is shown at the bottom. Validation of RNA-Seq data using RT-PCR with RNA extracted from cells depleted of each U2AF subunits and U2AF-related proteins (right panels in FIG. 12A and FIG. 12B).

FIG. 14A-FIG. 14D show U2AF control of RARA fusion partners.

FIG. 15D and FIG. 15E show inclusion levels of U2AF-repressed (FIG. 15D) and -activated (FIG. 15E) exons in lymphoblastoid cell lines (top). Cells were exposed to cold and heat shock at the indicated temperatures. ES, exon skipping; EI, exon inclusion.

FIG. 16A shows the location of transposed elements in intron 28 and schematics of NSE activation. Canonical exons are shown as grey boxes, the NSE as a white box, introns flanking the NSE as lines and their splicing by dotted lines. Transposed elements are shown as horizontal white rectangles below the primary transcript; UC, a unique sequence lacking recognizable transposons. Their deletions are numbered 1-6, which corresponds to lane numbers in panel B. RT PCR primers are denoted by black arrows. A scale is at the top. The NSE sequence is boxed in the lower panel. Constructs lacking the sense Alu (Alu+) repeatedly failed to ligate/propagate and were not examined. FIG. 16B shows deletion of antisense Alu and MER51 elements alters NSE activation. Wild-type (WT) and mutated constructs (designated 1-6) were transiently transfected into HEK293 cells (mock) depleted of U2AF35. NSE+/−, RNA products with/without NSE. Columns represent mean NSE inclusion (%), error bars SDs of 2 transfection experiments. Asterisks denote two-tailed P values <0.01 (t-test).

FIG. 17A-FIG. 17C show identification of intronic SSOs that activate or repress NSE. FIG. 17A shows the location of tested SSOs in intron 28 relative to transposed elements. For legend, see FIG. 16A. FIG. 17B shows the identification of intron 28 SSOs that alter NSE activation in exogenous transcripts. Illustrative SSOs are listed in Table 2. The "x" symbol denotes multiple negative controls, dotted line the average NSE inclusion, error bars SDs of two transfections experiments. Columns represent mean inclusion levels, asterisks show significant P values. FIG. 17C shows SSOs targeting single-stranded regions tended to repress endogenous NSE. r, Pearson correlation coefficient. The P value is in parentheses.

FIG. 18A shows NSE inclusion in HEK293 cells is inhibited upon exposure of SSO-NSE3/TMC-SA nanocomplexes. N/P ratio was 20, 40 and 80 (Sc=a scrambled control with the same modification, M=size marker). Error bars denote SDs of two transfections experiments. P values are shown at the top for the indicated comparisons. FIG. 18B shows NSE repression in VAVY cells exposed to SSO-NSE3/TMC-SA complexes.

FIG. 19 shows inverted repeats in the MER51 consensus sequence with ATM intron 28 (v, transversions; i, transitions). Most stable inverted repeats in the ATM MER51A are underlined and highlighted; purine-rich single-stranded regions are in red; the long terminal repeat homology originally described for the MER51 family is in italics. The aligned segment corresponds to deletion 4 shown in FIG. 16a. The MER51A consensus sequence is in the antisense orientation.

FIG. 20 illustrates exemplary synthetic DNA and RNA sequences.

FIG. 21 shows exemplary sequences of splicing reporter constructs mutated in NSE and PE.

FIG. 22 shows auxiliary splicing elements in NSE and PE.

FIG. 23 shows a summary of U2AF35-regulated transcripts involved in NMD.

DETAILED DESCRIPTION OF THE INVENTION

Figure 1A:
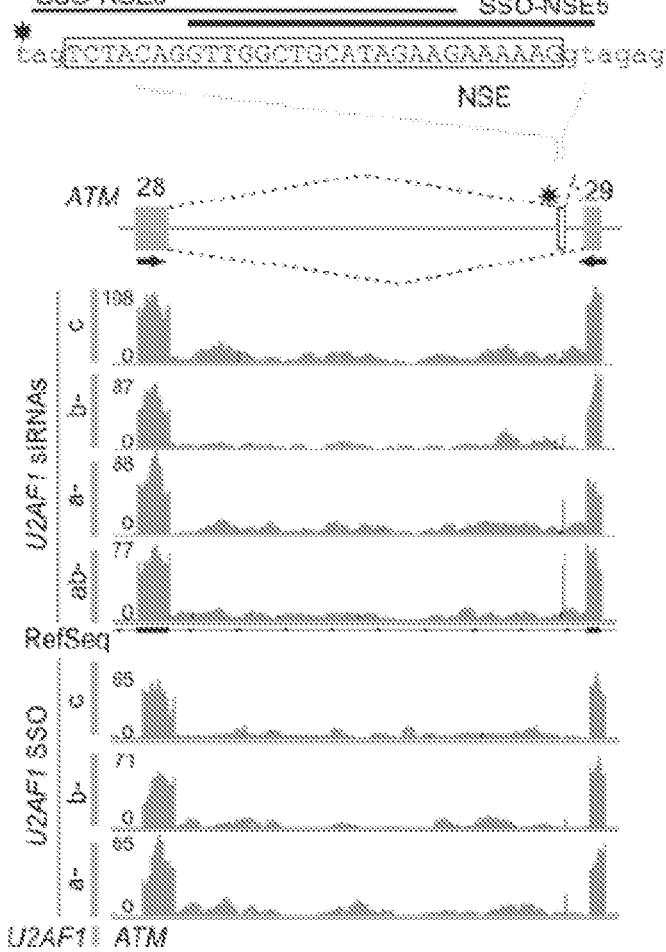
FIG. 1A-FIG. 1C illustrate an identification of a U2AF-repressed cryptic exon in ATM intron 28.

Intervening sequences or introns are removed by a large and highly dynamic RNA-protein complex termed the spliceosome, which orchestrates complex interactions between primary transcripts, small nuclear RNAs (snRNAs) and a large number of proteins. Spliceosomes assemble ad hoc on each intron in an ordered manner, starting with recognition of the 5' splice site (5' ss) by U1 snRNA or the 3'ss by the U2 pathway, which involves binding of the U2 auxiliary factor (U2AF) to the 3'ss region to facilitate U2 binding to the branch point sequence (BPS). U2AF is a stable heterodimer composed of a U2AF2-encoded 65-kD subunit (U2AF65), which binds the polypyrimidine tract (PPT), and a U2AF1-encoded 35-kD subunit (U2AF35), which interacts with highly conserved AG dinucleotides at 3' ss and stabilizes U2AF65 binding. In addition to the BPS/PPT unit and 3' ss/5' ss, accurate splicing requires auxiliary sequences or structures that activate or repress splice site recognition, known as intronic or exonic splicing enhancers or silencers. These elements allow genuine splice sites to be recognized among a vast excess of cryptic or pseudo-sites in the genome of higher eukaryotes, which have the same sequences but outnumber authentic sites by an order of magnitude. Although they often have a regulatory function, the exact mechanisms of their activation or repression are poorly understood.

Exome sequencing studies have revealed a highly restricted pattern of somatic mutations in U2AF1/U2AF2 and other genes involved in 3'ss recognition (SF3B1, ZRSR2, SF1, SF3A1, PRPF40B, and SRSF2) in cancer cells, most prominently myelodysplastic syndromes. These genes encode products that often interact during spliceosome assembly, suggesting the existence of shared pathways in oncogenesis, which is further supported by a high degree of mutual exclusivity of cancer-associated mutations. Genome-wide transcriptome profiling in leukemic samples carrying these mutations detected numerous alterations in splicing of mRNA precursors, however, key links between specific RNA processing defects and cancer initiation or progression have remained obscure, despite the great promise of these targets for therapeutic modulation. The interconnections between these RNA-binding proteins and DNA damage response (DDR) pathways remain to be fully characterized.

Mutations in traditional (BPS/PPT/3'ss/5'ss) and auxiliary splicing motifs often cause aberrant splicing, such as exon skipping or cryptic exon or splice-site activation, and contribute significantly to human morbidity and mortality. Both aberrant and alternative splicing patterns can be influenced by natural DNA variants in exons and introns, which play an important role in heritability of both Mendelian and complex traits. However, the molecular mechanisms that translate the allele- or haplotype-specific RNA expression to phenotypic variability as well as interactions between intronic and exonic variant alleles and trans-acting factors are largely obscure.

Antisense technology has now reached important clinical applications. For example, antisense splice-switching oligonucleotides (SSOs) targeting the ATM gene have been used to repair splicing mutations in ataxia-telangiectasia (A-T) and were successful in normalizing ATM protein levels (Du et al., 2011; Du et al., 2007).

A large fraction of both leukemias and solid tumors show deregulation of ATM expression (for example, Stankovic et al., 1999; Starczynski et al., 2003). Chemical inhibitors of ATM (wortmannin, CP-466722, KU-55933, and KU60019) have not reached clinical trials, largely because of nonspecific effects and/or high toxicity, although KU-559403 has shown good bioavailability and reliably conferred radiosensitivity.

In some instances, the ability to up or down regulate gene expression in a sequence-specific manner is desirable.

In certain embodiments, provided herein is a method of screening a subject or a population of subjects for susceptibility to functional-ATM protein deficiency, wherein the screening comprises determining the presence of a non-thymine variant residue rs609261 located at position −3 relative to the 3' splice site of NSE (cryptic or nonsense-mediated RNA decay switch exon in ATM intron 28) of the human genome, wherein the presence of a non-thymine variant residue rs609261 indicates that the subject (or group of subjects) has, or is susceptible to, functional-ATM protein deficiency.

The term "functional ATM-protein deficiency" means the reduction in the presence/expression of ATM protein that is functional in a subject, cell or tissue. Functional ATM-deficiency is the result of a functional variant rs609261 in ATM intron 28 that alters RNA processing of ATM precursor messenger RNA (pre-mRNA). Cytosine allele at rs609261 results in a higher inclusion of a nonsense-mediated RNA decay switch exon (termed here NSE) in ATM mRNA than a thymine allele at this position, limiting the expression of ATM protein more efficiently than the thymine allele. This limitation can be removed or modulated by novel SSOs that block access to NSE or to NSE-regulatory sequences in the same intron, leading to derepression or inhibition of ATM protein, respectively.

In some embodiments, provided herein is a method of selecting a subject or a population of subjects for treatment or prophylaxis, wherein the subject is susceptible to functional-ATM protein deficiency, the method comprising determining the presence of a non-thymine variant residue rs609261 located at position −3 relative to the 3' splice site of NSE (cryptic exon in ATM intron 28) of the human genome, wherein the presence of a non-thymine variant residue rs609261 indicates that the subject has, or is susceptible to, functional-ATM protein deficiency, and selecting such subject for treatment with an agent arranged to increase functional-ATM levels in the subject.

According to another aspect of the invention, there is provided a method of treatment or prevention of functional-ATM protein deficiency in a subject, the method comprising identifying the presence of a non-thymine variant residue rs609261 located at position −3 relative to the 3' splice site of NSE of the human genome, wherein the presence of a non-thymine variant residue rs609261 indicates that the subject has, or is susceptible to, functional-ATM protein deficiency, and administration of an agent to the subject, which is arranged to increase functional-ATM levels.

According to another aspect of the invention, there is provided a method of treatment or prevention of a condition associated with a functional-ATM protein deficiency, comprising the administration of a NSE repressor agent arranged to increase levels of functional ATM protein, wherein the agent is arranged to bind to a NSE in ATM intron 28 of the pre-mRNA transcript or to NSE-activating regulatory sequences in the same intron to decrease inclusion of the NSE in the mature transcript.

According to another aspect of the invention, there is provided a method of treatment or prevention of a condition associated with deregulation of ATM expression in a subject comprising the administration of a NSE-activator agent, wherein the NSE-activator agent is arranged to increase NSE inclusion in the ATM mature RNA transcript by binding to NSE-inhibiting regulatory motifs in ATM intron 28.

NSE-inhibiting regulatory motifs in ATM intron 28 may comprise sequences that compete with NSE for spliceosomal components, such as a 24 nucleotide pseudoexon (PE) located 3' of NSE in ATM intron 28 of the pre-mRNA transcript or U2AF65 binding site upstream of the pseudoexon.

According to another aspect of the invention, there is provided a method of treatment or prevention of cancer in a subject comprising the administration of a NSE-activator agent arranged to increase a cancer cell's susceptibility to DNA damaging agents that induce double strand DNA breaks, such as radiotherapy, wherein the NSE-activator agent is arranged to increase NSE inclusion in the ATM mature RNA by binding NSE regulatory motifs in ATM intron 28; and treating the subject with DNA damaging agents that cause double strand breaks, such as radiotherapy or chemotherapy.

According to another aspect of the invention, there is provided a method of increasing a cell's susceptibility to cytotoxic therapy, such as radiotherapy treatment, comprising the reduction of ATM protein expression by administration of a NSE-activator agent arranged to increase NSE inclusion in ATM mature RNA transcript by binding to regulatory motifs in ATM intron 28.

The regulatory motifs in ATM intron 28 may compete with NSE for spliceosomal components, wherein such motifs may comprise a 24 nucleotide pseudoexon (PE) located 3' of NSE in ATM intron 28 of the pre-mRNA transcript or U2AF65 binding site upstream of the pseudoexon.

According to another aspect of the invention, there is provided a method of tailoring functional ATM expression in a subject, cell or tissue, comprising the administration of a NSE-activator agent and/or a NSE-repressor agent described herein.

According to another aspect of the invention, there is provided use of rs609261 genotyping to predict a subject response to therapy for conditions associated with ATM deregulation.

According to another aspect of the invention, there is provided a composition comprising the NSE repressor agent of the invention herein.

According to another aspect of the invention, there is provided a composition comprising the NSE activator agent of the invention herein.

According to another aspect of the invention, there is provided a method of treatment or prevention of functional-ATM protein deficiency in a subject, the method comprising identifying the presence of a non-thymine variant residue rs609261 located at position −3 relative to the 3' splice site of NSE (cryptic exon in ATM intron 28) of the human genome, wherein the presence of a non-thymine variant residue rs609261 indicates that the subject has, or is susceptible to, functional-ATM protein deficiency, and administration of an agent to the subject, which is arranged to replace the non-thymine variant residue rs609261 with a thymine residue.

According to another aspect of the invention, there is provided a method of treatment or prevention of functional-ATM protein deficiency in a subject, the method comprising replacing a non-thymine variant residue rs609261 located at position −3 relative to the 3' splice site of NSE (cryptic exon in ATM intron 28) of the human genome with a thymine residue.

According to another aspect of the invention, there is provided a vector comprising the polynucleic acid polymer of the invention.

According to another aspect of the invention, there is provided a method of treatment or prevention of functional-ATM protein deficiency in a subject, the method comprising identifying the presence of a guanine variant residue at rs4988000 of the human genome, wherein the presence of a guanine variant residue at rs4988000 indicates that the subject has, or is susceptible to, functional-ATM protein deficiency, and administration of an agent to the subject, which is arranged to replace the guanine variant residue at rs4988000 with adenine.

According to another aspect of the invention, there is provided a method of treatment or prevention of functional-ATM protein deficiency in a subject, the method comprising replacing a guanine variant residue at rs4988000 of the human genome with an adenine residue.

According to a first aspect of the invention, there is provided a method of screening a subject or a population of subjects for susceptibility to functional-ATM protein deficiency, wherein the screening comprises determining the presence of a guanine variant residue at rs4988000 of the human genome, wherein the presence of a guanine variant residue at rs4988000 indicates that the subject (or group of subjects) has, or is susceptible to, functional-ATM protein deficiency.

According to another aspect of the invention, there is provided a method of selecting a subject or a population of subjects for treatment or prophylaxis, wherein the subject is susceptible to functional-ATM protein deficiency, the method comprising determining the presence of a guanine variant residue at rs4988000 of the human genome, wherein the presence of a guanine variant residue at rs4988000 indicates that the subject has, or is susceptible to, functional-ATM protein deficiency, and selecting such subject for treatment with an agent arranged to increase functional-ATM levels in the subject.

According to another aspect of the invention, there is provided a method of treatment or prevention of functional-ATM protein deficiency in a subject, the method comprising identifying the presence of a guanine variant residue at rs4988000 of the human genome, wherein the presence of a guanine variant residue at rs4988000 indicates that the subject has, or is susceptible to, functional-ATM protein deficiency, and administration of an agent to the subject, which is arranged to increase functional-ATM levels.

Figure 7:
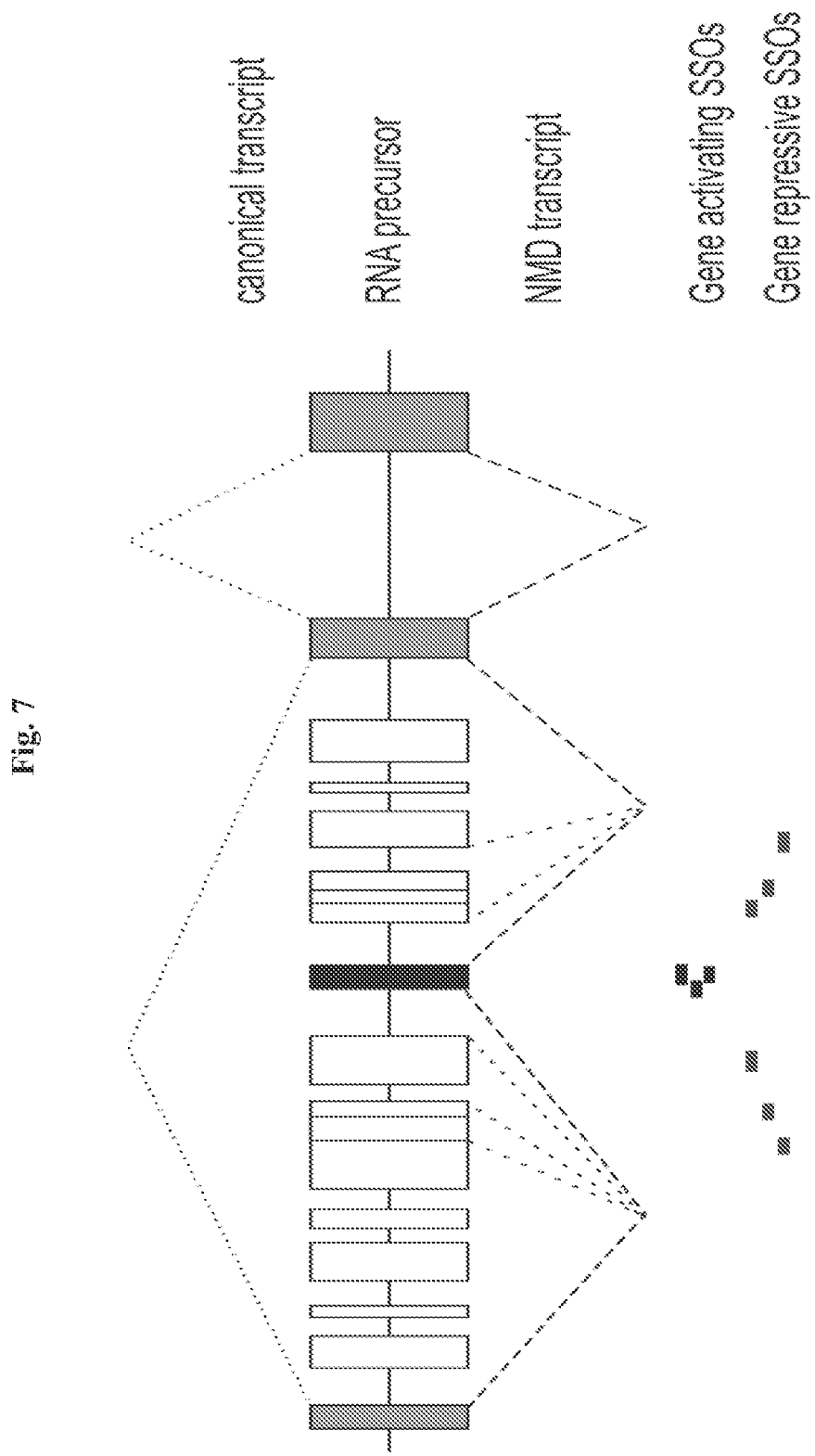
FIG. 7 shows SSO-based modulation of gene expression by pseudoexon targeting. Canonical exons are shown as grey boxes, a nonsense-mediated RNA decay (NMD) switch exon as a black box, pseudoexons as white boxes. Canonical splicing is shown by dotted lines. Pseudosplice sites competing with the NMD exon are shown below the RNA precursor. SSO activators/repressors are denoted by horizontal black/grey bars, respectively. Splicing regulatory motifs or secondary structures that compete with NMD switch exons for spliceosome components such as U2AF, heterogeneous nuclear ribonucleoproteins, or serine/arginine-rich proteins, for inclusion to mature transcripts are not shown for simplicity. They can be predicted by computational methods described in details previously (for example, Kralovicova, J. and Vorechovsky, I. (2007) Global control of aberrant splice site activation by auxiliary splicing sequences: evidence for a gradient in exon and intron definition. *Nucleic Acids Res.*, 35, 6399-6413, and references therein) or determined by experimental methods, including RNA crosslinking and immunoprecipitation, mutagenesis of splicing substrates and RNA folding studies.

According to another aspect of the invention, there is provided a method of screening for an agent or a combination of agents capable of modifying regulation of a gene's expression (FIG. 7) comprising identifying a nonsense-mediated RNA decay switch exon (NSE) that limits functional gene expression; identifying one or more splicing regulatory motifs upstream or downstream of the NSE that compete with the NSE for spliceosomal components, said regulatory motifs comprising cryptic splice sites or pseudoexons; targeting the one or more splicing regulatory motifs with antisense polynucleic acid that are arranged to hybridize to the splicing regulatory motifs through Watson-Crick base pairing; and determining if there is an increased or decreased inclusion of the NSE in a mature RNA transcript of the gene.

According to another aspect of the invention, there is provided a method of modulating gene's expression comprising providing an agent arranged to bind to NSE splicing regulatory motifs.

According to another aspect of the invention, there is provided an agent arranged to bind to a gene splicing regulatory motif of NSE, wherein the splicing regulatory motif controls inclusion of the NSE into a mature RNA transcript of the gene.

According to another aspect of the invention, provided herein is a method of a treatment or prevention of a disease pathology caused by an NSE inclusion in an mRNA gene transcript comprising providing an agent arranged to bind to a gene NSE splicing regulatory motif that controls inclusion of the NSE into a mature RNA transcript of the gene.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The determination may use any suitable assay or genetic analysis available to the skilled person. In some instances, detection is done at a nucleic acid level with nucleic acid-based techniques such as in situ hybridization and RT-PCR Sequencing technologies can include next-generation sequencing technologies such as Helicos True Single Molecule Sequencing (tSMS) (Harris T. D. et al., (2008) Science 320:106-109); 454 sequencing (Roche) (Margulies, M. et al., 2005, Nature, 437, 376-380); SOLiD technology (Applied Biosystems); SOLEXA sequencing (Illumina); single molecule, real-time (SMRT™) technology of Pacific Biosciences; nanopore sequencing (Soni G V and Meller A. (2007) Clin Chem 53: 1996-2001); semiconductor sequencing (Ion Torrent; Personal Genome Machine); DNA nanoball sequencing; sequencing using technology from Dover Systems (Polonator), and technologies that do not require amplification or otherwise transform native DNA prior to sequencing (e.g., Pacific Biosciences and Helicos), such as nanopore-based strategies (e.g., Oxford Nanopore, Genia Technologies, and Nabsys). Sequencing technologies can also include Sanger sequencing, Maxam-Gilbert sequencing, Shotgun sequencing, bridge PCR, mass spectrometry based sequencing, microfluidic based Sanger sequencing, microscopy-based sequencing, RNAP sequencing, or hybridization based sequencing.

Sequencing of a gene transcript of interest may also include an amplification step. Exemplary amplification methodologies include, but are not limited to, polymerase chain reaction (PCR), nucleic acid sequence based amplification (NASBA), self-sustained sequence replication (3 SR), loop mediated isothermal amplification (LAMP), strand displacement amplification (SDA), whole genome amplification, multiple displacement amplification, strand displacement amplification, helicase dependent amplification, nicking enzyme amplification reaction, recombinant polymerase amplification, reverse transcription PCR, ligation mediated PCR, or methylation specific PCR.

Additional methods that can be used to obtain a nucleic acid sequence include, e.g., whole-genome RNA expression array, enzyme-linked immunosorbent assay (ELISA), genome sequencing, de novo sequencing, Pacific Biosciences SMRT sequencing, immunohistochemistry (IHC), immunocytochemistry (ICC), mass spectrometry, tandem mass spectrometry, matrix-assisted laser desorption ionization time of flight mass spectrometry (MALDI-TOF MS), in-situ hybridization, fluorescent in-situ hybridization (FISH), chromogenic in-situ hybridization (CISH), silver in situ hybridization (SISH), digital PCR (dPCR), reverse transcription PCR, quantitative PCR (Q-PCR), single marker qPCR, real-time PCR, nCounter Analysis (Nanostring technology), Western blotting, Southern blotting, SDS-PAGE, gel electrophoresis, and Northern blotting.

According to another aspect of the invention, there is provided a method of treatment or prevention of functional-ATM protein deficiency in a subject, the method comprising identifying the presence of a non-thymine variant residue rs609261 located at position −3 relative to the 3' splice site of NSE (cryptic exon in ATM intron 28) of the human genome, wherein the presence of a non-thymine variant residue rs609261 indicates that the subject has, or is susceptible to, functional-ATM protein deficiency, and administration of an agent to the subject, which is arranged to increase functional-ATM levels.

According to another aspect of the invention, there is provided a method of treatment or prevention of a condition associated with a functional-ATM protein deficiency, comprising the administration of a NSE repressor agent arranged to increase levels of functional ATM protein, wherein the agent is arranged to bind to a NSE in ATM intron 28 of the pre-mRNA transcript to decrease inclusion of the NSE in the mature RNA transcript.

Decreasing inclusion of the NSE in the mature RNA transcript may provide an increase in functional ATM protein expression.

The method of treatment or prevention of functional-ATM protein deficiency in a subject or an at-risk population of subjects may be a method of treatment or prevention of a condition associated with functional-ATM protein deficiency. The condition may be any symptom of ataxia-telangiectasia; cerebellar ataxia; oculocutaneous angiectasia; cancer; immune deficiency; cellular radiosensitivity; or chromosomal instability. The cancer may comprise lymphoblastoid leukemias, or lymphomas. In one embodiment, the condition is ataxia-telangiectasia. In another embodiment, the condition is cancer. The cancer may comprise a non-Hodgkin or Hodgkin lymphoma.

In one embodiment, the NSE comprises the sequence tctacaggttggctgcatagaagaaaaag (SEQ ID NO: 57). The NSE repressor agent may be arranged to bind to NSE within the sequence agTCTACAGGTTGGCTGCATAGAAGAAAAAGgtagag (SEQ ID NO: 58) (respective 3' and 5' splice site dinucleotides of flanking intervening sequences are underlined). The NSE repressor agent may be arranged to bind to the 5' or 3' splice site of the NSE in ATM intron 28. In another embodiment, the NSE repressor agent is arranged to bind to the 3' splice site of the NSE in ATM intron 28. In another embodiment, the NSE repressor agent may be arranged to bind to NSE within the sequence tctt agTCTACAGGTTGGCTGCATAGAAGAAAAAGgtagag (SEQ ID NO: 59) (respective 3' and 5' splice site dinucleotides of flanking intervening sequences are underlined). In another embodiment, the NSE repressor agent may be arranged to bind to NSE within the sequence tctc agTCTACAGGTTGGCTGCATAGAAGAAAAAGgtagag (SEQ ID NO: 60) (respective 3' and 5' splice site dinucleotides of flanking intervening sequences are underlined).

According to another aspect of the invention, there is provided a method of treatment or prevention of a condition associated with deregulation of ATM expression in a subject comprising the administration of a NSE-activator agent, wherein the NSE-activator agent is arranged to increase NSE inclusion in ATM mature RNA transcript by binding to splicing regulatory motifs in ATM intron 28.

Increasing inclusion of the NSE in the mature RNA transcript may provide a decrease in functional ATM protein expression.

According to another aspect of the invention, there is provided a method of treatment or prevention of cancer in a subject comprising the administration of a NSE-activator agent arranged to increase a cancer cell's susceptibility to cytotoxic therapy with DNA damaging agents such as radiotherapy, wherein the NSE-activator agent is arranged to increase NSE inclusion in ATM mature RNA transcript by binding to splicing regulatory motifs in ATM intron 28; and treating the subject with the cytotoxic therapy, such as radiotherapy or chemotherapy.

Chemotherapy may comprise a therapeutic that induces double strand DNA breaks. The skilled person will understand that there are several chemotherapy/therapeutic agents that are capable of inducing double strand DNA breaks. In one embodiment, the chemotherapy agents may comprise bleomycin.

Increasing inclusion of the NSE in the mature RNA transcript may provide a decrease in functional ATM protein expression.

The radiotherapy or chemotherapy may be following the administration of the agent. The radiotherapy or chemotherapy may one or more days following the administration of the agent. The radiotherapy or chemotherapy may be one or more weeks following the administration of the agent.

In one embodiment the pseudoexon comprises the sequence tcatcgaatactttggaaataag.

According to another aspect of the invention, there is provided a method of increasing a cell's susceptibility to cytotoxic therapy with DNA damaging agents such as radiotherapy comprising the reduction of ATM protein expression by administration of a NSE-activator agent arranged to increase NSE inclusion in ATM mature RNA transcript by binding to NSE regulatory motifs in ATM intron 28.

In one embodiment the cell is a cancerous cell. In another embodiment the cell is a precancerous cell.

According to another aspect of the invention, there is provided a method of tailoring functional ATM expression in a subject, cell or tissue, comprising the administration of a NSE-activator agent and/or a NSE-repressor agent described herein.

Nonsense-Mediated mRNA Decay

Nonsense-mediated mRNA decay (NMD) is a surveillance pathway that exists in all eukaryotes. Its main function is to reduce errors in gene expression by eliminating mRNA transcripts that contain premature stop codons. NMD targets transcripts with premature stop codons but also a broad array of mRNA isoforms expressed from many endogenous genes, suggesting that NMD is a master regulator that drives both fine and coarse adjustments in steady-state RNA levels in the cell.

A nonsense-mediated RNA decay switch exon (NSE) is an exon or a pseudoexon that activates the NMD pathway if included in a mature RNA transcript A NSE inclusion in mature transcripts downregulates gene expression.

Cryptic (or pseudo-splice sites) have the same splicing recognition sequences as genuine splice sites but are not used in the splicing reactions. They outnumber genuine splice sites in the human genome by an order of a magnitude and are normally repressed by thus far poorly understood molecular mechanisms. Cryptic 5' splice sites have the consensus NNN/GUNNNN or NNN/GCNNNN where N is any nucleotide and/is the exon-intron boundary. Cryptic 3' splice sites have the consensus NAG/N. Their activation is positively influenced by surrounding nucleotides that make them more similar to the optimal consensus of authentic splice sites, namely MAG/GURAGU and YAG/G, respectively, where M is C or A, R is G or A, and Y is C or U.

Cryptic (or pseudo-) exons have the same splicing recognition sequences as genuine exons but are not used in the splicing reactions. They outnumber genuine exons by an order of a magnitude and are normally repressed by thus far poorly understood molecular mechanisms.

Splice sites and their regulatory sequences can be readily identified by a skilled person using suitable algorithms publicly available, listed for example in Kralovicova, J. and Vorechovsky, I. (2007) Global control of aberrant splice site activation by auxiliary splicing sequences: evidence for a gradient in exon and intron definition. *Nucleic Acids Res.*, 35, 6399-6413, (http://www.ncbi.nlm.nih.gov/pmc/articles/PMC2095810/pdf/gkm680.pdf).

The cryptic splice sites or splicing regulatory sequences may compete for RNA-binding proteins such as U2AF with a splice site of the NSE. In one embodiment, the agent may bind to the cryptic splice site or splicing regulatory sequences to prevent the binding of RNA-binding proteins and thereby favoring utilization of the NSE splice sites.

In one embodiment, the cryptic splice site may not comprise the 5' or 3' splice site of the NSE. The cryptic splice site may be at least 10 nucleotides upstream of the NSE 5' splice site. The cryptic splice site may be at least 20 nucleotides upstream of the NSE 5' splice site. The cryptic splice site may be at least 50 nucleotides upstream of the NSE 5' splice site. The cryptic splice site may be at least 100 nucleotides upstream of the NSE 5' splice site. The cryptic splice site may be at least 200 nucleotides upstream of the NSE 5' splice site.

The cryptic splice site may be at least 10 nucleotides downstream of the NSE 3' splice site. The cryptic splice site may be at least 20 nucleotides downstream of the NSE 3' splice site. The cryptic splice site may be at least 50 nucleotides downstream of the NSE 3' splice site. The cryptic splice site may be at least 100 nucleotides downstream of the NSE 3' splice site. The cryptic splice site may be at least 200 nucleotides downstream of the NSE 3' splice site.

The NSE Repressor Agent and NSE Activator Agent

The NSE repressor agent and/or NSE activator agent may comprise a polynucleic acid polymer. In one embodiment, the NSE repressor agent and/or NSE activator agent is an SSO (Splice Switching Oligonucleotide).

In an embodiment wherein the NSE repressor agent and/or NSE activator agent comprises a polynucleic acid polymer the following statements may apply equally to both the NSE repressor agent and the NSE activator agent unless otherwise indicated. The polynucleic acid polymer may be about 50 nucleotides in length. The polynucleic acid polymer may be about 45 nucleotides in length. The polynucleic acid polymer may be about 40 nucleotides in length. The polynucleic acid polymer may be about 35 nucleotides in length. The polynucleic acid polymer may be about 30 nucleotides in length. The polynucleic acid polymer may be about 24 nucleotides in length. The polynucleic acid polymer may be about 25 nucleotides in length. The polynucleic acid polymer may be about 20 nucleotides in length. The polynucleic acid polymer may be about 19 nucleotides in length. The polynucleic acid polymer may be about 18 nucleotides in length. The polynucleic acid polymer may be about 17 nucleotides in length. The polynucleic acid polymer may be about 16 nucleotides in length. The polynucleic acid polymer may be about 15 nucleotides in length. The polynucleic acid polymer may be about 14 nucleotides in length. The polynucleic acid polymer may be about 13 nucleotides in length. The polynucleic acid polymer may be about 12 nucleotides in length. The polynucleic acid polymer may be about 11 nucleotides in length. The polynucleic acid polymer may be about 10 nucleotides in length. The polynucleic acid polymer may be between about 10 and about 50 nucleotides in length. The polynucleic acid polymer may be between about 10 and about 45 nucleotides in length. The polynucleic acid polymer may be between about 10 and about 40 nucleotides in length. The polynucleic acid polymer may be between about 10 and about 35 nucleotides in length. The polynucleic acid polymer may be between about 10 and about 30 nucleotides in length. The polynucleic acid polymer may be between about 10 and about 25 nucleotides in length. The polynucleic acid polymer may be between about 10 and about 20 nucleotides in length. The polynucleic acid polymer may be between about 15 and about 25 nucleotides in length. The polynucleic acid polymer may be between about 15 and about 30 nucleotides in length. The polynucleic acid polymer may be between about 12 and about 30 nucleotides in length.

The sequence of the polynucleic acid polymer may be at least 50%, 55%, 60%, 65%, 70%, 75%, 80%, 85%, 90%, 91%, 92%, 93%, 94%, 95%, 96%, 97%, 98%, 99%, or 99.5% complementary to a target sequence of the partially processed mRNA transcript. The sequence of the polynucleic acid polymer may be 100% complementary to a target sequence of the pre-mRNA transcript.

The sequence of the polynucleic acid polymer may have 4 or less mismatches to a target sequence of the pre-mRNA transcript. The sequence of the polynucleic acid polymer may have 3 or less mismatches to a target sequence of the pre-mRNA transcript. The sequence of the polynucleic acid polymer may have 2 or less mismatches to a target sequence of the pre-mRNA transcript. The sequence of the polynucleic acid polymer may have 1 or less mismatches to a target sequence of the pre-mRNA transcript.

The polynucleic acid polymer may specifically hybridize to a target sequence of the pre-mRNA transcript. The specificity may be at least a 91%, 92%, 93%, 94%, 95%, 96%, 97%, 98%, 99%, 99.5% or 100% sequence complementarity of the polynucleic acid polymer to a target sequence of the pre-mRNA transcript. The hybridization may be under high stringent hybridization conditions.

The polynucleic acid polymer may have a sequence with at least 50%, 55%, 60%, 65%, 70%, 75%, 80%, 85%, 90%, 91%, 92%, 93%, 94%, 95%, 96%, 97%, 98%, 99%, or 99.5% sequence identity to a sequence illustrated in Table 2 or FIG. 20. The polynucleic acid polymer may have a sequence with 100% sequence identity to a sequence illustrated in Table 2 or FIG. 20. In some instances, the polynucleic acid polymer may have a sequence with at least 50%, 55%, 60%, 65%, 70%, 75%, 80%, 85%, 90%, 91%, 92%, 93%, 94%, 95%, 96%, 97%, 98%, 99%, or 99.5% sequence identity to a sequence illustrated in Table 2. In some cases, the polynucleic acid polymer may have a sequence with 100% sequence identity to a sequence illustrated in Table 2.

In some instances, the polynucleic acid polymer has a sequence with at least 50%, 55%, 60%, 65%, 70%, 75%, 80%, 85%, 90%, 91%, 92%, 93%, 94%, 95%, 96%, 97%, 98%, 99%, or 99.5% sequence identity to a sequence selected from SEQ ID NOs: 18-52. In some cases, the polynucleic acid polymer has a sequence with at least 50% sequence identity to a sequence selected from SEQ ID NOs: 18-52. In some cases, the polynucleic acid polymer has a sequence with at least 60% sequence identity to a sequence selected from SEQ ID NOs: 18-52. In some cases, the polynucleic acid polymer has a sequence with at least 70% sequence identity to a sequence selected from SEQ ID NOs: 18-52. In some cases, the polynucleic acid polymer has a sequence with at least 80% sequence identity to a sequence selected from SEQ ID NOs: 18-52. In some cases, the polynucleic acid polymer has a sequence with at least 85% sequence identity to a sequence selected from SEQ ID NOs: 18-52. In some cases, the polynucleic acid polymer has a sequence with at least 90% sequence identity to a sequence selected from SEQ ID NOs: 18-52. In some cases, the polynucleic acid polymer has a sequence with at least 91% sequence identity to a sequence selected from SEQ ID NOs: 18-52. In some cases, the polynucleic acid polymer has a sequence with at least 92% sequence identity to a sequence selected from SEQ ID NOs: 18-52. In some cases, the polynucleic acid polymer has a sequence with at least 93% sequence identity to a sequence selected from SEQ ID NOs: 18-52. In some cases, the polynucleic acid polymer has a sequence with at least 94% sequence identity to a sequence selected from SEQ ID NOs: 18-52. In some cases, the polynucleic acid polymer has a sequence with at least 95% sequence identity to a sequence selected from SEQ ID NOs: 18-52. In some cases, the polynucleic acid polymer has a sequence with at least 96% sequence identity to a sequence selected from SEQ ID NOs: 18-52. In some cases, the polynucleic acid polymer has a sequence with at least 97% sequence identity to a sequence selected from SEQ ID NOs: 18-52. In some cases, the polynucleic acid polymer has a sequence with at least 98% sequence identity to a sequence selected from SEQ ID NOs: 18-52. In some cases, the polynucleic acid polymer has a sequence with at least 99% sequence identity to a sequence selected from SEQ ID NOs: 18-52. In some cases, the polynucleic acid polymer has a sequence with at least 99.5% sequence identity to a sequence selected from SEQ ID NOs: 18-52. In some cases, the polynucleic acid polymer has a sequence with 100% sequence identity to a sequence selected from SEQ ID NOs: 18-52.

In some embodiments, a polynucleic acid polymer hybridizes to a motif within a transposed element, upstream of a transposed element, or downstream of a transposed element. In some instances, the transposed element is Alu, MER51, UC or L4C. In some instances, the transposed element is Alu (e.g., Alu– or Alu+) or MER51. In some cases, the transposed element is Alu (e.g., Alu– or Alu+). In other cases, the transposed element is MER51. In some instances, the polynucleic acid polymer hybridizes to a target motif within Alu (e.g., Alu– or Alu+). In other instances, the polynucleic acid polymer hybridizes to a target motif downstream of MER51. In some instances, the polynucleic acid polymer has a sequence with at least 50%, 55%, 60%, 65%, 70%, 75%, 80%, 85%, 90%, 91%, 92%, 93%, 94%, 95%, 96%, 97%, 98%, 99%, or 99.5% sequence identity to a sequence selected from SEQ ID NOs: 18-52.

In some embodiments, the polynucleic acid polymer hybridizes to a target motif that is either upstream or downstream of Alu (e.g., Alu− or Alu+). In some instances, the polynucleic acid polymer hybridizes to a target motif that is upstream of Alu. In some cases, the target motif is about 5, 10, 15, 20, 25, 30, 35, 40, 45, 50, 55, 60, 70, 80, 90, 100, 110, 120, 130, 140, 150, 180, 200, 250, 300, 350, 400, 450, 500, 600, 700, 800, or more bases upstream of Alu. In some cases, the target motif is about 5 or more bases upstream of Alu. In some cases, the target motif is about 10 or more bases upstream of Alu. In some cases, the target motif is about 20 or more bases upstream of Alu. In some cases, the target motif is about 30 or more bases upstream of Alu. In some cases, the target motif is about 40 or more bases upstream of Alu. In some cases, the target motif is about 50 or more bases upstream of Alu. In some cases, the target motif is about 80 or more bases upstream of Alu. In some cases, the target motif is about 100 or more bases upstream of Alu. In some cases, the target motif is about 150 or more bases upstream of Alu. In some cases, the target motif is about 200 or more bases upstream of Alu. In some cases, the target motif is about 300 or more bases upstream of Alu. In some cases, the target motif is about 500 or more bases upstream of Alu. In some cases, the target motif is about 800 or more bases upstream of Alu. In some instances, the polynucleic acid polymer has a sequence with at least 50%, 55%, 60%, 65%, 70%, 75%, 80%, 85%, 90%, 91%, 92%, 93%, 94%, 95%, 96%, 97%, 98%, 99%, or 99.5% sequence identity to a sequence selected from SEQ ID NOs: 18-52.

In some instances, the polynucleic acid polymer hybridizes to a target motif that is downstream of Alu (e.g., Alu− or Alu+). In some cases, the target motif is about 5, 10, 15, 20, 25, 30, 35, 40, 45, 50, 55, 60, 70, 80, 90, 100, 110, 120, 130, 140, 150, 180, 200, 250, 300, 350, 400, 450, 500, 600, 700, 800, or more bases downstream of Alu. In some cases, the target motif is about 5 or more bases downstream of Alu. In some cases, the target motif is about 10 or more bases downstream of Alu. In some cases, the target motif is about 20 or more bases downstream of Alu. In some cases, the target motif is about 30 or more bases downstream of Alu. In some cases, the target motif is about 40 or more bases downstream of Alu. In some cases, the target motif is about 50 or more bases downstream of Alu. In some cases, the target motif is about 80 or more bases downstream of Alu. In some cases, the target motif is about 100 or more bases downstream of Alu. In some cases, the target motif is about 150 or more bases downstream of Alu. In some cases, the target motif is about 200 or more bases downstream of Alu. In some cases, the target motif is about 300 or more bases downstream of Alu. In some cases, the target motif is about 500 or more bases downstream of Alu. In some cases, the target motif is about 800 or more bases downstream of Alu. In some instances, the polynucleic acid polymer has a sequence with at least 50%, 55%, 60%, 65%, 70%, 75%, 80%, 85%, 90%, 91%, 92%, 93%, 94%, 95%, 96%, 97%, 98%, 99%, or 99.5% sequence identity to a sequence selected from SEQ ID NOs: 18-52.

In some embodiments, the polynucleic acid polymer hybridizes to a target motif that is either upstream or downstream of MER51. In some instances, the polynucleic acid polymer hybridizes to a target motif that is upstream of MER51. In some cases, the target motif is about 5, 10, 15, 20, 25, 30, 35, 40, 45, 50, 55, 60, 70, 80, 90, 100, 110, 120, 130, 140, 150, 180, 200, 250, 300, 350, 400, 450, 500, 600, 700, 800, or more bases upstream of MER51. In some cases, the target motif is about 5 or more bases upstream of MER51. In some cases, the target motif is about 10 or more bases upstream of MER51. In some cases, the target motif is about 20 or more bases upstream of MER51. In some cases, the target motif is about 30 or more bases upstream of MER51. In some cases, the target motif is about 40 or more bases upstream of MER51. In some cases, the target motif is about 50 or more bases upstream of MER51. In some cases, the target motif is about 80 or more bases upstream of MER51. In some cases, the target motif is about 100 or more bases upstream of MER51. In some cases, the target motif is about 150 or more bases upstream of MER51. In some cases, the target motif is about 200 or more bases upstream of MER51. In some cases, the target motif is about 300 or more bases upstream of MER51. In some cases, the target motif is about 500 or more bases upstream of MER51. In some cases, the target motif is about 800 or more bases upstream of MER51. In some instances, the polynucleic acid polymer has a sequence with at least 50%, 55%, 60%, 65%, 70%, 75%, 80%, 85%, 90%, 91%, 92%, 93%, 94%, 95%, 96%, 97%, 98%, 99%, or 99.5% sequence identity to a sequence selected from SEQ ID NOs: 18-52.

In some instances, the polynucleic acid polymer hybridizes to a target motif that is downstream of MER51. In some cases, the target motif is about 5, 10, 15, 20, 25, 30, 35, 40, 45, 50, 55, 60, 70, 80, 90, 100, 110, 120, 130, 140, 150, 180, 200, 250, 300, 350, 400, 450, 500, 600, 700, 800, or more bases downstream of MER51. In some cases, the target motif is about 5 or more bases downstream of MER51. In some cases, the target motif is about 10 or more bases downstream of MER51. In some cases, the target motif is about 20 or more bases downstream of MER51. In some cases, the target motif is about 30 or more bases downstream of MER51. In some cases, the target motif is about 40 or more bases downstream of MER51. In some cases, the target motif is about 50 or more bases downstream of MER51. In some cases, the target motif is about 80 or more bases downstream of MER51. In some cases, the target motif is about 100 or more bases downstream of MER51. In some cases, the target motif is about 150 or more bases downstream of MER51. In some cases, the target motif is about 200 or more bases downstream of MER51. In some cases, the target motif is about 300 or more bases downstream of MER51. In some cases, the target motif is about 500 or more bases downstream of MER51. In some cases, the target motif is about 800 or more bases downstream of MER51. In some instances, the polynucleic acid polymer has a sequence with at least 50%, 55%, 60%, 65%, 70%, 75%, 80%, 85%, 90%, 91%, 92%, 93%, 94%, 95%, 96%, 97%, 98%, 99%, or 99.5% sequence identity to a sequence selected from SEQ ID NOs: 18-52.

Where reference is made to a polynucleic acid polymer sequence, the skilled person will understand that one or more substitutions may be tolerated, optionally two substitutions may be tolerated in the sequence, such that it maintains the ability to hybridize to the target sequence, or where the substitution is in a target sequence, the ability to be recognized as the target sequence. References to sequence identity may be determined by BLAST sequence alignment (www.ncbi.nlm.nih.gov/BLAST/) using standard/default parameters. For example, the sequence may have 99% identity and still function according to the invention. In other embodiments, the sequence may have 98% identity and still function according to the invention. In another embodiment, the sequence may have 95% identity and still function according to the invention.

A polynucleic acid polymer, such as the SSOs, may comprise RNA or DNA. The polynucleic acid polymer, such as the SSOs, may comprise RNA. The polynucleic acid polymer, such as the SSOs, may comprise natural or synthetic or artificial nucleotide analogues or bases, having equivalent complementation as DNA or RNA. The polynucleic acid polymer, such as the SSOs, may comprise combinations of DNA, RNA and/or nucleotide analogues. Nucleotide analogues may comprise PNA or LNA. In another embodiment, the nucleic acid, such as the SSOs, may comprise or consist of PMO.

In some instances, the synthetic or artificial nucleotide analogues or bases can comprise modifications at one or more of ribose moiety, phosphate moiety, nucleoside moiety, or a combination thereof. For example, a nucleotide base may be any naturally occurring, unmodified nucleotide base such as adenine, guanine, cytosine, thymine and uracil, or any synthetic or modified base that is sufficiently similar to an unmodified nucleotide base such that it is capable of hydrogen bonding with a base present on a target pre-mRNA. Examples of modified nucleotide bases include, without limitation, hypoxanthine, xanthine, 7-methylguanine, 5,6-dihydrouracil, 5-methylcytosine, and 5-hydroxymethoylcytosine.

Sometimes, the polynucleic acid polymers described herein also comprise a backbone structure that connects the components of an oligomer. The term "backbone structure" and "oligomer linkages" may be used interchangeably and refer to the connection between monomers of the polynucleic acid polymer. In naturally occurring oligonucleotides, the backbone comprises a 3'-5' phosphodiester linkage connecting sugar moieties of the oligomer. The backbone structure or oligomer linkages of the polynucleic acid polymers described herein may include (but are not limited to) phosphorothioate, phosphorodithioate, phosphoroselenoate, phosphorodiselenoate, phosphoroanilothioate, phosphoraniladate, phosphoramidate, and the like. See e.g., LaPlanche et al., Nucleic Acids Res. 14:9081 (1986); Stec et al., J. Am. Chem. Soc. 106:6077 (1984), Stein et al; Nucleic Acids Res. 16:3209 (1988), Zon et al., Anti Cancer Drug Design 6:539 (1991); Zon et al; Oligonucleotides and Analogues: A Practical Approach, pp. 87-108 (F. Eckstein, Ed., Oxford University Press, Oxford England (1991)); Stec et al., U.S. Pat. No. 5,151,510; Uhlmann and Peyman, Chemical Reviews 90:543 (1990).

In embodiments, the stereochemistry at each of the phosphorus internucleotide linkages of the polynucleic acid polymer backbone is random. In embodiments, the stereochemistry at each of the phosphorus internucleotide linkages of the polynucleic acid polymer backbone is controlled and is not random. For example, U.S. Pat. App. Pub. No. 2014/0194610, "Methods for the Synthesis of Functionalized Nucleic Acids," incorporated herein by reference, describes methods for independently selecting the handedness of chirality at each phosphorous atom in a nucleic acid oligomer. In embodiments, a polynucleic acid polymer described herein comprises a polynucleic acid polymer having phosphorus internucleotide linkages that are not random. In embodiments, a composition used in the methods of the invention comprises a pure diastereomeric polynucleic acid polymer. In embodiments, a composition used in the methods of the invention comprises a polynucleic acid polymer that has diastereomeric purity of at least about 90%, at least about 91%, at least about 92%, at least about 93%, at least about 94%, at least about 95%, at least about 96%, at least about 97%, at least about 98%, at least about 99%, about 100%, about 90% to about 100%, about 91% to about 100%, about 92% to about 100%, about 93% to about 100%, about 94% to about 100%, about 95% to about 100%, about 96% to about 100%, about 97% to about 100%, about 98% to about 100%, or about 99% to about 100%.

In embodiments, the polynucleic acid polymer has a nonrandom mixture of Rp and Sp configurations at its phosphorus internucleotide linkages. For example, a mix of Rp and Sp may be required in antisense oligonucleotides to achieve a balance between good activity and nuclease stability (Wan, et al., 2014, "Synthesis, biophysical properties and biological activity of second generation antisense oligonucleotides containing chiral phosphorothioate linkages," Nucleic Acids Research 42(22): 13456-13468, incorporated herein by reference). In embodiments, a polynucleic acid polymer described herein comprises about 5-100% Rp, at least about 5% Rp, at least about 10% Rp, at least about 15% Rp, at least about 20% Rp, at least about 25% Rp, at least about 30% Rp, at least about 35% Rp, at least about 40% Rp, at least about 45% Rp, at least about 50% Rp, at least about 55% Rp, at least about 60% Rp, at least about 65% Rp, at least about 70% Rp, at least about 75% Rp, at least about 80% Rp, at least about 85% Rp, at least about 90% Rp, or at least about 95% Rp, with the remainder Sp, or about 100% Rp. In embodiments, a polynucleic acid polymer described herein comprises about 10% to about 100% Rp, about 15% to about 100% Rp, about 20% to about 100% Rp, about 25% to about 100% Rp, about 30% to about 100% Rp, about 35% to about 100% Rp, about 40% to about 100% Rp, about 45% to about 100% Rp, about 50% to about 100% Rp, about 55% to about 100% Rp, about 60% to about 100% Rp, about 65% to about 100% Rp, about 70% to about 100% Rp, about 75% to about 100% Rp, about 80% to about 100% Rp, about 85% to about 100% Rp, about 90% to about 100% Rp, or about 95% to about 100% Rp, about 20% to about 80% Rp, about 25% to about 75% Rp, about 30% to about 70% Rp, about 40% to about 60% Rp, or about 45% to about 55% Rp, with the remainder Sp.

In embodiments, a polynucleic acid polymer described herein comprises about 5-100% Sp, at least about 5% Sp, at least about 10% Sp, at least about 15% Sp, at least about 20% Sp, at least about 25% Sp, at least about 30% Sp, at least about 35% Sp, at least about 40% Sp, at least about 45% Sp, at least about 50% Sp, at least about 55% Sp, at least about 60% Sp, at least about 65% Sp, at least about 70% Sp, at least about 75% Sp, at least about 80% Sp, at least about 85% Sp, at least about 90% Sp, or at least about 95% Sp, with the remainder Rp, or about 100% Sp. In embodiments, a polynucleic acid polymer described herein comprises about 10% to about 100% Sp, about 15% to about 100% Sp, about 20% to about 100% Sp, about 25% to about 100% Sp, about 30% to about 100% Sp, about 35% to about 100% Sp, about 40% to about 100% Sp, about 45% to about 100% Sp, about 50% to about 100% Sp, about 55% to about 100% Sp, about 60% to about 100% Sp, about 65% to about 100% Sp, about 70% to about 100% Sp, about 75% to about 100% Sp, about 80% to about 100% Sp, about 85% to about 100% Sp, about 90% to about 100% Sp, or about 95% to about 100% Sp, about 20% to about 80% Sp, about 25% to about 75% Sp, about 30% to about 70% Sp, about 40% to about 60% Sp, or about 45% to about 55% Sp, with the remainder Rp.

Nucleotide analogues or artificial nucleotide base may comprise a nucleic acid with a modification at a 2' hydroxyl group of the ribose moiety. The modification can be a 2'-O-methyl modification or a 2'-O-methoxyethyl (2'-O-MOE) modification. The 2'-O-methyl modification can add a methyl group to the 2' hydroxyl group of the ribose moiety whereas the 2'O-methoxyethyl modification can add a methoxyethyl group to the 2' hydroxyl group of the ribose moiety. Exemplary chemical structures of a 2'-O-methyl modification of an adenosine molecule and 2'O-methoxyethyl modification of an uridine are illustrated below.

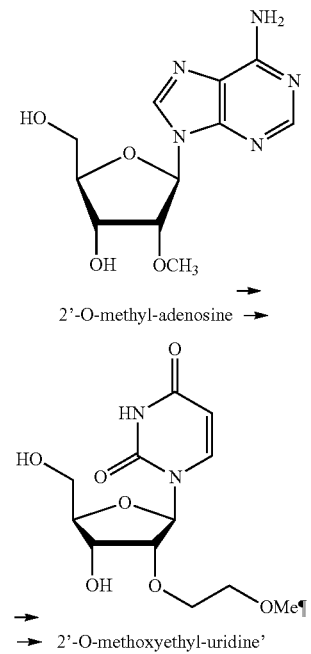

2'-O-methyl-adenosine

2'-O-methoxyethyl-uridine'

An additional modification at the 2' hydroxyl group can include a 2'-O-aminopropyl sugar conformation which can involve an extended amine group comprising a propyl linker that binds the amine group to the 2' oxygen. This modification can neutralize the phosphate derived overall negative charge of the oligonucleotide molecule by introducing one positive charge from the amine group per sugar and can thereby improve cellular uptake properties due to its zwitterionic properties. An exemplary chemical structure of a 2'-O-aminopropyl nucleoside phosphoramidite is illustrated below.

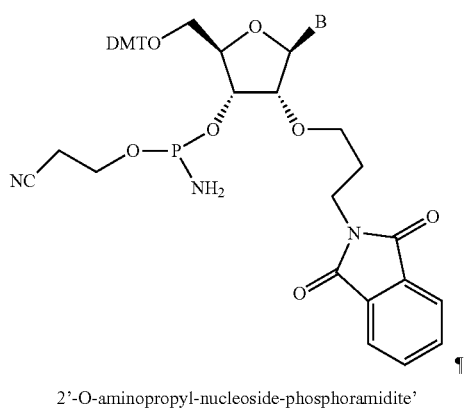

2'-O-aminopropyl-nucleoside-phosphoramidite'

Another modification at the 2' hydroxyl group can include a locked or bridged ribose conformation (e.g., locked nucleic acid or LNA) where the 4' ribose position can also be involved. In this modification, the oxygen molecule bound at the 2' carbon can be linked to the 4' carbon by a methylene group, thus forming a 2'-C,4'-C-oxy-methylene-linked bicyclic ribonucleotide monomer. Exemplary representations of the chemical structure of LNA are illustrated below. The representation shown to the left highlights the chemical connections of an LNA monomer. The representation shown to the right highlights the locked 3'-endo (3E) conformation of the furanose ring of an LNA monomer.

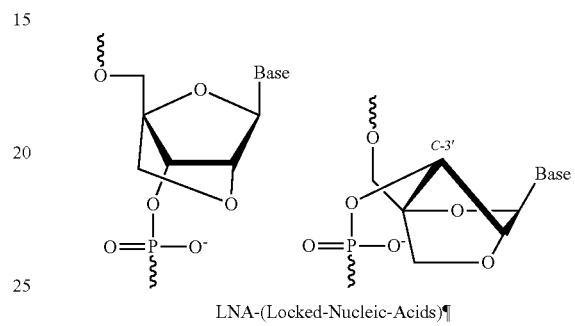

LNA-(Locked-Nucleic-Acids)

A further modification at the 2' hydroxyl group may comprise ethylene nucleic acids (ENA) such as for example 2'-4'-ethylene-bridged nucleic acid, which locks the sugar conformation into a C3'-endo sugar puckering conformation. ENA are part of the bridged nucleic acids class of modified nucleic acids that also comprises LNA. Exemplary chemical structures of the ENA and bridged nucleic acids are illustrated below.

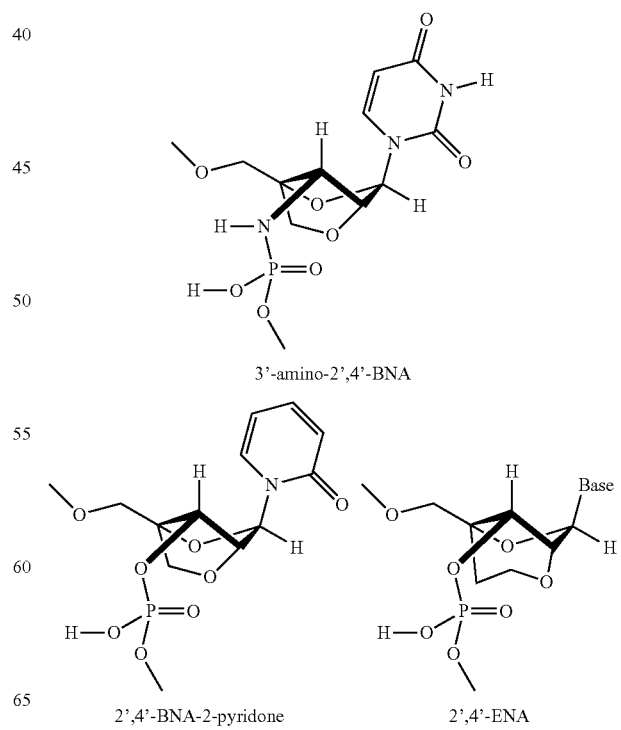

3'-amino-2',4'-BNA

2',4'-BNA-2-pyridone          2',4'-ENA

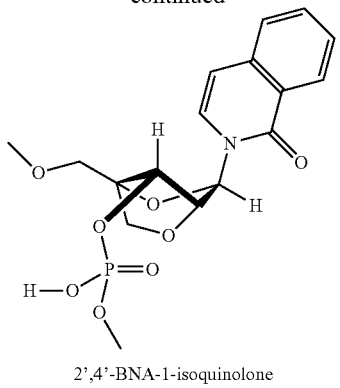

2',4'-BNA-1-isoquinolone

Still other modifications at the 2' hydroxyl group can include 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-0-NMA).

Nucleotide analogues may further comprise Morpholinos, peptide nucleic acids (PNAs), methylphosphonate nucleotides, thiolphosphonate nucleotides, 2'-fluoro N3-P5'-phosphoramidites, 1', 5'-anhydrohexitol nucleic acids (HNAs), or a combination thereof. Morpholino or phosphorodiamidate morpholino oligo (PMO) comprises synthetic molecules whose structure mimics natural nucleic acid structure by deviates from the normal sugar and phosphate structures. Instead, the five member ribose ring can be substituted with a six member morpholino ring containing four carbons, one nitrogen and one oxygen. The ribose monomers can be linked by a phosphordiamidate group instead of a phosphate group. These backbone alterations can remove all positive and negative charges making morpholinos neutral molecules that can cross cellular membranes without the aid of cellular delivery agents such as those used by charged oligonucleotides.

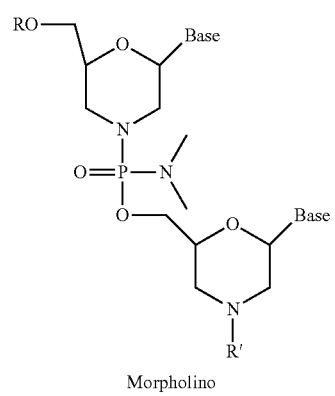

Morpholino

Peptide nucleic acid (PNA) does not contain sugar ring or phosphate linkage. Instead, the bases can be attached and appropriately spaced by oligoglycine-like molecules, therefore, eliminating a backbone charge.

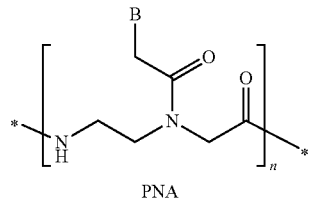

PNA

Modification of the phosphate backbone may also comprise methyl or thiol modifications such as methylphosphonate nucleotide and. Exemplary thiolphosphonate nucleotide (left) and methylphosphonate nucleotide (right) are illustrated below.

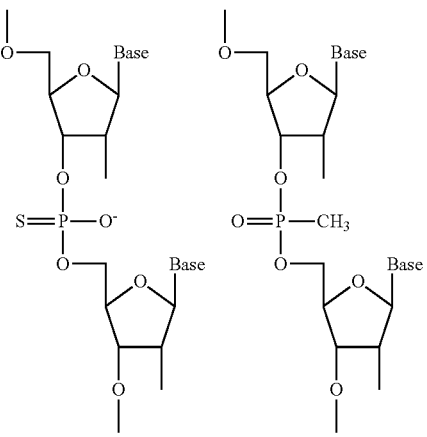

Furthermore, exemplary 2'-fluoro N3-P5'-phosphoramidites is illustrated as:

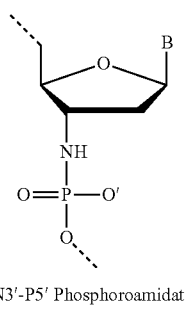

N3'-P5' Phosphoroamidate

And exemplary hexitol nucleic acid (or 1', 5'-anhydrohexitol nucleic acids (HNA)) is illustrated as:

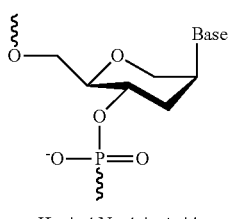

Hexitol Nucleic Acid

In addition to modification of the ribose moiety, phosphate backbone and the nucleoside, the nucleotide analogues can also be modified by for example at the 3' or the 5' terminus. For example, the 3' terminus can include a 3' cationic group, or by inverting the nucleoside at the 3'-terminus with a 3'-3' linkage. In another alternative, the 3'-terminus can be blocked with an aminoalkyl group, e.g., a 3' C5-aminoalkyl dT. The 5'-terminus can be blocked with an aminoalkyl group, e.g., a 5'-O-alkylamino substituent. Other 5' conjugates can inhibit 5'-3' exonucleolytic cleavage. Other 3' conjugates can inhibit 3'-5' exonucleolytic cleavage.

Unless specified otherwise, the left-hand end of single-stranded nucleic acid (e.g., pre-mRNA transcript, oligonucleotide, SSO, etc.) sequences is the 5' end and the left-hand direction of single or double-stranded nucleic acid sequences is referred to as the 5' direction. Similarly, the right-hand end or direction of a nucleic acid sequence (single or double stranded) is the 3' end or direction. Generally, a region or sequence that is 5' to a reference point in a nucleic acid is referred to as "upstream," and a region or sequence that is 3' to a reference point in a nucleic acid is referred to as "downstream." Generally, the 5' direction or end of an mRNA is where the initiation or start codon is located, while the 3' end or direction is where the termination codon is located. In some aspects, nucleotides that are upstream of a reference point in a nucleic acid may be designated by a negative number, while nucleotides that are downstream of a reference point may be designated by a positive number. For example, a reference point (e.g., an exon-exon junction in mRNA) may be designated as the "zero" site, and a nucleotide that is directly adjacent and upstream of the reference point is designated "minus one," e.g., "−1," while a nucleotide that is directly adjacent and downstream of the reference point is designated "plus one," e.g., "+1."

In some cases, one or more of the artificial nucleotide analogues described herein are resistant toward nucleases such as for example ribonuclease such as RNase H, deoxyribonuclease such as DNase, or exonuclease such as 5'-3' exonuclease and 3'-5' exonuclease when compared to natural polynucleic acid polymers. In some instances, artificial nucleotide analogues comprising 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-0-DMAP), T-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, 2'-fluoro N3-P5'-phosphoramidites, or combinations thereof are resistant toward nucleases such as for example ribonuclease such as RNase H, deoxyribonuclease such as DNase, or exonuclease such as 5'-3' exonuclease and 3'-5' exonuclease. 2'-O-methyl modified polynucleic acid polymer may be nuclease resistance (e.g., RNase H, DNase, 5'-3' exonuclease or 3'-5' exonuclease resistance). 2'O-methoxyethyl (2'-O-MOE) modified polynucleic acid polymer may be nuclease resistance (e.g., RNase H, DNase, 5'-3' exonuclease or 3'-5' exonuclease resistance). 2'-O-aminopropyl modified polynucleic acid polymer may be nuclease resistance (e.g., RNase H, DNase, 5'-3' exonuclease or 3'-5' exonuclease resistance). 2'-deoxy modified polynucleic acid polymer may be nuclease resistance (e.g., RNase H, DNase, 5'-3' exonuclease or 3'-5' exonuclease resistance). T-deoxy-2'-fluoro modified polynucleic acid polymer may be nuclease resistance (e.g., RNase H, DNase, 5'-3' exonuclease or 3'-5' exonuclease resistance). 2'-O-aminopropyl (2'-O-AP) modified polynucleic acid polymer may be nuclease resistance (e.g., RNase H, DNase, 5'-3' exonuclease or 3'-5' exonuclease resistance). 2'-O-dimethylaminoethyl (2'-O-DMAOE) modified polynucleic acid polymer may be nuclease resistance (e.g., RNase H, DNase, 5'-3' exonuclease or 3'-5' exonuclease resistance). 2'-O-dimethylaminopropyl (2'-O-DMAP) modified polynucleic acid polymer may be nuclease resistance (e.g., RNase H, DNase, 5'-3' exonuclease or 3'-5' exonuclease resistance). T-O-dimethylaminoethyloxyethyl (2'-O-DMAEOE) modified polynucleic acid polymer may be nuclease resistance (e.g., RNase H, DNase, 5'-3' exonuclease or 3'-5' exonuclease resistance). 2'-O—N-methylacetamido (2'-O-NMA) modified polynucleic acid polymer may be nuclease resistance (e.g., RNase H, DNase, 5'-3' exonuclease or 3'-5' exonuclease resistance). LNA modified polynucleic acid polymer may be nuclease resistance (e.g., RNase H, DNase, 5'-3' exonuclease or 3'-5' exonuclease resistance). ENA modified polynucleic acid polymer may be nuclease resistance (e.g., RNase H, DNase, 5'-3' exonuclease or 3'-5' exonuclease resistance). HNA modified polynucleic acid polymer may be nuclease resistance (e.g., RNase H, DNase, 5'-3' exonuclease or 3'-5' exonuclease resistance). Morpholinos may be nuclease resistance (e.g., RNase H, DNase, 5'-3' exonuclease or 3'-5' exonuclease resistance). PNA can be resistant to nucleases (e.g., RNase H, DNase, 5'-3' exonuclease or 3'-5' exonuclease resistance). Methylphosphonate nucleotides modified polynucleic acid polymer may be nuclease resistance (e.g., RNase H, DNase, 5'-3' exonuclease or 3'-5' exonuclease resistance). Thiolphosphonate nucleotides modified polynucleic acid polymer may be nuclease resistance (e.g., RNase H, DNase, 5'-3' exonuclease or 3'-5' exonuclease resistance). Polynucleic acid polymer comprising 2'-fluoro N3-P5'-phosphoramidites may be nuclease resistance (e.g., RNase H, DNase, 5'-3' exonuclease or 3'-5' exonuclease resistance).

In some instances, one or more of the artificial nucleotide analogues described herein have increased binding affinity toward their mRNA target relative to an equivalent natural polynucleic acid polymer. The one or more of the artificial nucleotide analogues comprising 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O-NMA) modified, LNA, ENA, PNA, HNA, morpholino, methylphosphonate nucleotides, thiolphosphonate nucleotides, or 2'-fluoro N3-P5'-phosphoramidites can have increased binding affinity toward their mRNA target relative to an equivalent natural polynucleic acid polymer. 2'-O-methyl modified polynucleic acid polymer can have increased binding affinity toward their mRNA target relative to an equivalent natural polynucleic acid polymer. 2'-O-methoxyethyl (2'-O-MOE) modified polynucleic acid polymer can have increased binding affinity toward their mRNA target relative to an equivalent natural polynucleic acid polymer. 2'-O-aminopropyl modified polynucleic acid polymer can have increased binding affinity toward their mRNA target relative to an equivalent natural polynucleic acid polymer. 2'-deoxy modified polynucleic acid polymer can have increased binding affinity toward their mRNA target relative to an equivalent natural polynucleic acid polymer. T-deoxy-2'-fluoro modified polynucleic acid polymer can have increased binding affinity toward their mRNA target relative to an equivalent natural polynucleic acid polymer. 2'-O-aminopropyl (2'-O-AP) modified polynucleic acid polymer can have increased binding affinity toward their mRNA target relative to an equivalent natural polynucleic acid polymer. 2'-O-dimethylaminoethyl (2'-O-DMAOE) modified polynucleic acid polymer can have increased binding affinity toward their mRNA target relative to an equivalent natural polynucleic acid polymer. 2'-O-dimethylaminopropyl (2'-O-DMAP) modified polynucleic acid polymer can have increased binding affinity toward their mRNA target relative to an equivalent natural polynucleic acid polymer. T-O-dimethylaminoethyl-oxyethyl (2'-O-DMAEOE) modified polynucleic acid polymer can have increased binding affinity toward their mRNA target relative to an equivalent natural polynucleic acid polymer. 2'-O—N-methylacetamido (2'-O-NMA) modified polynucleic acid polymer can have increased binding affinity toward their mRNA target relative to an equivalent natural polynucleic acid polymer. LNA modified polynucleic acid polymer can have increased binding affinity toward their mRNA target relative to an equivalent natural polynucleic acid polymer. ENA modified polynucleic acid polymer can have increased binding affinity toward their mRNA target relative to an equivalent natural polynucleic acid polymer. PNA modified polynucleic acid polymer can have increased binding affinity toward their mRNA target relative to an equivalent natural polynucleic acid polymer. HNA modified polynucleic acid polymer can have increased binding affinity toward their mRNA target relative to an equivalent natural polynucleic acid polymer. Morpholino modified polynucleic acid polymer can have increased binding affinity toward their mRNA target relative to an equivalent natural polynucleic acid polymer. Methylphosphonate nucleotides modified polynucleic acid polymer can have increased binding affinity toward their mRNA target relative to an equivalent natural polynucleic acid polymer. Thiolphosphonate nucleotides modified polynucleic acid polymer can have increased binding affinity toward their mRNA target relative to an equivalent natural polynucleic acid polymer. Polynucleic acid polymer comprising 2'-fluoro N3-P5'-phosphoramidites can have increased binding affinity toward their mRNA target relative to an equivalent natural polynucleic acid polymer. The increased affinity can be illustrated with a lower Kd, a higher melt temperature (Tm), or a combination thereof.

In additional instances, a polynucleic acid polymer described herein may be modified to increase its stability. In an embodiment where the polynucleic acid polymer is RNA, the polynucleic acid polymer may be modified to increase its stability. The polynucleic acid polymer may be modified by one or more of the modifications described above to increase its stability. The polynucleic acid polymer may be modified at the 2' hydroxyl position, such as by 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), or 2'-O—N-methylacetamido (2'-O-NMA) modification or by a locked or bridged ribose conformation (e.g., LNA or ENA). The polynucleic acid polymer may be modified by 2'-O-methyl and/or 2'-O-methoxyethyl ribose. The polynucleic acid polymer may also include morpholinos, PNAs, HNA, methylphosphonate nucleotides, thiolphosphonate nucleotides, or 2'-fluoro N3-P5'-phosphoramidites to increase its stability. Suitable modifications to the RNA to increase stability for delivery will be apparent to the skilled person.

A polynucleic acid polymer described herein can be constructed using chemical synthesis and/or enzymatic ligation reactions using procedures known in the art. For example, a polynucleic acid polymer can be chemically synthesized using naturally occurring nucleotides or variously modified nucleotides designed to increase the biological stability of the molecules or to increase the physical stability of the duplex formed between the polynucleic acid polymer and target nucleic acids. Exemplary methods can include those described in: U.S. Pat. Nos. 5,142,047; 5,185,444; WO2009099942; or EP1579015. Additional exemplary methods can include those described in: Griffey et al., "2'-O-aminopropyl ribonucleotides: a zwitterionic modification that enhances the exonuclease resistance and biological activity of antisense oligonucleotides," *J. Med. Chem.* 39(26):5100-5109 (1997)); Obika, et al., "Synthesis of 2'-0, 4'-C-methyleneuridine and -cytidine. Novel bicyclic nucleosides having a fixed C3, -endo sugar puckering". Tetrahedron Letters 38 (50): 8735 (1997); Koizumi, M. "ENA oligonucleotides as therapeutics". Current opinion in molecular therapeutics 8 (2): 144-149 (2006); and Abramova et al., "Novel oligonucleotide analogues based on morpholino nucleoside subunits-antisense technologies: new chemical possibilities," *Indian Journal of Chemistry* 48B:1721-1726 (2009). Alternatively, the polynucleic acid polymer can be produced biologically using an expression vector into which a polynucleic acid polymer has been subcloned in an antisense orientation (i.e., RNA transcribed from the inserted polynucleic acid polymer will be of an antisense orientation to a target polynucleic acid polymer of interest).

A polynucleic acid polymer may be bound to any nucleic acid molecule, such as another antisense molecule, a peptide, or other chemicals to facilitate delivery of the polynucleic acid polymer and/or target the nucleic acid to a specific tissue, cell type, or cell developmental stage. The polynucleic acid polymer may be bound to a protein or RNA. The protein tethered to the polynucleic acid polymer may comprise a splicing factor to enhance, inhibit or modulate splicing and intron removal. RNA tethered to the polynucleic acid polymer may comprise an aptamer or any structure that enhance, inhibit or modulate splicing and intron removal. The polynucleic acid polymer may be isolated nucleic acid.

A polynucleic acid polymer may be conjugated to, or bound by, a delivery vehicle suitable for delivering the polynucleic acid polymer to cells. The cells may be a specific cell type, or specific developmental stage. The delivery vehicle may be capable of site specific, tissue specific, cell specific or developmental stage-specific delivery. For example, the delivery vehicle may be a cell specific viral particle, or component thereof, alternatively, the delivery vehicle may be a cell specific antibody particle, or component thereof. The polynucleic acid polymer may be targeted for delivery to beta cells in the pancreas. The polynucleic acid polymer may be targeted for delivery to thymic cells. The polynucleic acid polymer may be targeted for delivery to malignant cells. The polynucleic acid polymer may be targeted for delivery to pre-malignant cells (that are known to develop into overt malignant phenotypes within a foreseeable future, such as pre-leukemias and myelodysplastic syndromes or histopathologically defined precancerous lesions or conditions.

A polynucleic acid polymer may be conjugated to, or bound by, a nanoparticle-based delivery vehicle. A nanoparticle may be a metal nanoparticle, e.g., a nanoparticle of scandium, titanium, vanadium, chromium, manganese, iron, cobalt, nickel, copper, zinc, yttrium, zirconium, niobium, molybdenum, ruthenium, rhodium, palladium, silver, cadmium, hafnium, tantalum, tungsten, rhenium, osmium, iridium, platinum, gold, gadolinium, aluminum, gallium, indium, tin, thallium, lead, bismuth, magnesium, calcium, strontium, barium, lithium, sodium, potassium, boron, silicon, phosphorus, germanium, arsenic, antimony, and combinations, alloys or oxides thereof. Sometimes a nanoparticle may be prepared from polymeric materials. Illustrative polymeric materials include, but are not limited to, poly(ethylenimine) (PEI), poly(alkylcyanoacrylates), poly(amidoamine) dendrimers (PAMAM), poly(ε-caprolactone) (PCL), poly(lactic-co-glycolic acid) (PLGA), or polyesters (poly(lactic acid) (PLA). Sometimes a nanoparticle may be further coated with molecules for attachment of functional elements. In some cases, a coating comprises chondroitin sulfate, dextran sulfate, carboxymethyl dextran, alginic acid, pectin, carragheenan, fucoidan, agaropectin, porphyran, karaya gum, gellan gum, xanthan gum, hyaluronic acids, glucosamine, galactosamine, chitin (or chitosan), polyglutamic acid, polyaspartic acid, lysozyme, cytochrome C, ribonuclease, trypsinogen, chymotrypsinogen, α-chymotrypsin, polylysine, polyarginine, histone, protamine, graphene, ovalbumin or dextrin or cyclodextrin. A nanoparticle may include a core or a core and a shell, as in a core-shell nanoparticle. Sometimes, a nanoparticle may have at least one dimension of less than about 500 nm, 400 nm, 300 nm, 200 nm, or 100 nm.

In some embodiments, a polynucleic acid polymer may be formulated with a nanoparticle-based delivery vehicle for delivery to a site of interest (e.g., a malignant tissue site or a cell with deregulated protein expression). In some cases, a polynucleic acid polymer may be formulated with a nanoparticle-based delivery vehicle to facilitate and/or enable transport across the blood-brain barrier (BBB).

Sometimes, a polynucleic acid polymer is coupled to a substance, known in the art to promote penetration or transport across the blood-brain barrier, e.g., an antibody to the transferrin receptor. In some embodiments, the polynucleic acid polymer is linked with a viral vector, e.g., to render the compound more effective or increase transport across the blood-brain barrier. In some embodiments, osmotic blood brain barrier disruption is assisted by infusion of sugars, e.g., meso erythritol, xylitol, D(+) galactose, D(+) lactose, D(+) xylose, dulcitol, myo-inositol, L(−) fructose, D(−) mannitol, D(+) glucose, D(+) arabinose, D(−) arabinose, cellobiose, D(+) maltose, D(+) raffinose, L(+) rhamnose, D(+) melibiose, D(−) ribose, adonitol, D(+) arabitol, L(−) arabitol, D(+) fucose, L(−) fucose, D(−) lyxose, L(+) lyxose, and L(−) lyxose, or amino acids, e.g., glutamine, lysine, arginine, asparagine, aspartic acid, cysteine, glutamic acid, glycine, histidine, leucine, methionine, phenylalanine, proline, serine, threonine, tyrosine, valine, and taurine. Methods and materials for enhancing blood brain barrier penetration are described, e.g., in U.S. Pat. Nos. 4,866,042, 6,294,520 and 6,936,589, each incorporated herein by reference.

In one embodiment the polynucleic acid polymer may be bound to a chemical molecule (e.g., non-peptide or nucleic acid based molecule), such as a drug. The drug may be a small molecule (e.g., having a MW of less than 900 Da).

In one embodiment of the invention, the delivery vehicle may comprise a cell penetrating peptide (CPP). For example, the polynucleic acid polymer may be bound or complexed with a CPP. The skilled person will understand that any suitable CPP may be conjugated with the polynucleic acid polymer to aid delivery of the polynucleic acid polymer to and/or into cells. Such CPPs may be any suitable CPP technology described by Boisguérin et al., Advanced Drug Delivery Reviews (2015), which is herein incorporated by reference. Suitable delivery vehicles for conjugation to the polynucleic acid polymer are also described in Lochmann et al., ((*European Journal of Pharmaceutics and Biopharmaceutics* 58 (2004) 237-251), which is herein incorporated by reference).

The CPP may be an arginine and/or lysine rich peptide, for example, wherein the majority of residues in the peptide are either lysine or arginine. The CPP may comprise a poly-L-lysine (PLL). Alternatively, the CPP may comprise a poly-arginine. Suitable CPPs may be selected from the group comprising Penetratin; R6-Penetratin; Transportan; oligo-argininies; F-3; B-peptide; B-MSP; Pip peptides, such as Pip1, Pip2a, Pip2b, Pip5e, Pip5f, Pip5h, Pip5j; Pip5k, Pip5l, Pip5m, Pip5n, Pip5o, Pip6a, Pip6b, Pip6c, Pip6d, Pip6e, Pip6f, Pip6g, or Pip6h; peptide of sequence PKKKRKV; Penatratin; Lys4; SPACE; Tat; Tat-DRBD (dsRNA-binding domain); (RXR)4; (RFF)3RXB; (KFF)3K; RgF2; T-cell derived CPP; Pep-3; PEGpep-3; MPG-8; MPG-8-Chol; PepFect6; PSRHH; R15; and Chol-R9; or functional variants thereof (e.g., see Boisguérin et al., Advanced Drug Delivery Reviews (2015)).

In one embodiment, the CPP comprises or consists of a Pip peptide. The Pip peptide may be selected from the group comprising Pip1, Pip2a, Pip2b, Pip5e, Pip5f, Pip5h, Pip5j; Pip5k, Pip5l, Pip5m, Pip5n, Pip5o, Pip6a, Pip6b, Pip6c, Pip6d, Pip6e, Pip6f, Pip6g, and Pip6h.

In one embodiment of the invention, the delivery vehicle may comprise a peptide-based nanoparticle (PBN), wherein a plurality of CPPs (for example one or more suitable CPPs discussed herein) form a complex with the polynucleic acid polymer through charge interactions. Such nanoparticles may be between about 50 nm and 250 nm in size. In one embodiment the nanoparticles may be about 70-200 nm in size. In another embodiment the nanoparticles may be about 70-100 nm in size or 125-200 nm in size.

In one embodiment, the polynucleic acid polymer may be complexed with a delivery vehicle, for example by ionic bonding. Alternatively, the polynucleic acid polymer may be covalently bound to the delivery vehicle. Conjugation/binding methods are described in Lochmann et al., ((*European Journal of Pharmaceutics and Biopharmaceutics* 58 (2004) 237-251), which is herein incorporated by reference). For example, a conjugation method may comprise introducing a suitable tether containing a reactive group (e.g., —NH$_2$ or —SH$_2$) to the polynucleic acid polymer and to add the delivery vehicle, such as a peptide, post-synthetically as an active intermediate, followed by carrying out the coupling reaction in aqueous medium. An alternative method may comprise carrying out the conjugation in a linear mode on a single solid-phase support.

The delivery vehicle and polynucleic acid polymer may be thiol and/or maleimide linked, such as thiol-maleimide linked. The conjugation of the polynucleic acid polymer and the delivery vehicle may be by click-chemistry, such as reaction of azido or 2'-O-propyargyl functional groups and alkyne groups on the respective molecules to be conjugated. In one embodiment, the delivery vehicle and polynucleic acid polymer may be linked by a thioether bridge. In another embodiment, the delivery vehicle and polynucleic acid polymer may be linked by a disulphide bridge. The skilled person will readily identify suitable linking groups or reactions for conjugation of polynucleic acid polymer and the delivery vehicle, such as a peptide.

In one embodiment the NSE repressor agent may comprise an SSO of the sequence cuucuaugcagccaaccuguagacu (SSO-NSE3) (SEQ ID NO: 53), or a nucleic acid analogue thereof. In one embodiment the NSE repressor agent may comprise an SSO of the sequence accuuuuucuucuaugcagccaac (SSO-NSE5) (SEQ ID NO: 54), or a nucleic acid analogue thereof. The skilled person will note that NSE3 (cuucuaugcagccaaccuguagacu) (SEQ ID NO: 53) and NSE5 (accuuuuucuucuaugcagccaac) (SEQ ID NO: 54) overlap in sequence. In one embodiment, the NSE repressor agent may comprise an SSO having a sequence of, or within, this overlapping sequence (i.e. accuuuuucuucuaugcagccaaccuguagacu) (SEQ ID NO: 55).

In one embodiment, the NSE repressor or activator agent comprises or consists of any one SSO selected from the group comprising:

```
(SSO A2)
                                    (SEQ ID NO: 18)
aacuuaaagguuauaucuc;

(SSO A4)
                                    (SEQ ID NO: 19)
uauaaauacgaauaaaucga;

(SSO A9)
                                    (SEQ ID NO: 21)
caacacgacauaaccaaa;

(SSO A11)
                                    (SEQ ID NO: 23)
aacauuucuauuuaguuaaaagc;

(SSO A17)
                                    (SEQ ID NO: 26)
uuaguauuccuugacuuua;

(SSO A23)
                                    (SEQ ID NO: 32)
gguaugagaacuauagga;

(SSO A25)
                                    (SEQ ID NO: 34)
gguaauaagugucacaaa;

(SSO A26)
guaucauacauuagaagg;

(SSO B2)
gacugguaaauaauaaacauaauuc;

(SSO B4)
auauauuagagauacaucagcc;

(SSO B11)
ugugggugaccacagcuu;

(SSO AN3)
uuagagaaucauuuuaaauaagac;
and cuguaaaagaaaauaga (PEkr),
or combinations thereof
```

In another embodiment, the NSE activator agent comprises or consists of any one SSO selected from the group comprising:

```
(SSO A2)
                                    (SEQ ID NO: 18)
aacuuaaagguuauaucuc;

(SSO A4)
                                    (SEQ ID NO: 19)
uauaaauacgaauaaaucga;

(SSO A9)
                                    (SEQ ID NO: 21)
caacacgacauaaccaaa;
```

```
(SSO A23)
                                    (SEQ ID NO: 32)
gguaugagaacuauagga;

(SSO A25)
                                    (SEQ ID NO: 34)
gguaauaagugucacaaa;

(SSO A26)
                                    (SEQ ID NO: 35)
guaucauacauuagaagg;

(SSO B11)
                                    (SEQ ID NO: 45)
ugugggugaccacagcuu;
and (SEQ ID NO: 56)
cuguaaaagaaaauaga (PEkr),
or combinations thereof
```

The NSE activator agent may comprise or consist of an SSO of the sequence aacuuaaagguuauaucuc (SSO A2) (SEQ ID NO: 18). The NSE activator agent may comprise or consist of an SSO of the sequence uauaaauacgaauaaaucga (SSO A4) (SEQ ID NO: 19). The NSE activator agent may comprise or consist of an SSO of the sequence caacacgacauaaccaaa (SSO A9) (SEQ ID NO: 21). The NSE activator agent may comprise or consist of an SSO of the sequence gguaugagaacuauagga (SSO A23) (SEQ ID NO: 32). The NSE activator agent may comprise or consist of an SSO of the sequence gguaauaagugucacaaa (SSO A25) (SEQ ID NO: 34). The NSE activator agent may comprise or consist of an SSO of the sequence guaucauacauuagaagg (SSO A26) (SEQ ID NO: 35). The NSE activator agent may comprise or consist of an SSO of the sequence ugugggugaccacagcuu (SSO B11) (SEQ ID NO: 45).

In one embodiment the NSE-activator agent may comprise the SSO PEkr herein described. In one embodiment the NSE-activator agent may comprise an SSO of the sequence CUGUAAAAGAAAAUAGA (PEkr) (SEQ ID NO: 56). PEkr may also be referred to as PEdel and it is understood that these terms are interchangeable.

In one embodiment, the NSE repressor agent comprises or consists of any one SSO selected from the group comprising:

```
(SSO-NSE3)
                                    (SEQ ID NO: 53)
cuucuaugcagccaaccuguagacu;

(SSO-NSE5)
                                    (SEQ ID NO: 54)
accuuuuucuucuaugcagccaac;

(SSO A11)
                                    (SEQ ID NO: 23)
aacauuucuauuuaguuaaaagc;

(SSO A17)
                                    (SEQ ID NO: 26)
uuaguauuccuugacuuua;

(SSO B2)
                                    (SEQ ID NO: 37)
gacugguaaauaauaaacauaauuc;

(SSO B4)
                                    (SEQ ID NO: 39)
auauauuagagauacaucagcc;
and
```

-continued (SSO AN3)

(SEQ ID NO: 51)
uuagagaaucauuuuaaauaagac,
or combinations thereof

The NSE repressor agent may comprise or consist of an SSO of the sequence cuucuaugcagccaaccuguagacu (SSO-NSE3) (SEQ ID NO: 53). The NSE repressor agent may comprise or consist of an SSO of the sequence accuuuuucuucuaugcagccaac (SSO-NSE5) (SEQ ID NO: 54). The NSE repressor agent may comprise or consist of an SSO of the sequence aacauuucuauuuaguuaaaagc (SSO A11) (SEQ ID NO: 23). The NSE repressor agent may comprise or consist of an SSO of the sequence uuaguauuccuugacuuua (SSO A17) (SEQ ID NO: 26). The NSE repressor agent may comprise or consist of an SSO of the sequence gacugguaaauaauaaacauaauuc (SSO B2) (SEQ ID NO: 37). The NSE repressor agent may comprise or consist of an SSO of the sequence auauauuagagauacaucagcc (SSO B4) (SEQ ID NO: 39). The NSE repressor agent may comprise or consist of an SSO of the sequence uuagagaaucauuuuaaauaagac (SSO AN3) (SEQ ID NO: 51).

In one embodiment the NSE repressor agent, such as an SSO, may be arranged to bind to guanine variant residue at rs4988000.

The skilled person will understand that combinations of two or more SSOs described herein may be provided and/or used for treatment. For example, combinations of two, three, four, five or more NSE repressor agents may be provided or combinations of two, three, four, five or more NSE activating agents may be provided.

Where reference is made to reducing NSE inclusion in the mature RNA, the reduction may be complete, e.g., 100%, or may be partial. The reduction may be clinically significant. The reduction/correction may be relative to the level of NSE inclusion in the subject without treatment, or relative to the amount of NSE inclusion in a population of similar subjects. The reduction/correction may be at least 10% less NSE inclusion relative to the average subject, or the subject prior to treatment. The reduction may be at least 20% less NSE inclusion relative to an average subject, or the subject prior to treatment. The reduction may be at least 40% less NSE inclusion relative to an average subject, or the subject prior to treatment. The reduction may be at least 50% less NSE inclusion relative to an average subject, or the subject prior to treatment. The reduction may be at least 60% less NSE inclusion relative to an average subject, or the subject prior to treatment. The reduction may be at least 80% less NSE inclusion relative to an average subject, or the subject prior to treatment. The reduction may be at least 90% less NSE inclusion relative to an average subject, or the subject prior to treatment.

Where reference is made to increasing active-ATM protein levels, the increase may be clinically significant. The increase may be relative to the level of active-ATM protein in the subject without treatment, or relative to the amount of active-ATM protein in a population of similar subjects. The increase may be at least 10% more active-ATM protein relative to the average subject, or the subject prior to treatment. The increase may be at least 20% more active-ATM protein relative to the average subject, or the subject prior to treatment. The increase may be at least 40% more active-ATM protein relative to the average subject, or the subject prior to treatment. The increase may be at least 50% more active-ATM protein relative to the average subject, or the subject prior to treatment. The increase may be at least 80% more active-ATM protein relative to the average subject, or the subject prior to treatment. The increase may be at least 100% more active-ATM protein relative to the average subject, or the subject prior to treatment. The increase may be at least 200% more active-ATM protein relative to the average subject, or the subject prior to treatment. The increase may be at least 500% more active-ATM protein relative to the average subject, or the subject prior to treatment.

The terms active-ATM and functional-ATM may be used interchangeably herein.

According to another aspect of the invention, there is provided use of rs609261 genotyping to predict a subject response to therapy for conditions associated with ATM deregulation.

The conditions associated with ATM deregulation may comprise A-T or cancer.

In one embodiment, the presence of an rs609261 cytosine residue is associated with a higher NSE activation, less efficient response of ATM to DNA double-strand break signaling, a higher cancer risk and lower survival relative to non-cytosine residue at the same position.

According to another aspect of the invention, there is provided a composition comprising the NSE repressor agent of the invention herein.

According to another aspect of the invention, there is provided a composition comprising the NSE activator agent of the invention herein.

In one embodiment, the composition is a pharmaceutically acceptable formulation.

The composition may comprise at least one other biologically active molecule in addition to the polynucleic acid polymer. The biologically active molecule may be drug or a pro-drug. The biologically active molecule may comprise nucleic acid or amino acid. The biologically active molecule may comprise a small molecule (e.g., a molecule of <900 Daltons).

In some embodiments, pharmaceutical formulations described herein are administered to a subject by an enteral administration route, by a parenteral administration route, or by a topical administration route. In some cases, pharmaceutical formulations described herein are administered to a subject by an enteral administration route. In other cases, pharmaceutical formulations described herein are administered to a subject by a parenteral administration route. In additional cases, pharmaceutical formulations described herein are administered to a subject by a topical administration route.

Illustrative administration routes include, but are not limited to, parenteral (e.g., intravenous, subcutaneous, intramuscular, intra-arterial, intracranial, intracerebral, intracerebroventricular, intrathecal, or intravitreal), oral, intranasal, buccal, topical, rectal, transmucosal, or transdermal administration routes. In some instances, the pharmaceutical composition describe herein is formulated for parenteral (e.g., intravenous, subcutaneous, intramuscular, intra-arterial, intracranial, intracerebral, intracerebroventricular, intrathecal, or intravitreal) administration. In other instances, the pharmaceutical composition describe herein is formulated for oral administration. In still other instances, the pharmaceutical composition describe herein is formulated for intranasal administration.

Pharmaceutical formulations described herein may include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical formulations may include a carrier or carrier materials which may include any commonly used excipients in pharmaceutics and should be selected on the basis of compatibility with the composition disclosed herein, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. Pharmaceutically compatible carrier materials may include, but are not limited to, acacia, gelatin, colloidal silicon dioxide, calcium glycerophosphate, calcium lactate, maltodextrin, glycerin, magnesium silicate, polyvinylpyrrolidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. Liposomes can include sterically stabilized liposomes, e.g., liposomes comprising one or more specialized lipids. These specialized lipids can result in liposomes with enhanced circulation lifetimes. Sometimes, a sterically stabilized liposome can comprise one or more glycolipids or is derivatized with one or more hydrophilic polymers, such as a polyethylene glycol (PEG) moiety. See, e.g., *Remington: The Science and Practice of Pharmacy*, Nineteenth Ed (Easton, Pa.: Mack Publishing Company, 1995); Hoover, John E., Remington's *Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999).

According to another aspect of the invention, there is provided a method of treatment or prevention of functional-ATM protein deficiency in a subject, the method comprising identifying the presence of a non-thymine variant residue rs609261 located at position −3 relative to the 3' splice site of NSE (cryptic exon in ATM intron 28) of the human genome, wherein the presence of a non-thymine variant residue rs609261 indicates that the subject has, or is susceptible to, functional-ATM protein deficiency, and administration of an agent to the subject, which is arranged to replace the non-thymine variant residue rs609261 with a thymine residue.

According to another aspect of the invention, there is provided a method of treatment or prevention of functional-ATM protein deficiency in a subject, the method comprising replacing a non-thymine variant residue rs609261 located at position −3 relative to the 3' splice site of NSE (cryptic exon in ATM intron 28) of the human genome with a thymine residue.

In one embodiment, replacing the non-thymine variant residue rs609261 may comprise administration of an agent to the subject, which is arranged to replace the non-thymine variant residue rs609261 with a thymine residue.

The agent for replacement of the non-thymine residue may be a genomic editing molecule, such as CRISPR-Cas9, or a functional equivalent thereof, together with an appropriate RNA molecule arranged to target rs609261.

According to another aspect of the invention, there is provided a method of treatment or prevention of functional-ATM protein deficiency in a subject, the method comprising identifying the presence of a guanine variant residue at rs4988000 of the human genome, wherein the presence of a guanine variant residue at rs4988000 indicates that the subject has, or is susceptible to, functional-ATM protein deficiency, and administration of an agent to the subject, which is arranged to replace the guanine variant residue at rs4988000 with adenine.

According to another aspect of the invention, there is provided a method of treatment or prevention of functional-ATM protein deficiency in a subject, the method comprising replacing a guanine variant residue at rs4988000 of the human genome with an adenine residue.

In one embodiment, replacing the guanine variant residue at rs4988000 may comprise administration of an agent to the subject, which is arranged to replace the guanine variant residue at rs4988000 with an adenine residue.

The agent for replacement of the guanine residue may be a genomic editing molecule, such as CRISPR-Cas9, or a functional equivalent thereof, together with an appropriate RNA molecule arranged to target rs4988000.

According to a first aspect of the invention, there is provided a method of screening a subject or a population of subjects for susceptibility to functional-ATM protein deficiency, wherein the screening comprises determining the presence of a guanine variant residue at rs4988000 of the human genome, wherein the presence of a guanine variant residue at rs4988000 indicates that the subject (or group of subjects) has, or is susceptible to, functional-ATM protein deficiency.

According to another aspect of the invention, there is provided a method of selecting a subject or a population of subjects for treatment or prophylaxis, wherein the subject is susceptible to functional-ATM protein deficiency, the method comprising determining the presence of a guanine variant residue at rs4988000 of the human genome, wherein the presence of a guanine variant residue at rs4988000 indicates that the subject has, or is susceptible to, functional-ATM protein deficiency, and selecting such subject for treatment with an agent arranged to increase functional-ATM levels in the subject.

According to another aspect of the invention, there is provided a method of treatment or prevention of functional-ATM protein deficiency in a subject, the method comprising identifying the presence of a guanine variant residue at rs4988000 of the human genome, wherein the presence of a guanine variant residue at rs4988000 indicates that the subject has, or is susceptible to, functional-ATM protein deficiency, and administration of an agent to the subject, which is arranged to increase functional-ATM levels.

The methods of the invention herein may comprise blocking a guanine variant residue at rs4988000, for example using an SSO.

PE contains a natural DNA variant rs4988000 (G/A), which also influences NSE recognition (FIG. 4H). Transfections of C and T minigenes systematically mutated at rs4988000 revealed that the rare A allele decreased NSE inclusion on each pre-mRNA, both in U2AF35- and mock-depleted cells. Therefore, replacement of the guanine residue with adenine will decrease NSE inclusion, and increase the level of functional ATM-protein.

The highest NSE inclusion is produced by the haplotype that is most frequent in Caucasians (CG), followed by haplotypes CA>TG>TA (referring tors609261 and rs4988000 respectively). Therefore, the methods and compositions of the invention may be used in combination (concurrently or sequentially) to modify a CG haplotype to CA, TG, or TA. In one embodiment, the methods and compositions of the invention may be used to modify a CG haplotype to TA. In one embodiment, the methods and compositions of the invention may be used to modify a CA haplotype to TG or TA. In one embodiment, the methods and compositions of the invention may be used to modify a CA haplotype to TA. In one embodiment, the methods and compositions of the invention may be used to modify a TG haplotype to TA.

The methods and compositions of the invention may also be used in combination (concurrently or sequentially) to identify a CG haplotype in a subject, and optionally treat or select the patient according to the invention. The methods and compositions of the invention may also be used in combination (concurrently or sequentially) to identify a CA haplotype in a subject, and optionally treat or select the patient according to the invention. The methods and compositions of the invention may also be used in combination (concurrently or sequentially) to identify a TG haplotype in a subject, and optionally treat or select the patient according to the invention.

According to another aspect of the invention, there is provided a method of modifying regulation of NSE inclusion in a mature RNA transcript, the method comprising the insertion or deletion of one or more splicing regulatory motifs upstream or downstream of the NSEs that compete with the NSE for spliceosomal components, said regulatory motifs comprising cryptic splice sites or pseudo-exons.

According to another aspect of the invention, there is provided a method of modifying regulation of a functional protein expression, wherein the functional protein expression is regulated by NSE inclusion in a mature RNA transcript of the gene encoding protein, the method comprising the insertion or deletion of one or more splicing regulatory motifs upstream or downstream of the NSE that compete with the NSE for spliceosomal components, said regulatory motifs comprising cryptic splice sites or pseudo-exons.

In one embodiment, the insertion or deletion of one or more splicing regulatory motifs is in genomic DNA of ATM intron 28.

The insertion of one or more splicing regulatory motifs may cause a reduction in NSE inclusion in the mature RNA transcript. The deletion of one or more splicing regulatory motifs may cause an increase in NSE inclusion in the mature RNA transcript.

The insertion or deletion of one or more splicing regulatory motifs may comprise the use of genome editing technology, such as CRISPR-Cas9. CRISPR-Cas9 may be provided with an appropriate targeting RNA molecule.

The subject or cells that are treated or screened according to the invention may be mammalian. In one embodiment, the subject is a human. In one embodiment, the cells are human.

Kits and articles of manufacture are provided herein for use with one or more methods described herein. The kits can contain one or more of the polynucleic acid polymers described herein.

According to another aspect of the invention, there is provided a kit comprising one or more oligonucleotide probes for identifying rs609261 and/or rs4988000 variants.

The skilled person will be familiar with techniques for probing the presence or absence of genetic sequence features. For example, the oligonucleotide probes may comprise primers for use in PCR amplifying a region of a nucleic acid comprising rs609261 and/or rs4988000. In another embodiment the oligonucleotide probes may directly bind rs609261 or rs4988000, wherein the binding may be detectable. The binding of the probe may be detectable for example using SERS or SERRS technology.

The kits can also include a carrier, package, or container that is compartmentalized to receive one or more containers such as vials, tubes, and the like, each of the container(s) comprising one of the separate elements, such as the polynucleic acid polymers and reagents, to be used in a method described herein. Suitable containers include, for example, bottles, vials, syringes, and test tubes. The containers can be formed from a variety of materials such as glass or plastic.

The articles of manufacture provided herein contain packaging materials. Examples of pharmaceutical packaging materials include, but are not limited to, bottles, tubes, bags, containers, bottles, and any packaging material suitable for a selected formulation and intended mode of administration and treatment.

A kit typically includes labels listing contents and/or instructions for use, and package inserts with instructions for use. A set of instructions will also typically be included.

According to another aspect of the invention, there is provided a vector comprising the polynucleic acid polymer of the invention.

The vector may comprise a viral vector. The viral vector may comprise adeno-associated viral vector. The vector may comprise any virus that targets the polynucleic acid polymer to malignant cells or specific cell type.

Indications

In some instances, compositions and methods described herein are used to treat a genetic disorder or condition such as a hereditary disease. Compositions and methods described herein can be used to treat a genetic disorder or condition such as a hereditary disease that is characterized by an impaired production of a protein. Compositions and methods described herein can be used to treat a genetic disorder or condition such as a hereditary disease that is characterized by a defective splicing.

Compositions and methods described herein can also be used to treat a genetic disorder or condition such as an autosomal dominant disorder, an autosomal recessive disorder, X-linked dominant disorder, X-linked recessive disorder, Y-linked disorder, mitochondrial disease, or multifactorial or polygenic disorder. Compositions and methods described herein can be used to treat an autosomal dominant disorder, an autosomal recessive disorder, X-linked dominant disorder, X-linked recessive disorder, Y-linked disorder, mitochondrial disease, or multifactorial or polygenic disorder, in which the disorder or condition is characterized by an impaired production of a protein. Compositions and methods described herein can also be used to treat an autosomal dominant disorder, an autosomal recessive disorder, X-linked dominant disorder, X-linked recessive disorder, Y-linked disorder, mitochondrial disease, or multifactorial or polygenic disorder, in which the disorder or condition is characterized by a defective splicing.

The condition associated with deregulated ATM expression may comprise cancer. Compositions and methods described herein can be used to treat cancer. In one embodiment the cancer comprises breast cancer. Cancer can be a solid tumor or a hematologic malignancy. A solid tumor can be a sarcoma or a carcinoma. Sarcoma can be a cancer of bone, cartilage, fat muscle, vascular or hematopoietic tissues. Exemplary sarcoma can include alveolar rhabdomyosarcoma, alveolar soft part sarcoma, ameloblastoma, angiosarcoma, chondrosarcoma, chordoma, clear cell sarcoma of soft tissue, dedifferentiated liposarcoma, desmoid, desmoplastic small round cell tumor, embryonal rhabdomyosarcoma, epithelioid fibrosarcoma, epithelioid hemangioendothelioma, epithelioid sarcoma, esthesioneuroblastoma, Ewing sarcoma, extrarenal rhabdoid tumor, extraskeletal myxoid chondrosarcoma, extraskeletal osteosarcoma, fibrosarcoma, giant cell tumor, hemangiopericytoma, infantile fibrosarcoma, inflammatory myofibroblastic tumor, Kaposi sarcoma, leiomyosarcoma of bone, liposarcoma, liposarcoma of bone, malignant fibrous histiocytoma (MFH), malignant fibrous histiocytoma (MFH) of bone, malignant mesenchymoma, malignant peripheral nerve sheath tumor, mesenchymal chondrosarcoma, myxofibrosarcoma, myxoid liposarcoma, myxoinflammatory fibroblastic sarcoma, neoplasms with perivascular epitheioid cell differentiation, osteosarcoma, parosteal osteosarcoma, neoplasm with perivascular epitheioid cell differentiation, periosteal osteosarcoma, pleomorphic liposarcoma, pleomorphic rhabdomyosarcoma, PNET/extraskeletal Ewing tumor, rhabdomyosarcoma, round cell liposarcoma, small cell osteosarcoma, solitary fibrous tumor, synovial sarcoma, telangiectatic osteosarcoma.

Carcinoma can be a cancer developed from epithelial cells. Exemplary carcinoma can include adenocarcinoma, squamous cell carcinoma, adenosquamous carcinoma, anaplastic carcinoma, large cell carcinoma, small cell carcinoma, anal cancer, appendix cancer, bile duct cancer (i.e., cholangiocarcinoma), bladder cancer, brain tumor, breast cancer, cervical cancer, colon cancer, cancer of Unknown Primary (CUP), esophageal cancer, eye cancer, fallopian tube cancer, gastroenterological cancer, kidney cancer, liver cancer, lung cancer, medulloblastoma, melanoma, oral cancer, ovarian cancer, pancreatic cancer, parathyroid disease, penile cancer, pituitary tumor, prostate cancer, rectal cancer, skin cancer, stomach cancer, testicular cancer, throat cancer, thyroid cancer, uterine cancer, vaginal cancer, or vulvar cancer. Hematologic malignancy is a malignancy of the blood system and can include T-cell based and B-cell based malignancies. Exemplary hematologic malignancy can include myeloid leukemia, myeloproliferative neoplasias, peripheral T-cell lymphoma not otherwise specified (PTCL-NOS), anaplastic large cell lymphoma, angioimmunoblastic lymphoma, cutaneous T-cell lymphoma, adult T-cell leukemia/lymphoma (ATLL), blastic NK-cell lymphoma, enteropathy-type T-cell lymphoma, hematosplenic gamma-delta T-cell lymphoma, lymphoblastic lymphoma, nasal NK/T-cell lymphomas, treatment-related T-cell lymphomas, chronic lymphocytic leukemia (CLL), small lymphocytic lymphoma (SLL), high risk CLL, non-CLL/SLL lymphoma, prolymphocytic leukemia (PLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis.

According to another aspect of the invention, there is provided a method of a treatment or prevention of a disease pathology caused by an NSE inclusion in a pre-mRNA gene transcript comprising providing an agent arranged to bind to a cryptic splice site of a pseudoexon present on the pre-mRNA gene transcript, wherein the cryptic splice site is capable of regulating inclusion of a nonsense-mediated RNA decay switch exon (NSE) into a mature RNA transcript of the gene.

Wherein the binding of the agent to the cryptic splice site of the pseudoexon present on the pre-mRNA gene transcript reduces the NSE inclusion.

The method may comprise a step of determining if a disease pathology is caused by an NSE inclusion in a gene transcript prior to treatment.

The skilled person will understand that optional features of one embodiment or aspect of the invention may be applicable, where appropriate, to other embodiments or aspects of the invention.

EXAMPLES

Embodiments of the invention will now be described in more detail, by way of example only, with reference to the accompanying figures. These examples are provided for illustrative purposes only and not to limit the scope of the claims provided herein.

Abbreviations

NSE nonsense-mediated RNA decay switch exon in ATM intron 28
PE a 24-nt pseudoexon located 3' of NSE in ATM intron 28
NMD nonsense-mediated RNA decay
A-T ataxia-telangiectasia
ATM gene deficient in ataxia-telangiectasia
SSO splice-switching oligonucleotide
DSB double-strand DNA break
DDR DNA damage response
MIR mammalian-wide interspersed repeat
BPS branch point sequence
PPT polypyrimidine tract
IR ionizing radiation
U2AF auxiliary factor of U2 small nuclear ribonucleoprotein
U2AF35 a 35-kD subunit of U2AF encoded by U2AF1
U2AF65 a 65-kD subunit of U2AF encoded by U2AF2
snRNA small nuclear RNAs Example 1

Summary

Phenotypic diversity and susceptibility to genetic disease is influenced by natural intronic variants, but their interactions with RNA-binding proteins are largely unknown. Here a single-nucleotide polymorphism in a detained ATM intron was shown to gain functionality in cells lacking the auxiliary factor of U2 small nuclear ribonucloprotein (U2AF). Each U2AF subunit was required for repression of a nonsense-mediated RNA decay switch exon (NSE) in ATM intron 28. NSE was activated to a greater degree in the presence of cytosine than thymine at rs609261 located at position −3 relative to the NSE 3' splice site. The cytosine allele, which is predominant in Caucasians, resulted in a more efficient NSE-mediated inhibition of ATM expression than thymine, the principal allele in Asian populations. NSE activation was deregulated in leukemic cells and was influenced by the amino acid identity at U2AF35 residue 34. Exploiting competition between NSE and a downstream pseudoexon, splice-switching oligonucleotides (SSOs) that repress or activate NSE to modulate ATM expression were identified. Using RNA-Seq, U2AF-regulated exon usage in the ATM signaling pathway was shown to be centered on the MRN/ATM-CHEK2-CDC25-cdc2/cyclin B axis and that U2AF preferentially controls RNA processing of transcripts involved in cancer-associated fusions and chromosomal translocations. These results reveal important links between 3' splice-site control and ATM-dependent response to double strand DNA breaks, illustrate functional plasticity of intronic variants in response to RNA-binding factors, demonstrate versatility of SSOs to modify gene expression by targeting pseudo-splice sites in introns and may explain ethnic differences in cancer risk and survival.

Introduction

Here, U2AF was shown to repress a nonsense-mediated decay (NMD) switch exon (NSE) in the ATM gene (ataxia-telangiectasia, A-T, mutated) and other proteins involved in 3' ss recognition that regulate NSE inclusion in mature transcripts were identified. The extent to which this event limits ATM expression depends on a common C/T variant rs609261 located in the NSE 3'ss consensus deep in intron 28. Also identified are intronic cis-elements that control NSE inclusion in mature transcripts and splice-switching oligonucleotides (SSOs) that modulate NSE activation by targeting a competing pseudoexon in the same intron. Using RNA-Seq, it was next shown that the U2AF-mediatedregulation of DNA damage response (DDR) pathway is centered on the ATM-CHEK2-CDC25-cdc2/cyclin B axis, suggesting that it has coevolved with cellular responses to double-strand DNA breaks (DSBs). Finally, a preferential involvement of U2AF-regulated transcripts is demonstrated in cancer-associated gene fusions and chromosome translocations.

Results

Identification of a U2AF-Repressed Cryptic Exon in ATM

It has been recently shown that depletion of each U2AF subunit resulted in down- and upregulation of a large number of exons that were predominantly alternatively spliced. When inspecting global RNA processing changes in cells depleted of U2AF35, an unexpectedly strong activation of a cryptic, 29-nt ATM exon that was not annotated by RefSeq (termed NSE, FIG. 1A) was found. The NSE activation was observed also in cells individually depleted of each U2AF35 isoform with isoform-specific small interfering RNAs (siRNAs) and with SSOs targeting 3'ss of alternatively spliced U2AF1 exons Ab and 3, which encode isoform U2AF35b and U2AF35a, respectively (FIG. 1A). Validation of RNA-Seq data using RT-PCR showed that NSE was present in ~10-20% of polyadenylated transcripts in untreated HEK293 cells, similar to levels observed in lymphoblastoid cell lines. The NSE inclusion levels increased to ~75% in cultures depleted of ~90% U2AF35 and to ~50% in cells depleted of ~75% U2AF65 (FIG. 1B), were siRNA dose-dependent and inversely correlated with the amount of available U2AF heterodimers (FIG. 1C), consistent with the requirement of each U2AF subunit for NSE repression. Inspection of RNA-Seq data revealed retention of intronic sequences surrounding NSE (FIG. 1A), suggesting that intron 28 is 'detained' and could be spliced post-transcriptionally. Retention levels of intron 28 were affected neither by SSO- nor siRNA-mediated depletion of U2AF35 (FIG. 1A) and no other cryptic exon in this gene was activated to the same extent as NSE. Thus, NSE plays a key role in the exon-centric regulation of ATM expression by U2AF.

NSE Activation and ATM Expression is Modified by Rs609261

Examination of genomic sequences surrounding NSE revealed that position −3 relative to the NSE 3'ss is polymorphic (r5609261, FIG. 2A) in which thymine (T) is predominant in African and Asian populations and cytosine (C) in Caucasians (FIG. 2A). The base identity at this position is important for universal exon recognition, with a CAG>TAG>AAG>GAG hierarchy of exon inclusion levels both at authentic and U2AF35-dependent 3'ss. To confirm that the NSE usage is allele-specific, splicing of two reporter constructs that contained C or T at this position was examined following transient transfections into human embryonic kidney (HEK) 293 cells (FIG. 2B). The T construct yielded lower NSE inclusion than the C reporter, both in untreated cells and cells individually depleted of each U2AF subunit (FIG. 2C).

To test whether the allele-specific NSE usage results in differential protein expression in cells lacking U2AF35, DNA was first sequenced from available cell lines across rs609261 to obtain transfectable cells homozygous for each allele. HEK293 cells were found to be homozygous for the C allele and HeLa cells were homozygous for the T allele (FIG. 2D). Immunoblots from the U2AF35-depleted cells and untreated controls confirmed efficient depletion in each cell line and a greater U2AF-mediated decline of ATM expression in the presence of the C allele than the T allele (FIG. 2E,F). Depletion of UPF1, a key component of the NMD pathway, revealed a dose-dependent increase of NSE inclusion in ATM mature RNAs (FIG. 2G). No signal from a putative truncated ATM was detected on immunoblots from depleted cells.

Because U2AF-repressed and -activated exons show preferential responses to U2AF-related proteins, HEK293 cells were depleted of PUF60 and CAPERa, and several heterogeneous nuclear RNPs, including hnRNP A1. PUF60 interacts with uridine-rich motifs at 3'ss and hnRNP A1 forms a ternary complex with the U2AF heterodimer on AG-containing U-rich RNAs. Depletion of either PUF60 or hnRNP A1 increased NSE inclusion (FIG. 2H) while PUF60 overexpression led to NSE skipping (FIG. 2I). Thus, the rs609261- and population-dependent NSE activation deep in ATM intron 28 is regulated by U2AF, PUF60 and hnRNP A1, demonstrating how functionality of a common intronic polymorphism varies with cellular levels of RNA-binding proteins that facilitate 3'ss recognition.

NSE Inhibition by SSOs Promotes ATM Expression

To test if NSE activation in cells lacking U2AF can be repressed to restore ATM expression, the C-allele reporter construct was individually cotransfected with SSOs targeting each NSE splice site (FIG. 1A). SSOs were modified at each phosphorothioate linkage and 2'-O-methyl ribose and were designed to avoid the PPT of NSE, stable Mfold-predicted stems and rs609261. Each SSO diminished NSE inclusion in a dose-dependent manner both in exogenous (FIG. 3A) and endogenous (FIG. 3B) transcripts and the SSO targeting the NSE 3'ss was more efficient than the SSO bridging its 5'ss at the same concentrations.

Figure 8:
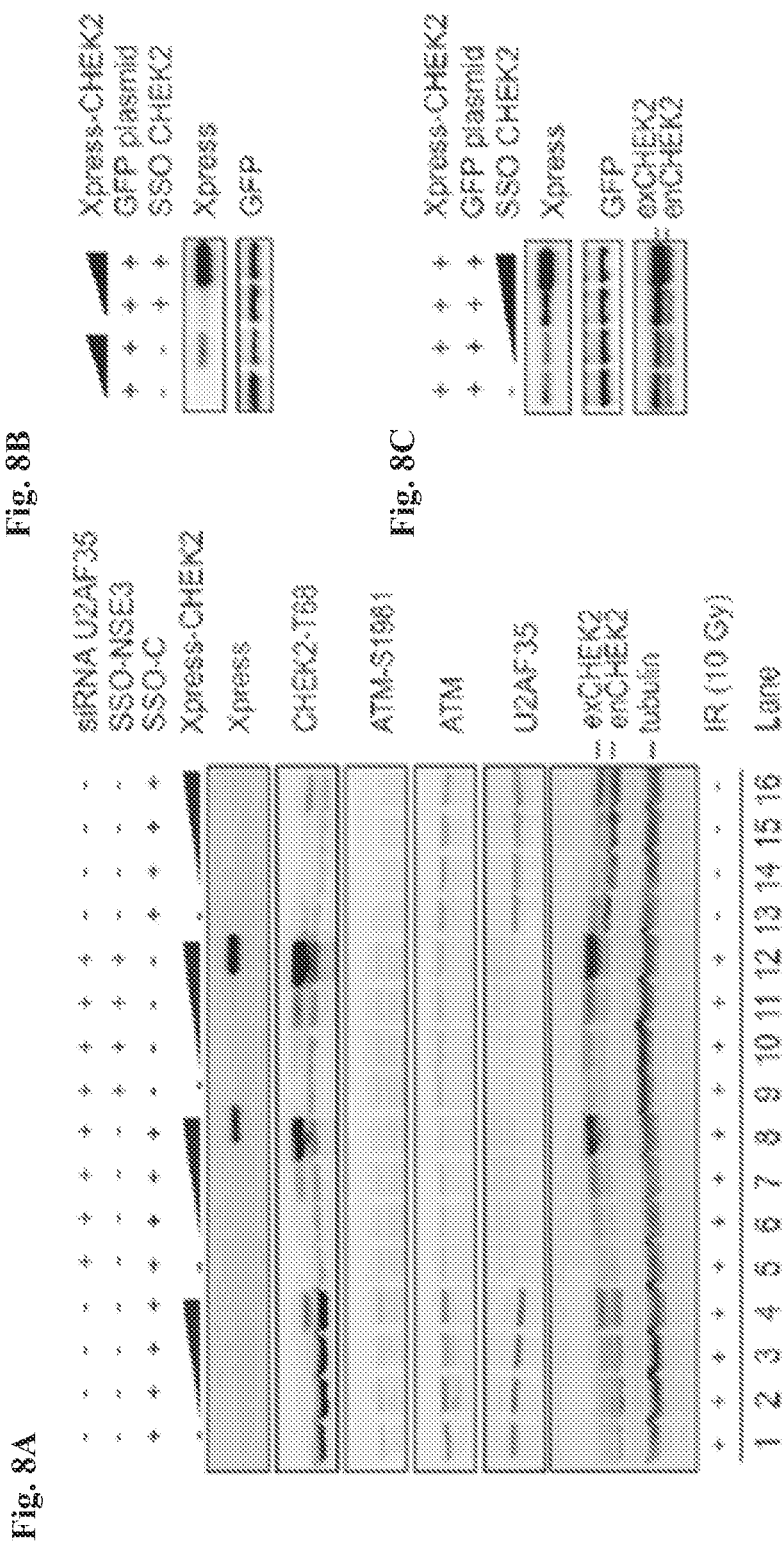
FIG. 8A-FIG. 8C show SSO-mediated NSE repression enhances ATM expression.

Whether the NSE 3'ss SSO can increase ATM protein expression and activation in cells exposed to ionizing radiation (IR) was next examined. The low ATM expression in cells lacking U2AF35 was partially rescued by this SSO, both in unexposed and IR-exposed cells (lanes 1 vs 2 and 5 vs 6, FIG. 3C, lanes 5-8 vs 9-12, FIG. 8A) and the increase was dose-dependent (FIG. 4D). Following IR, activated ATM autophosphorylated at S1981 showed reduced signal in depleted cells as compared to untreated cells (lane 6 vs 8, FIG. 3C, and lanes 1-4 vs 5-8, FIG. 8A). Exposure to the NSE 3'ss SSO slightly increased also activated ATM (lanes 5-8 vs 9-12, FIG. 8A, lane 5 vs 6, FIG. 3C). To begin to explore putative effects of SSO-mediated NSE repression on ATM signaling, wild type CHEK2 was also overexpressed in (mock) irradiated cells (mock) depleted of U2AF (FIG. 8A). CHEK2 is a serine/threonine kinase phosphorylated by ATM at T68 in response to DNA double-strand breaks (DSBs). However, cells lacking U2AF had markedly lower levels of endogenous CHEK2 compared to controls, which did not appear to be altered by the NSE 3'ss SSO (lanes 1-4 vs 5-8 vs 9-12) whereas exogenous CHEK2 was increased in depleted cells both in IR-exposed and -unexposed cells (lanes 1-4 vs 5-8, see also FIG. 5 and FIG. 8B,C further below).

Taken together, NSE activation was efficiently inhibited by SSOs that block access to NSE splice sites and do not support RNase H cleavage. The more efficient SSO partially rescued the NSE-mediated inhibition of ATM.

Activation of a NMD Switch Exon is Influenced by a Downstream Pseudoexon

Figures 4A, 4B:
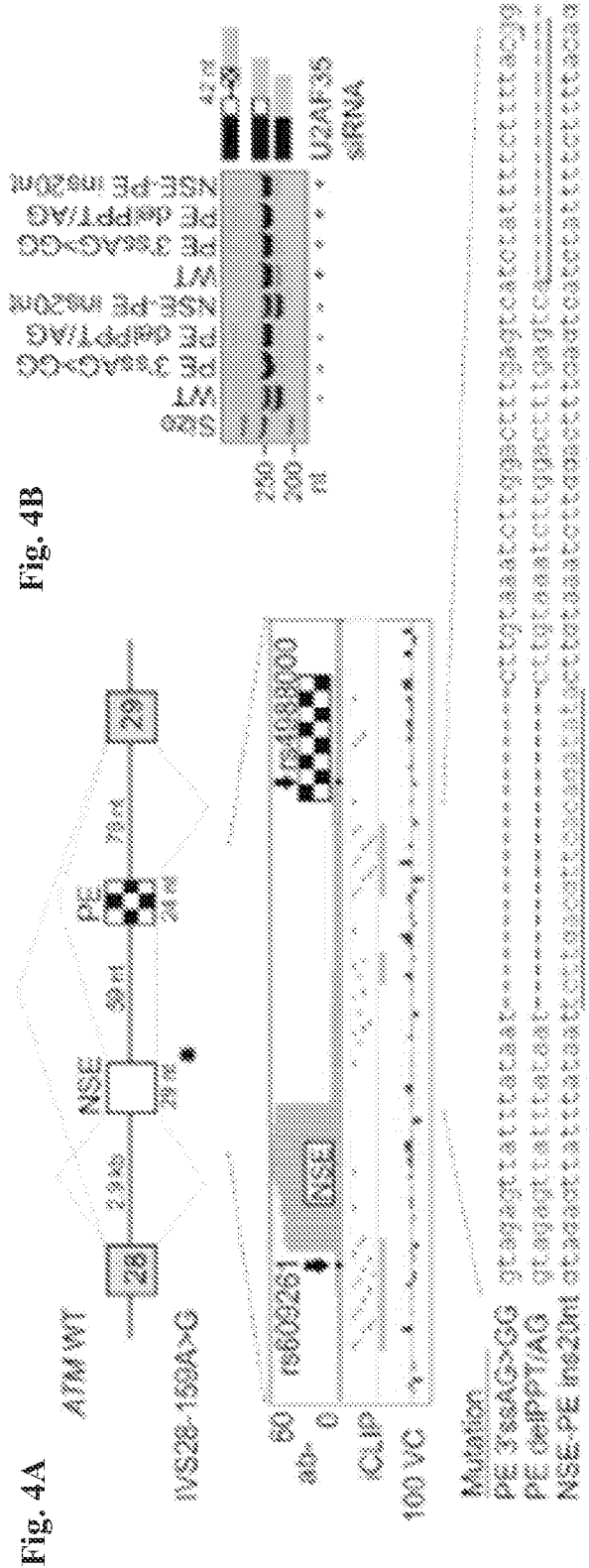

To identify intronic regulatory cis-elements that control NSE inclusion in mature transcripts, a previously reported A-T mutation IVS28-159A>G was utilized. This mutation was observed to activate the NSE 3'ss while repressing its 5'ss and promoting a downstream 5'ss instead, introducing a 112-nt cryptic exon in the mRNA. There is a strong 3'ss consensus preceded by optimal BPS/PPT motifs observed within this exon, which may bind U2AF and activate a smaller, 24-nt pseudoexon (termed PE; FIG. 4A). Examination of published RNA crosslinking/immunoprecipitation data in ATM showed U2AF65 binding upstream and downstream of NSE and upstream of PE, suggesting that NSE activation may be controlled by competition between partially productive spliceosomes assembled at the PE 3'ss and the NSE 3'ss. The two 3'ss are conserved in mammals but are separated by a distance smaller than the minimal size of human introns, sterically preventing simultaneous recognition of NSE and PE (FIG. 4A). In agreement with this hypothesis, deletion of the PE PPT/3'ss introduced in the C minigene, which should alleviate NSE repression through diminished U2AF binding to PE, increased NSE inclusion (FIG. 4B). This deletion also brought about retention of the intron that separates NSE and PE, mimicking the splicing pattern of the A-T mutation IVS28-159A>G. Increasing the intron length from 59 to 79 nt, thereby overcoming a steric hindrance imposed by the insufficient distance between the two pseudo-3'ss, also improved NSE inclusion and diminished the intron retention (FIG. 4B).

Figure 21:
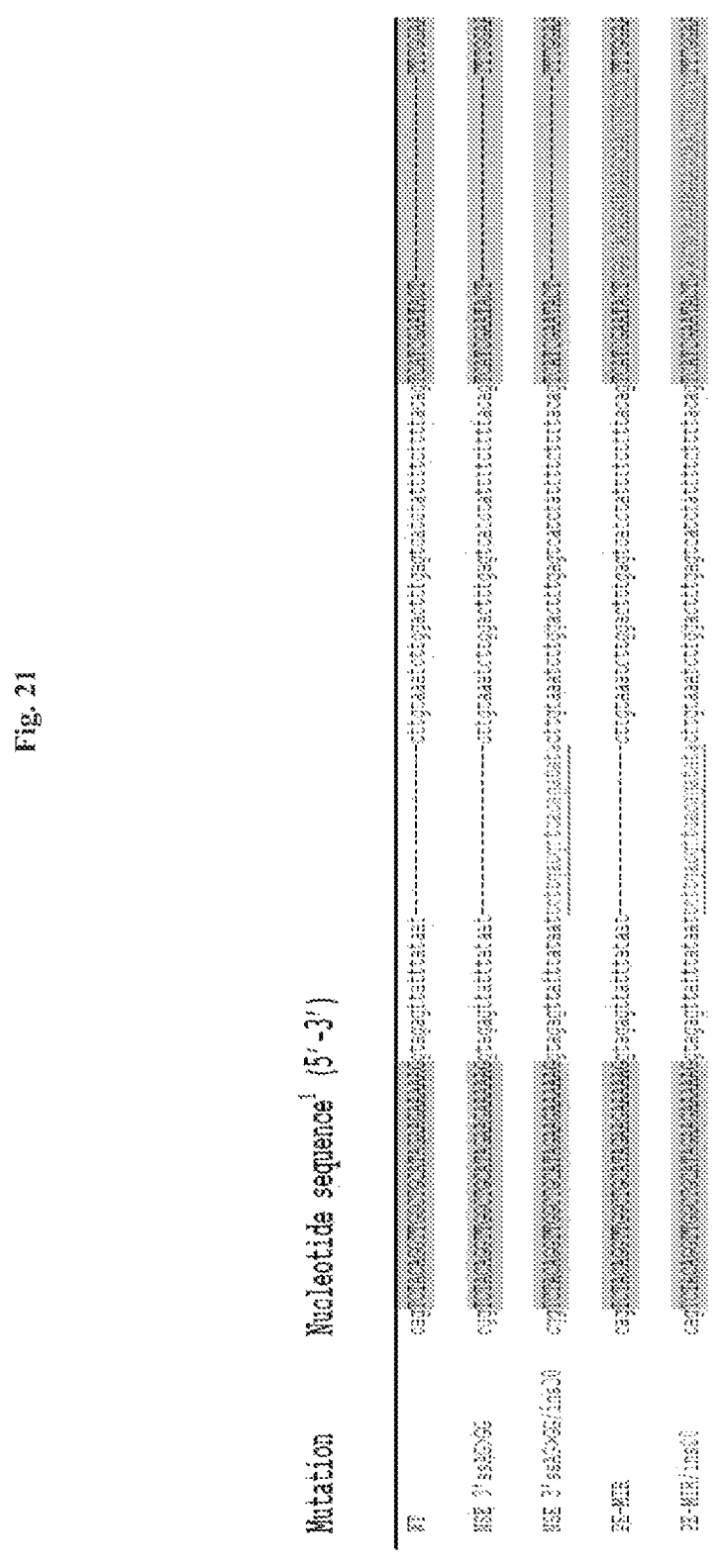

To test if NSE inactivation can influence PE inclusion in mRNA, the NSE 3'ss was first eliminated. This mutation activated a cryptic 3'ss 7-nt downstream of the authentic NSE 3'ss (lanes 1, 2 and 6, 7, FIG. 4C, FIG. 21). This cryptic 3'ss showed a diminished requirement for U2AF. Because extending the intron length between NSE and PE on this background failed to activate PE (FIG. 4C, lanes 3 and 8) and PE lacks exonic splicing enhancers and has a suboptimal BPS (FIG. 22), a 24-nt stem loop derived from a mammalian-wide interspersed repeat (MIR) was inserted in the middle of PE. This MIR hairpin acts as a nearly universal exon definition module through an exposed splicing enhancer in a terminal RNA triloop. The enlarged PE was strongly activated in mock-depleted cells, but was outcompeted by NSE in cells lacking U2AF35 (lanes 4 and 9), indicating that NSE inclusion is more dependent on U2AF35 than PE. The construct containing both the MIR insertion in PE and the extended intron finally generated mRNAs containing both NSE and PE (lanes 5 and 10).

Intronic SSOs Targeting Competing Pseudoexons to Modulate Gene Expression

Next, the MIR reporter was employed to test the impact of NSE and PE SSOs on exon usage and ATM expression. FIG. 4D shows that the NSE 3'ss SSO repressed transcripts containing NSE and upregulated those with PE whereas the opposite effect was found for SSOs targeting the MIR enhancer loop in PE. The same pattern was observed for the reporter in which NSE and PE were separated by a distance insufficient for their simultaneous inclusion in mRNA (FIG. 4E). These results suggested that SSOs targeting PE and/or U2AF65 binding sites upstream of PE may potentially promote NSE inclusion and reduce ATM expression while the NSE SSOs should have the opposite effect. This approach would provide a broad strategy to modulate gene expression in either direction by antisense-based targeting of competing pseudoexons, one of which is critical for gene regulation. To test this concept, SSOs targeting PE 3'ss and 5' ss were examined. Although each PE SSO induced NSE skipping, both on exogenous and endogenous transcripts (FIG. 4F), SSOs targeting U2AF65 binding sites just upstream of PE (FIG. 4A), i.e. the NSE-repressing sequence (construct delPPT/AG, FIG. 4B), reduced PE inclusion and slightly increased NSE in the MIR reporter (FIG. 4G). In contrast, a longer oligo extended in the 5' direction (SSO-PEBP, FIG. 20) did not show any effect.

PE contains a natural DNA variant rs4988000 (G/A), which may also influence NSE recognition (FIG. 4H). Transfections of C and T minigenes systematically mutated at rs4988000 revealed that the rare A allele decreased NSE inclusion on each pre-mRNA, both in U2AF35- and mock-depleted cells. Thus, the highest NSE inclusion was produced by the haplotype that is most frequent in Caucasians (CG), followed by haplotypes CA>TG>TA.

Taken together, the haplotype-dependent activation of the U2AF-repressed NSE can be modified by SSOs that target U2AF65 intronic binding sites upstream of competing pseudo-3' ss, potentially providing a general method to manipulate exon-centric gene expression by antisense-based targeting of NMD switch exons and their regulatory motifs in introns.

Regulation of ATM Signaling by U2AF: DSBs at the Focal Point

Figure 9:
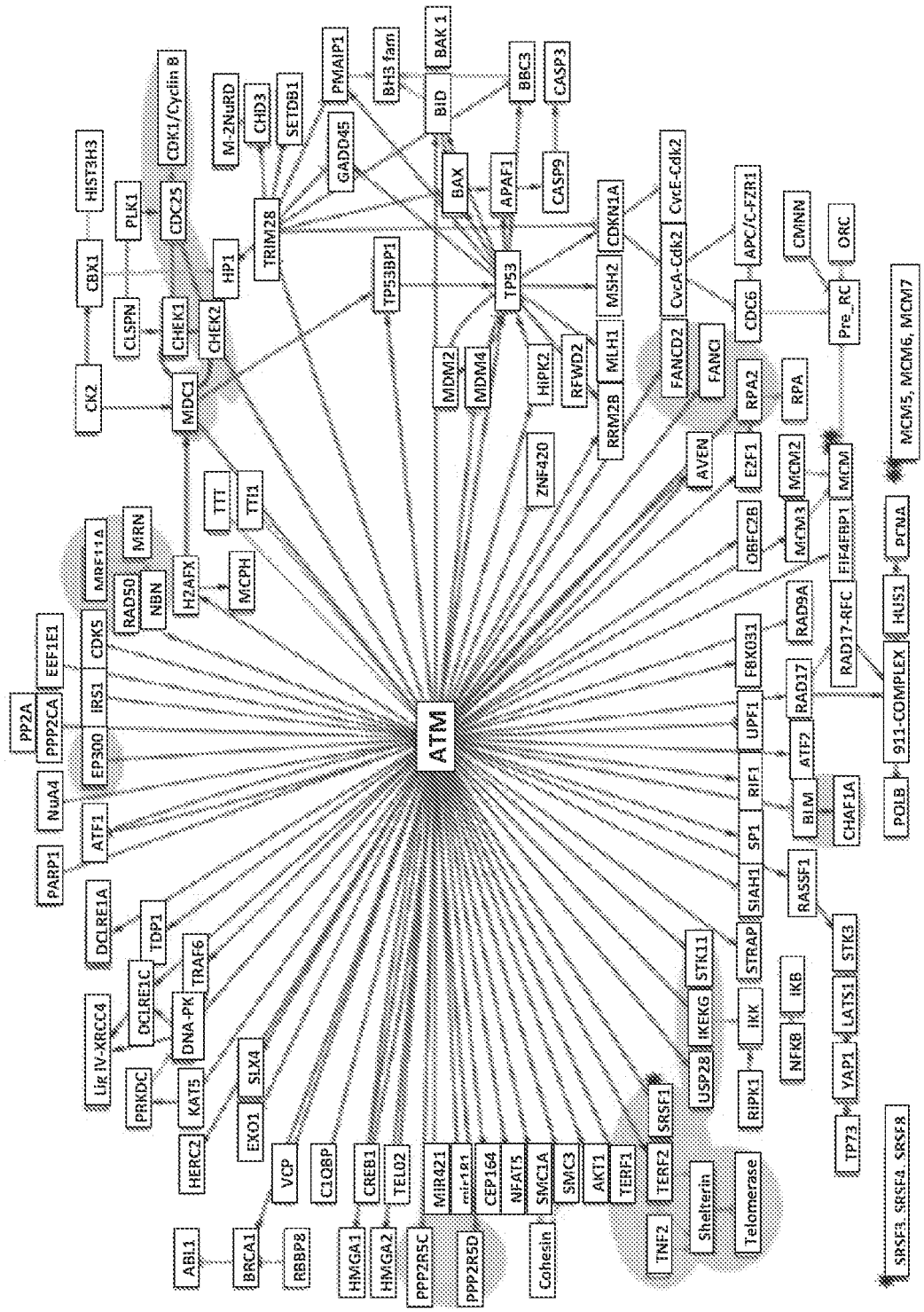
FIG. 9 illustrates an exemplary map of U2AF-regulated functional ATM interactions. U2AF-regulated ATM signaling network is highlighted by red arrows/pink background. Genes up-/downregulated in cells depleted of U2AF35 are shown in red/dark green, respectively. Genes exhibiting significantly altered exon usage are shown in yellow. The ATM signaling map shows ATM-interacting proteins (purple)/protein complexes (light green). Arrows correspond to activation, T-shaped edges to inhibition and open circles denote unknown regulations. Containment links are shown as green edges.

Because ATM is a key apical kinase in the DDR pathway and NMD switch exons often regulate genes encoding protein interaction partners, U2AF35-induced RNA processing changes of currently known ATM substrates and other constituents of the ATM signaling network were systematically characterized. Interestingly, although genes involved in the DDR and cell cycle control that contained U2AF35-dependent exons were only marginally enriched (FDR=0.08), each component in the ATM-CHEK2-CDC25-CDC2/cyclin B axis showed RNA processing alterations (FIG. 5A, FIG. 9). This pathway is critical for ATM signaling of DSBs.

First, reduced ATM expression in cells lacking U2AF (FIG. 8) was associated with decreased CHEK2 mRNA, increased retention of CHEK2 intron 10, and skipping of exons 9 and 11 (FIG. 5A). RNA processing alterations of known CHEK2 substrates were limited to genes regulating the cell cycle (CDC25A, CDC25B, CDC25C and TTK; FIG. 5A, S3A-B, 11A) and were not apparent in genes involved in DNA repair (BRCA1/2, XRCC1, FOXM1, TRIM28) or p53 signaling (TP53, MDM4, CABIN1, STRAP, AATF). CHEK2 exon 9 skipping, which would be predicted to activate NMD, was only marginally increased 24 hrs after IR and did not contribute to the decline of total CHEK2 observed as early as 30 min after IR (FIGS. 5B and 5C). As CHEK2 exon 9 inclusion was increased only for the highest concentration of UPF1 siRNAs (FIG. 5D), HEK293 cells were transfected with an SSO targeting its 3' ss. This treatment induced exon 9 skipping and reduced expression of the CHEK2 protein, however, it also increased NSE activation (FIG. 5E). In contrast, SSOs targeting NSE or PE did not have any effect on CHEK2 exon 9 inclusion (FIG.

5F). Exon 9 skipping, but not NSE, was also dramatically increased in cells lacking SF3B1 (FIG. 5G). To address why exogenous expression of CHEK2 was increased in cells lacking U2AF35 as compared to controls (FIG. 8A), HEK293 cells were cotransfected with the CHEK2-repressing SSO and a CHEK2-expressing plasmid (FIGS. 8B, and 8C). Reduced endogenous CHEK2 was associated with a significant increase of exogenous CHEK2 also in U2AF-proficient cells, pointing to a tight homeostatic regulation of the total CHEK2 protein in the cell.

Figure 10A:
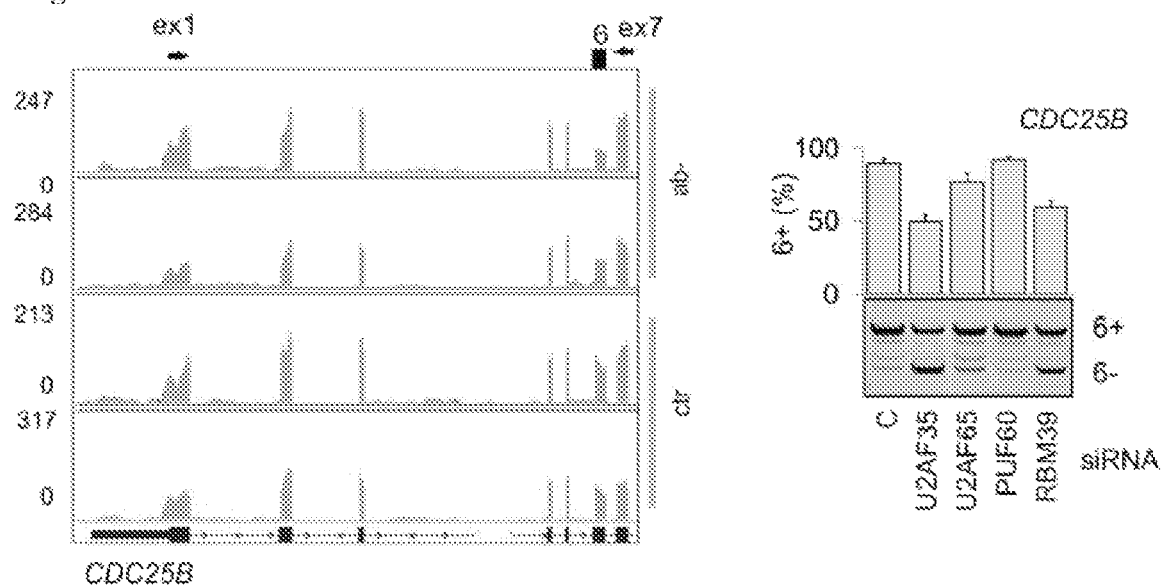
FIG. 10A-FIG. 10B show exon usage in CDC25B and CDC25C in cells depleted of U2AF35. Genomic browser views of RNA-Seq data in control (ctr) and depleted (ab−) cells (left panels in FIG. 10A and FIG. 10B). PCR primers are shown by arrows, differentially used exons are denoted by black rectangles. RefSeq exon annotation is shown at the bottom. Validation of RNA-Seq data using RT-PCR with RNA extracted from cells depleted of each U2AF subunits and U2AF-related proteins (right panels in FIG. 10A and FIG. 10B).
Figure 10B:
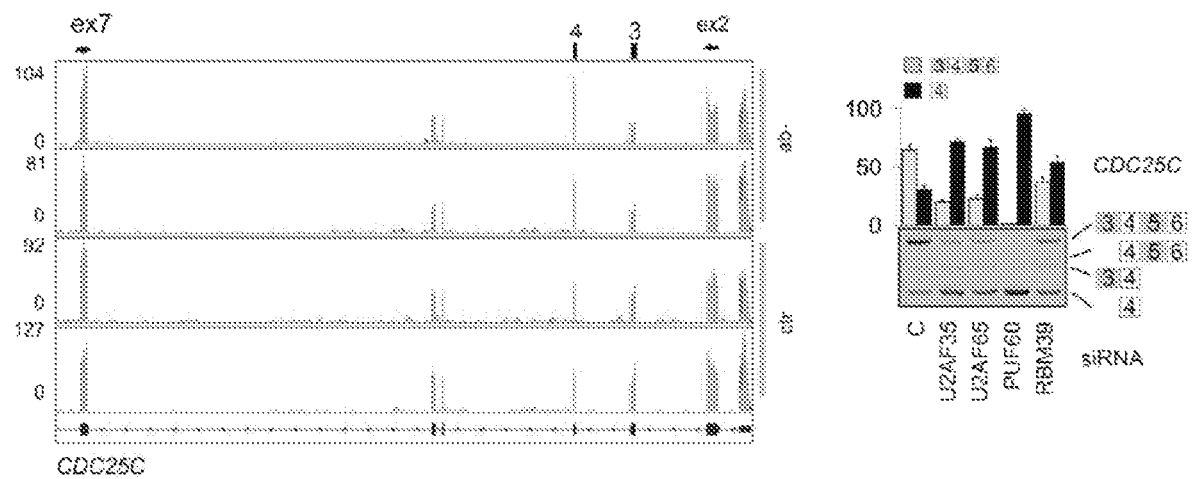
Figure 11A:
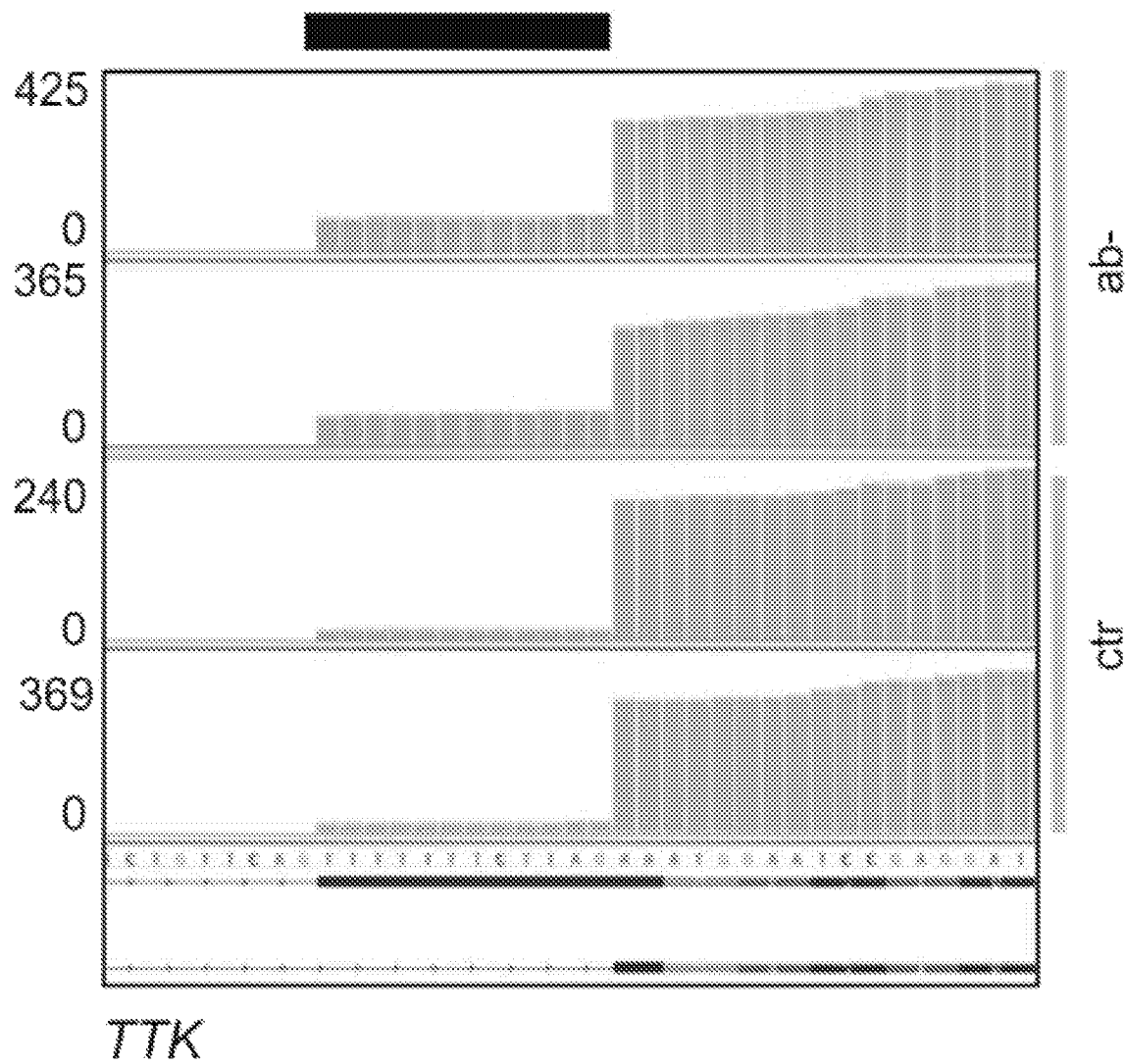
FIG. 11A-FIG. 11C shows U2AF-regulated exon usage in TTK, PIN1 and CDK1. Genomic browser views of RNA-Seq data in control (ctr) and depleted (ab−) cells (in FIG. 11A, left panel of FIG. 11B, and FIG. 11C). PCR primers are shown by arrows, differentially used exons are denoted by black rectangles. RefSeq exon annotation is shown at the bottom. Validation of RNA-Seq data using RT-PCR with RNA extracted from cells depleted of each U2AF subunits and U2AF-related proteins (right panel in FIG. 11B).
Figure 11B:
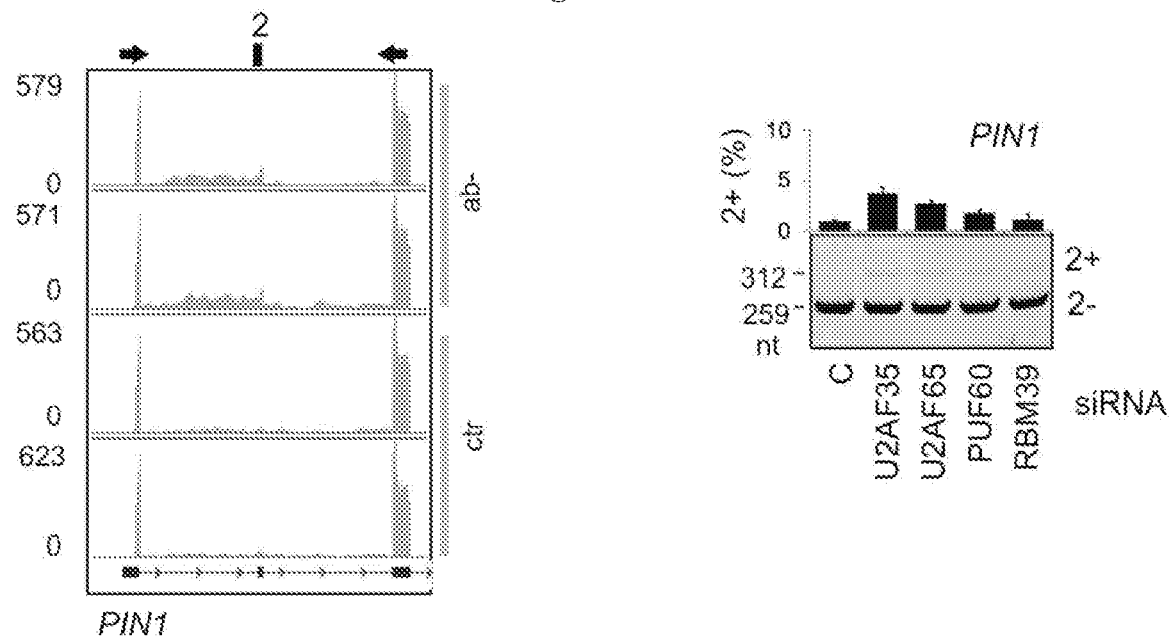
Figure 11C:
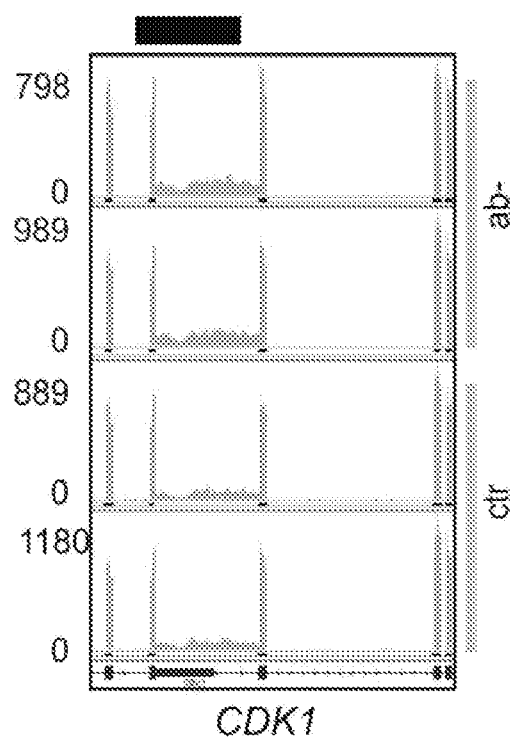
Figure 12A:
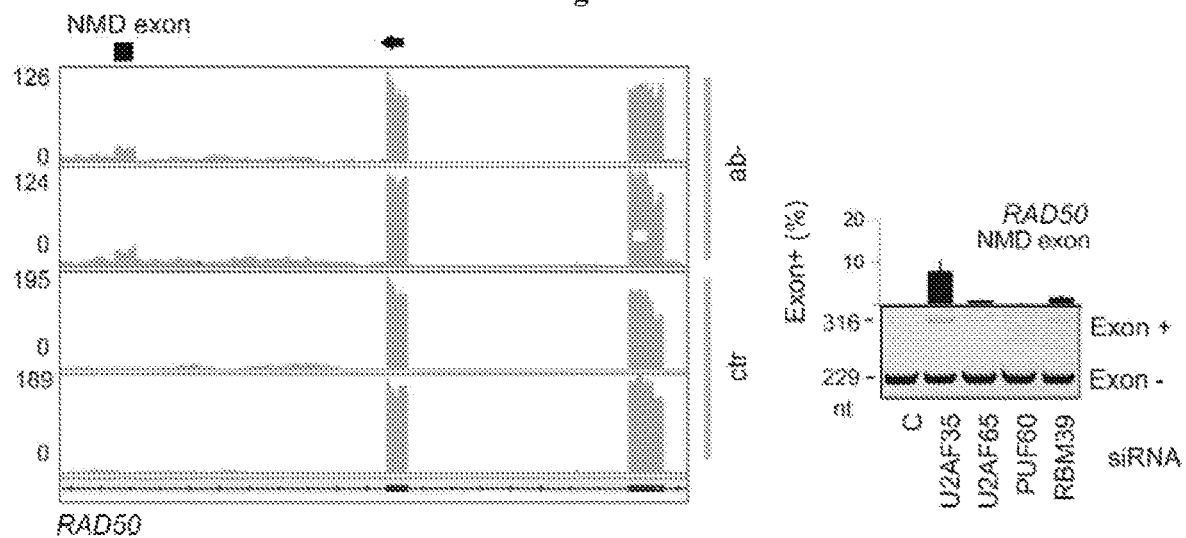
Figure 12B:
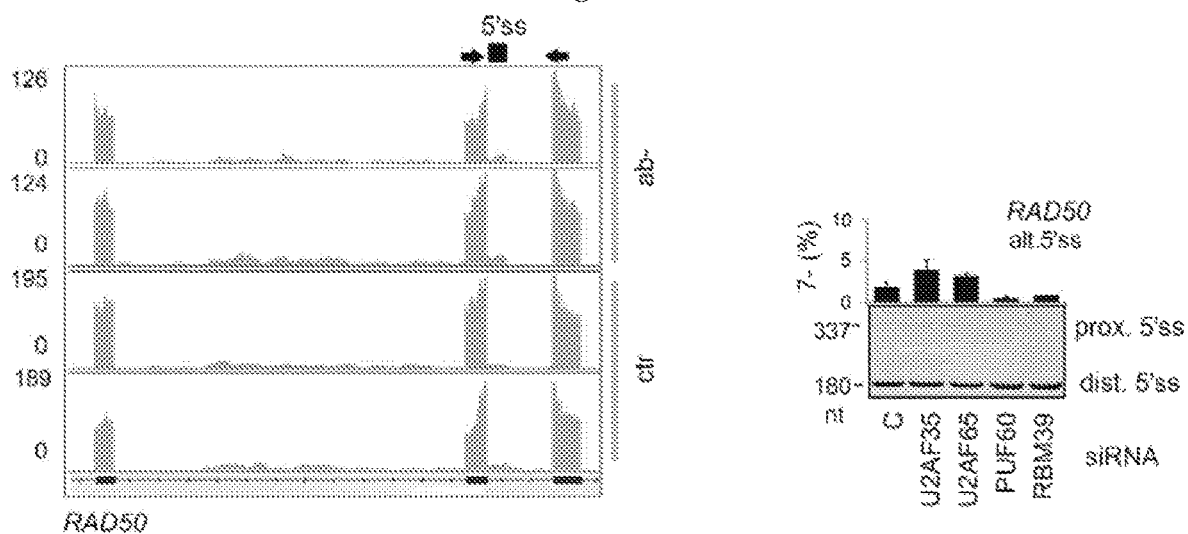

Second, U2AF was required for full activation of CDC25A exon 6 (FIG. 5A), which encodes a residue (S178) that is phosphorylated by CHEK2 and CHEK1, facilitating binding of 14-3-3. U2AF35 was also required for inclusion of exon 3 of CDC25B and CDC25C (FIGS. 10A and 10B), confirming previous microarray data. CDC25B exon 3 encodes multiple phosphorylated residues, including a B-domain residue 5169, phosphorylated by MAPKAP kinase 2 and pEg3. This isoform localizes to the centrosomes and accumulates during mitosis. CDC25C exon 3 encodes T67 phosphorylated by cdc2/cyclin B as a part of the auto amplification loop. Phosphorylated T67 in CDC25C creates a binding site recognized by the WW domain of PIN1, which sustained activation of a U2AF-repressed NMD switch exon (FIG. 11B), possibly modifying catalytic activity of this abundant peptidyl-prolyl isomerase. Finally, cyclin B1 and B2 mRNAs were upregulated in cells lacking U2AF35 as well as cyclin B1-interacting protein (CCNB1IP1, also known as HEI10), although their RNA processing pattern did not appear to be altered (FIG. 5A). Cyclin B upregulation was associated with a detained CDK1 intron (FIG. 11C), which may be spliced post-transcriptionally.

ATM recruitment to DSB is facilitated by the MRN complex, consisting of MRE11, RAD50 and NBN. NBN showed no obvious RNA processing changes in cells lacking U2AF35, but RAD50 mRNA was downregulated, possibly through activation of a NMD switch exon and/or additional splicing alterations (FIG. 12A-C and FIG. 9). The last MRE11A exon was upregulated as a result of a promotion of distal alternative polyadenylation site in depleted cells, which is present in most cell types, but not in B cells. DEXSeq analysis did not detect significant RNA processing changes in transcripts encoding other members of the phosphatidylinositol 3 kinase-like family of serine/threonine protein kinases (ATR and PRKDC), nor in BRCA1/2, RNF 168 and the ATM interactor ATMIN. Additional ATM interacting partners with altered exon or gene expression included RPS6, SRSF 1 and other SR proteins, EP300, RPA2, BLM, FANCD2 and FANCI, PPP2R5C and PPP2R5D, and SMC3, a central component of the cohesin complex (FIG. 9).

Figure 13A:
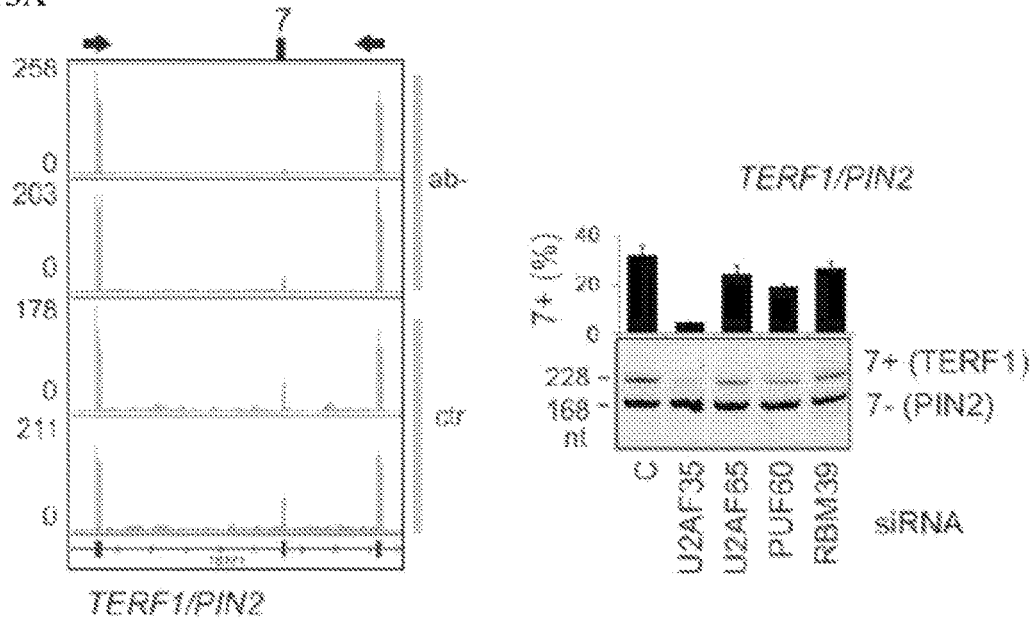
FIG. 13A-FIG. 13B show U2AF35-controlled exon usage of the peptidyl-prolyl isomerase PIN2 and components of the shelterin complex.
Figure 13B:
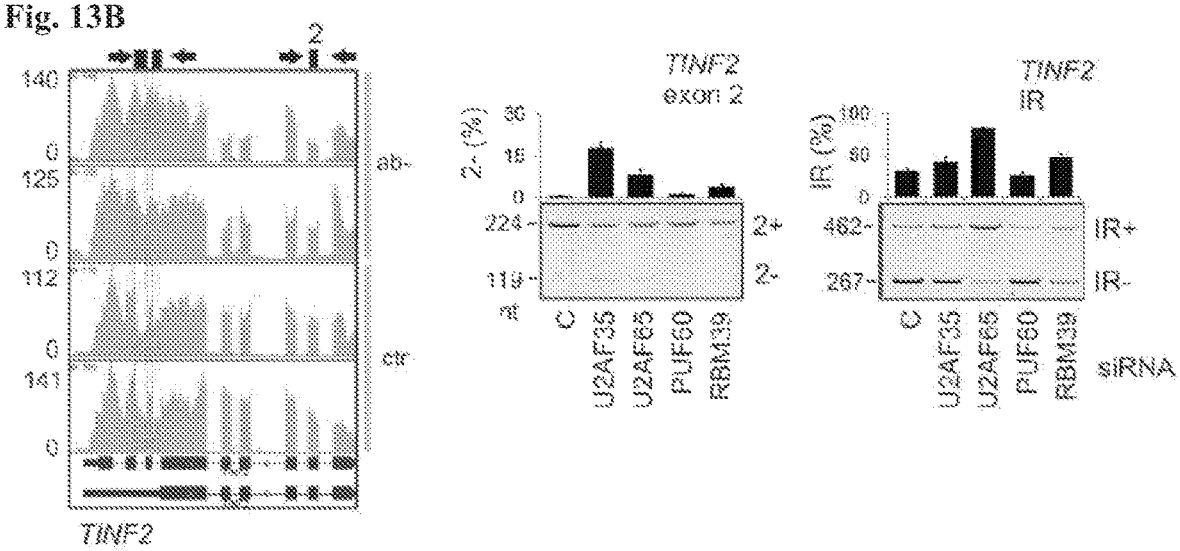

Depletion of U2AF35 was associated with preferential alterations of genes/exons involved in chromatin modification, which have numerous functional links to ATM signaling (FIG. 9). For example, the INO80 chromatin remodeling complex is phosphorylated by ATM and is functionally linked to checkpoint regulators, including CHEK2. U2AF inhibited INO80C isoforms containing 54-nt exons that encode peptides that are absent in the yeast Ies6 homolog, which is critical to INO80 function in vivo and is likely to alter heterodimer formation with ACTR5 and nucleosome binding. Expression of multiple components of the INO80 complex was altered in depleted cells, including ACTR5, ACTL6A and RUVL2B. Many INO80 subunits localize preferentially in telomeres and their mutations result in telomere elongation. U2AF is required for full inclusion of TERF1 exon 7 in mRNA (FIG. 13A), regulating the abundance of TRF1 (exon 7+)/PIN2 (exon 7-) isoforms, important components of the shelterin complex. Exon 7 encodes multiple phosphorylated serine residues and both isoforms can heterodimerize through the dimerization domain. TRF1 binding to telomeres is promoted by ATM inhibition whereas ATM-mediated phosphorylation impairs TRF1 interaction with telomeric DNA. TRF1 association with telomeres is also negatively regulated by RAD50. TRF1-interacting TIF2 is another shelterin protein localized in nuclear matrix and encoded by TINF2. TIF2 exists in at least two isoforms produced by alternative splicing, termed TIN2S and TIN2L. TIN2L contains an extra NM binding domain and associates more strongly with the nuclear matrix than TIF2S, which is encoded by a transcript with retained 3' introns that form a long 3' untranslated region. This mRNA isoform was repressed by U2AF (FIG. 13B).

Collectively, these results show that the MRN/ATM-CHEK2-CDC25-cdc2/cyclin B axis is at the center of the U2AF35-mediated control of DDR, although the U2AF regulation extends into additional ATM substrates involved in chromatin modification and telomere length control.

Figure 14A:
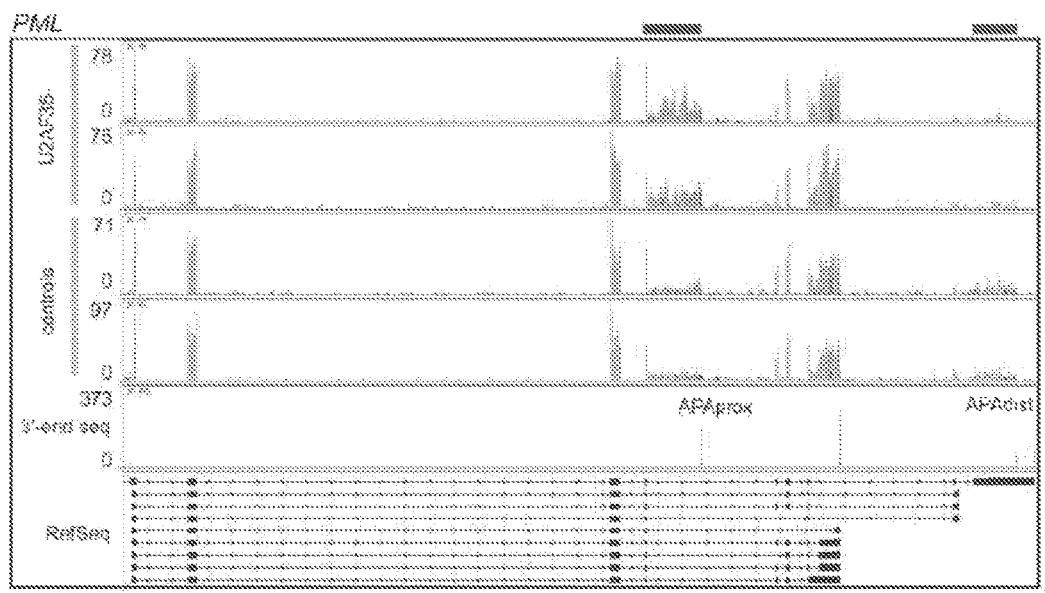

U2AF Preferentially Controls RNA Processing of Transcripts Involved in Leukemia-Associated Fusions CHEK2 phosphorylates PML (Promyelocytic Leukemia) and appears to require PML for subsequent autophosphorylation. Depletion of U2AF35 promoted the use of proximal alternative polyadenylation site of PML, leading to the upregulation of the shortest PML isoform, which lacks the last exon coding for the nuclear export signal (FIG. 14A). The long and short PML isoforms have distinct functions; for example, nuclear PML isoforms, but not the cytoplasmic isoform, are positive regulators of IFNγ signaling. The C-terminus of the longest PML isoform specifically interacts with AML1 to enhance AML1-mediated transcription, suggesting that U2AF deficiency could impair PML-AML1 interactions. PML also binds PIN1 and this interaction promotes PML degradation in a phosphorylation-dependent manner. U2AF depletion increased a PIN1 NMD exon (FIG. 11 B), potentially limiting expression of this highly abundant peptidyl-prolyl isomerase, which interacts with many phosphoproteins to regulate mitosis, including phosphorylated CDC25.

Figure 14B:
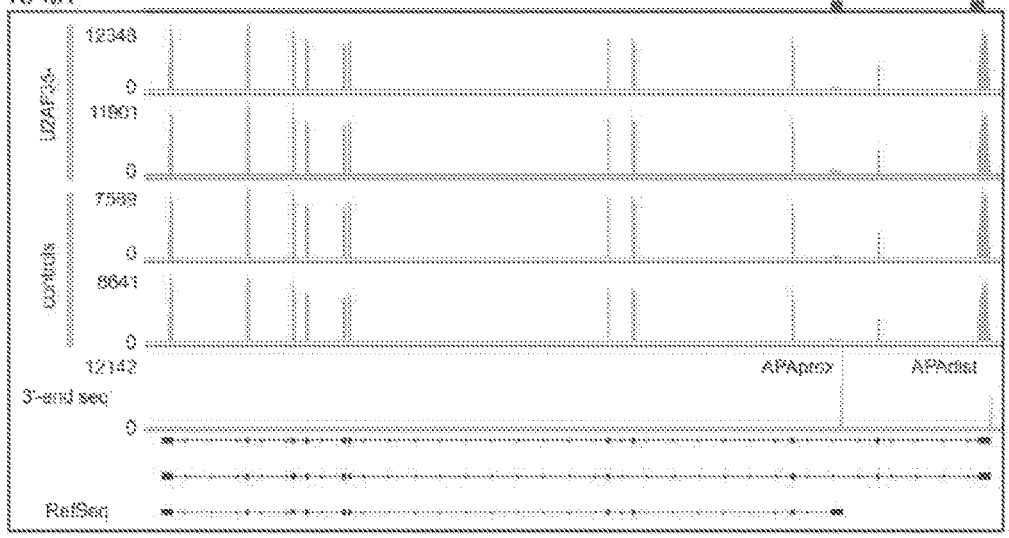

Apart from PML, U2AF35 depletion upregulated other RARA partners, including NPM1 (FIG. 14B). This event was associated with promotion of a proximal polyadenylation site, thus increasing the abundance of shorter, presumably more stable transcripts. An alternatively spliced exon of BCOR, a BCL6 corepressor that forms BCOR-RARA fusions and interacts with several histone deacetylases to increase BCL6 transcriptional repression, was also downregulated (FIG. 14C).

Interestingly, the overlap between U2AF35-sensitive genes/exons and 1,187 genes involved in cancer-associated gene fusions and 300 genes involved in recurrent chromosome translocations was greater than expected, with more significant P values observed for genes with differentially used exons than those implicated by Cufflinks at the transcript level (Table 1). Similarly, sharing of genes frequently mutated in the myelodysplastic syndrome and genes differentially expressed upon U2AF35 depletion was significantly higher than expected (P<0.01, hypergeometric test). Thus, RNA processing of transcripts involved in cancer-associated gene fusions and chromosome translocations is preferentially regulated by U2AF.

Figure 6:
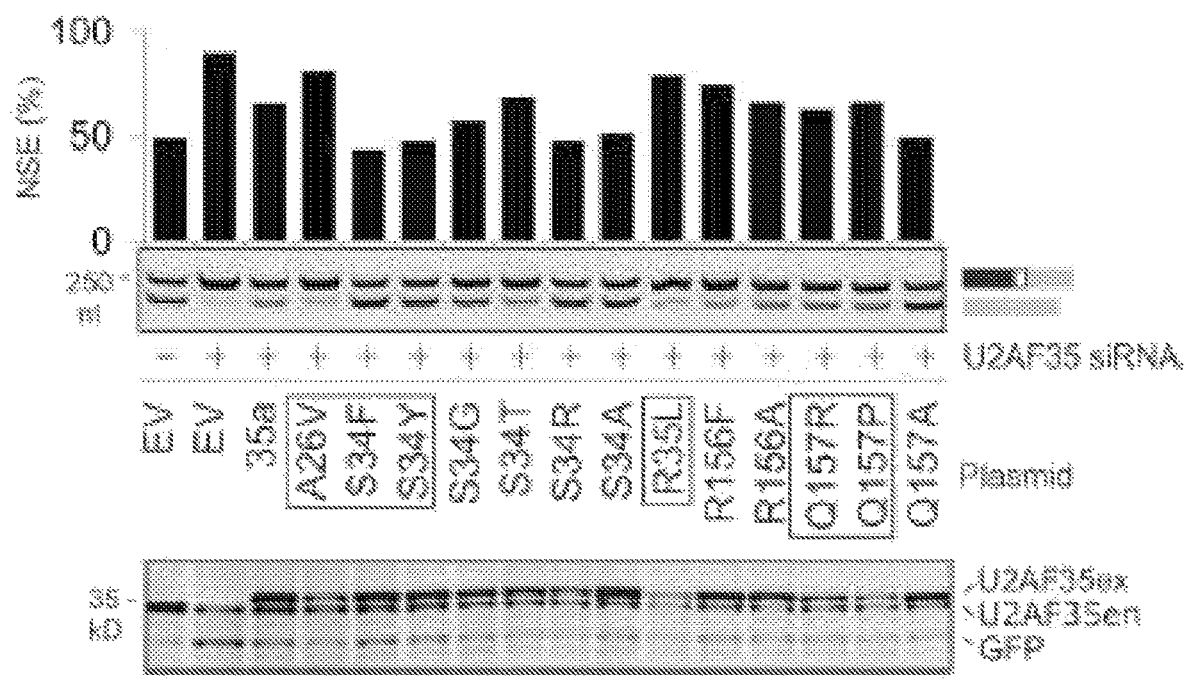
FIG. 6 shows rescue of NSE repression by cancer-associated mutations in U2AF35. Rescue of U2AF35-dependent NSE splicing of the C minigene by zinc finger 1 and 2 substitutions in U2AF35 (upper panel). All substitutions were made in the U2AF1a construct (35a). Cancer-associated mutations (bottom) are boxed; splice products are to the right Immunoblot with U2AF35 and GFP antibodies is shown in the lower panel (ex=exogenous; en=endogenous U2AF35).

To test the function of cancer-associated U2AF1 mutations in NSE splicing, reconstitution experiments were performed with wild-type and mutated U2AF35 constructs that were cotransfected with the C minigene into cells (mock)-depleted of U2AF35 (FIG. 6). NSE activation was repressed by either U2AF35 isoform to a similar extent, as well as U2AF35a containing substitutions of S34 in the zinc finger 1 domain, the most frequently mutated U2AF35 residue in cancer. In contrast, only a partial rescue was achieved by substitutions of Q157 in the second zinc finger domain where these mutations are less frequent. Other S34 mutations failed to fully reconstitute the defect, including S34T and substitutions with small amino acids, although a large residue at this position (S34R) was efficient. Thus, the identity of the residue at position 34 of U2AF35 is important for NSE recognition.

Figure 15A:
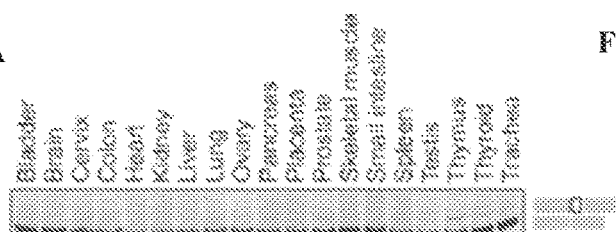
FIG. 15A-FIG. 15E show NSE activation in normal tissue and leukemic cells. NSE inclusion levels were measured in 19 human tissues (FIG. 15A) and 17 AML/CMML bone marrow samples (FIG. 15B) using primers ATM-F and ATM-R (FIG. 1, FIG. 20). Exon inclusion was quantified. Means were compared with an unpaired t-test (FIG. 15C).
Figure 15B:
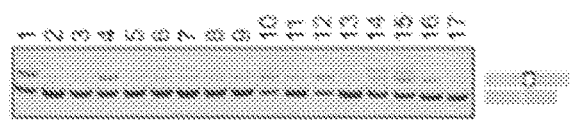
Figure 15C:
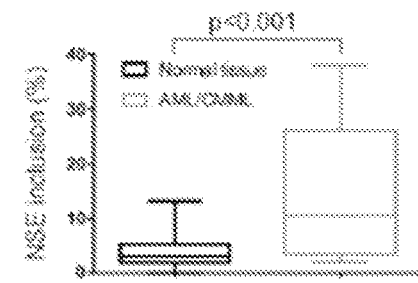
Figure 15D:
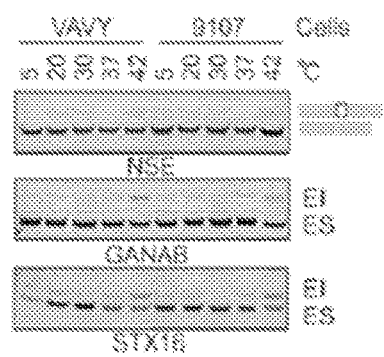
Figure 15E:
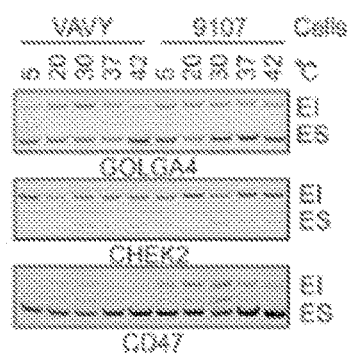

Finally, a low degree of NSE activation was detected in diverse human tissues, both in hexamer-primed samples and polyadenylated transcripts (FIG. 15A). The proportion of NSE-containing RNAs was on average higher in leukemic cells than in normal cells, with some samples exhibiting very high levels not observed in normal tissues (FIGS. 15B and 15C), potentially contributing to reduced ATM expression previously observed both in leukemias and solid tumors. NSE inclusion was also examined in polyadenylated RNAs extracted from a panel of lymphoblastoid cell lines exposed to cold and heat shock at the indicated temperatures prior to lysis (FIGS. 15D and 15E). Interestingly, NSE appeared to be activated to a minor extent by exposing cells to 42° C. but not at subphysiological temperatures (FIG. 15D), suggesting that markedly higher NSE inclusion levels in malignant cells are unlikely to be explained by a cold shock encountered during storage of patients' samples. Since proteomic profiling of Jurkat cells exposed to a heat stress at 43° C. revealed diminished expression of several proteins including U2AF35a, these results further support U2AF35 as a specific NSE repressor.

Discussion

The work described herein significantly expands currently known links between RNA processing and DDR pathways (FIGS. 5 and 9). An alternative splicing-coupled NMD switch exon critical for ATM expression was identified (FIGS. 1 and 3) and its importance in cancer risk was examined (FIG. 2, FIGS. 6 and 15). How intronic haplotypes influence inclusion of this exon in mature transcripts and their functional dependence on cellular levels of RNA-binding proteins involved in 3'ss selection was also shown (FIGS. 2 and 4H). Finally, SSOs were identified that modulate activation of this exon by targeting its regulatory sequences and propose a novel antisense strategy to modify gene expression.

U2AF is an important 3'ss recognition complex and a critical regulator of alternative splicing. In addition to expanding protein-protein interactions, alternative splicing has evolved to fine-tune quantitative gene expression through NMD, in agreement with alterations of many NMD exons in cells lacking this factor (FIGS. 1, 5 and 13). Peptides encoded by alternatively spliced exons are enriched in disordered regions and post-translation modification (PTM) sites, which are required for dynamic and reversible switching between two or more isoforms. Conversely, PTMs regulate numerous splicing factors, including proteins involved in NSE regulation. This complexity represents a clear challenge ahead and can be exemplified by the observed NSE activation upon targeting of CHEK2 exon 9 (FIG. 5E). Reduced CHEK2 expression may alter interactions with other kinases such as CDK11, which is constitutively phosphorylated at S737 in a CHEK2-dependent manner and interacts with U2AF65 and PUF60, creating a regulatory loop that controls NSE levels (FIG. 2H,I).

Figure 1B:
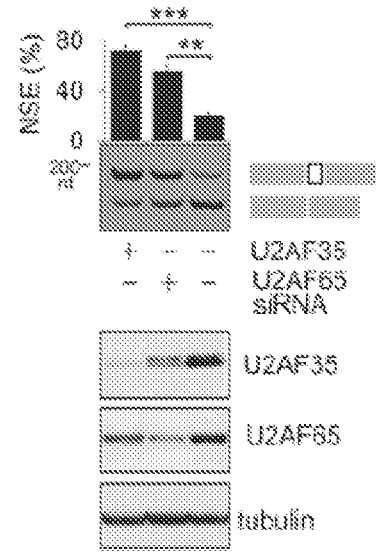
Figure 1C:
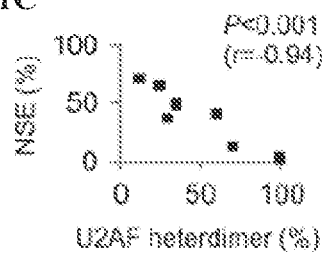

These results suggest that U2AF is an integral part of the DDR control, contributing to fine-tuning of its PTM network and subject to PTMs itself. U2AF35 was found among proteins that showed increased phosphorylation at S59 upon DNA damage. This serine residue is present only in U2AF35a and is replaced by alanine in U2AF35b. Exogenous expression of U2AF35b was higher than U2AF35a and the relative abundance of U2AF35b increased upon depletion of U2AF65, suggesting that the two U2AF35 isoforms may differentially interact with U2AF65 and may not have equivalent roles in DDR. However, U2AF35- and U2AF65-regulated exons vastly overlap and most, but not all, RNA processing changes found in U2AF35 depleted cells are attributable to the lack of the U2AF heterodimer, including the NSE activation (FIG. 1C).

U2AF-repressed exons have a distinct 3'ss organization and response to U2AF-related proteins as compared to U2AF-activated exons, suggesting that the exon repression involves direct RNA binding. This is supported by the observed NSE activation on exogenous transcripts that do not undergo NMD and by the SSO-induced NSE blockage (FIGS. 2 and 4). NSE lacks AG dinucleotides between the predicted BPS and 3'ss, its AG exclusion zone is longer than the average and has an unusual stretch of 5 conserved guanines upstream of the BPS, which may contribute to stable secondary structures across 3'ss that might be required for the repression. The adenine-rich 3' portions of both NSE and PE are more conserved in evolution than their 5' parts (FIG. 4A), potentially providing important ligand interactions, given the propensity of adenine to occupy unpaired positions in structured RNAs. Interestingly, primate NSEs have uridine at position −3 and longer PPT than lower mammals, which have cytosine at this position. Although direct RNA binding appears to be the simplest explanation for exon repression by U2AF, U2AF35 depletion led to downregulation of several proteins involved in NMD (Table S4), which may contribute to NSE activation on endogenous transcripts. In addition, physical interactions between U2AF65 and the C-terminus of TRF1 or other components of the ATM signaling network may also participate in NSE regulation.

Apart from U2AF1/U2AF2, additional genes involved in 3'ss selection have been found mutated in cancer. Interestingly, chronic lymphocytic leukemias with SF3B1 mutation were associated with a cryptic 3'ss activation of ATM exon 46, leading to ATM truncation. Recently, splicing of an EZH2 exon as a result of cancer-associated SRSF2 mutation was implicated in impaired hematopoietic differentiation and the same NMD exon was upregulated also upon U2AF35 depletion (FIG. 12D). Whether these exons are targets of a common 3'ss recognition pathway underlying leukemogenesis remains to be established. In contrast, NSE inclusion did not appear altered in cells depleted of SF3B1, which produced almost complete skipping of CHEK2 exon 9 (FIG. 5G).

Because NSE activation may restrict ATM expression both in normal and cancer cells (FIGS. 1, 2, and 15) and ATM is a limiting factor in the DDR pathway, cytosine at rs609261 may confer a relative ATM deficiency not only in (pre-)malignant cells but also in the germline. ATM kinase activity appears to be a good predictor of A-T severity, however, the diversity of A-T alleles does not fully account for the spectrum of clinical symptoms. Genes involved in NSE activation (FIG. 1, 2) might contribute to clinical heterogeneity of A-T patients, particularly those with 'leaky' mutations. Natural variants modifying NSE inclusion (FIGS. 2C-F and 4H) may also contribute to the phenotypic complexity of A-T or even A-T heterozygotes that lack overt clinical features but may display increased radiosensitivity and cancer risk, consistent with the central focus of U2AF-regulated exon usage within the ATM signaling network (FIG. 9).

These results predict that NSE activation is on average more efficient in Caucasians than in Asian populations as a result of a higher frequency of the C allele at rs609261 in the former (FIG. 2A). Asian Americans have lower mortality rates for common malignancies than Caucasians that persist over a long-period of time. The risk of hematopoietic malignancies also varies greatly by ethnic group and their incidence is the highest in white populations, including non-Hodgkin and Hodgkin lymphomas, which are associated with A-T. This trend also persists in migrants and continues in subsequent generations. Although lymphoblastoid leukemias, lymphomas and other cancer types show distinct incidence rates across Asian and Caucasian populations, no significant ethnic differences in the age-standardized incidence rates were found for myeloid leukemias, which does not appear to be more prevalent in A-T, unlike lymphoid malignancies or other cancers. Asian cancer patients respond more favorably than Caucasian patients to cytotoxic therapy and have on average a longer median survival. Asian cancer patients were also reported to have a lower prevalence of some gene fusions than Caucasians, potentially reflecting their capacity to respond to DSBs. rs609261 showed the lowest p-value of ATM variants in Cochrane-Armitage tests of association with glioma. rs2235006 (ATM allele F582L), which is located only ~35 kb upstream of rs609261 in a region of minimal recombination, was associated with a high risk (OR 11.2) of chronic lymphocytic leukemia. This study genotyped 1467 coding nonsynonymous SNPs in 865 candidate genes and implicated variants in genes encoding the ATM-BRCA2-CHEK2 DDR axis as the most significant risk pathway. Allelic association studies of nonagenarians/centenarians and younger controls also suggested association between ATM and longevity. Finally, ethnic differences were noted also for mutation rates in genes frequently altered in hematological malignancies; for example, SF3B1 mutations in chronic lymphocytic leukemias were less frequent in Chinese than in European populations.

Although these considerations collectively support the importance of rs609261-dependent NSE activation in cancer risk and survival, the U2AF- and hnRNP A1-dependency of NSE inclusion (FIG. 2H, S8B) demonstrates that it is by no means fixed. Variable expression patterns of these proteins from one malignancy to another would imply a 'capricious functionality' of this variant. Many more polymorphic sites with this attribute are likely to be established in future, contributing not only to the inter-individual variability of gene expression through restrictive capacity of 'poison' cryptic exons, but potentially also to the 'missing heritability' of complex traits and failures of genome-wide association studies, particularly in cancer.

Although RNA-Seq is a powerful tool to examine global transcriptome in response to DNA damage, rigorous standards that correctly estimate biological and statistical significance of the observed alterations in RNA processing are yet to be implemented. Given a high stringency of the DEXSeq algorithm, the existence of additional biologically important RNA processing events responsive to U2AF cannot be excluded. For example, upregulation of a proximal polyadenylation site in CHEK1, which was coupled with upregulation of 24-nt and 27-nt exons in CLASP1, would implicate the ATM apoptotic pathway. These events were not detected by DEXSeq but were see genomic browsers and require confirmation. The apoptotic pathways are of particular interest in the myelodysplastic syndrome which shows susceptibility of myeloid progenitors to the programmed cell death and where deregulation of genes involved in ATM signaling was found in more advanced but not initial clinical stages. Interestingly, U2AF1 mutations were also found to be more frequent in advanced stages and were associated with shorter survival. This study also highlights current limitations of incomplete transcript annotation and the importance of examining cryptic exons in RNA-Seq data. Future RNA-Seq studies should therefore attempt at global detection of NMD events associated with alternative splicing, which has been hindered by the instability of stop codon-containing transcripts.

Finally, this study demonstrates efficient repression of a key NMD switch exon in ATM by SSOs that also increased ATM protein levels (FIG. 3A-D, FIG. 8). It also reveals competing regulatory motifs of NSE in the same intron (FIG. 4A-C, H) that could be exploited as a target for SSO-mediated modulation of gene expression (FIG. 4D-G). This approach can be combined with genome-editing such as CRISPR-Cas9 to delete or introduce splicing regulatory motifs or protein binding sites implicated by minigene studies (FIG. 4C) and should also help us to find efficient intronic SSOs with desired outcomes for RNA processing. The search for such SSOs is more challenging than for those targeting human exons. For example, most SSOs systematically covering SMN2 exon 7 stimulated exon skipping, an event exploited for treatment of spinal muscular atrophy, however, −20% induced exon inclusion. By analogy, the desired stimulation of intron splicing was found only for 10% of SSOs targeting INS intron 1 while the majority failed to show this effect. The proposed strategy takes advantage of a much higher information content of human auxiliary splicing sequences as compared to lower organisms and should be greatly facilitated by future global pre-mRNA folding studies. For example, unlike the SSO that efficiently blocked the NSE 3'ss (SSO-NSE3, FIG. 3A,B), a partially overlapping morpholino extending only 7-nt into NSE failed to repress the same 3'ss to rescue splicing of mutation IVS28-159A>G, despite targeting U2AF binding sites (FIG. 4A). This suggests that the morpholino oligo may have blocked access to structures or motifs that are not responsible for exon activation, but exon repression, in agreement with these finding (FIG. 1A-C). Administration of antisense-based RNA processing activators or inhibitors that target or avoid binding sites of splicing factors in introns could be exploited therapeutically to shape beneficial or detrimental consequences of NMD in cancer cells. This approach is supported by a broad recognition that NMD serves primarily a regulatory function across a wide range of transcripts and may also promote translation of NMD substrates that produce truncated polypeptides, which may stimulate anti-tumor immunity.

Material and Methods

Plasmid Constructs

ATM minigenes were prepared by cloning −0.9-kb amplicons into XhoI/XbaI sites of the U2AF1 construct. Cloning primers are shown in Table S1. Full inserts were sequenced to confirm the identity of intended changes and exclude undesired mutations. PUF60 expression vectors were also used. The hnRNP A1 construct was a generous gift of Gideon Dreyfuss (University of Pennsylvania).

Cell Cultures and Transfections

Cell cultures were maintained in standard conditions in DMEM supplemented with 10% (v/v) bovine calf serum (Life Technologies). Depletion of U2AF subunits and U2AF35 isoforms with small interfering RNAs (siRNAs) and splice-switching oligonucleotides (SSOs), were carried out following a time course experiment that established depletion levels of each isoform. Oligo(ribo)nucleotides and siRNAs are listed in Table S1. Transfections were carried out in 6- or 12-well plates using jetPRIME (Polyplus) according to manufacturer's recommendations. The cells were harvested 48 hrs after the second hit, except for those exposed to IR, which received a single hit. For SF3B1 depletion, HEK293 cells were exposed to a siRNAs mixture (S23850, S23852, and S223598 (LifeTechnologies)) and were harvested 48 hrs later.

RNA-Seq

Analysis of differential exon usage was performed using DEXSeq (v. 1.12.1), based on q-values less than 0.05. Differential gene and isoform expression between sample sets was analyzed with Cufflinks (v. 2.1.1), which normalizes the reads using a fragments per kilobase of exon model per million reads measure. Selection of significantly differentially expressed genes was made on the basis of FDR-adjusted P-values (q<0.05).

NSE Expression in Human Tissues and Cell Lines

The FirstChoice human total RNA survey panel containing total RNA samples from 19 different tissues was purchased from LifeTechnologies. Each tissue sample contained a pool of RNAs from different donors. Lymphoblastoid cell lines were exposed to cold and heat shock. Total RNA samples were reverse transcribed with the Moloney murine leukemia virus reverse transcriptase (Promega) and random hexamer or oligo-d(T) primers. cDNA samples were amplified using primers shown in FIG. 20. Total RNA extracted from leukocytes from bone marrow samples of randomly selected patients with acute myeloid leukemia or chronic myelomonocytic leukemia was reverse transcribed with random hexamer primers. The study was approved by the National Research Ethics Service (UK) Committee South West.

Splice-Switching Oligonucleotides

SSOs were designed to maximize interactions with single-stranded regions and avoid secondary structures predicted by Mfold. All SSOs were purchased from Eurofins, diluted in water and their aliquots were stored at −80° C. All transfections were carried out with jetPRIME (Polyplus) according to manufacturer's recommendations.

Exposure of Cell Cultures to Ionizing Irradiation (Mock)-depleted HEK293 cells were exposed to IR 48 hours after the first hit using a Gulmay Medical (X-Strahl) D3225 Orthovoltage X-ray system at a dose-rate of 0.63 Gy/min at room temperature. The actual dose rate was monitored by a constancy meter. Cells were harvested as indicated in figure legends.

Immunoblotting

Antibodies against ATM (D2E2), ATM-pS1981 (D6H9), CHEK2 (D9C6) and CHEK2pThr68 (C13C1) were purchased from the Cell Signaling Technology, Inc. RBM39 antibodies were purchased from Thermo Fisher Scientific (PAS-31103). Antibodies detecting X-press tag, U2AF35, U2AF65, and tubulin were used. SF3B1 immunoblotting was performed with mouse monoclonal anti-SAP155 antibody (D138-3, MBL). Preparation of cell lysates and immunoblotting was carried out.

TABLE 1

U2AF35-dependent transcripts are more common than expected among genes involved in cancer-associated gene fusions and recurrent chromosomal translocations

| Database | Source | Number of Genes | Overlap with U2AF35-sensitive exons[2] | P-value/representation factor[3] | Overlap with U2AF35-sensitive transcripts[2] | P-value/representation factor[3] |
|---|---|---|---|---|---|---|
| ChimerDB 2.0 | [69] | 1187 | 66 | P <0.00004/1.7 | 204 | P <0.02/1.1 |
| Genes involved in recurrent structural abnormalities in cancer | [70] | 300 | 19 | P <0.006/1.9 | 56 | P <0.05/1.2 |

[1]Gene list downloaded on 2 Apr. 2014.
[2]Exon- and gene-level analysis of RNA-Seq data was carried out for 23,263 genes using DEX-Seq and Cufflinks, respectively.
[3]Number of overlapping genes divided by the expected number of overlapping genes drawn from two independent groups. A representation factor >1 indicates a greater overlap than expected of two independent groups, the value <1 indicates less overlap than expected. P-values were derived by hypergeometric tests.

Example 2—Antisense Macrowalk Targeting a Regulated Nonsense-Mediated RNA Decay Switch Exon in the ATM Gene Summary ATM is an important cancer susceptibility gene that encodes a critical kinase of the DNA damage response (DDR) pathway. ATM deficiency results in ataxia-telangiectasia (A-T), a rare genetic syndrome exhibiting a high susceptibility to lymphoid malignancies. ATM expression is limited by a nonsense-mediated RNA decay (NMD) switch exon (termed NSE) located in intron 28, which is tightly controlled by the spliceosome. NSE inclusion in mature transcripts can be modulated by splice-switching oligonucleotides (SSOs), but their optimal targets in the intron are unknown and their delivery to lymphoid cells has not been tested. Here a systematic search for efficient SSOs targeting intron 28 to identify NSE activators and inhibitors was employed. Discovery of these antisense compounds was assisted by a segmental deletion analysis of intronic transposed elements, revealing NSE repression upon removal of a distant antisense Alu and NSE activation upon elimination of a long terminal repeat transposon MER51A. Efficient NSE repression upon SSO delivery with chitosan-based nanoparticles to embryonic and lymphoblastoid cells was also demonstrated, opening a possibility for NSE-mediated modulation of ATM expression in cancer and A-T. Taken together, these results highlight an important role of transposed elements in regulating NMD switch exons and the power of intronic SSOs to modify gene expression.

Introduction

Eukaryotic genes contain intervening sequences or introns that need to be removed by a large and highly dynamic RNA protein complex termed the spliceosome to ensure accurate protein synthesis. The cell requires excessive energy and time to complete transcription of intron containing precursor messenger RNAs (pre-mRNAs) from at least a quarter of the human genome and also needs to synthesize non-coding RNAs and >200 different spliceosomal proteins to achieve this task. Although once regarded a 'selfish' or 'junk' DNA, introns are now recognized as critical functional components of eukaryotic genes that enhance gene expression, regulate alternative RNA processing, mRNA export and RNA surveillance. They are also an important source of new gene-coding and -regulatory sequences and noncoding RNAs, including microRNAs and circular RNAs. Their removal process is tightly coupled with transcription, mRNA export and translation, with most human introns eliminated from pre-mRNA co-transcriptionally, however, their potential as targets for nucleic acid therapy is only beginning to be unleashed.

Spliceosomes assemble ad hoc on each intron in an ordered manner, starting with recognition of the 5' splice site (5'ss) by U1 small nuclear RNP or the 3' ss by the U2 pathway. In addition to traditional splice site recognition sequences (5'ss, branch point, polypyrimidine tracts and 3' ss), accurate splicing requires auxiliary sequences or structures that activate or repress splice sites, known as intronic or exonic splicing enhancers or silencers. These elements allow genuine splice sites to be recognized among a vast excess of cryptic or pseudo-sites in eukaryotic genomes that have similar sequences but outnumber authentic sites by an order of magnitude. Activation of cryptic splice sites can introduce premature termination codons (PTCs) in translational reading frames that may lead to genetic disease. Such transcripts are usually recognized by a NMD pathway and downregulated. However, cryptic exons and NMD have also an important role in controlling the expression of naturally occurring transcripts and for differentiation stage-specific splicing switches, as exemplified by terminal stages of hematopoiesis. In addition, cryptic splice sites may permit unproductive or partial spliceosome assemblies that may compete with natural splice sites, facilitating their accurate selection at a single-nucleotide resolution. Cryptic splice sites activating such 'pseudo-exons' (also known as 'poison' or 'NMD switch' exons) that limit gene expression and regulate the pool of mRNA isoforms could thus provide interesting targets for nucleic acid therapeutics, however, exploitation of such approaches is in its infancy.

Splice-switching oligonucleotides (SSOs) are antisense reagents that modulate intron splicing by binding splice-site recognition or regulatory sequences and competing with cis- and trans-acting factors for their targets. They have been shown to restore aberrant RNA processing, modify the relative abundance of existing mRNA isoforms or produce novel splice variants that are not normally expressed by the cell. Most SSOs employed in pre-clinical and clinical development have targeted exonic sequences. Functional intronic SSOs are more difficult to identify, unless SSOs block access to intronic cryptic splice sites activated by a disease-causing mutation. First, a large fraction of intronic sequences may not affect RNA processing, despite the wealth of intronic auxiliary splicing motifs in the human genome. In addition, their identification is costly and inefficient in long introns. Most exonic SSOs designed to induce exon skipping have usually a desired effect. For example, most SSOs systematically covering SMN2 exon 7 stimulated exon skipping, a prerequisite for antisense therapy of spinal muscular atrophy, however, ~20% increased exon inclusion. By contrast, stimulation of intron splicing was found only for ~10% of SSOs targeting INS intron 1 while the majority failed to show this effect. Identification of effective SSOs may be facilitated by global pre-mRNA folding and ultraviolet crosslinking and immunoprecipitation studies that identify binding sites for components of the spliceosome or the exon junction complex. However, these binding sites may not reflect optimal antisense targets and their resolution may not be sufficient. Thus, a search for intronic SSOs with desired effects on RNA processing remains challenging.

The RNA-Seq studies have recently revealed activation of a NMD switch exon (termed NSE) deep in ATM intron 28 in cells depleted of each subunit of the auxiliary factor of U2 small nuclear RNP (U2AF). U2AF binds to polypyrimidine tracts coupled with highly conserved 3'ss AG dinucleotides at intron ends and this binding promotes U2 recruitment to the branch site and formation of lariat introns. However, the recent identification of a large number of exons that were activated in cells depleted of each U2AF subunit (U2AF35 and U2AF65) and exhibited a distinct 3'ss organization suggested that a subset of both canonical and NMD switch exons is repressed by U2AF, similar to exon-repressing and -activating activities found for a growing number of RNA binding proteins. The NSE levels were responsive to knockdown of additional splicing factors involved in 3'ss recognition and were influenced by two natural DNA variants (r54988000 and r5609261) located in the NSE itself and its 3'ss, respectively. SSOs that modulate NSE inclusion levels in the ATM mRNA by targeting NSE and its competing pseudoexon in the same intron have also been identified. The ATM NSE provides an interesting and promising target for anticancer therapy for several reasons: (i) the ATM kinase is activated in response to double-strand breakage, mobilizing an extensive signaling network with a broad range of targets, influencing cellular sensitivity to DNA-damaging agents; (ii) the U2AF-regulated exon usage in the ATM signaling pathway was centered on the MRN/ATM-CHEK2-CDC25 axis and preferentially involved transcripts implicated in cancer-associated gene fusions and chromosomal translocations; and (iii) the ATM NSE activation limits ATM expression in cells lacking each U2AF subunit. However, optimal NSE SSOs are unknown and their delivery to lymphoid cells has not been tested.

In the present study, SSOs covering the entire intron 28 were systematically screened and additional SSOs that activate or repress NSE and could be exploited as putative NSE-based ATM inhibitors and activators in therapeutic strategies were identified. Distant transposed elements in the same intron that influence NSE inclusion were also identified. Finally, efficient NSE repression upon SSO delivery to embryonic and lymphoblastoid cell lines using chitosan-based nanoparticles was also shown.

Materials and Methods

Plasmid Constructs

Reporter constructs containing full ATM intron 28 and flanking exons were cloned in the HindIII/XbaI site of pCR3.1 (Invitrogen) using amplification primers ATM26 and ATM27 (Table 2). Deletion constructs (FIG. 16) were obtained by overlap extension PCR with mutagenic primers (Table 2). Hybrid ATM minigenes were prepared by cloning ~0.9-kb amplicons containing NSE and exon 29 into XhoI/XbaI sites of the U2AF1 construct. Plasmids were propagated in *E. coli* (DH5a) and plasmid DNA was extracted with the Gene JET Plasmid Miniprep kit (ThermoScientific). Full inserts were sequenced to confirm the identity of intended changes and exclude undesired mutations.

Splice-Switching Oligonucleotides (SSOs)

To test SSOs with both endogenous and exogenous pre-mRNAs, SSOs were designed to avoid transposed elements in intron 28. Transposons were confirmed in sequences of the constructs using RepeatMasker. The SSO GC content was at least 24% (mean 31%) and their average length was ~20 nt. The SSOs comprehensively covered three unique regions in ATM intron 28 (termed A, B and AN, FIG. 17), avoiding only homopolymeric tracts. SSOs (Eurofins) were modified at each ribose by 2'-O-methyl and by a phosphorothioate at each end linkage to ensure adequate stability for the ex vivo screening. SSOs were diluted in double distilled water and quantified using Nanodrop (ThermoScientific). Their normalized aliquots were stored at −80° C.

Determination of PU Values

The PU (probability of unpaired) values estimate RNA single-strandedness using the equilibrium partition function by considering all possible RNA structures of short sequences, permitting their comparison at each nucleotide position. Higher PU values indicate a higher single-strandedness of an RNA motif. The PU values were computed as described using the three intronic regions and their 30-nt flanks as an input. PU values for each position of an SSO target were averaged and correlated with SSO-induced NSE inclusion levels.

Preparation of Stearylated Trimethyl Chitosan

Trimethyl chitosan, originally derived from ultrapure chitosan obtained from *Agaricus bisporus*, was provided by KitoZyme (Belgium).

Purified products had the number average molecular weight (Mn) of 43.3±5.5 kDa and the polydispersity index (Mw/Mn) of 2.4±0.3, as determined by gel permeation chromatography in a 0.33 M $NaCH_3COOH$/0.28 M $CH_3COOH$ eluent at a flow rate of 1 mL/min. The degrees of acetylation and quaternization, determined by the Fourier-transform infrared spectroscopy and 1H-nuclear magnetic resonance spectroscopy ($^1H$ NMR), respectively, were 11.1±0.9% and 30.1±4.6%. Trimethyl chitosan was functionalized with N-succinimidyl stearate (Santa Cruz Biotechnologies), achieving a final degree of substitution of 2.1±0.6% (mol %), as determined by 1H NMR.

Formation of Nanocomplexes

The nanocomplexes were prepared by mixing equal volumes (30 μL) of SSO and polymer solutions. Briefly, SSOs were diluted in buffer A (20 mM HEPES, pH 7.3, 5% (w/v) glucose) and supplemented with 1 M $Na_2SO_4$ to a final concentration of 50 mM. Both the polymer and SSO solutions were heated at 60° C. for 5 min before mixing with vortex at 1,000 rpm for 15 s. The tested complexes were prepared with molar ratios of quaternized amines (N) to phosphate groups (P) of 20, 40 and 80, as previously optimized, and had a hydrodynamic diameter between 110-130 nm for N/P ratios between 20-80. The complexes were allowed to stabilize for 30 min at room temperature before adding to a 240 μL of the culture medium (DMEM) without serum and antibiotics. Final concentration of SSOs in chitosan-containing cultures was 300 nM. Twenty four hours after transfections, 300 μL of the culture medium with serum/antibiotics was added. The cells were harvested 24 hrs later.

Cell cultures and transfections. HEK293 and lymphoblastoid VAVY cells were maintained in standard culture conditions in DMEM supplemented with 10% (v/v) bovine calf serum. Cells were seeded at 70% confluency 24 hrs prior to transfections. Transfections of wild-type and deletion constructs were carried out in 12- or 24-well plates using jetPRIME (Polyplus) according to manufacturer's recommendations. The cells were harvested 24 hrs later for total RNA extraction. Each SSO was transfected with or without the full-length ATM construct at 50 nM and cells were harvested 48 hours later for RNA extraction.

Analysis of spliced products. RNA samples were isolated using TRI-reagent (Ambion). Total RNA samples from chitosan experiments were extracted with the RNeasy kit (Qiagen). RNA was quantified and 1 μg of total RNA was reverse transcribed with the Moloney murine leukemia virus reverse transcriptase (Promega) and random hexamer or oligo-d(T) primers. Exogenous cDNA samples were amplified using primers PL4 and ATM-F and endogenous products were amplified with primers ATM-F and ATM-R (Table 2). Spliced products were separated on agarose and polyacrylamide gels and their signal intensities were measured. Statistical analysis was carried out with Stat200 (BioSoft, UK).

TABLE 2

Oligonucleotide primers

| Primer | 5'-3' sequence | SEQ ID NO: | Primer | 5'-3' sequence | SEQ ID NO: |
|---|---|---|---|---|---|
| Cloning primers | | | A16 | caaccaguuugcauucgu | 25 |
| ATM26 | ataaagcttcttgttataaggttttgattcc | 1 | A17 | uuaguauuccuugacuuua | 26 |
| ATM27 | atatctagatgtacataccctgaaaagtcac | 2 | A18 | uucuguacacuguuuaguauucc | 27 |
| RT-PCR primers | | | A19 | gaagagggagugaagguu | 28 |
| PL4 | agtcgaggctgatcagcgg | 3 | A20 | aaagcuuggugagauuga | 29 |
| ATM-F | gagggtaccagagacagtgggatggc | 4 | A21 | uuucuugaaaaguggaaagcuug | 30 |
| ATM-R | ggctcatgtaacgtcatcaat | 5 | A22 | uggaaugagggacgguuguuuuc | 31 |

TABLE 2-continued

Oligonucleotide primers

| Primer | 5'-3' sequence | SEQ ID NO: | Primer | 5'-3' sequence | SEQ ID NO: |
|---|---|---|---|---|---|
| Mutagenic primers | | | A23 | gguaugagaacuauagga | 32 |
| del-1F | atacaatttaccataatttacttttgaattatgtt | 6 | A24 | aaacaaacagcaggguau | 33 |
| del-1R | aagtaaattatggtaaattgtatcatacattag | 7 | A25 | gguaauaagugucacaaa | 34 |
| del-2F | ccttgccagaccagtttcctagttatctatattgaac | 8 | A26 | guaucauacauuagaagg | 35 |
| del-2R | taactaggaaactggtctggcaaggtggctta | 9 | B1 | ucaaaaguaaauuauggucu | 36 |
| del-3F | cttcaagggaccttggccgggtgcggtggct | 10 | B2 | gacugguaaauaauaaacauaauuc | 37 |
| del-3R | gcacccggccaaggtcccttgaagtttatctaa | 11 | B3 | aaauguauacuggagaagacu | 38 |
| del-4F | acacaaacaaagcttaggtactacttgtcaccttcta | 12 | B4 | auauauuagagauacaucagcc | 39 |
| del-4R | agaaagaaacctaagctngtngtgtgtntatacaa | 13 | B5 | gacaaacauuuaaugaauacucaa | 40 |
| del-5F | tgcctcatttacgtcatacaacttaatgatagacct | 14 | B6 | uugacuccuucuuugacaaacau | 41 |
| del-5R | ttaagttgtatgacgtaaatgaggcagggcaa | 15 | B7 | uuuaaauccuuccuuacuu | 42 |
| del-6F | tgatacaatttacctcatacaacttaatgatagacct | 16 | B8 | gauuauaaaacaaacgaagc | 43 |
| del-6R | attaagttgtatgaggtaaattgtatcatacattag | 17 | B10 | uguuuaauauaaguugcuucaa | 44 |
| 2'-O-methyl/PTO SSOs[a] | | | B11 | ugugggugaccacagcuu | 45 |
| A2 | aacuuaaagguuauaucuc | 18 | B12 | ucccuuacuuauauccaa | 46 |
| A4 | uauaaauacgaauaaaucga | 19 | B13 | ccaaguuugguuacuuauc | 47 |
| A8 | cauggguuggcuaugcuag | 20 | B14 | gaaguuuaucuaauauugacc | 48 |
| A9 | caacacgacauaaccaaa | 21 | AN1 | ggucuaucauuaaguugauga | 49 |
| A10 | aagccaaucagagggagaca | 22 | AN2 | uuaaauaagacuucaggucua | 50 |
| A11 | aacauuucuauuuaguuaaaagc | 23 | AN3 | uuagagaaucauuuaaauaagac | 51 |
| A15 | ucguguauuacaacaguuaa | 24 | AN4 | cuuaauccaauucuucaauuuuag | 52 |

[a]PTO, phosphorothioate

Results

Figure 16A:
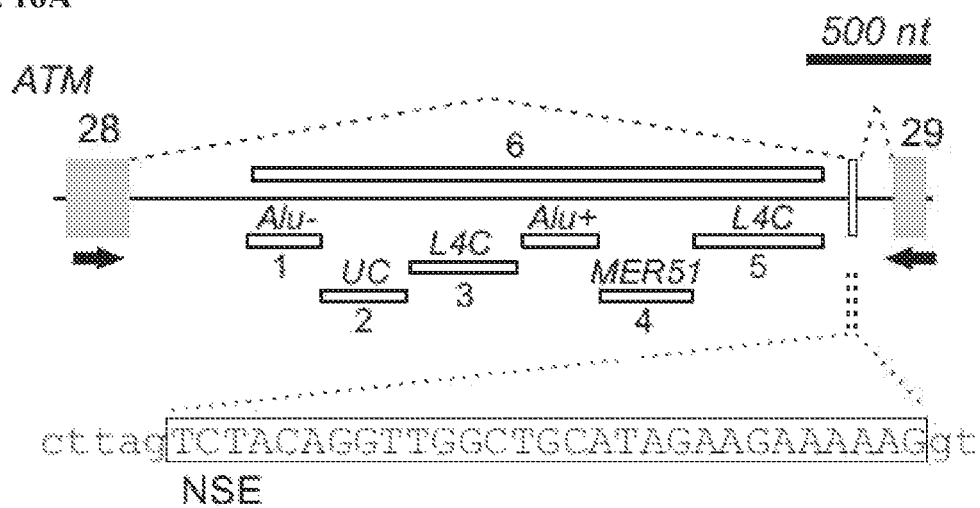
FIG. 16A-FIG. 16B show identification of transposed elements in ATM intron 28 that influence NSE activation.

SSOs targeting either 3' or 5' ss of the NSE efficiently repress this exon in a haplotype dependent manner. To facilitate identification of optimal intronic SSOs that activate NSE, splicing reporter constructs with the entire ATM intron 28 (FIG. 16A) were first prepared. The construct was obtained by PCR using the HEK293 DNA as a template. The reference sequence (hg19) of intron 28 is ~3,100 nt long, which is similar to the average human intron. Transposed elements occupy ~64% of intron 28, filling completely its middle part, except for a ~350 nt region in the 5' half of the intron and exonic flanks (FIG. 16A). Plasmid DNA sequencing revealed the same organization of transposed elements without any additional transposon copies. It also showed the C and G allele at rs4988000 and rs609261, respectively, indicating that the construct contains the haplotype most permissive for NSE inclusion in the ATM mRNA. After transfections into HEK293 cells, total RNA was extracted and reverse transcribed prior to amplification with a vector primer PL4 (Table 2) and an exon primer (FIG. 16A). Examination of spliced products showed that most transcripts entirely lacked intronic sequences (NSE-) whereas ~36% mRNA contained NSE (FIG. 16B, lane 1), a fraction slightly higher than for a hybrid reporter reported previously.

To determine the importance of transposed elements for NSE inclusion, each transposon from intron 28 was individually deleted using overlap-extension PCR (deletions 1-5, FIG. 16A). A large middle part of the intron was also deleted along with all transposons, leaving the NSE and its upstream sequences intact (~75% of the intron, deletion 6). Transfection of validated mutated constructs, which all had identical genotypes to the wildtype construct at rs4988000 and rs609261, revealed that the large deletion promoted NSE-containing transcripts (deletion 6, FIG. 16B). Deletion of the MER51 element increased NSE inclusion to a lesser extent. In contrast, deletion of the antisense Alu inhibited NSE while deletion of long interspersed repeats (deletions 3 and 5) or a unique intronic segment (deletion 2) had no effect on NSE activation. The variability of NSE inclusion levels was much higher following a two-hit knockdown of U2AF35, with a significant increase of NSE levels maintained only for deletion 6 (FIG. 16B), consistent with a major stress component of NSE responses. A series of SSOs were then designed targeting three intronic regions that have unique sequences in the genome (termed A, B and AN) while avoiding a predicted branch site upstream of NSE (FIG. 17A, Table 2). Each SSO was modified with 2'-O-methyl at each ribose and phosphorothioate at each end linkage to ensure their RNase H resistance and sufficient stability in transient transfections. As positive and negative controls, SSO-NSE3 was used, which was highly efficient in blocking the NSE 3' ss, and a series of scrambled SSOs and SSOs targeting other genes, including INS and BTK which were not expressed in HEK293 cells, as confirmed by RNA-Seq. Each SSO was individually transfected with or without the wild-type ATM construct.

Measurements of spliced products revealed that SSO-NSE3 yielded the most efficient NSE repression (FIG. 17B). About a half of tested SSOs significantly altered NSE inclusion levels as compared to controls, with similar numbers of repressor and activator SSOs. The Pearson correlation coefficient between replicate transfections was highly significant, reaching 0.88 (P<10-8); however, the overall correlation between exogenous and endogenous NSE levels was only 0.35 (P<0.01).

Figure 16B:
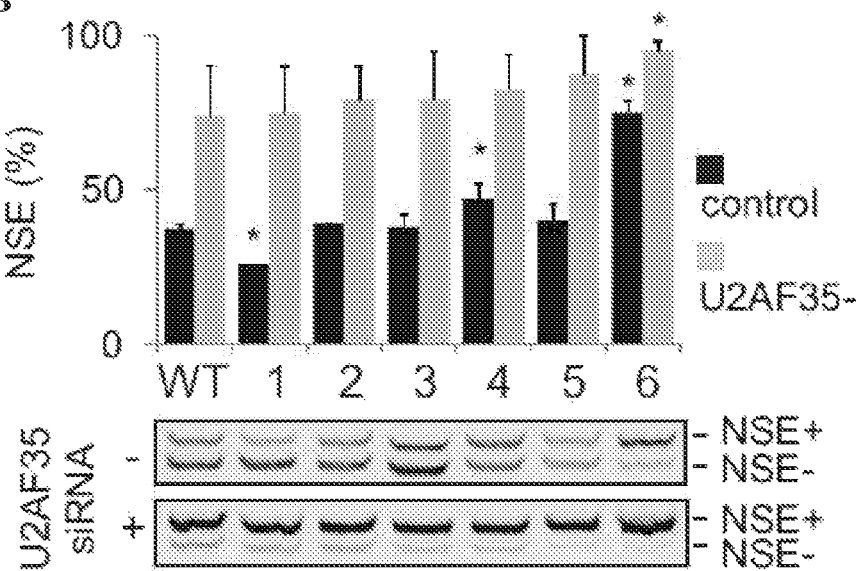
Figure 17C:
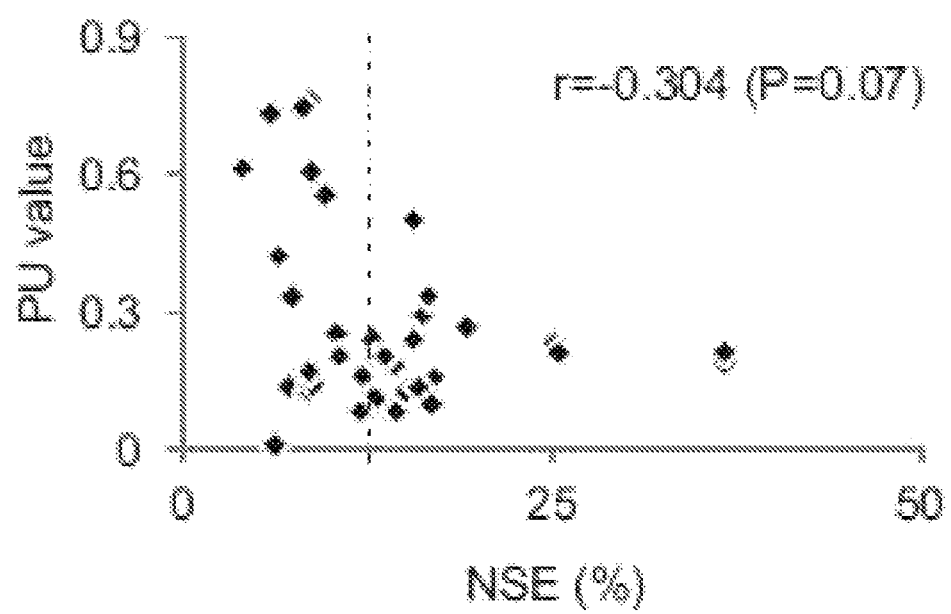

Experiments in FIG. 16 showed that the NSE inclusion is controlled by distant splicing regulatory sequences within and outside transposons. Experimentally determined splicing enhancer and silencer motifs in their natural pre-mRNA context occur preferentially in single-stranded regions, suggesting that they are more accessible to RNA binding proteins or other ligands that control exon selection. Preferential targeting of SSOs to unpaired regions could thus improve a search for intronic SSOs. To test this assumption, NSE inclusion levels induced by each SSO were correlated with their average PU values (FIG. 17C). These values estimate single-strandedness of their RNA targets using an equilibrium partition function, with higher values signaling a higher probability of single-stranded conformation. Interestingly, SSO targets with higher average PU values tended to induce exon skipping, suggesting that efficient blocking of unpaired interactions as far as 2 kb from the exon can impair its activation.

The experiments described above identified a small set of intronic SSOs that activated NSE inclusion in mature exogenous and endogenous transcripts. Since NSE can limit ATM expression through NMD, activator and repressor SSOs could serve as tunable gene-specific inhibitors. Transient ATM repression by NSE-activating SSOs could be advantageous for cancer treatment by inhibiting the double-strand break signaling pathway and radiosensitization.

To test if ATM SSOs can be delivered to cells that have much lower transfection efficiency than HEK293 cells, a stearylated trimethylated chitosan (TMC-SA) was employed. Chitosan is a natural copolymer of D-glucosamine and N-acetyl-D-glucosamine known for biocompatibility, biodegradability and low toxicity and immunogenicity. When trimethylated, chitosan acquires a permanent positive charge that improves its solubility at neutral pH. Stearylation was found necessary for formation of stable nanocomplexes with SSOs and their transfection activity in a HeLa/pLuc705 system, which makes use of a luciferase gene interrupted by a mutated HBB1 intron.

Figure 18A:
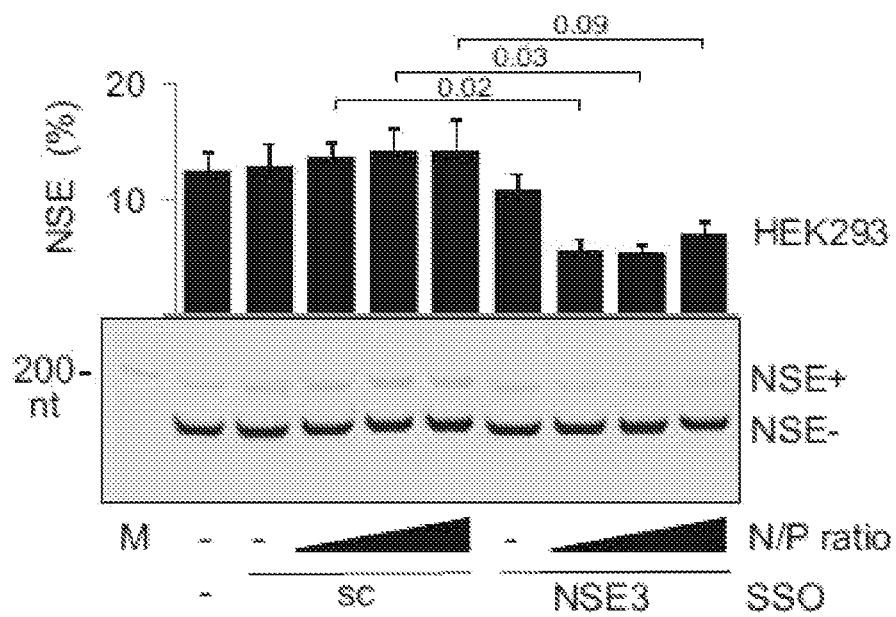
FIG. 18A-FIG. 18B show TMC-SA-assisted delivery of SSO-NSE3 to human cell lines leads to NSE repression.
Figure 18B:
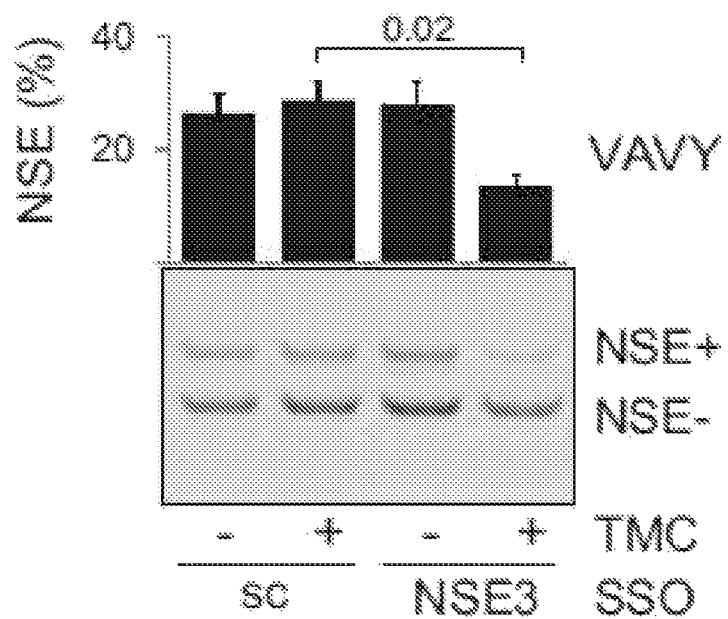

Whether TMC-SA can facilitate delivery of SSO-NSE3 into HEK293 cells was first tested. FIG. 18A shows reduction of NSE levels following exposure to SSO-NSE3-TMC nanoparticles as compared to a scrambled SSO. This decline was significant for the TMC-SA/SSO-NSE3 (N/P) ratios of 20 and 40. The NSE decline was also apparent when comparing NSE inclusion in cells exposed to uncomplexed SSO-NSE3, consistent with their significant uptake by this highly transfectable cell line. However, the reduction of NSE levels was less efficient for TMC-SA/SSO-NSE3 than for the same oligo transfected with jetPrime to the same cell line at a lower final concentration. A significant NSE repression upon exposure to TMC-SA/SSO-NSE3 nanocomplexes was observed also for a lymphoblastoid cell line where uncomplexed SSO-NSE3 failed to reduce NSE (FIG. 18B). Collectively, these results provide the first proof-of-principle that a chitosan-based delivery system of intronic SSOs can repress NMD switch exons in human cells.

Discussion

This work shows the first example of transposed elements that promote and repress activation of a NMD switch exon (FIG. 16). Alu sequences themselves have a propensity to exonize through 3' ss or 5' ss activation or auxiliary splicing motifs, which contributes significantly to human morbidity. They can also be exonized by outlying deletions and cause genetic disease, suggesting that they can promote inclusion of distant intronic sequences in mature transcripts. This is further supported by a higher fraction of Alus that flank alternatively spliced exons than those spliced constitutively. Although the exact mechanism of these distant effects is not understood, secondary structure of these GC-rich transcripts is likely to play a major role.

Mutation-induced exonizations have been shown for all other classes of transposed elements, including more ancient short interspersed elements termed mammalian interspersed repeats. In the present study, an intronic transposed element with the highest similarity to MER51A (Medium Reiterated frequency repeat, family 51) repressed NSE, acting as a buffer to counteract the Alu– mediated NSE activation (FIGS. 16A and 16B). The ATM MER51 is relatively GC-rich (~44%), which may facilitate intramolecular interactions with GC-rich Alus during co-transcriptional folding. The element contains several inverted repeats, possibly forming stable hairpins containing exposed purine-rich loops that may control NSE inclusion (FIG. 19). About 250,000 copies of recognizable MER sequences were estimated to exist in the human genome and many were found in mature transcripts of protein-coding genes, contributing to the diversity of protein interactions. A mutation-induced MER exonization event was also shown to cause Gitelman syndrome. The 3' part of MER51 is similar to a long terminal repeat of retroviruses (FIG. 19), which account for ~15% of disease-causing exonizations. The origin of most MERs was placed after the decline of mammalian interspersed repeats before the spread of Alus, coinciding with expansion of mammals and suggesting that MERs may offer insight into early mammalian radiation. However, the molecular mechanisms underlying MER-mediated exon activation are not understood and will require further studies. Taken together, these results suggest that the interplay of transposed elements in long introns could influence inclusion levels of many NMD switch exons, fine-tuning gene expression.

In this work, candidate sequence-specific ATM inhibitors that act by promoting a regulated NMD switch exon critical for ATM expression were also identified (FIG. 17). ATM inhibitors sensitize cancer cells to cytotoxic therapy that induces double-strand breaks, including local radiotherapy, which is an integral part of treatment regimens of many cancer types. Although chemical ATM inhibitors showed a great promise for cancer radiotherapy, their undesired pharmacokinetic profiles, high toxicity or poor efficacy have hampered their progression into the clinic. In contrast, newly identified SSOs target unique sequences in the human genome, their mechanism of action is well-defined and they can be delivered to cells using natural biodegradable compounds (FIG. 18). In addition, the availability of NSE-activating and -repressing SSOs provides an opportunity to titrate gene expression more accurately than chemical inhibitors. The approach described herein makes use of SSO-mediated modulation of cryptic exons that activate NMD. These exons are usually present in natural transcripts at very low levels but their inclusion levels can be efficiently upregulated in response to various stimuli. Recently, a gene-specific antisense inhibition of NMD employed SSOs targeting exon junction complex deposition sites, thus permitting NMD repression without relying on skipping of a PTC-containing exon. The two approaches, the former relying on intronic sequence and the latter one on exonic targets, might complement each other in the future to expand the repertoire of antisense strategies that inhibit NMD.

The average length of SSOs employed in the screening was close to the minimum for unique targets (Table 2). The short SSOs may induce more off-target effects than longer SSOs, which could contribute to the low correlation between inclusion levels of endogenous and exogenous NSE transcripts. Apart from the possible suboptimal target specificity, intron 28 splicing and NSE inclusion can be influenced by adjacent introns that were absent in exogenous transcripts. In addition, intron 28 splicing may not be entirely co-transcriptional and folding and folding kinetics of RNAs transcribed from different promoters are likely to be distinct, contributing to the low correlation. Nevertheless, this study clearly demonstrates a wealth of candidate intronic target sites for SSOs in the human genome, consistent with a higher information content of intronic auxiliary splicing sequences as compared to lower organisms, which have smaller introns with a lower regulatory potential for alternative splicing. Although SSO-NSE3 and other SSOs can repress endogenous NSE-containing mRNAs (FIGS. 17B and 17C) and NMD transcripts with the relative abundance as low as ~1% can contribute to the mRNA consumption, it remains to be tested if their reduction can lead to a sustained increase of ATM protein levels in normal cells. This approach may have a potential to alleviate phenotypic consequences of leaky A-T alleles in a mutation-independent manner, especially in homozygous A-T patients carrying the C allele at rs609261, which facilitates 3' ss recognition of the NSE. Finally, chitosan-based nanoparticles have been shown to penetrate the blood-brain barrier and accumulate in cerebellum without affecting histomorphology, opening a possibility to deliver NSE repressors and putative ATM activators to neural cells to ameliorate cerebellar symptoms of AT.

What is claimed is:

1. A method of modulating protein expression, comprising:
   contacting a non-sense mediated RNA decay switch exon (NSE)-activator agent to a target motif within a pre-processed mRNA transcript;
   wherein the NSE-activator agent comprises a polynucleic acid polymer or a small molecule that interacts with the target motif within the pre-processed mRNA transcript;
   wherein the target motif is within an intron that contains the NSE and that is between two canonical exons;
   wherein the pre-processed mRNA transcript is processed to form a processed mRNA transcript,
   wherein the NSE-activator agent promotes inclusion of an NSE into the processed mRNA transcript;
   wherein the processed mRNA transcript is translated; and
   wherein the inclusion of the NSE into the processed mRNA transcript downregulates protein expression relative to protein expression of an equivalent processed mRNA transcript lacking the NSE.

2. The method of claim 1, wherein the NSE-activator agent promotes activation of a 5' or a 3' splice site of the NSE.

3. The method of claim 1, wherein the target motif is within the NSE.

4. The method of claim 1, wherein the target motif at least partially overlaps with the NSE.

5. The method of claim 1, wherein the target motif comprises a 5' end of the NSE.

6. The method of claim 1, wherein the target motif comprises a 3' end of the NSE.

7. The method of claim 1, wherein the target motif is upstream of a 5' end of the NSE.

8. The method of claim 1, wherein the target motif is downstream of a 3' end of the NSE.

9. The method of claim 1, wherein the target motif does not comprise a 5' end or a 3' end of the NSE.

10. The method of claim 1, wherein the pre-processed mRNA transcript is a mutant pre-processed mRNA transcript.

11. The method of claim 1, wherein pre-processed mRNA transcript is a wild-type pre-processed mRNA transcript.

12. The method of claim 1, wherein the NSE-activator agent binds to a cryptic splice site within the pre-processed mRNA transcript.

13. The method of claim 1, wherein the NSE-activator agent comprises a polynucleic acid polymer that hybridizes to the target motif within the pre-processed mRNA transcript.

14. The method of claim 1, wherein the target motif is from 7 to 100 nucleotides in length.

15. The method of claim 13, wherein the target motif is from 10 to 50 nucleotides in length.

16. The method of claim 1, wherein the NSE-activator agent binds to a mutated nucleotide of the pre-processed mRNA transcript.

17. The method of claim 13, wherein the polynucleic acid polymer is modified at a nucleoside moiety, at a phosphate moiety, at a 5' terminus, at a 3' terminus, or a combination thereof.

18. The method of claim 13, wherein the polynucleic acid polymer comprises an artificial nucleotide selected from the group consisting of 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), 2'-O—N-methylacetamido (2-O-NMA), a locked nucleic acid (LNA), an ethylene nucleic acid (ENA), a peptide nucleic acid (PNA), a 1',5'-anhydrohexitol nucleic acid (HNA), a morpholino, a methylphosphonate nucleotide, a thiolphosphonate nucleotide, and a 2'-fluoro N3-P5'-phosphoramidite.

19. The method of claim 13, wherein contacting comprises expressing the polynucleic acid polymer from a vector encoding the polynucleic acid polymer.

20. The method of claim 19, wherein the vector is a viral vector.

21. The method of claim 20, wherein the viral vector is adeno-associated viral vector.

22. The method of claim 1, wherein the pre-processed mRNA transcript is an endogenous pre-processed mRNA transcript.

23. The method of claim 1, wherein a protein translated from the equivalent processed mRNA transcript lacking the NSE is a wild-type protein.

24. The method of claim 1, wherein a protein translated from the equivalent processed mRNA transcript lacking the NSE is a mutant protein.

25. The method of claim 1, wherein a protein translated from the equivalent processed mRNA transcript lacking the NSE is a full-length protein.

26. The method of claim 1, wherein the NSE-activator agent comprises a genomic editing molecule.

27. The method of claim 26, wherein contacting comprises expressing the genomic editing molecule from a polynucleotide encoding the genomic editing molecule.

28. The method of claim 27, wherein the genomic editing molecule is CRISPR-Cas9.

29. The method of claim 1, wherein the NSE-activator agent is associated with a delivery vehicle suitable for delivering the NSE-activator agent to cells.

30. The method of claim 29, wherein the delivery vehicle comprises a cell-penetrating peptide.

31. The method of claim 29, wherein the delivery vehicle comprises a viral vector.

32. A method of treating or preventing a disease or condition in a subject in need thereof, the method comprising administering to the subject a pharmaceutical composition that comprises:
(i) a non-sense mediated RNA decay switch exon (NSE)-activator agent or a vector encoding the NSE-activator agent, wherein the NSE-activator agent comprises a polynucleic acid polymer or a small molecule that interacts with a target motif within a pre-processed mRNA transcript to promote inclusion of an NSE into a processed mRNA transcript, wherein the target motif is within an intron that contains the NSE and that is between two canonical exons; and
(ii) a pharmaceutically acceptable excipient and/or a delivery vehicle;
wherein the disease or condition is treated or prevented in the subject by the administration of the NSE-activator agent that decreases expression of a protein that is encoded by the pre-processed mRNA transcript.

33. The method of claim 32, wherein the disease or condition is cancer or a genetic disorder or condition selected from an autosomal dominant disorder, an autosomal recessive disorder, an X-linked dominant disorder, an X-linked recessive disorder, a Y-linked disorder, a mitochondrial disease, a multifactorial disorder and a polygenic disorder.

34. The method of claim 33, wherein the disease or condition is an autosomal dominant disorder.

35. The method of claim 32, wherein the NSE-activator agent promotes activation of a 5' or a 3' splice site of the NSE.

36. The method of claim 32, wherein the target motif is within the NSE or at least partially overlaps with the NSE.

37. The method of claim 32, wherein the target motif comprises a 5' end of the NSE or 3' end of the NSE.

38. The method of claim 32, wherein the target motif is upstream of a 5' end of the NSE or downstream of a 3' end of the NSE.

39. The method of claim 32, wherein the target motif does not comprise a 5' or 3' end of the NSE.

40. The method of claim 32, wherein the NSE-activator agent binds to a mutated nucleotide of the pre-processed mRNA transcript.

41. The method of claim 32, wherein the pre-processed mRNA transcript is a mutant pre-processed mRNA transcript.

42. The method of claim 32, wherein the pharmaceutical composition comprises the NSE-activator agent, wherein the NSE-activator agent comprises a polynucleic acid polymer that hybridizes to the target motif within the pre-processed mRNA transcript.

43. The method of claim 42, wherein the target motif is from 10 to 50 nucleotides in length.

44. The method of claim 32, wherein the pharmaceutical composition comprises the vector encoding the NSE-activator agent, wherein the NSE-activator agent comprises a polynucleic acid polymer that hybridizes to the target motif within the pre-processed mRNA transcript, and wherein the vector is a viral vector.

45. The method of claim 32, wherein the pharmaceutical composition further comprises a genomic editing molecule or a polynucleotide encoding the genomic editing molecule.

46. The method of claim 32, wherein the NSE-activator agent is associated with a delivery vehicle suitable for delivering the NSE-activator agent to cells, wherein the delivery vehicle comprises a cell-penetrating peptide or a viral vector.

47. A pharmaceutical composition comprising:
(i) a non-sense mediated RNA decay switch exon (NSE)-activator agent or a vector encoding the NSE-activator agent, wherein the NSE-activator agent comprises a polynucleic acid polymer or a small molecule that interacts with a target motif within a pre-processed mRNA transcript to promote inclusion of an NSE into a processed mRNA transcript,
wherein the target motif is within an intron that contains the NSE and that is between two canonical exons; and
(ii) a pharmaceutically acceptable excipient and/or a delivery vehicle.

* * * * *